(12) United States Patent
Dvorak et al.

(10) Patent No.: US 9,115,117 B2
(45) Date of Patent: Aug. 25, 2015

(54) SUBSTITUTED PIPERIDINE COMPOUNDS AND THEIR USE AS OREXIN RECEPTOR MODULATORS

(71) Applicant: JANSSEN PHARMACEUTICA NV, New Brunswick, NJ (US)

(72) Inventors: Curt A. Dvorak, Poway, CA (US); Brock T. Shireman, Poway, CA (US)

(73) Assignee: JANSSEN PHARMACEUTICA NV (BE)

( * ) Notice: Subject to any disclaimer, the term of this patent is extended or adjusted under 35 U.S.C. 154(b) by 0 days.

(21) Appl. No.: 14/206,662

(22) Filed: Mar. 12, 2014

(65) Prior Publication Data

US 2014/0275095 A1   Sep. 18, 2014

Related U.S. Application Data

(60) Provisional application No. 61/780,302, filed on Mar. 13, 2013.

(51) Int. Cl.

| | |
|---|---|
| A61K 31/495 | (2006.01) |
| C07D 401/12 | (2006.01) |
| C07D 401/14 | (2006.01) |
| C07D 413/14 | (2006.01) |
| C07D 413/12 | (2006.01) |
| C07D 417/14 | (2006.01) |

(52) U.S. Cl.
CPC ............ *C07D 401/12* (2013.01); *C07D 401/14* (2013.01); *C07D 413/12* (2013.01); *C07D 413/14* (2013.01); *C07D 417/14* (2013.01)

(58) Field of Classification Search
CPC .................................................. C07D 401/12
USPC ........................................ 514/249; 544/284
See application file for complete search history.

(56) References Cited

U.S. PATENT DOCUMENTS

2009/0163485 A1* 6/2009 Knust et al. ................ 514/230.2

FOREIGN PATENT DOCUMENTS

| WO | WO 2008/065626 | * | 6/2008 |
|---|---|---|---|
| WO | WO 2008/065626 A | | 6/2008 |
| WO | WO 2009/133522 A | | 11/2009 |
| WO | WO 2010/048012 | * | 4/2010 |
| WO | WO 2010/048012 A | | 4/2010 |
| WO | WO 2010/048016 A | | 4/2010 |
| WO | WO 2010/063663 A | | 6/2010 |
| WO | WO 2010/122151 A | | 10/2010 |
| WO | WO 2011/050198 A | | 4/2011 |
| WO | WO 2011/050200 A | | 4/2011 |
| WO | WO 2013/059222 A | | 4/2013 |
| WO | WO 2014/066196 | * | 5/2014 |

OTHER PUBLICATIONS

King, Med. Chem. Principle and Practice (1994), pp. 206-208.*
Ammoun et al, "Distinct Recognition of OX1 and OX2 Receptors by Orexin Peptides", *Journal of Pharmacology and Experimental Therapeutics* (2003) 305(2):507-514.
Arendt et al, "Depressive Behavior and Activation of the Orexin/Hypocretin System", *Behavioral Neuroscience* (2013) 127(1):86-94.
Borgland et al, "Orexin A in the VTA Is Critical for the Induction of Synaptic Plasticity and Behavioral Sensitization to Cocaine", *Neuron* (2006) 49:589-601.
Brundin et al, "Reduced orexin levels in the cerebrospinal fluid of suicidal patients with major depressive disorder", *European Neuropsychopharmacology* (2007) 17:573-579.
Chemelli et al, "Narcolepsy in orexin Knockout Mice: Molecular Genetics of Sleep Regulation", Cell (1999) 98:437-451.
Chen et al, "Pressor effects of orexins injected intracisternally and to rostral ventrolateral medulla of anesthetized rats", *American Journal of Physiol. Regulatory Integrative Comp. Physiol.* (2000) 278:R692-R697.
De Lecea, Chatper 3, "Hypocretins and the neurobiology of sleep-wake mechanisms", *Progress in Brain Research* (2012) vol. 198, A. Shekhar (Ed.), pp. 15-24.
Fortuyn et al, "Anxiety and mood disorders in narcolepsy: a case-control study", *General Hopsital Psychiatry* (2010) 32:49-56.
Hara et al, "Genetic Ablation of Orexin Neurons in Mice Results in Narcolepsy, Hypophagia, and Obesity", *Neuron* (2001) 30:345-354.
Harris et al, "A role for lateral hypothalamic orexin neurons in reward seeking", *Nature* (2005) 437:556-559.
Harris et al, "Lateral hypothalamic orexin neurons are critically involved in learning to associate an environment with morphine reward", *Behavioural Brain Research* (2007) 183:43-51.
Hollander et al, "Insular hypocretin transmission regulates nicotine reward", *Proc Natl Acad Sci USA (PNAS)* (2008) 105(49) 19480-19485.
Johnson et al, "A key role for orexin in panic anxiety", *Nature Medicine* (2010) 16(1):111-116.
Johnson et al, "Activation of the Orexin I Receptor is a Critical Component of CO2-Medidated Anxiety and Hypertension but not Bradycardia", *Neuropsychopharmacology* (2012) 37:1911-1922.

(Continued)

Primary Examiner — Taofiq A Solola

(57) ABSTRACT

The present invention is directed to compounds of Formula I:

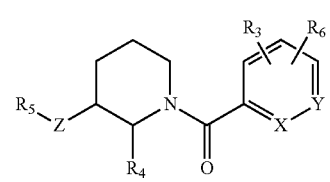

wherein X is $CR_1$ or N; Y is $CR_2$ or N; Z is NH or O; $R_1$ is alkoxy, triazolyl, oxazolyl, isoxazolyl, oxadiazolyl, or pyrimidinyl; $R_2$ is H, alkyl, or halo; $R_3$ is H, alkyl, alkoxy, halo, triazolyl, oxazolyl, or pyrimidinyl; $R_4$ is alkyl; $R_5$ is pyridyl; benzoxazolyl; pyrimidinyl; pyridazinyl; quinoxalinyl; pyrazinyl; or quinazolinyl; wherein the pyridyl; benzoxazolyl; pyrimidinyl; pyridazinyl; quinoxalinyl; pyrazinyl; or quinazolinyl is optionally substituted with one or two substituents independently selected from the group consisting of alkyl, halo, or phenyl; and $R_6$ is H or alkyl. Methods of making the compounds of Formula I are also described. The invention also relates to pharmaceutical compositions comprising compounds of Formula I. Methods of using the compounds of the invention are also within the scope of the invention.

57 Claims, No Drawings

(56) References Cited

OTHER PUBLICATIONS

Johnson et al, Chatper 9, "Orexin, stress, and anxiety/panic states", *Progress in Brain Research* (2012) vol. 198, A. Shekhar (Ed.), pp. 133-161.

Kirchgessner et al, "Orexin Synthesis and Response in the Gut", *Neuron* (1999) 24:941-951.

Kukkonen, "Physiology of the orexinergic/hypocretinergic system: a revisit in 2012", *American Journal of Physiol. Cell Physiol.* (2013) 304:C2-C32.

Langmead et al, "Characterisation of the binding of [3H]-SB-674042, a novel nonpeptide antagonist, to the human orexin-1 receptor", *British Journal of Pharmacology* (2004) 141:340-346.

Lawrence et al, "The orexin system regulates alcohol-seeking in rats", *British Journal of Pharmacology* (2006) 148:752-759.

Lin et al, "The Sleep Disorder Canine Narcolepsy Is Caused by a Mutation in the Hypocretin (Orexin) Receptor 2 Gene", *Cell* (1999) 98:365-376.

Mahler et al, Chatper 7, "Multiple roles for orexin/hypocretin in addiction", *Progress in Brain Research* (2012) vol. 198, A. Shekhar (Ed.), pp. 79-121.

Malherbe et al, "Biochemical and behavioural characterization of EMPA, a novel high-affinity, selective antagonist for the OX2 receptor", *British Journal of Pharmacology* (2009) 156:1326-1341.

Marcus et al, "Differential Expression of Orexin Receptors 1 and 2 in the Rat Brain", *Journal of Comparative Neurology* (2001) 435:6-25.

Mignot et al, "Complex HLA-DR and -DQ Interactions Confer Risk of Narcolepsy-Cataplexy in Three Ethnic Groups", *American Journal Human Genetics* (2001) 68:686-699.

Mignot et al, "Narcolepsy and the HLA System", *New England Journal of Medicine* (2001) 344(9):692.

Nakamura et al, "Orexin-induced hyperlocomotion and stereotypy are mediated by the dopaminergic system", *Brain Research* (2000) 873:181-187.

Narita et al, "Direct Involvement of Orexinergic Systems in the Activation of the Mesolimbic Dopamine Pathway and Related Behaviros Induced by Morphine", *Journal of Neuroscience* (2006) 26(2):398-405.

Peyron et al, "Neurons Containing Hypocretin (Orexin) Project to Multiple Neuronal Systems", *Journal of Neuroscience* (1998) 18(23):9996-10015.

Peyron et al, "A mutation in a case of early onset narcolepsy and a generalized absence of hypocretin peptides in human narcoleptic brains", *Nature Medicine* (2000) 6(9):991-997.

Piper et al, "The novel brain neuropeptide, orexin-A, modulates the sleep-wake cycle of rats", *European Journal of Neuroscience* (2000) 12:726-730.

Rengasamy et al, "New Building Block for Polyhydroxylated Peperidine: Total Synthesis of 1,6-Dideoxynojirimycin", *Journal of Organic Chemistry* (2008) 73(7):2898-2901.

Sakurai et al, "Orexins and Orexin Receptors: A Family of Hyopthalamic Neuropeptides and G Protein-Coupled Receptors that Regulate Feeding Behavior", *Cell* (1998) 92:573-585.

Salomon et al, "Diurnal Variation of Cerebrospinal Fluid Hypocretin-1-(Orexin-A) Levels in Control and Depressed Subjects", *Biological Psychiatry* (2003) 54:96-104.

Samson et al, "Cardiovascular Regulatory Actions of the Hypocretins in Brain", *Brain Research* (1999) 831:248-253.

Sharf et al, "Orexin Mediates the Expression of Precipitated Morphine Withdrawal and Concurrent Activation of the Nucleus Accumbens Shell", *Biological Psychiatry* (2008) 64:175-183.

Shirasaka et al, "Sympathetic and cardiovascular actions of orexins in conscious rats", *American Journal of Physiol.(Regulatory Integrative Comp. Physiol. 46)* (1999) 277:R1780-R1785.

Shoblock et al, "Selective blockade of the orexin-2 receptor attenuates ethanol self-administration, place preference, and reinstatement", *Psychopharmacology* (2011) 215:191-203.

Strawn et al, "Low cerebrospinal fluid and plasma orexin-A (hypocretin-1) concentrations in combat-related posttraumatic stress disorder", *Psychoneuroendocrinology* (2010) 35:1001-1007.

Takahashi et al, "Stimulation of Gastric Acid Secretion by Centrally Administered Orexin-A in Conscious Rats", *Biochemical and Biophysical Research Communications* (1999) 254:623-627.

Trivedi et al, "Distribution of orexin receptor mRNA in the rat brain", *FEBS Letters* (1998) 438:71-75.

Van Den Pol, "Hypothalamic Hypocretin (Orexin): Robust Innervation of the Spinal Cord", *Journal of Neuroscience* (1999) 19(8):3171-3182.

Yamanaka et al, "Orexins Activate Histaminergic Neurons via the Orexin 2 Receptor", Biochemical and Biophysical Research Communications (2002) 290:1237-1245.

\* cited by examiner

SUBSTITUTED PIPERIDINE COMPOUNDS AND THEIR USE AS OREXIN RECEPTOR MODULATORS

CROSS REFERENCE TO RELATED APPLICATIONS

This application claims the benefit of U.S. Provisional Application No. 61/780,302, filed Mar. 13, 2013, which is incorporated herein by reference in its entirety.

TECHNICAL FIELD

The present invention is directed to substituted piperidine compounds, pharmaceutical compositions comprising them, methods of making them, and methods of using them for the modulation of the orexin receptor for the treatment of disease states, disorders, and conditions mediated by orexin receptor activity.

BACKGROUND

Orexin/hypocretin signaling is mediated by two receptors and two peptide agonists. The peptides (orexin-A and orexin-B) are cleavage products of the same gene, pre-pro orexin. In the central nervous system, neurons producing pre-pro orexin are found solely in the periformical nucleus, the dorsal hypothalamus, and the lateral hypothalamus (Peyron et al., 1998, *J. Neurosci.* 18: 9996-10015). Orexigenic cells in these regions project to many areas of the brain, extending rostrally to the olfactory bulbs and caudally to the spinal cord (Van den Pol, 1999, *J. Neurosci.* 19: 3171-3182).

The orexins bind to two high affinity receptors, referred to as orexin-1 and orexin-2 receptors. Orexin-1 and orexin-2 receptors are G-protein-coupled, seven transmembrane receptors that share over 64% amino acid sequence identity with one another. Both receptors are generally excitatory, the common cellular response to orexin-induced receptor activation being increases in intracellular calcium. Homology between the species orthologs is high and there are no known pharmacological differences. Orexin-A and -B are usually considered equal ligands for orexin-2 receptor but orexin-B is thought to be 5- to 100-fold weaker ligand than orexin-A at the orexin-1 receptor (Sakurai et al., 1998, Cell 92: 573-585; Ammoun et al., 2003, *J. Pharmacol. Exp. Ther.* 305: 507-514).

Many regions of the brain have fairly selective expression of the orexin-1 or orexin-2 receptors (Marcus et al., 2001, *J. Comp Neurology* 435, 6-25; Trivedi et al., 1998, *FEBS Letters*, 438, 71-75). Orexin-1 receptors are selective for the limbic system (bed nucleus of the stria terminalis and amygdala), cingulate cortex and noradrenergic neurons in the locus coeruleus. Conversely, the orexin-2 receptor is almost the exclusive orexin receptor in the histaminergic neurons in the tuberomammilary nucleus which play a critical role in wake promotion; in paraventricular neurons and the parabrachial nucleus. In other brain regions like the dorsal raphe, the ventral tegmental area or the prefontal cortex both receptors are coexpressed.

The broad CNS distribution of cells producing orexin, as well as cells expressing the orexin receptors, suggests involvement of orexin in a number of physiological functions, including feeding and metabolism, regulation of wakefulness and sleep, sympathetic activation and stress response (de Lecea, 2012, *Progress in Brain Research*, 198, 15-24; Kukkonen, 2013, *Am J. Physiol. Cell Physiol.*, 304, C2-C32). Orexin also plays a key role regulating motivation and reward associated with food intake and with drugs of abuse (Mahler et al., 2012, *Progress in Brain Research*, 198, 79-121).

Several lines of evidence indicate that the orexin system is an important modulator of arousal. Rodents administered orexin intracerebroventricularly spend more time awake (Piper et al., 2000, *J. Neurosci.* 12: 726-730. Orexin-mediated effects on arousal have been linked to orexin neuronal projections to histaminergic neurons in the tuberomammillary nucleus (Yamanaka et al., 2002, *Biochem. Biophys. Res. Comm.* 290: 1237-1245). Rodents whose pre-pro orexin gene has been knocked out, or whose orexigenic neurons have been killed, display altered sleep/wake cycles similar to narcolepsy (Chemelli et al., 1999, *Cell* 98: 437-451; Hara et al., 2001, *Neuron* 30: 345-354). Dog models of narcolepsy have been shown to have mutant or non-functional orexin-2 receptors (Lin et al., 1999, *Cell* 98: 365-376). Orexin signaling as a target for sleep-promoting therapies was further validated clinically by findings of attenuated orexin levels and loss of orexinergic neurons in human narcoleptic patients (Mignot et al., 2001, *Am. J. Hum. Genet.* 68: 686-699; Minot & Thorsby, 2001, *New England J. Med.* 344: 692) or, in rare cases, to mutations in the orexin-2 gene (Peyron et al., 2000, *Nature Med.* 6: 991-997). Disorders of the sleep-wake cycle are therefore likely targets for orexin-2 receptor modulator activity. Examples of sleep-wake disorders that may be treated by agonists or other modulators that up-regulate orexin-2 receptor-mediated processes include narcolepsy, jet lag (sleepiness) and sleep disorders secondary to neurological disorders such as depression. Examples of disorders that may be treated by antagonists or other modulators that down-regulate orexin-2 receptor-mediated processes include insomnia, restless leg syndrome, jet lag (wakefulness) and sleep disorders secondary to neurological disorders such as mania, schizophrenia, pain syndromes and the like.

Evidence has accumulated to demonstrate a clear involvement of orexin signaling in reward pathways associated with drug dependence (Mahler et al., 2012, *Progress in Brain Research*, 198, 79-121). Orexinergic neurons send projections to the ventral tegmental area and other brain regions involved in reward processing. Orexin ligands mediate reward behavior, and antagonizing these effects with a selective orexin-1 receptor antagonist in various preclinical model of addiction has suggested that these actions are mediated through orexin-1 receptor. Specifically, a selective orexin-1 antagonist attenuates morphine conditioned place preference and reinstatement (Harris et al., 2005, *Nature*, 437, 556-5599; Narita et al., 2006, *J Neurosci.*, 26, 398-405; Harris et al., 2007, *Behav Brain Res*, 183, 43-51), stress-induced cocaine reinstatement, cocaine-induced behavioral and synaptic plasticity (Borgland et al., 2006, *Neuron*, 49, 589-601), and intake and cue and stress-induced reinstatement of ethanol (Lawrence et al., 2006, *Br J Pharmacol*, 148, 752-759), in addition to attenuating precipitated morphine withdrawal (Sharf et al., 2008, *Biol Psychiatry*, 64, 175-183) and nicotine self-administration (Hollander et al., 2008, *Proc Natl Acad Sci USA.*, 105, 19480-19485). Another recent study has also suggested a role for OX2R (Shoblock et al., 2011, *Psychopharmacology*, 215, 191-203).

Orexin's role in more complex emotional behavior is also emerging (Johnson et al., 2012, *Progress in Brain Research*, 198, 133-161). Changes in orexin levels in patients with panic and posttraumatic stress disorders have been noted as have changes in the prevalence of anxiety behaviors in narcoleptic patients (Johnson et al., 2010, *Nature Medicine*, 16, 111-115; Fortuyn et al., 2010, *General Hospital Psychiatry*, 32, 49-56; Strawn et al., 2010, *Psychoneuroendocrinology*, 35, 1001-1007). Lactate infusion or acute hypercapnia, which causes panic in humans, and are used as an animal model of panic, activates orexin neurons in the periformical hypothalamus. This activation correlates with anxiety in the social interaction test or open field test. Blocking orexin signaling with either siRNA or selective orexin-1 receptor antagonists attenuates panic-like responses to lactate (Johnson et al., 2010, *Nature Medicine,* 16, 111-115; Johnson et al., 2012, *Neuropsychopharmacology,* 37, 1911, 1922).

Cerebral spinal fluid (CSF) levels of orexin are lower in depressed or suicidal patients, and the level of orexin inversely correlates with illness severity (Brundin et al., 2007, *European Neuropsychopharmacology,* 17, 573-579; Salomon et al., 2003, *Biol Psychiatry,* 54, 96-104). A positive correlation between orexin-1 receptor mRNA in the amygdala and depressive behavior in the forced swim test in mice has been reported (Arendt, 2013, *Behavioral Neuroscience,* 127, 86-94).

The orexin system also interacts with brain dopamine systems. Intracerebroventricular injections of orexin in mice increase locomotor activity, grooming and stereotypy; these behavioral effects are reversed by administration of D2 dopamine receptor antagonists (Nakamura et al., 2000, *Brain Res.* 873: 181-187). Therefore, orexin receptor modulators may be useful to treat various neurological disorders; e.g., agonists or up-regulators to treat catatonia, antagonists or down-regulators to treat Parkinson's disease, Tourette's syndrome, anxiety, delerium and dementias.

Orexins and their receptors have been found in both the myenteric and submucosal plexus of the enteric nervous system, where orexins have been shown to increase motility in vitro (Kirchgessner & Liu, 1999, *Neuron* 24: 941-951) and to stimulate gastric acid secretion in vitro (Takahashi et al., 1999, *Biochem. Biophys. Res. Comm.* 254: 623-627). Orexin effects on the gut may be driven by a projection via the vagus nerve (van den Pol, 1999, supra), as vagotomy or atropine prevent the effect of an intracerebroventricular injection of orexin on gastric acid secretion (Takahashi et al., 1999, supra). Orexin receptor antagonists or other down-regulators of orexin receptor-mediated systems are therefore potential treatments for ulcers, irritable bowel syndrome, diarrhea and gastroesophageal reflux.

Body weight may also be affected by orexin-mediated regulation of appetite and metabolism. Some effects of orexin on metabolism and appetite may be mediated in the gut, where, as mentioned, orexins alter gastric motility and gastric acid secretion. Orexin antagonists therefore are likely to be useful in treatment of overweight or obesity and conditions related to overweight or obesity, such as insulin resistance/type II diabetes, hyperlipidemia, gallstones, angina, hypertension, breathlessness, tachycardia, infertility, sleep apnea, back and joint pain, varicose veins and osteoarthritis. Conversely, orexin agonists are likely to be useful in treatment of underweight and related conditions such as hypotension, bradycardia, ammenorrhea and related infertility, and eating disorders such as anorexia and bulimia.

Intracerebroventricularly administered orexins have been shown to increase mean arterial pressure and heart rate in freely moving (awake) animals (Samson et al., 1999, *Brain Res.* 831: 248-253; Shirasaka et al., 1999, *Am. J. Physiol.* 277: R1780-R1785) and in urethane-anesthetized animals (Chen et al., 2000, *Am. J. Physiol.* 278: R692-R697), with similar results. Orexin receptor agonists may therefore be candidates for treatment of hypotension, bradycardia and heart failure related thereto, while orexin receptor antagonists may be useful for treatment of hypertension, tachycardia and other arrhythmias, angina pectoris and acute heart failure.

From the foregoing discussion, it can be seen that the identification of orexin receptor modulators, will be of great advantage in the development of therapeutic agents for the treatment of a wide variety of disorders that are mediated through these receptor systems.

SUMMARY

The present invention is directed to compounds of Formula I:

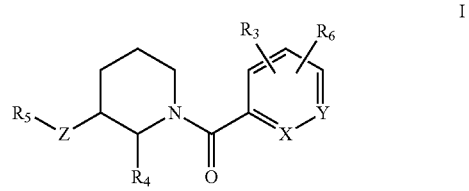

wherein X is $CR_1$ or N; Y is $CR_2$ or N; Z is NH or O; $R_1$ is alkoxy, triazolyl, oxazolyl, isoxazolyl, oxadiazolyl, or pyrimidinyl; $R_2$ is H, alkyl, or halo; $R_3$ is H, alkyl, alkoxy, halo, triazolyl, oxazolyl, or pyrimidinyl; $R_4$ is alkyl; $R_5$ is pyridyl; benzoxazolyl; pyrimidinyl; pyridazinyl; quinoxalinyl; pyrazinyl; or quinazolinyl; wherein the pyridyl; benzoxazolyl; pyrimidinyl; pyridazinyl; quinoxalinyl; pyrazinyl; or quinazolinyl is optionally substituted with one or two substituents independently selected from the group consisting of alkyl, halo, or phenyl; and $R_6$ is H or alkyl.

Methods of making the compounds of Formula I are also described. The invention also relates to pharmaceutical compositions comprising compounds of Formula I. Methods of using the compounds of the invention are also within the scope of the invention.

DETAILED DESCRIPTION OF ILLUSTRATIVE EMBODIMENTS

The invention may be more fully appreciated by reference to the following description, including the following glossary of terms and the concluding examples.

The term "alkyl" refers to a straight- or branched-chain alkyl group having from 1 to 12 carbon atoms in the chain. Examples of alkyl groups include methyl (Me) ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. Alkyl groups of the invention can be substituted with, for example, halogen atoms. One exemplary substitutent is fluoro. Preferred substituted alkyl groups of the invention include trihalogenated alkyl groups such as trifluoromethyl groups.

Alkyl groups of the invention can also refer to "cycloalkyl" moieties. Cycloalkyl refers to monocyclic, non-aromatic hydrocarbon groups having from 3 to 7 carbon atoms. Examples of cycloalkyl groups include, for example, cyclopropyl, cyclobutyl, cyclopentyl, cyclohexyl, 1-methylcyclopropyl, 2-methylcyclopentyl, and the like.

The term "alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on.

The term "benzoxazolyl" represents the following moiety:

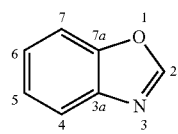

The benoxazolyl moiety can be attached through any one of the 2-, 4-, 5-, 6-, or 7-position carbon atoms.

The term "halogen" represents chlorine, fluorine, bromine, or iodine. The term "halo" represents chloro, fluoro, bromo, or iodo.

The term "isoxazolyl" represents the following moiety:

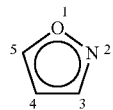

The isoxazolyl moiety can be attached through any one of the 3-, 4-, or 5-position carbon atoms. Isoxazolyl groups of the invention can be optionally substituted with, for example, one or two alkyl groups, for example, one or two methyl groups.

The term "oxazolyl" represents the following moiety:

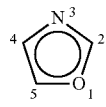

The oxazolyl moiety can be attached through any one of the carbon atoms.

The term "oxadiazolyl" represents a 1,2,3-oxadiazole, 1,2,4-oxadiazole, 1,2,5-oxadiazole, or 1,3,4-oxadiazole moiety:

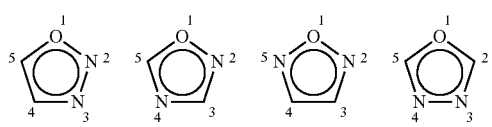

The oxadiazolyl moieties can be attached through any one of the carbon or nitrogen atoms. Within the scope of the invention, "oxadiazolyl" groups can be substituted with an alkyl group, preferably a methyl group.

The term "phenyl" represents the following moiety:

The term "pyridyl" represents the following moiety:

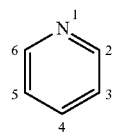

The pyridyl moiety can be attached through any one of the 2-, 3-, 4-, 5-, or 6-position carbon atoms.

The term "pyrimidinyl" represents the following moiety:

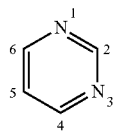

The pyrimidinyl moiety can be attached through any one of the 2-, 4-, 5-, or 6-position carbon atoms. Within the scope of the invention, "pyrimidinyl" groups of the invention can be substituted with halogen, for example fluoro.

The term "pyrazinyl" represents the following moiety:

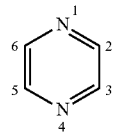

The pyrazinyl moiety can be attached through any one of the 2-, 3-, 5-, or 6-position carbon atoms.

The term "pyridazinyl" represents the following moiety:

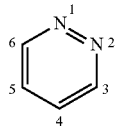

The pyridazinyl moiety can be attached through any one of the 3-, 4-, 5-, or 6-position carbon atoms.

The term "pyrazolyl" represents the following moiety:

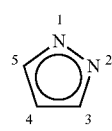

The pyrazolyl moiety can be attached through any one of the 1-, 2-, 3-, 4-, or 5-position carbon atoms. Pyrazolyl groups of the invention can be optionally substituted with, for example, one or two alkyl groups, for example, one or two methyl groups.

The term "quinoxalinyl" represents the following moiety:

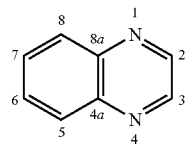

The quinoxalinyl moiety can be attached through any one of the 2-, 3-, 5-, 6-, 7-, or 8-position carbon atoms.

The term "quinazolinyl" represents the following moiety:

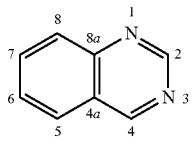

The quinoxalinyl moiety can be attached through any one of the 2-, 4-, 5-, 6-, 7-, or 8-position carbon atoms.

The term "triazolyl" represents a 1,2,3-triazole or a 1,2,4-triazole moiety:

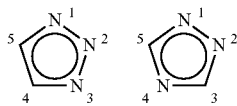

The triazolyl moieties can be attached through any one of their atoms.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like.

"Pharmaceutically acceptable vehicle" refers to a diluent, adjuvant, excipient or carrier with which a compound of the invention is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

"Subject" includes humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Compounds of the present invention," and equivalent expressions, are meant to embrace compounds of the Formula (I) as described herein, which expression includes the pharmaceutically acceptable salts, and the solvates, e.g., hydrates, where the context so permits. Similarly, reference to intermediates, whether or not they themselves are claimed, is meant to embrace their salts, and solvates, where the context so permits.

As used herein, the term "isotopic variant" refers to a compound that contains unnatural proportions of isotopes at one or more of the atoms that constitute such compound. For example, an "isotopic variant" of a compound can be radiolabeled, that is, contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. Radiolabeled compounds of the invention can be used in diagnostic methods such as Single-photon emission computed tomography (SPECT). The radioactive isotopes tritium, i.e. $^3$H, and carbon-14, i.e. $^{14}$C, are particularly useful for their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds of the invention, radioactive or not, are intended to be encompassed within the scope of the invention.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of r electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The present invention is directed to compounds of Formula I:

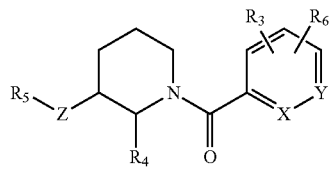

wherein
X is $CR_1$ or N;
Y is $CR_2$ or N;
Z is NH or O;
$R_1$ is alkoxy, triazolyl, oxazolyl, isoxazolyl, oxadiazolyl, or pyrimidinyl
$R_2$ is H, alkyl, or halo;
$R_3$ is H, alkyl, alkoxy, halo, triazolyl, oxazolyl, or pyrimidinyl;
$R_4$ is alkyl;
$R_5$ is pyridyl; benzoxazolyl; pyrimidinyl; pyridazinyl; quinoxalinyl; pyrazinyl; or quinazolinyl;
  wherein the pyridyl; benzoxazolyl; pyrimidinyl; pyridazinyl; quinoxalinyl; pyrazinyl; or quinazolinyl is optionally substituted with one or two substituents independently selected from the group consisting of alkyl, halo, or phenyl; and
$R_6$ is H or alkyl.

Enantiomers and diastereomers of the compounds of Formula I are also within the scope of the invention. Also within the scope of the invention are the pharmaceutically acceptable salts of the compounds of Formula I, as well as the pharmaceutically acceptable salts of the enantiomers and diastereomers of the compounds of Formula I.

In preferred embodiments of the invention, Z is NH. In other preferred embodiments of the invention, Z is O.

Preferably, in the compounds of the invention, $R_4$ is an alkyl group containing from 1 to 6 carbon atoms ($C_{1-6}$alkyl). Examples of preferred alkyl groups for $R_4$ include methyl, ethyl, and propyl. In exemplary embodiments of the invention, $R_4$ is methyl.

In some embodiments of the invention, X is $CR_1$ and Y is $CR_2$.

In other embodiments of the invention, X is N and Y is $CR_2$.

In still other embodiments, X is $CR_1$ and Y is N.

In yet other embodiments, X and Y are each N.

In those embodiments of the invention wherein X is $CR_1$, for example, those embodiments wherein X is $CR_1$ and Y is $CR_2$ or X is $CR_1$ and Y is N, $R_1$ is alkoxy, preferably methoxy, ethoxy, or propoxy.

In those embodiments of the invention wherein X is $CR_1$, for example, those embodiments wherein X is $CR_1$ and Y is $CR_2$ or X is $CR_1$ and Y is N, $R_1$ is triazolyl, with 1,2,3-triazolyl being preferred. In preferred embodiments, the 1,2,3-triazolyl is attached through the 2-position nitrogen atom. In other embodiments, the 1,2,3-triazolyl is attached through the 1-position nitrogen atom.

In those embodiments of the invention wherein X is $CR_1$, for example, those embodiments wherein X is $CR_1$ and Y is $CR_2$ or X is $CR_1$ and Y is N, $R_1$ is oxazolyl, which can be attached through any available atom, preferably attached through the 2-position carbon.

In those embodiments of the invention wherein X is $CR_1$, for example, those embodiments wherein X is $CR_1$ and Y is $CR_2$ or X is $CR_1$ and Y is N, $R_1$ is isoxazolyl, which can be attached through any available atom.

In those embodiments of the invention wherein X is $CR_1$, for example, those embodiments wherein X is $CR_1$ and Y is $CR_2$ or X is $CR_1$ and Y is N, $R_1$ is oxadiazolyl, preferably 1,2,4-oxadiazolyl attached through the 5-position carbon, although any oxadiazolyl, attached through any available carbon, is within the scope of the invention. The oxadiazolyl group can optionally be substituted with $C_{1-6}$alkyl, for example methyl. In exemplary embodiments, the substituted oxadiazolyl moiety is 1,2,4-oxadiazolyl substituted with methyl.

In those embodiments of the invention wherein X is $CR_1$, for example, those embodiments wherein X is $CR_1$ and Y is $CR_2$ or X is $CR_1$ and Y is N, $R_1$ is pyrimidinyl, which can be attached through any available atom. The pyrimidinyl can be optionally substituted with, for example, halogen such as fluoro. Preferably, the pyrimidinyl moiety is attached through the 2-position carbon.

In preferred embodiments of the invention wherein Y is $CR_2$, for example, those embodiments wherein X is $CR_1$ and Y is $CR_2$ or X is N and Y is $CR_2$, $R_2$ is H.

In some embodiments of the invention wherein Y is $CR_2$, for example, those embodiments wherein X is $CR_1$ and Y is $CR_2$ or X is N and Y is $CR_2$, $R_2$ is halo, preferably F, Cl, or Br, with F being more preferred.

In those embodiments of the invention wherein Y is $CR_2$, for example, those embodiments wherein X is $CR_1$ and Y is $CR_2$ or X is N and Y is $CR_2$, $R_2$ is alkyl. Preferably, the alkyl group has from one to six carbon atoms ($C_{1-6}$alkyl). In exemplary embodiments, $R_2$ is methyl.

In some embodiments of the invention, $R_3$ is H. In other embodiments, $R_3$ is alkyl, preferably methyl. In some embodiments, the alkyl group can be substituted with, for example, one or more halogen atoms. One exemplary substituted alkyl group is trifluoromethyl.

In yet other embodiments, $R_3$ is alkoxy, preferably methoxy or ethoxy. In still other embodiments, $R_3$ is halo, preferably F, Br, or Cl, with F and Br being more preferred.

In other exemplary embodiments of the invention, $R_3$ is triazolyl, with 1,2,3-triazolyl being preferred. In some embodiments, the 1,2,3-triazolyl is attached through the 2-position nitrogen atom. In other embodiments, the 1,2,3-triazolyl is attached through the 1-position nitrogen atom.

In still other embodiments of the invention, $R_3$ is oxazolyl, which can be attached through any available atom, preferably attached through the 2-position carbon.

In yet other embodiments, $R_3$ is pyrimidinyl, which can be attached through any available atom. The pyrimidinyl can be optionally substituted with, for example, halogen such as fluoro. Preferably, the pyrimidinyl moiety is attached through the 2-position carbon.

In some embodiments of the invention, $R_5$ is pyridyl, optionally substituted with one or two substituents independently selected from the group consisting of alkyl, halo, or phenyl. The pyridyl can be attached through any one of the 2-, 3-, or 4-position carbon atoms. In those embodiments where the pyridyl is substituted, the substitutents are independently selected from alkyl, for example methyl, substituted alkyl, for example, trihaloalkyl such as trifluoromethyl, and halo such as F, Br, and Cl.

In some embodiments of the invention, $R_5$ is benzoxazolyl, which can be attached through any available atom, and which can be optionally substituted with one or two substituents independently selected from the group consisting of alkyl, halo, or phenyl. In those embodiments where the benzoxazolyl is substituted, the substituents are independently selected from alkyl, for example methyl, substituted alkyl, for example, trihaloalkyl such as trifluoromethyl, and halo such as F, Br, and Cl.

In some embodiments of the invention, $R_5$ is pyrimidinyl, optionally substituted with one or two substituents independently selected from the group consisting of alkyl, halo, or phenyl. The pyrimidinyl can be attached through any one of the 2-, 4-, or 5-position carbon atoms. In those embodiments where the pyrimidinyl is substituted, the substitutents are independently selected from alkyl, for example methyl, substituted alkyl, for example trihaloalkyl such as trifluoromethyl, and halo such as F, Br, and Cl.

In some embodiments of the invention, $R_5$ is pyridazinyl, optionally substituted with one or two substituents independently selected from the group consisting of alkyl, halo, or phenyl. The pyridazinyl can be attached through any one of the 3- or 4-position carbon atoms. In those embodiments where the pyridazinyl is substituted, the substitutents are independently selected from alkyl, for example methyl, substituted alkyl, for example trihaloalkyl such as trifluoromethyl, and halo such as F, Br, and Cl.

In some embodiments of the invention, $R_5$ is quinoxalinyl, optionally substituted with one or two substituents independently selected from the group consisting of alkyl, halo, or phenyl. The quinoxalinyl can be attached through any one of the 2-, 3-, 5-, or 6-position carbon atoms. In those embodiments where the quinoxalinyl is substituted, the substitutents are independently selected from alkyl, for example methyl, substituted alkyl, for example trihaloalkyl such as trifluoromethyl, and halo such as F, Br, and Cl.

In some embodiments of the invention, $R_5$ is pyrazinyl, optionally substituted with one or two substituents independently selected from the group consisting of alkyl, halo, or phenyl. The pyrazinyl can be attached through any one of the 2- or 3-position carbon atoms. In those embodiments where the pyrazinyl is substituted, the substitutents are independently selected from alkyl, for example methyl, substituted alkyl, for example trihaloalkyl such as trifluoromethyl, and halo such as F, Br, and Cl.

In some embodiments of the invention, $R_5$ is quinazolinyl, optionally substituted with one or two substituents independently selected from the group consisting of alkyl, halo, or phenyl. The quinazolinyl can be attached through any one of the 2-, 4-, 5-, 6-, 7-, or 8-position carbon atoms. In those embodiments where the quinazolinyl is substituted, the substitutents are independently selected from alkyl, for example methyl, substituted alkyl, for example trihaloalkyl such as trifluoromethyl, and halo such as F, Br, and Cl.

In preferred embodiments of the invention, $R_6$ is H. In other embodiments of the invention, $R_6$ is alkyl, preferably methyl.

The invention relates to methods of using the compounds described herein to treat subjects diagnosed with or suffering from a disease, disorder, or condition mediated by orexin receptor activity. These methods are accomplished by administering to the subject a compound of the invention.

Diseases, disorders, and conditions mediated by orexin receptor activity include disorders of the sleep-wake cycle, insomnia, restless legs syndrome, jet-lag, disturbed sleep, sleep disorders secondary to neurological disorders, mania, depression, manic depression, schizophrenia, pain syndromes, fibromyalgia, neuropathic pain, catatonia, Parkinson's disease, Tourette's syndrome, anxiety, delirium, dementia, overweight, obesity, or conditions related to overweight or obesity, insulin resistance, type II diabetes, hyperlipidemia, gallstones, angina, hypertension, breathlessness, tachycardia, infertility, sleep apnea, back and joint pain, varicose veins, osteoarthritis, hypertension, tachycardia, arrhythmias, angina pectoris, acute heart failure, ulcers, irritable bowel syndrome, diarrhea gastroesophageal reflux, mood disorders, post-traumatic stress disorder, panic disorders, attention deficit disorders, cognitive deficiencies, or substance abuse.

Compounds of the invention are particularly suited for the treatment of mood disorders, post-traumatic stress disorder, panic disorders, attention deficit disorders, cognitive deficiencies, or substance abuse.

Sleep disorders include, but are not limited to, sleep-wake transition disorders, insomnia, restless legs syndrome, jet-lag, disturbed sleep, and sleep disorders secondary to neurological disorders (e.g., manias, depressions, manic depression, schizophrenia, and pain syndromes (e.g., fibromyalgia, neuropathic).

Metabolic disorders include, but are not limited to, overweight or obesity and conditions related to overweight or obesity, such as insulin resistance, type II diabetes, hyperlipidemia, gallstones, angina, hypertension, breathlessness, tachycardia, infertility, sleep apnea, back and joint pain, varicose veins and osteoarthritis.

Neurological disorders include, but are not limited to, Parkinson's disease, Alzheimer's disease, Tourette's Syndrome, catatonia, anxiety, delirium and dementias.

In treatment methods according to the invention, an effective amount of a pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the compounds of the invention may be used in combination with additional active ingredients in the treatment of the above conditions. The additional active ingredients may be coadministered separately with a compound of the invention or included with such an agent in a pharmaceutical composition according to the invention. In an exemplary embodiment, additional active ingredients are those that are known or discovered to be effective in the treatment of conditions, disorders, or diseases mediated by orexin activity, such as another orexin modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention.

The compounds of the invention are used, alone or in combination with one or more additional active ingredients, to formulate pharmaceutical compositions of the invention. A pharmaceutical composition of the invention comprises: (a) an effective amount of at least one compound in accordance with the invention; and (b) a pharmaceutically acceptable excipient.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and diglycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000.mu.g/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Scheme 1

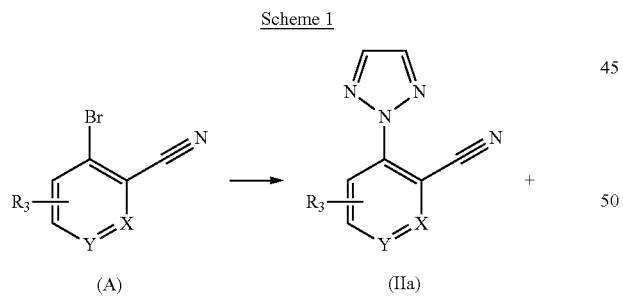

(A)　　　　(IIa)

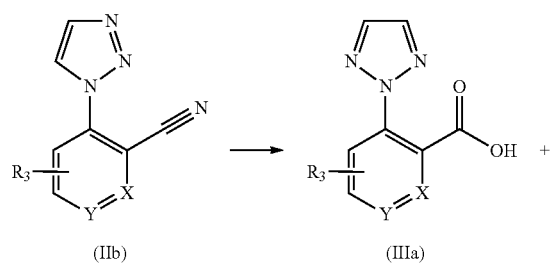

(IIb)　　　　(IIIa)

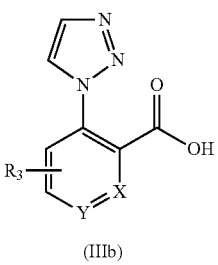

(IIIb)

Intermediate compounds of formulas (IIIa) and (IIIb) are prepared, as outlined in Scheme 1, from commercially available or synthetically accessible compounds of formula (A). Compounds of formulas (IIa) and (IIb), are obtained by reacting a compound of formula (A), where $R_3$ is —H, -alkyl, or -alkoxy, with commercially available 1,2,3-triazole, in the presence of, for example, $K_2CO_3$ in DMF or dioxane, at temperatures ranging from about 60° C. to about 100° C. Compounds of formulas (IIIa) and (IIIb) are obtained by reacting compounds of formula (II) in the presence of a base such as NaOH in a solvent such as EtOH at temperatures ranging from about 80° C. to about 100° C. One skilled in the art will recognize that 1,2,3-triazole can exist in two tautomeric forms defined as 2H-[1,2,3]triazole and 1H-[1,2,3]triazole thus accounting for the formation of (IIIa) and (IIIb).

Scheme 2

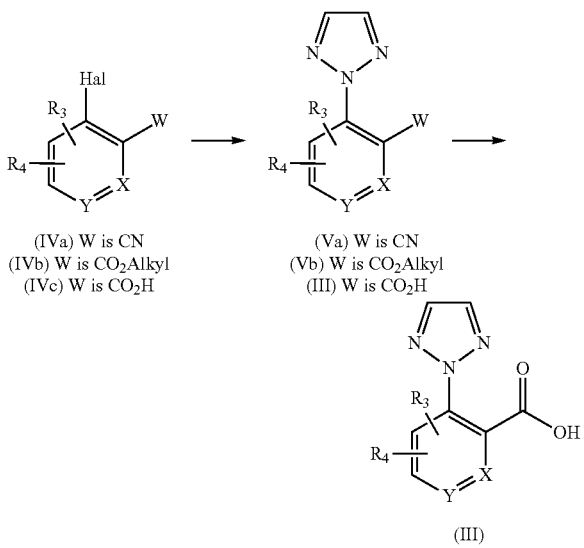

(IVa) W is CN　　　(Va) W is CN
(IVb) W is $CO_2$Alkyl　　(Vb) W is $CO_2$Alkyl
(IVc) W is $CO_2$H　　　(III) W is $CO_2$H (III)

Intermediate compounds of formula (III) can be prepared, as outlined in Scheme 2, from commercially available or synthetically accessible compounds of formula ($IV_{a-c}$). Compounds of formulas (Va), (Vb) and (III) are obtained by reacting compounds of formula (IVa), (IVb) and (IVc) where Hal is —Br, or —I; W is $CO_2$H, $CO_2$Alkyl, or CN and $R_3$ and $R_4$ are —H, halo, —$C_{1-4}$alkyl, —$C_{1-4}$alkoxy and $R_3$ and $R_4$, together with the atoms to which they are attached, form a 6-membered aryl or 6-membered heteroaryl ring, with commercially available 1,2,3-triazole, in the presence of, for example, copper(I)iodide, $Cs_2CO_3$ and trans-N,N'-dimethyl-1,2-cyclohexanediamine in for example, DMF or dioxane, at temperatures ranging from about 60° C. to about 120° C. Compounds of formula (IVc) can be converted to the corresponding esters (Vb) by treatment with, for example, alkyl iodide in the presence of a base such as $K_2CO_3$ in a solvent such as DMF. Compounds of formula (III) are also obtained by reacting compounds of formula (Va) and (Vb) in the presence of a base such as NaOH in a solvent such as EtOH at temperatures ranging from about 80° C. to about 100° C.

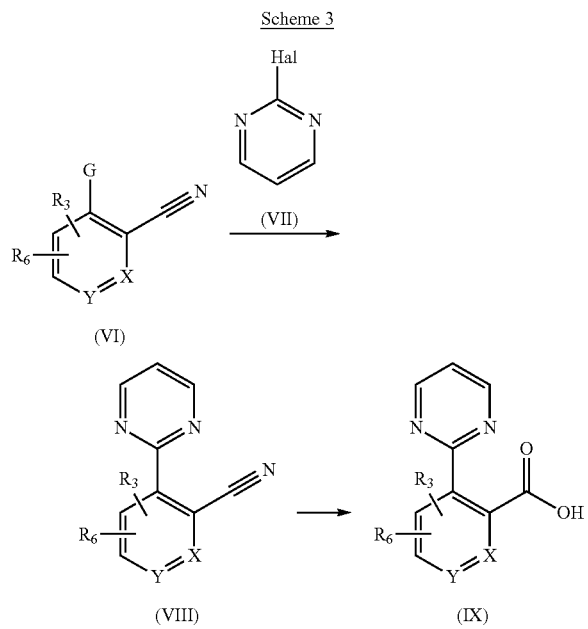

Intermediate compounds of formula (IX) are prepared, as outlined in Scheme 3, from commercially available or synthetically accessible compounds of formula (VI) where X is $CR_1$ or N, Y is $CR_2$ or N, $R_1$ and $R_2$ are H, alkyl, halo or alkoxy, $R_3$ is —H, halo, -alkyl, -alkoxy and $R_6$ is H or alkyl, G is $SnBu_3$ or 4,4,5,5 tetramethyl-1, dioxaboralane and Hal is Cl, or Br, preferably Br in this case. Compounds of formula (VIII) are obtained by reacting a compound of formula (VI) with commercially available (VII) in the presence of a catalyst such as 1,1'-Bis(di-tert-butylphosphino)ferrocene palladium dichloride and a base such as $Na_2CO_3$ in a solvent such as 2-MeTHF or THF at temperatures ranging from about 60° C. to about 90° C. Compounds of formula (IX) are obtained by reacting a compound of formula (VIII) in the presence of a base such as NaOH in a solvent such as MeOH at temperatures ranging from about 80° C. to about 100° C. or acids such as $H_2SO_4$ in solvents such as $H_2O$ at temperatures ranging from 80 to 100° C.

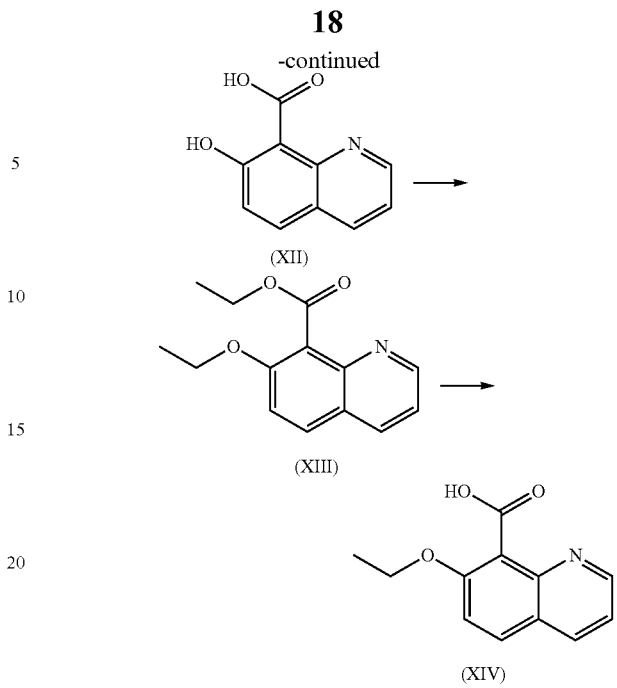

Intermediate compound (XIV) is prepared, as outlined in Scheme 4, from commercially available compound (X). Compound (XI) is obtained by reacting compound (X) with commercially available acrolein in a solvent such as 1,4 dioxane at temperatures of about 200° C. in, for example, a microwave reactor. Compound (XII) can be prepared from compound (XI) by treatment with an acid such as HBr in a solvent such as toluene at a temperature of about 90° C. Compound (XIII) can be obtained by treatment of compound (XII) with, for example, commercially available iodoethane and a base such as $K_2CO_3$ in a solvent such as DMF at temperatures ranging from about 45° C. to about 65° C. Compound (XIV) is obtained by treating compound (XIII) with a base such as NaOH in a solvent such as MeOH at temperatures ranging from about 80° C. to about 100° C.

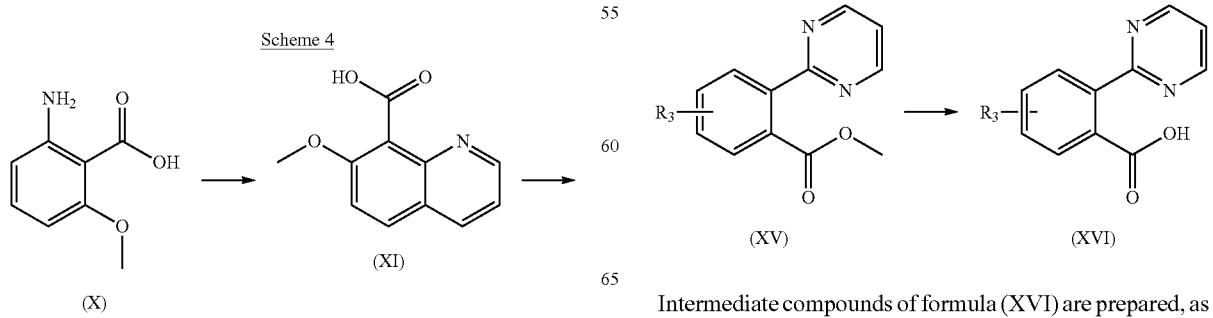

Intermediate compounds of formula (XVI) are prepared, as outlined in Scheme 5, from a commercially available or synthetically accessible compounds of formula (XIV) where $R_3$ is —H, -alkyl, or -alkoxy and Hal is Cl or Br. Compounds of formula (XV) are obtained by reacting a compound of formula (XIV) with commercially available (VII) in the presence of a catalyst such as Pd(dppf)Cl$_2$ and a base such as Na$_2$CO$_3$ in a solvent such as 2-MeTHF at temperatures ranging from about 75° C. to about 150° C. Compounds of formula (XVI) are obtained by reacting a compound of formula (XV) in the presence of a base such as NaOH in a solvent such as MeOH at temperatures ranging from about 80° C. to about 100° C.

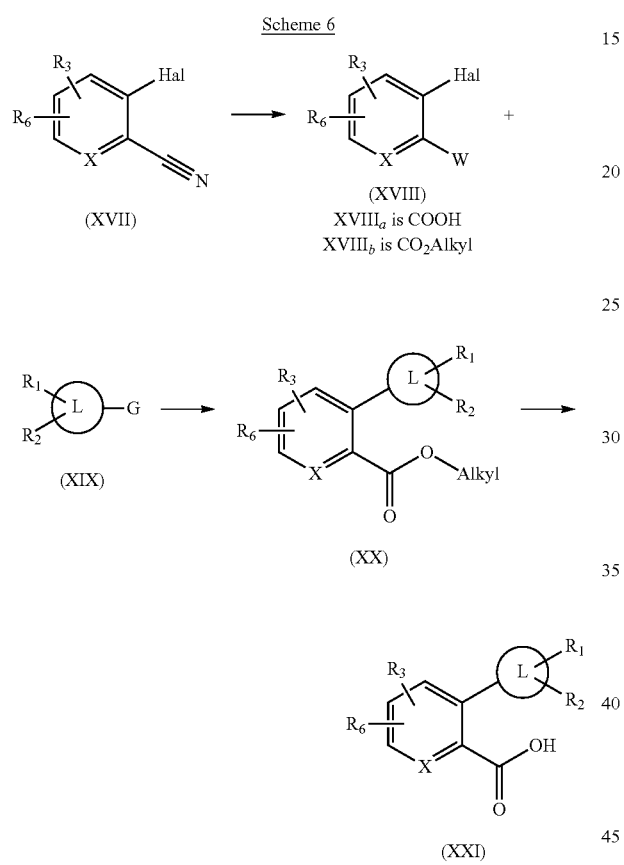

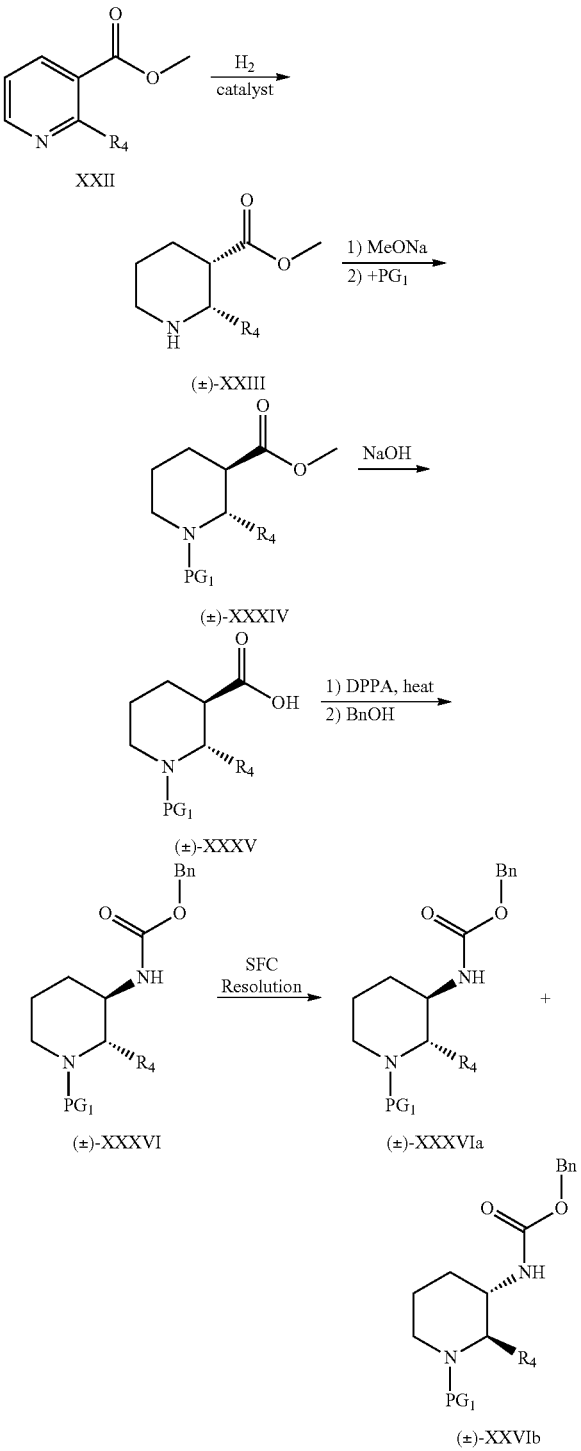

Intermediate compounds of formula (XXI) can be prepared, as outlined in Scheme 6, from a commercially available or synthetically accessible compounds of formula (XVII) where Hal is Br or I; and where $R_3$ is —H, halo, -alkyl, -alkoxy and $R_6$ is H or alkyl. Compounds of formula (XVIIIa) can be converted to the corresponding ester (XVIIIb) by treatment with, for example, thionyl chloride in a solvent such as MeOH. Compounds of the formula (XX) are obtained by reacting compounds of formula (XVIIIb) with commercially available compounds of the formula XIX where L is a heterocyle such as pyrazole, pyridyl, or oxazole; G is SnBu$_3$ or 4,4,5,5 tetramethyl-1, dioxaboralane and $R_1$ and $R_2$ are —H, -alkyl, or -alkoxy in the presence of a catalyst such as Pd(Ph$_3$P)$_4$ and a base such as Na$_2$CO$_3$ in a mixture of solvents such as DME and H$_2$O at temperatures ranging from about 100° C. to about 150° C. Compounds of formula (XXI) are obtained by reacting a compound of formula (XX) in the presence of a base such as NaOH in a solvent such as MeOH at temperatures ranging from about 80° C. to about 100° C.

Referring to Scheme 7, compounds of formula (+)-(XXXVIa) and (−)-(XXXVIb) were synthesized from compounds of formula (XXII) where PG1 is, for example, a Boc protecting group, $R_4$ is alkyl and Bn represents a benzyl group, —CH$_2$Ph. Treatment of compounds of formula (XXII) with hydrogen in the presence of, for example, a metal catalyst such as PtO$_2$, Pd/C, or Pd(OH)$_2$ in solvents such as AcOH provide compounds of formula (±)-(XXIII) as a mixture of diastereomers favoring the cis diastereomer of formula (±)-(XXIII). Compounds of formula (±)-(XXXIV) were synthesized from compounds of formula (±)-(XXIII) upon treatment with a base such as sodium methoxide in solvents such as methanol at reflux temperature. The amine in these compounds was protected as PG1 using reagents such as Boc$_2$O in the presence of bases such as Na$_2$CO$_3$ in solvents such as THF and water. Compounds of formula (±)-(XXXV) were synthesized from compounds of formula (±)-(XXXIV) by treatment with bases such as sodium hydroxide, lithium hydroxide or potassium hydroxide in solvents such as water, THF or methanol. Compounds of formula (±)-(XXXVI) were synthesized from compounds of formula (±)-(XXXV) by treatment with, for example, DPPA in solvents such as toluene in the presence of bases such as TEA at temperatures ranging from about 70-110° C. followed by, for example, benzyl alcohol followed by continued heating to temperatures ranging from about 70-110° C. Compounds of formula (±)-(XXXVI) were resolved into individual enantiomers using SFC chromatography on a chiral SFC(CHIRALPAK AD-H 5 mM 250×30 mm) column to provide compounds of formula (+)-(XXXVIa) and (−)-(XXXVIb).

Scheme 8

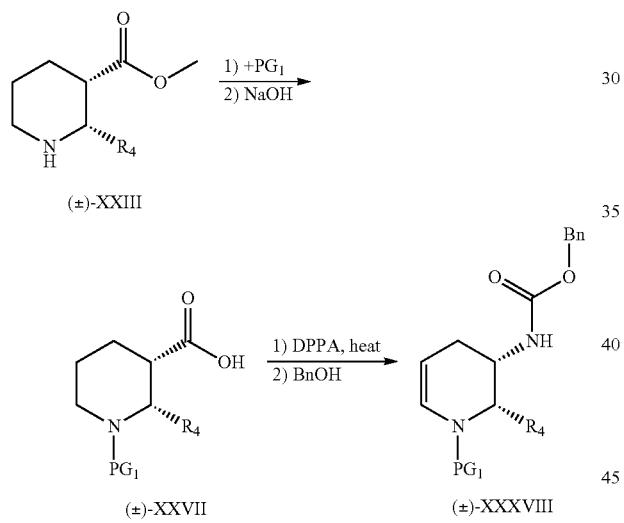

Referring to Scheme 8, compounds of formula (±)-(XXXVIII) were synthesized from compounds of formula (±)-(XXIII) where PG1 is, for example, a Boc protecting group, R4 is alkyl and Bn represents a benzyl group, —CH$_2$Ph. The amine in compounds of formula (±)—(XXIII) was protected as PG1 using reagents such as Boc$_2$O in the presence of bases such as Na$_2$CO$_3$ in solvents such as THF and water. Compounds of formula (±)-(XXXVII) were synthesized from compounds of formula (±)-(XXIII) by treatment with bases such as sodium hydroxide, lithium hydroxide, or potassium hydroxide in solvents such as water, THF, or methanol after protection with PG1 as described. Compounds of formula (±)-(XXXVIII) were synthesized from compounds of formula (±)-(XXXVII) by treatment with, for example, DPPA in solvents such as toluene in the presence of bases such as TEA at temperatures ranging from about 70-110° C. followed by benzyl alcohol followed by continued heating to temperatures ranging from about 70-110° C.

Scheme 9

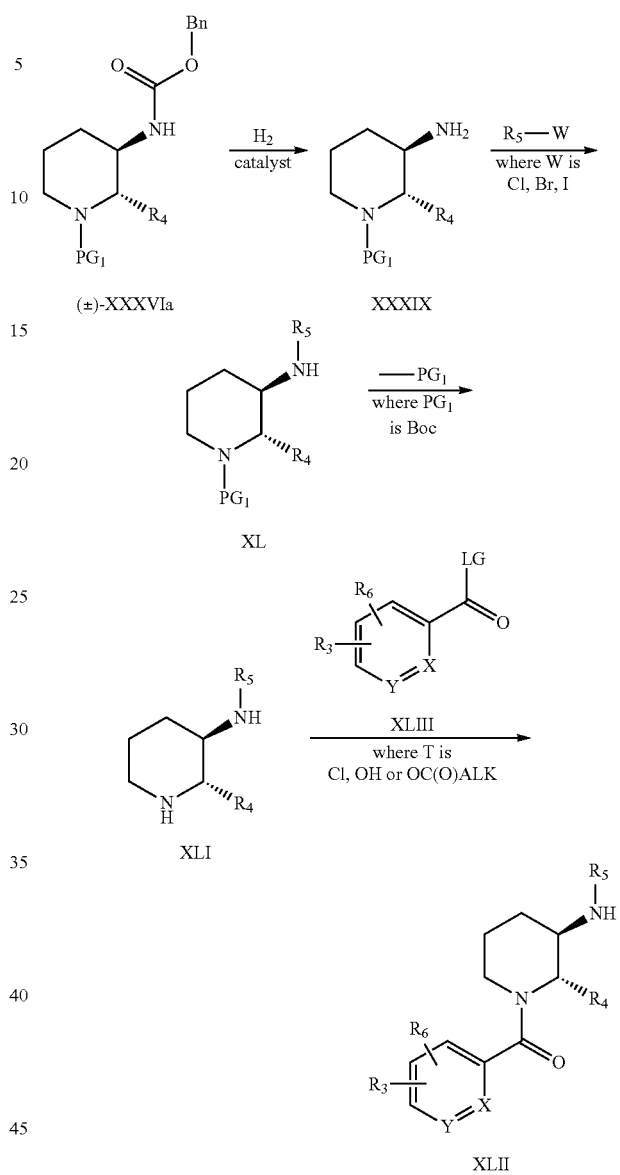

Referring to Scheme 9, compounds of formula XLII were synthesized from compounds of formula (±)-(XXXVIa) where PG1 is, for example, a Boc protecting group, R$_4$ is alkyl, LG is Cl, OH or OC(O)ALK, W is Cl, Br or I and Bn represents a benzyl group, —CH$_2$Ph. Compounds of formula (XXXIX) were obtained from compounds of formula (±)-(XXXVIa) by treatment with, for example, Pd catalysts such as 10 wt % Pd/C wet Degussa under an atmosphere of H$_2$ in a solvent such as EtOH to give compound of formula (XXXIX). Compounds of formula (XL) were obtained from compounds of formula (XXXIX) using compounds R$_5$—W in a suitable solvent such as DMSO or DMF in the presence of a base such as K$_2$CO$_3$ at a temperature of about 70° C. Compounds of formula (XL) were also obtained when compounds of formula (XXXIX) and R$_5$—W were treated with, for example, Pd catalysts such as Pd(OAc)$_2$ or Pd(dba)$_2$, ligands such as racemic BINAP or Q-PHOS, a base such as sodium tert-butoxide in a solvent such as toluene at a temperature of about 70° C. Compounds of formula (XLI) were obtained from compounds of formula (XL) when treated with an acid such as HCl or TFA in a suitable solvent such as EtOAc or DCM at room temperature. Compounds of formula (XLII) were obtained from compounds of formula (XLI) using compounds of formula (XLIII) in a suitable solvent such as DMF or DCM in the presence of a peptide coupling reagent such as HATU, HBTU or T3P, a base such as DIPEA, a solvent such as DMF, ACN, THF or DCM at a temperature ranging from rt to about 45° C. One skilled in the art will recognize similar chemistry can be done with compounds of formula (±)-XXXVI to give compounds of formula (±)-XLII.

Scheme 10

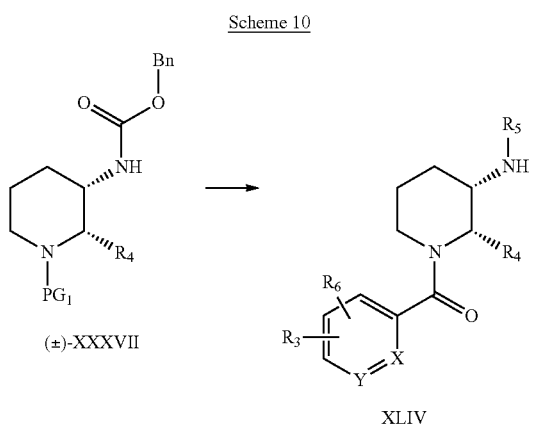

Referring to Scheme 10 compounds of formula (±)-XLIV were synthesized from compounds of formula (±)-XXXVIII using similar chemistry as described for the compounds in Scheme 9.

Scheme 11

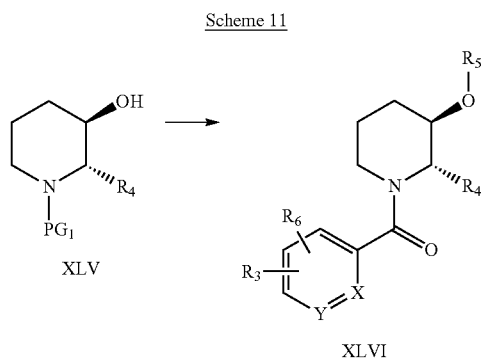

Referring to Scheme 11 compounds of formula (±)-XLV were synthesized from compounds of formula (±)-XLVI (J. Org. Chem. 2008, 73, 2898) using similar chemistry as described for the compounds in Scheme 9.

EXAMPLES

| Abbreviations | |
|---|---|
| Term | Acronym |
| High-pressure liquid chromatography | HPLC |
| Thin layer chromatography | TLC |
| Diisopropylethylamine | DIPEA |

-continued

| Abbreviations | |
|---|---|
| Term | Acronym |
| Tetrahydrofuran | THF |
| Dimethyl sulfoxide | DMSO |
| Benzyl alcohol | BnOH |
| n-Butyl alcohol | nBuOH |
| tert-Butylcarbamoyl | Boc |
| Di-tert-butyl dicarbonate | $BOC_2O$ |
| Dichloromethane | DCM |
| Trifluoroacetic acid | TFA |
| Acetic Acid | HOAc, AcOH |
| N,N-Dimethylformamide | DMF |
| Methanol | MeOH |
| Ethanol | EtOH |
| Acetonitrile | ACN |
| Ethyl Acetate | EtOAc, or EA |
| Triethylamine | TEA |
| Methanesulfonyl chloride | MsCl |
| 2-(1H-9-Azobenzotriazole-1-yl)-1,1,3,3-tetramethylaminium hexafluorophosphate | HATU |
| N,N,N',N'-Tetramethyl-O-(1H-benzotriazol-1-yl)uronium hexafluorophosphate | HBTU |
| Methyl Tertiary Butyl Ether | MTBE |
| Diisopropyl azodicarboxylate | DIAD |
| Diphenylphosphoryl azide | DPPA |
| Toluene | $PhCH_3$ |
| N-Methyl-2-pyrrolidone | NMP |
| 4,5-Bis(diphenylphosphino)-9,9-dimethylxanthene | Xantphos |
| 1,2,3,4,5-Pentaphenyl-1'-(di-t-butylphosphino)ferrocene | CTC-Q-Phos or QPHos |
| Bis(dibenzylideneacetone)palladium(0) | $Pd(dba)_2$ |
| Tris(dibenzylideneacetone)dipalladium(0) | $Pd_2(dba)_3$ |
| 1,1'-Bis(di-tert-butylphosphino)ferrocene palladium dichloride | $PdCl_2(dtbpf)$ |
| 1-Propanephosphonic anhydride or 2,4,6-Tripropyl-1,3,5,2,4,6-trioxatriphosphorinane-2,4,6-trioxide | T3P |

Chemistry:

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as $Na_2SO_4$ or $MgSO_4$, filtered and concentrated. Where mixtures, solutions, and extracts were "concentrated", they were typically concentrated on a rotary evaporator under reduced pressure. Reactions under microwave irradiation conditions were carried out in a Biotage Initiator or CEM Discover instrument.

Melting point determinations were performed in open capillary tubes on a FP62 or MP50 apparatus (Mettler-Toledo). Melting points were measured with a temperature gradient of 10° C./minute. Maximum temperature was 300° C. The melting point was read from a digital display.

Normal-phase flash column chromatography (FCC) was performed on silica gel ($SiO_2$) using prepackaged cartridges, eluting with the indicated solvents.

Where compounds were purified by "Prep HPLC" the method employed was either:

Preparative reverse-phase high performance liquid chromatography (HPLC) was performed on a Gilson HPLC with an Xterra Prep $RP_{18}$ (5 m, 30×100 mm, or 50×150 mm)

column, and a gradient of 10 to 99% acetonitrile/water (20 mM $NH_4OH$) over 12 to 18 min, and a flow rate of 30 mL/min.

or

Preparative reverse-phase high performance liquid chromatography (HPLC) was performed on a Agilent 1100 Series HPLC with an XBridge C18 column (5 μm, 30×100 mm), mobile phase of 5% ACN in 20 mM $NH_4OH$ (hold for 2 min) then ramp 5-99% ACN over 15 min, hold at 99% ACN for 5 min. and a flow rate of 40 mL/min.

or

Preparative reverse-phase high performance liquid chromatography (HPLC) was performed on a Agilent 1100 Series HPLC with an XBridge C18 column (5 μm, 50×100 mm), mobile phase of 5% ACN in 20 mM NH4OH (hold for 2 min) then ramp 5-99% ACN over 15 min, hold at 99% ACN for 5 min. and a flow rate of 80 mL/min.

or

Preparative reverse-phase high performance liquid chromatography (HPLC) was performed on a Gilson HPLC with an Xterra Prep $RP_{18}$ (5 μm, 30×100 mm, or 50×150 mm) column, and a gradient of 10 to 99% acetonitrile/water (20 mM $NH_4OH$) over 12 to 18 min, and a flow rate of 30 mL/min.

Analytical chromatography data was acquired using an Agilent 1100 HPLC, with an Inertsil ODS-3 3 mm 4.6×50 mm column, purchased from GL Sciences (Part #1010L050W046). Samples were run using a gradient profile of 10-99% acetonitrile (ACN) in water, each containing 0.05% trifluoroacetic acid (TFA) over 1.6 minutes, then holding at 99% acetonitrile for 0.3 minutes. Flow rate was 5 mL/min and column temperature was set to 50° C. (Method A).

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. The format of the $^1H$ NMR data below is: chemical shift in ppm downfield of the tetramethylsilane reference (multiplicity, coupling constant J in Hz, integration).

Chemical names were generated using ChemDraw Ultra 12.0 (CambridgeSoft Corp., Cambridge, Mass.) or ACD/Name Version 10.01 (Advanced Chemistry Development, Toronto, Ontario, Canada).

Where compounds were purified by "SFC Chromatography" the method employed was either:

On preparative APS 1010 system with autoprep option from Berger instrument, consisted of two varian SD-1 pumps (walnut creek, CA, USA), one of which was extensively modified to pump $CO_2$, a special pump head heat exchanger, a julabo FT 401 chiller (labortechnik GmbH, Sellback, Germany), a model SCM 2500 phase separator (berger instruments) with selection valve and set of collection vessels in a Bodan robot. A model Knauer 2500 UV detector with high pressure flow cell (berlin, germany). Sample were applied using a six-port injection valve (Valco, Houston, Tex., USA)) with a 5 ml sample loop and a model YP-300 syringue pump (cavro, san Jose, Calif.).

or

On a SFC-PICLAB-PREP 200 (PIC SOLUTION, Avignon, France). Modifier was pump with a model K1800 Knauer (Berlin, germany), with 100 ml Pump Head. The $CO_2$ was pump with 2 lewa pumps (Leonberg Germany). Cooling of the pump head and the CO2 line was achieved by a coil alimented by a Huber chiller (Offenburg/Germany). Sample injections were made using 6 switching valves (Valco, Houston, Tex., USA) and a 5 ml sample loop. The system is managed by a PLC automation system.

Intermediates

| Intermediate | Name | Structure | Reference |
|---|---|---|---|
| A-1 | 4-fluoro-2-(2H-1,2,3-triazol-2-yl)benzoic acid | 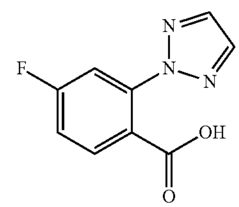 [SMILES: O=C(O)c1ccc(F)cc1-n1nccn1] | Prepared according to WO 2011/050198 Intermediate 4. |
| A-2 | 2-fluoro-6-(pyrimidin-2-yl)benzoic acid | 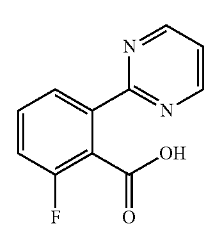 [SMILES: O=C(O)c1c(F)cccc1-c1ncccn1] | WO 2011/050198 Intermediate 14. |
| A-3 | 3-fluoro-2-(2H-1,2,3-triazol-2-yl)benzoic acid | 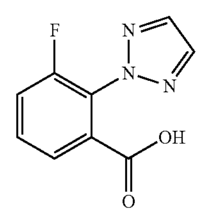 [SMILES: O=C(O)c1cccc(F)c1-n1nccn1] | WO 2011/050198 Intermediate 5. |

-continued

| Intermediate | Name | Structure | Reference |
|---|---|---|---|
| A-4 | 2-(2H-1,2,3-triazol-2-yl)benzoic acid | 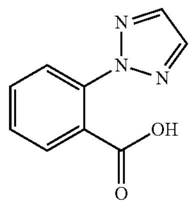 [SMILES: O=C(O)c1ccccc1-n1nccn1] | WO 2011/050198 Intermediate 2. |
| A-5 | 5-methyl-2-(pyrimidin-2-yl)benzoic acid | 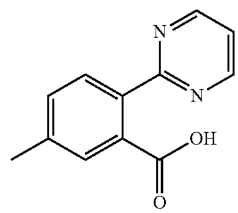 [SMILES: Cc1ccc(-c2ncccn2)c(C(=O)O)c1] | WO 2011/050198 Intermediate 50. |
| A-6 | 5-methyl-2-(2H-1,2,3-triazol-2-yl)benzoic acid | 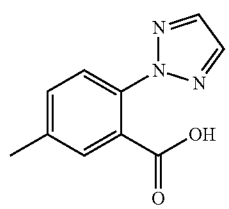 | WO 2011/050198 Intermediate 8. |
| A-7 | 5-fluoro-2-(pyrimidin-2-yl)benzoic acid | 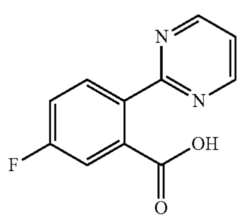 [SMILES: O=C(O)c1cc(F)ccc1-c1ncccn1] | WO 2011/050198 Intermediate 13. |
| A-8 | 6-methyl-2-(2H-1,2,3-triazol-2-yl)nicotinic acid | 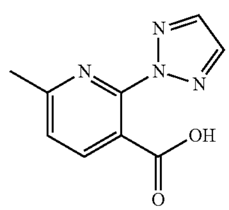 | WO 2011/050198 Intermediate 70 |
| A-9 | 6-methyl-2-(1H-1,2,3-triazol-1-yl)nicotinic acid | 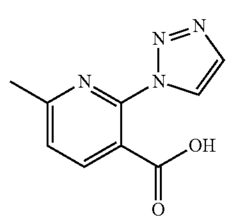 | WO 2011/050198 Intermediate 71 |
| A-10 | 4-methoxy-2-(2H-1,2,3-triazol-2-yl)benzoic acid | 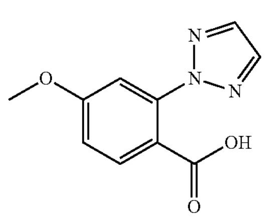 [SMILES: COc1ccc(C(=O)O)c(-n2nccn2)c1] | WO 2011/050198 Intermediate 54 |

-continued

| Intermediate | Name | Structure | Reference |
|---|---|---|---|
| A-11 | 4-methyl-2-(2H-1,2,3-triazol-2-yl)benzoic acid | 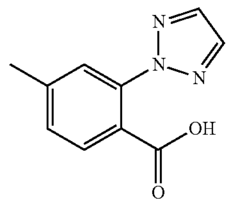 | Analogous Intermediate A-4 using 2-bromo-4-methylbenzoic acid |
| A-12 | 3-ethoxy-6-methylpicolinic acid | 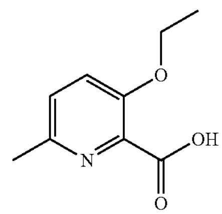 | WO 2010/063663 Description 39 |
| A-13 | 5-chloro-2-(2H-1,2,3-triazol-2-yl)benzoic acid | 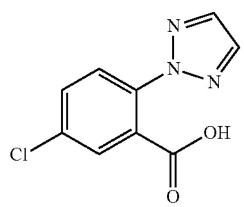 [SMILES: O=C(O)c1cc(Cl)ccc1-n1nccn1] | WO 2011/050198 Intermediate 9. |
| A-14 | 5-methoxy-2-(2H-1,2,3-triazol-2-yl)benzoic acid | 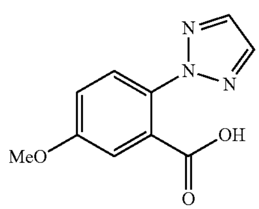 [SMILES: COc1ccc(-n2nccn2)c(C(=O)O)c1] | WO 2011/050198 Intermediate 10. |
| A-15 | 3-methyl-2-(2H-1,2,3-triazol-2-yl)benzoic acid | 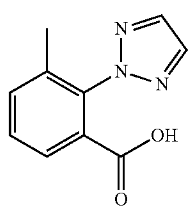 | WO 2011/050198 Intermediate 82. |
| A-16 | 3-(2H-1,2,3-triazol-2-yl)picolinic acid | 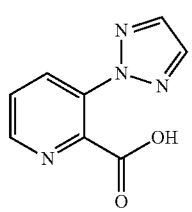 [SMILES: O=C(O)c1ncccc1-n1nccn1] | WO 2011/050198 Intermediate 72. |
| A-17 | 5-methyl-3-(oxazol-2-yl)picolinic acid | 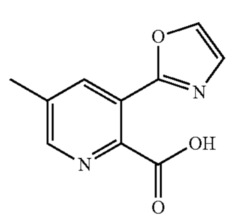 | Prepared analogous to intermediate A-18 |

| Intermediate | Name | Structure | Reference |
|---|---|---|---|
| A-18 | 6-methyl-3-(oxazol-2-yl)picolinic acid | 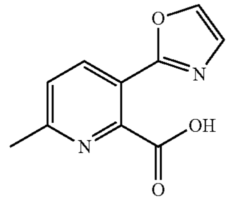 | Prepared as described below |
| A-19 | 6-methyl-3-(pyrimidin-2-yl)picolinic acid | 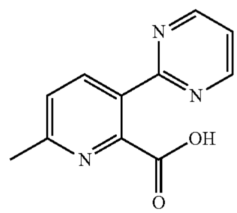 [SMILES: Cc1ccc(-c2ncccn2)c(C(=O)O)n1] | WO 2010/063663 Description 69 |
| A-20 | 5-methyl-3-(pyrimidin-2-yl)picolinic acid | 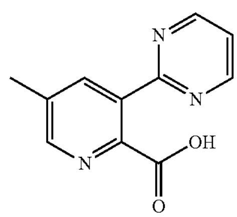 [SMILES: Cc1cnc(C(=O)O)c(-c2ncccn2)c1] | Prepared analogous to intermediate A-19 using 3-bromo-5-methylpicolinonitrile |

Intermediate A-18:
6-methyl-3-(oxazol-2-yl)picolinic acid

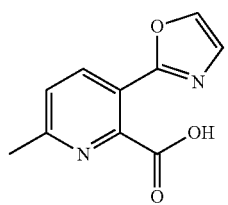

Step A: 3-bromo-6-methylpicolinic acid. To 3-bromo-6-methylpicolinonitrile (4 g, 20.3 mmol) in EtOH (40 mL) in a sealed tube was added aqueous 4M NaOH (15 mL). The reaction was heated at 90° C. for 24 h. Additional aqueous 4M NaOH was added and heating continued at 90° C. for 24 h. The reaction was cooled to rt, acidified to pH=3 with 1N HCl (aq), concentrated and used without further purification in subsequent steps. MS (ESI) mass calcd. for $C_7H_6BrNO_2$, 216.0; m/z found 218 [M+H]$^+$.

Step B: Methyl 3-bromo-6-methylpicolinate. To the title compound of step A (10.3 g, 20 mmol) in MeOH (50 mL) was added thionyl chloride (4.4 mL, 60 mmol). The reaction was heated at reflux overnight, cooled to rt and concentrated. Purification via silica gel chromatography (0-15% EtOAc in heptane) gave the title compound (1.9 g, 40%). MS (ESI) mass calcd. for $C_8H_8BrNO_2$, 230.1; m/z found 232 [M+H]$^+$.

Step C: Methyl 6-methyl-3-(oxazol-2-yl)picolinate. In a microwave vial was dissolved the title compound of step B (185 mg, 0.8 mmol) and 2-(tributylstannyl)oxazole (0.22 mL, 1 mmol) in $PhCH_3$ (2.4 mL). The solution was degassed with $N_2$ and $Pd(PPh_3)_4$ (92 mg, 0.1 mmol) were added. The reaction was purged with $N_2$ and heated at 120° C. for 20 m using microwave irradiation. The reaction was cooled to rt, filtered through a pad of celite and purified via silica gel chromatography (0-40% EtOAc in hexanes) to give the title compound of step A (333 mg, 67%). The mixture was diluted with $H_2O$ and extracted with EtOAc. The combined organics were dried ($MgSO_4$) and purified via silica gel chromatography (0-50% EtOAc in heptane) to give the title compound (56 mg, 32%). MS (ESI) mass calcd. for $C_{11}H_{10}N_2O_3$, 218.2; m/z found 219.1 [M+H]$^+$.

Step D: 6-methyl-3-(oxazol-2-yl)picolinic acid. To the title compound of step C (56 mg, 0.3 mmol) was added MeOH (0.6 mL) and 2M $NaOH_{(aq)}$ (0.6 mL). After 1 h at rt, 1M $HCl_{(aq)}$ was added. The reaction mixture was concentrated to give the title compound (52 mg) that was used without further purification in subsequent steps. MS (ESI) mass calcd. for $C_{10}H_8N_2O_3$, 204.2; m/z found 205.1 [M+H]$^+$.

Intermediate A-21:
5-methyl-3-(2H-1,2,3-triazol-2-yl)picolinic acid

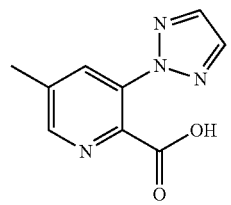

Step A: 5-methyl-3-(2H-1,2,3-triazol-2-yl)picolinonitrile. To 2-bromo-6-methyl-3-(2H-1,2,3-triazol-2-yl)pyridine (1.5 g, 7.6 mmol) in DMF (19 mL) was added $K_2CO_3$ (1.2 g, 8.4 mmol) and 2H-1,2,3-triazole (440 µL, 7.6 mmol). The mixture was heated to 100° C. for 16 h, cooled to rt and extracted with EtOAc (2×). The combined organics were dried (Na2SO4) and concentrated. Purification via silica gel chromatography (5-60% EtOAc in hexanes) gave the title compound (490 mg, 35%) and 5-methyl-3-(1H-1,2,3-triazol-1-yl)picolinonitrile (387 mg, 27%).

Step B: (sodium 5-methyl-3-(2H-1,2,3-triazol-2-yl)picolinate). To a solution of the title compound of Step A (489 mg, 2.6 mmol) in EtOH (7 mL) was added 4 N NaOH (660 µL, 2.6 mmol). The mixture was heated at 100° C. for 24 h. The reaction mixture was concentrated in vacuo to a white solid which was used without further purification in subsequent steps.

Intermediate A-22:
6-methyl-3-(2H-1,2,3-triazol-2-yl)picolinic acid

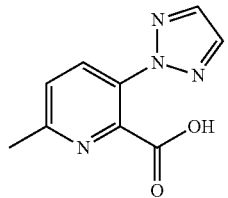

Step A: 6-methyl-3-(2H-1,2,3-triazol-2-yl)picolinonitrile. To 3-bromo-5-methylpicolinonitrile (2.2 g, 11 mmol) in DMF (28 mL) was added $K_2CO_3$ (1.7 g, 12 mmol) and 2H-1,2,3-triazole (650 µL, 11 mmol). The mixture was heated to 100° C. for 36 h, cooled to rt and extracted with EtOAc. The combined organics were dried (Na2SO4) and concentrated. Purification via silica gel chromatography (10-100% EtOAc in hexanes) gave the title compound (1 g, 48%).

Step B: 6-methyl-3-(2H-1,2,3-triazol-2-yl)picolinic acid. To a solution of the title compound of Step A (730 mg, 4 mmol) in EtOH (10 mL) was added 4 N NaOH (1 mL, 4 mmol). The mixture was heated at 100° C. for 24 h. The reaction mixture was concentrated in vacuo to a white solid which was used without further purification in subsequent steps.

| A-23 | 2-fluoro-6-(2H-1,2,3-triazol-2-yl)benzoic acid | 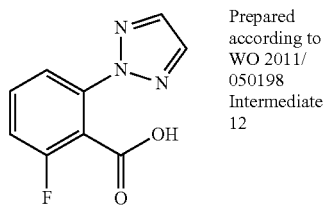 | Prepared according to WO 2011/050198 Intermediate 12 |
| A-24 | 5-fluoro-2-(2H-1,2,3-triazol-2-yl)benzoic acid | 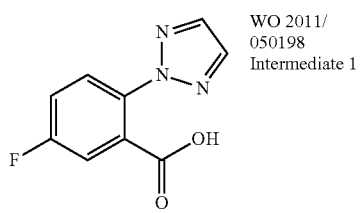 | WO 2011/050198 Intermediate 1 |

Intermediate B-1: trans-(±)-tert-butyl-3-(((benzyloxy)carbonyl)amino)-2-methylpiperidine-1-carboxylate

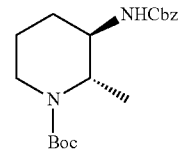 [SMILES: C[C@H]1[C@H](NC(=O)OCc2ccccc2)CCCN1C(=O)OC(C)(C)C]

Step A: trans-(±)-1-(tert-butoxycarbonyl)-2-methylpiperidine-3-carboxylic acid. Methyl 2-methylnicotinate (28.6 g, 190 mmol) and $PtO_2$ (430 mg) in AcOH (500 mL) was stirred under an atmosphere of $H_2$ for 48 h. Additional $PtO_2$ was added and the reaction continued for an additional 24 h. Then the reaction catalyst was filtered through a pad of celite and the filtrate concentrated. The resulting residue was partitioned between 2M NaOH (aq) and DCM. The organic layer was extracted with DCM (2×). The combined organic layers were dried (MgSO4) and concentrated to give 27.2 g of a residue.

To this residue in MeOH (450 mL) was added sodium methoxide (4.5 M in MeOH, 56 mL, 260 mmol). The reaction was heated at reflux for 15 h, then cooled to rt, concentrated, H2O was added and the mixture extracted with DCM. The combined organics were dried (MgSO4) and concentrated to give 23.9 g of product that was dissolved in THF (300 mL) and H2O (60 mL). Then, Na2CO3 (38.3 g, 456 mmol) was added followed by Boc2O (33.2 g, 152 mmol). After stirring overnight, the mixture was diluted with H2O and extracted with DCM. The combined organics were dried (MgSO4) and concentrated to give 39.2 g of material (9:1 trans:cis isomers).

To this material in THF (300 mL) and H2O (100 mL) was added LiOH (7.3 g, 305 mmol). After stirring overnight, the mixture was diluted with H2O and extracted with DCM. The organic extract was discarded. The aqueous layer was acidified with HCl and extracted with DCM. The combined organics were dried (MgSO4) and concentrated. Purification via silica gel chromatography (0-100% EtOAc in heptane) gave the title compound (30.2 g) as a ~86:13 mixture of trans:cis diastereomers. MS (ESI) mass calcd. for $C_{12}H_{21}NO_4$, 243.2; m/z found 188.1 [M−55]$^+$.

Step B: trans-(+)-tert-butyl 3-(((benzyloxy)carbonyl)amino)-2-methylpiperidine-1-carboxylate. To the title compound of step A (10 g, 41 mmol) in $PhCH_3$ (60 mL) was added DIPEA (7.4 mL, 43 mmol) and the mixture heated at 50° C. for 1 h. Then DPPA (8.9 mL, 41 mmol) in $PhCH_3$ was added dropwise and the mixture heated at 75° C. for 2 h and BnOH (4.5 mL, 43 mmol) and the mixture stirred at 80° C. for 20 h. The reaction was allowed to cool to rt, diluted with saturated NaHCO3 (aq) and extracted with PhCH3. The combined organics were dried (MgSO4). Purification via silica gel chromatography (0-20% EtOAc in hexanes) gave the title compound (2.6 g, 18%). MS (ESI) mass calcd. for $C_{19}H_{28}N_2O_4$, 348.2; m/z found 249.2 [M−100]$^+$, 293.2 [M−55]$^+$. $^1$H NMR (400 MHz, CDCl$_3$) 7.39-7.30 (m, 5H), 5.24-5.00 (m, 3H), 4.35-4.22 (m, 1H), 4.01-3.85 (m, 1H), 3.74-3.51 (m, 1H), 2.89-2.71 (m, 1H), 1.87-1.30 (m, 13H), 1.19 (d, J=7.0 Hz, 3H).

Example B-2

(2R*,3S*)-tert-butyl 3-(((benzyloxy)carbonyl)amino)-2-methylpiperidine-1-carboxylate

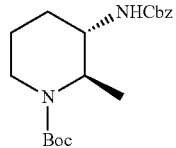 [SMILES: C[C@@H]1[C@@H](NC(=O)OCc2ccccc2)CCCN1C(=O)OC(C)(C)C]

and (2S*,3R*)-tert-butyl 3-(((benzyloxy)carbonyl)amino)-2-methylpiperidine-1-carboxylate.

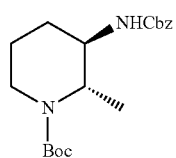

The title compounds were obtained by chiral SFC(CHIRAL-PAK AD-H 5 μM 250×30 mm) resolution of Intermediate B-1 (38.2 g) using 93% CO$_2$/7% MeOH as the mobile phase to give enantiomer A (18.8 g, 1st eluting enantiomer) and enantiomer B (19.3 g, 2$^{nd}$ eluting enantiomer).

Enantiomer A: $[\alpha]_D^{20}$-31.9° (c 0.7, DMF). MS (ESI) mass calcd. for C$_{19}$H$_{28}$N$_2$O$_4$, 348.2; m/z found 349.2 [M+H]$^+$. $^1$H NMR consistent with intermediate B-1.

Enantiomer B: $[\alpha]_D^{20}$+28.0° (c 0.96, DMF). MS (ESI) mass calcd. for C$_{19}$H$_{28}$N$_2$O$_4$, 348.2; m/z found 349.2 [M+H]$^+$. $^1$H NMR consistent with intermediate B-1.

Intermediate B-3: trans-(±)-tert-butyl-3-amino-2-methylpiperidine-1-carboxylate

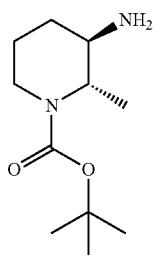

Intermediate B-1 (8.9 g, 25.4 mmol) and wet 10 wt % Pd/C (880 mg) in MeOH (200 mL) was stirred under an atmosphere of H$_2$ overnight. The reaction catalyst was filtered through a pad of celite and the filtrate concentrated to give the title compound (5.7 g) that was used without further purification. MS (ESI) mass calcd. for C$_{11}$H$_{22}$N$_2$O$_2$, 214.3; m/z found 159.1 [M−55]$^+$. $^1$H NMR (400 MHz, CDCl$_3$) 4.19-4.08 (m, 1H), 4.00-3.88 (m, 1H), 2.91-2.72 (m, 2H), 1.86-1.61 (m, 1H), 1.61-1.33 (m, 12H), 1.15 (d, J=7.0 Hz, 3H).

Intermediate B-4: (2S*,3R*)-tert-butyl 3-amino-2-methylpiperidine-1-carboxylate

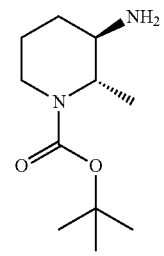

Prepared analogous to Intermediate B-3 substituting intermediate B-1 with intermediate (+)-B-2 (enantiomer B).

Intermediate B-5: (2R*,3S*)-tert-butyl 3-amino-2-methylpiperidine-1-carboxylate

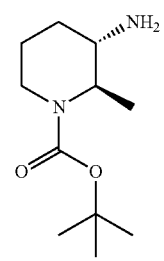

Prepared analogous to Intermediate B-3 substituting intermediate B-1 with intermediate (−)-B-2 (enantiomer A).

Intermediate B-6: cis-(±)-tert-butyl-3-amino-2-methylpiperidine-1-carboxylate

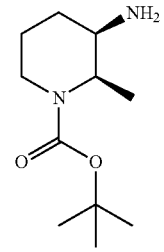

Step A: cis-(±)-1-(tert-butoxycarbonyl)-2-methylpiperidine-3-carboxylic acid. Methyl 2-methylnicotinate (100 g, 662 mmol) and PtO$_2$ (1.5 g) in AcOH (300 mL) was stirred under an atmosphere of H$_2$ for 7 days. The reaction catalyst was filtered and the filtrate concentrated. The resulting residue was partitioned between saturated NaHCO$_3$ (aq) and DCM. The organic layer was extracted with DCM (4×200 mL). The combined organic layers were dried (Na$_2$SO$_4$) and concentrated to give 80 g of a residue.

To this residue in THF (200 mL) was added DIPEA (37 mL, 200 mmol) and Boc$_2$O (32 g, 150 mmol). After stirring overnight, the mixture was concentrated, diluted with H₂O and extracted with EtOAc. The combined organics were dried (NaSO₄) and concentrated. Purification via silica gel chromatography (10% EtOAc in petroleum ethers) gave cis-(±)-1-tert-butyl 3-methyl 2-methylpiperidine-1,3-dicarboxylate.

To the crude mixture of cis-(±)-1-tert-butyl 3-methyl-2-methylpiperidine-1,3-dicarboxylate from above in MeOH (150 mL) was added 2M NaOH (aq.). The reaction was heated at 70° C. for 2 h, cooled to rt, concentrated, treated with H₂O (400 mL) and extracted with MTBE (100 mL). The aqueous layer was then acidified to pH=6 with 1N HCl (aq) and concentrated. To this was added MeOH (400 mL) and concentrated to give the title compound (5 g) as a white solid.

Step B: cis-(±)-tert-butyl 3-(((benzyloxy)carbonyl)amino)-2-methylpiperidine-1-carboxylate. To the title compound of step A (5.3 g, 21 mmol) in PhCH₃ was added DIPEA (4.3 mL, 26 mmol) and DPPA (7.2 g, 26 mmol). The mixture was heated at reflux overnight, cooled to rt, concentrated and treated with 20% KOH (aq). The mixture was heated at 100° C. for 2 h, cooled to rt and extracted with DCM (2×). The combined organics were dried (Na2SO4), concentrated and purified via silica gel chromatography (10% MeOH in DCM) to give the title compound (1.5 g).

Example 1

(±)-trans-(3-((4,6-dimethylpyrimidin-2-yl)amino)-2-methylpiperidin-1-yl)(4-fluoro-2-(2H-1,2,3-triazol-2-yl)phenyl)methanone

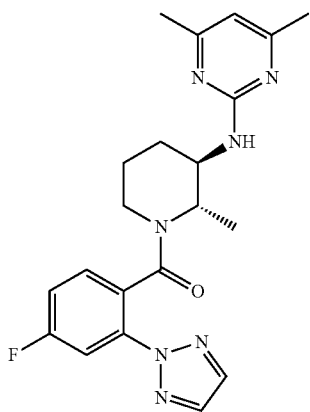 [SMILES: Cc1cc(C)nc(N[C@@H]2CCCN(C(=O)c3ccc(F)cc3-n3nccn3)[C@H]2C)n1]

Step A: (±)-tert-butyl-3-((4,6-dimethylpyrimidin-2-yl)amino)-2-methylpiperidine-1-carboxylate. To a microwave vial was weighed intermediate B-3 (260 mg, 1.2 mmol), 2-chloro-4,6-dimethylpyrimidine (208 mg, 1.5 mmol), Pd(dba)₂ (17 mg, 0.03 mmol), CTC-Q-Phos (27 mg, 0.06 mmol) and sodium tert-butoxide (175 mg, 1.8 mmol). The vial was capped, evacuated, refilled with N₂ (2×) and PhCH₃ was added. The reaction was then heated in the microwave at 150° C. for 120 min. The mixture was then cooled to rt, directly applied to and purified via silica gel chromatography (1-7% 2M NH₃/MeOH in CH₂Cl₂) to give the title compound (205 mg, 53%) as a brown oil. MS (ESI) mass calcd. for C₁₇H₂₈N₄O₂, 320.2; m/z found 321.2 [M+H]⁺. 1H(CDCl3): 6.30 (s, 1H), 5.39-5.25 (m, 1H), 4.46-4.31 (m, 1H), 4.10-3.85 (m, 2H), 2.94-2.71 (m, 1H), 2.34-2.20 (m, 6H), 1.87-1.62 (m, 3H), 1.52-1.33 (m, 10H), 1.22 (d, J=7.0 Hz, 2.5H), 1.09-1.01 (m, 0.5H).

Step B: (±)-trans-4,6-dimethyl-N-(2-methylpiperidin-3-yl)pyrimidin-2-amine. To the title compound from Step A (75 mg, 0.23 mmol) in DCM (4 mL) was added TFA (4 mL). Upon completion (~3 h), the reaction was concentrated, neutralized with 5% Na₂CO₃ (aq) and extracted with DCM (3×). The combined organics were dried (Na₂SO₄) to give the title compound (52 mg) which was used without further purification. MS (ESI) mass calcd. for C₁₂H₂₀N₄, 220.2; m/z found 221.1 [M+H]⁺.

Step C: (±)-trans-(3-((4,6-dimethylpyrimidin-2-yl)amino)-2-methylpiperidin-1-yl)(4-fluoro-2-(2H-1,2,3-triazol-2-yl)phenyl)methanone. To the title compound from Step B (29 mg, 0.13 mmol) in DMF (1.3 mL) was added TEA (0.022 mL, 0.16 mmol), intermediate A-1 (30 mg, 0.14 mmol) and HATU (55 mg, 0.14 mmol). Upon completion of the reaction, purification was performed using Agilent prep method A to give the title compound (29 mg, 55% yield). MS (ESI) mass calcd. for C₂₁H₂₄FN₇O, 409.2; m/z found 410.0 [M+H]⁺. HPLC Rₜ=0.85 (Analytical Method A).

Example 2

(±)-trans-(3-((4,6-dimethylpyrimidin-2-yl)amino)-2-methylpiperidin-1-yl)(2-fluoro-6-(pyrimidin-2-yl)phenyl)methanone

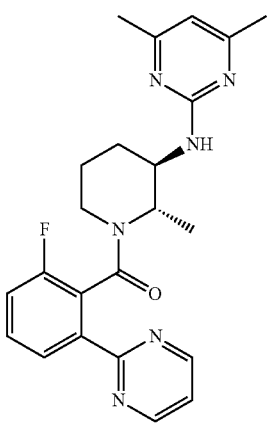 [SMILES: Cc1cc(C)nc(N[C@@H]2CCCN(C(=O)c3c(F)cccc3-c3ncccn3)[C@H]2C)n1]

The title compound was prepared analogous to Example 1 substituting intermediate A-1 with intermediate A-2. MS (ESI) mass calcd. for C₂₃H₂₅FN₆O, 420.2; m/z found 421.2 [M+H]⁺.

Example 3

(±)-trans-(3-((4,6-dimethylpyrimidin-2-yl)amino)-2-methylpiperidin-1-yl)(2-fluoro-6-(2H-1,2,3-triazol-2-yl)phenyl)methanone

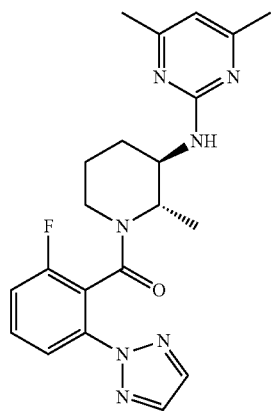

The title compound was prepared analogous to example 1 substituting intermediate A-1 with intermediate A-23. MS (ESI) mass calcd. for $C_{21}H_{22}FN_7O$, 407.5; m/z found 408.2 [M+H]$^+$. HPLC R$_t$=0.85 (Analytical Method A).

Example 4

(±)-trans-(2-(2H-1,2,3-triazol-2-yl)phenyl)(3-((4,6-dimethylpyrimidin-2-yl)amino)-2-methylpiperidin-1-yl)methanone

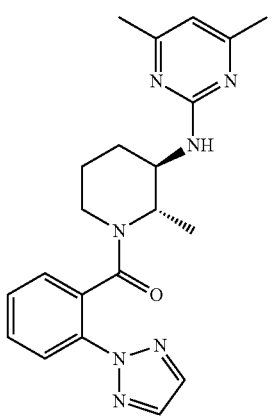 [SMILES: Cc1cc(C)nc(N[C@@H]2CCCN(C(=O)c3ccccc3-n3nccn3)[C@H]2C)n1]

The title compound was prepared analogous to example 1 substituting intermediate A-1 with intermediate A-4. MS (ESI) mass calcd. for $C_{21}H_{25}N_7O$, 391.2; m/z found 392.2 [M+H]$^+$ Example 5

(±)-trans-(3-((4,6-dimethylpyrimidin-2-yl)amino)-2-methylpiperidin-1-yl)(5-fluoro-2-(2H-1,2,3-triazol-2-yl)phenyl)methanone

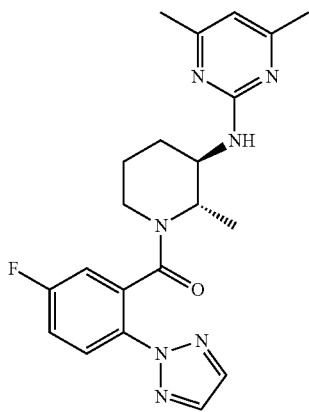 [SMILES: Cc1cc(C)nc(N[C@@H]2CCCN(C(=O)c3cc(F)ccc3-n3nccn3)[C@H]2C)n1]

The title compound was prepared analogous to Example 1 substituting intermediate A-1 with intermediate A-24. MS (ESI) mass calcd. for $C_{21}H_{24}FN_7O$, 409.2; m/z found 410.2 [M+H]$^+$ Example 6

(±)-trans-(3-((4,6-dimethylpyrimidin-2-yl)amino)-2-methylpiperidin-1-yl)(5-methyl-2-(pyrimidin-2-yl)phenyl)methanone

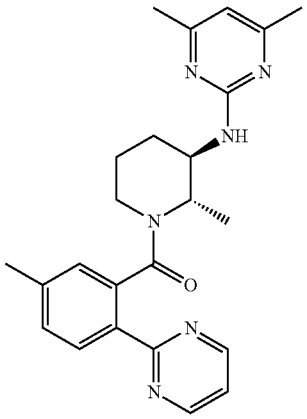

The title compound was prepared analogous to Example 1 substituting intermediate A-1 with intermediate A-5. MS (ESI) mass calcd. for $C_{24}H_{28}N_6O$, 416.2; m/z found 417.2 [M+H]$^+$.

Example 7

(±)-trans-(5-methyl-2-(pyrimidin-2-yl)phenyl)(2-methyl-3-((6-methyl-2-(trifluoromethyl)pyrimidin-4-yl)amino)piperidin-1-yl)methanone

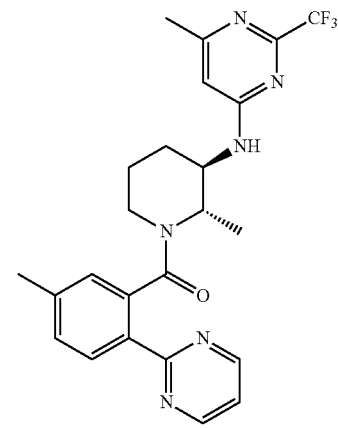 [SMILES: Cc1ccc(-c2ncccn2)c(C(=O)N2CCC[C@@H](Nc3cc(C)nc(C(F)(F)F)n3)[C@@H]2C)c1]

Step A: (±)-tert-butyl-2-methyl-3-((6-methyl-2-(trifluoromethyl)pyrimidin-4-yl)amino)piperidine-1-carboxylate.
To intermediate B-3 (135 mg, 0.63 mmol) in DMF (1.5 mL) was added Cs$_2$CO$_3$ (308 mg, 0.95 mmol) and 4-chloro-6-methyl-2-(trifluoromethyl)pyrimidine (149 mg, 0.76 mmol). The flask was then heated with an oil bath at 70° C. for 18 h. The reaction was allowed to cool to rt, diluted with H$_2$O and extracted with EtOAc (2×). The combined organics were washed with brine and dried (Na$_2$SO$_4$). Silica gel chromatography (EtOAc in hexanes) gave the title compound (111 mg, 47%). MS (ESI) mass calcd. for $C_{17}H_{25}F_3N_4O_2$, 374.2; m/z found 275.2 [M+H−100]+. 1H NMR (CDCl$_3$): 6.24 (s, 1H), 5.44 (s, 1H), 4.48-4.31 (m, 1H), 4.15-3.60 (m, 2H), 2.97-2.78 (m, 1H), 2.42 (s, 3H), 1.85 (s, 2H), 1.74-1.32 (m, 10H), 1.26 (d, J=7.0 Hz, 3H).

Step B: (±)-trans-6-methyl-N-(2-methylpiperidin-3-yl)-2-(trifluoromethyl)pyrimidin-4-amine. The title compound was prepared analogous to example 1, Step B substituting (±)-tert-butyl-3-((4,6-dimethylpyrimidin-2-yl)amino)-2-methylpiperidine-1-carboxylate with the title compound from Step A.

Step C: (±)-trans-(5-methyl-2-(pyrimidin-2-yl)phenyl)(2-methyl-3-((6-methyl-2-(trifluoromethyl)pyrimidin-4-yl)amino)piperidin-1-yl)methanone. The title compound was prepared analogous to example 1, Step C substituting intermediate A-1 with intermediate A-5 and (±)-4,6-dimethyl-N-(2-methylpiperidin-3-yl)pyrimidin-2-amine with the title compound of Step B. MS (ESI) mass calcd. for $C_{24}H_{25}F_3N_6O$, 470.2; m/z found 471.2 [M+H]$^+$.

Example 8

(±)-trans-(5-methyl-2-(2H-1,2,3-triazol-2-yl)phenyl)(2-methyl-3-((6-methyl-2-(trifluoromethyl)pyrimidin-4-yl)amino)piperidin-1-yl)methanone

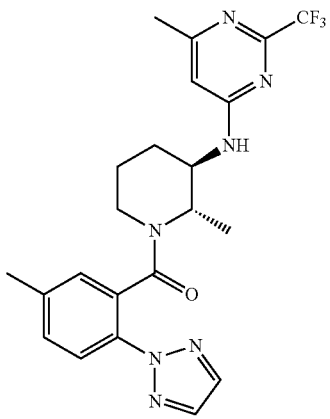 [SMILES: Cc1ccc(-n2nccn2)c(C(=O)N2CCC[C@@H](Nc3cc(C)nc(C(F)(F)F)n3)[C@@H]2C)c1]

The title compound was prepared analogous to Example 7 substituting intermediate A-5 with intermediate A-6. MS (ESI) mass calcd. for $C_{22}H_{24}F_3N_7O$, 459.2; m/z found 460.2 [M+H]$^+$.

Example 9

(±)-trans-(5-fluoro-2-(pyrimidin-2-yl)phenyl)(2-methyl-3-((6-methyl-2-(trifluoromethyl)pyrimidin-4-yl)amino)piperidin-1-yl)methanone

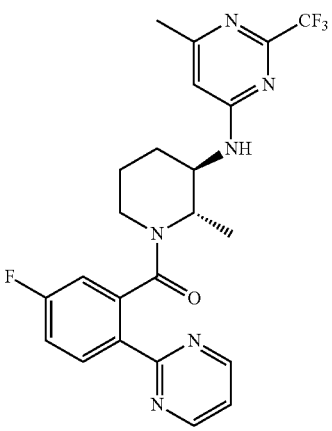 [SMILES: Cc1cc(N[C@@H]2CCCN(C(=O)c3cc(F)ccc3-c3ncccn3)[C@H]2C)nc(C(F)(F)F)n1]

The title compound was prepared analogous to Example 7 substituting intermediate A-5 with intermediate A-7. MS (ESI) mass calcd. for $C_{23}H_{22}F_4N_6O$, 474.2; m/z found 475.2 [M+H]$^+$.

Example 10

(±)-trans-(2-fluoro-6-(2H-1,2,3-triazol-2-yl)phenyl)(2-methyl-3-((4-(trifluoromethyl)pyrimidin-2-yl)amino)piperidin-1-yl)methanone

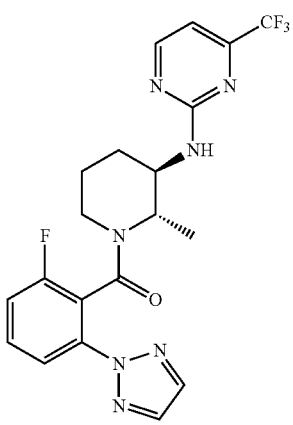 [SMILES: C[C@H]1[C@H](Nc2nccc(C(F)(F)F)n2)CCCN1C(=O)c1c(F)cccc1-n1nccn1]

The title compound was prepared analogous to Example 7 substituting 4-chloro-6-methyl-2-(trifluoromethyl)pyrimidine with 2-chloro-4-(trifluoromethyl)pyrimidine and intermediate A-5 with intermediate A-23. MS (ESI) mass calcd. for $C_{20}H_{19}F_4N_7O$, 449.2; m/z found 450.2 [M+H]$^+$.

Example 11

(±)-trans-(6-methyl-2-(1H-1,2,3-triazol-1-yl)pyridin-3-yl)(2-methyl-3-((4-(trifluoromethyl)pyrimidin-2-yl)amino)piperidin-1-yl)methanone

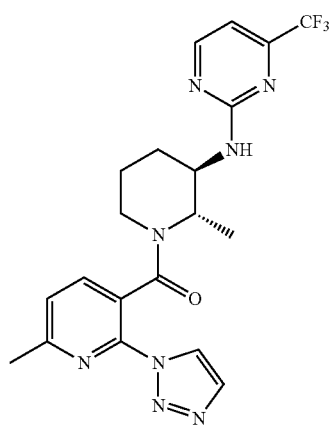 [SMILES: Cc1ccc(C(=O)N2CCC[C@@H](Nc3nccc(C(F)(F)F)n3)[C@@H]2C)c(-n2ccnn2)n1]

The title compound was prepared analogous to Example 10 substituting intermediate A-23 with intermediate A-9. MS (ESI) mass calcd. for $C_{20}H_{21}F_3N_8O$, 446.2; m/z found 447.2 [M+H]+.

Example 12

(±)-trans-(2-(2H-1,2,3-triazol-2-yl)phenyl)(2-methyl-3-((5-(trifluoromethyl)pyridin-2-yl)amino)piperidin-1-yl)methanone

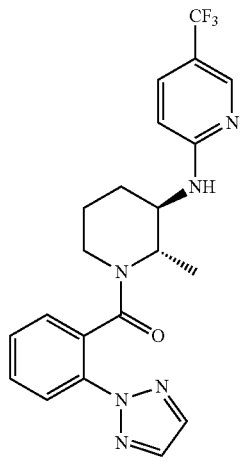

Step A: trans-(±)-tert-butyl-2-methyl-3-((5-(trifluoromethyl)pyridin-2-yl)amino)piperidine-1-carboxylate. To intermediate B-3 (3 g, 14 mmol) in DMSO (100 mL) was added 2-fluoro-5-(trifluoromethyl)pyridine (3.4 g, 21 mmol) and DIPEA (4.8 mL, 28 mmol). The reaction was then heated at 100° C. for 4 h. The reaction was allowed to cool to rt, diluted with saturated NaHCO$_3$ (aq) and extracted with DCM. The combined organics were washed with brine and dried (MgSO$_4$). Silica gel chromatography (EtOAc in heptane) gave the title compound (2.7 g, 54%). MS (ESI) mass calcd. for $C_{17}H_{24}F_3N_3O_2$, 359.2; m/z found 360.2 [M+H]+.

Step B. trans-(±)-2-methylpiperidin-3-yl)-5-(trifluoromethyl)pyridin-2-amine. Prepared analogous to Example 1 substituting (±)-tert-butyl-3-((4,6-dimethylpyrimidin-2-yl)amino)-2-methylpiperidine-1-carboxylate with the title compound from Step A. MS (ESI) mass calcd. for $C_{12}H_{16}F_3N_3$, 259.1; m/z found 260.2 [M+H]+.

Step C. (±)-trans-tert-butyl-2-methyl-3-((5-(trifluoromethyl)pyridin-2-yl)amino)piperidine-1-carboxylate. Prepared analogous to Example 1 substituting (±)-trans-(3-((4,6-dimethylpyrimidin-2-yl)amino)-2-methylpiperidin-1-yl)(4-fluoro-2-(2H-1,2,3-triazol-2-yl)phenyl)methanone with the title compound from Step B, intermediate A-1 with intermediate A-4 and HATU with HBTU. MS (ESI) mass calcd. for $C_{21}H_{21}F_3N_6O$, 430.2; m/z found 431.2 [M+H]+. MP=154.7° C. (Mixture of 4 isomers, undefined ratio). $^1$H NMR (300 MHz, DMSO) δ 8.36 (d, J=21.8 Hz, 0.44H), 8.24 (d, J=12.9 Hz, 0.36H), 8.08 (d, J=1.3 Hz, 1.62H), 7.97 (s, 0.47H), 7.91 (d, J=8.2 Hz, 0.41H), 7.83-7.32 (m, 4.20H), 7.32-7.21 (m, 0.48H), 7.06-6.96 (m, 0.47H), 6.82 (d, J=8.9 Hz, 0.76H), 6.71 (dd, J=13.9, 7.0 Hz, 0.59H), 6.60 (s, 0.10H), 6.15 (d, J=8.8 Hz, 0.10H), 4.93 (d, J=6.0 Hz, 0.12H), 4.68 (q, J=6.8 Hz, 0.39H), 4.41 (t, J=13.4 Hz, 0.65H), 4.17-3.83 (m, 0.78H), 3.81-3.61 (m, 0.73H), 3.20 (d, J=14.4 Hz, 0.35H), 2.94 (t, J=11.7 Hz, 0.52H), 2.85-2.66 (m, 0.46H), 2.19-1.49 (m, 3.53H), 1.49-1.22 (m, 2.07H), 0.74 (d, J=6.9 Hz, 1.40H).

Example 13

(±)-trans-(4-methyl-2-(2H-1,2,3-triazol-2-yl)phenyl)(2-methyl-3-((5-(trifluoromethyl)pyridin-2-yl)amino)piperidin-1-yl)methanone

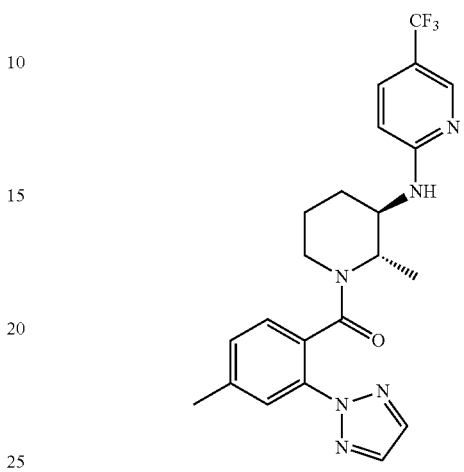

Prepared analogously to Example 12 substituting intermediate A-4 with intermediate A-11. MS (ESI) mass calcd. for C22H23F3N6O, 444.2; m/z found 445.2 [M+H]+. MP=136.4° C. (Mixture of 4 isomers, undefined ratio). 1H NMR (300 MHz, DMSO) δ 8.41 (d, J=20.3 Hz, 0.34H), 8.28 (d, J=13.4 Hz, 0.34H), 8.21-7.94 (m, 2.16H), 7.88-7.67 (m, 1.27H), 7.60 (dd, J=12.3, 7.4 Hz, 0.92H), 7.53-7.21 (m, 1.81H), 6.96-6.72 (m, 1.41H), 6.60 (s, 0.11H), 6.51 (d, J=7.4 Hz, 0.53H), 6.17 (s, 0.11H), 4.96 (s, 0.11H), 4.72 (d, J=7.3 Hz, 0.34H), 4.42 (d, J=14.1 Hz, 0.68H), 4.11 (s, 0.45H), 3.98 (s, 0.20H), 3.77 (d, J=6.8 Hz, 0.56H), 3.67 (dd, J=12.1, 6.0 Hz, 0.68H), 3.26 (d, J=13.4 Hz, 0.34H), 2.96 (t, J=11.7 Hz, 0.50H), 2.86-2.71 (m, 0.50H), 2.49 (s, 1.07H), 2.43 (s, 0.33H), 2.26 (s, 1.24H), 2.18-1.52 (m, 3.57H), 1.53-1.33 (m, 0.90H), 1.30 (d, J=7.0 Hz, 0.94H), 0.76 (d, J=6.9 Hz, 1.57H).

Example 14

(4-methyl-2-(2H-1,2,3-triazol-2-yl)phenyl)((2S,3R)-2-methyl-3-((5-(trifluoromethyl)pyridin-2-yl)amino)piperidin-1-yl)methanone

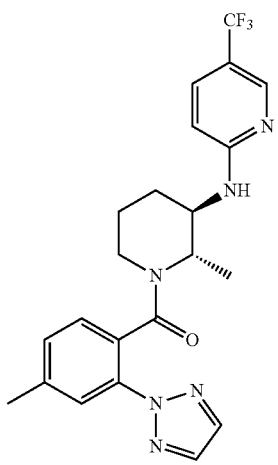

Prepared analogously to Example 13 substituting intermediate B-3 with intermediate B-4. MS (ESI) mass calcd. for $C_{22}H_{23}F_3N_6O$, 444.2; m/z found 445.2 [M+H]+. MP=119.4° C.

Example 15

(4-methyl-2-(2H-1,2,3-triazol-2-yl)phenyl)((2R,3S)-2-methyl-3-((5-(trifluoromethyl)pyridin-2-yl)amino)piperidin-1-yl)methanone

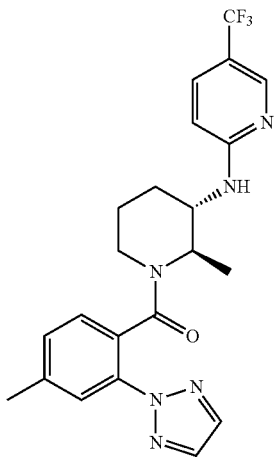 [SMILES: Cc1ccc(C(=O)N2CCC[C@H](Nc3ccc(C(F)(F)F)cn3)[C@H]2C)c(-n2nccn2)c1]

Prepared analogously to Example 13 substituting intermediate B-3 with intermediate B-5. MS (ESI) mass calcd. for C$_{22}$H$_{23}$F$_3$N$_6$O, 444.2; m/z found 445.2 [M+H]$^+$. MP=130.4° C. (Mixture of 4 isomers, undefined ratio). $^1$H NMR (300 MHz, CDCl$_3$) δ 8.38 (s, 0.2H), 8.33 (s, 0.100H), 8.21 (s, 0.35H), 8.09 (s, 0.45H), 7.96 (s, 0.70H), 7.92 (s, 0.30H), 7.86-7.68 (m, 0.70H), 7.70-7.43 (m, 0.50H), 7.44-7.09 (m, 3.40H), 6.84 (d, J=7.7 Hz, 0.10H), 6.52 (d, J=7.7 Hz, 0.100H), 6.47-6.33 (m, 0.30H), 6.24 (d, J=9.0 Hz, 0.10H), 6.08 (d, J=8.8 Hz, 0.70H), 5.31-5.08 (m, 0.35H), 5.08-4.82 (m, 0.20H), 4.70 (br d, J=13.7 Hz, 0.50H), 4.26-4.05 (m, 0.90H), 3.99 (br s, 0.40H), 3.93-3.80 (m, 0.20H), 3.60 (br s, 0.10H), 3.49 (br d, J=9.6 Hz, 0.30H), 3.34-3.12 (m, 0.35H), 3.02-2.70 (m, 0.70H), 2.45 (d, J=7.4 Hz, 2.00H), 2.14-1.73 (m, 2.00H), 1.73-1.01 (m, 3.80H), 1.01-0.76 (m, 2.00H), 0.71 (d, J=7.0 Hz, 0.20H). The signal corresponding to the NH group was not observed.

Example 16

(±)-trans-(3-ethoxy-6-methylpyridin-2-yl)(2-methyl-3-((5-(trifluoromethyl)pyridin-2-yl)amino)piperidin-1-yl)methanone

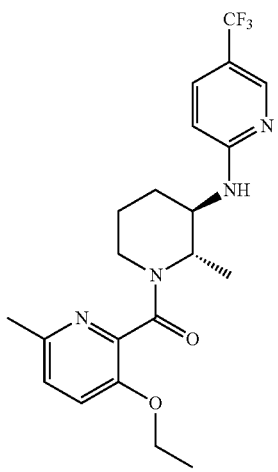 [SMILES: CCOc1ccc(C)nc1C(=O)N1CCC[C@@H](Nc2ccc(C(F)(F)F)cn2)[C@@H]1C]

Prepared analogously to Example 12 substituting intermediate A-4 with intermediate A-12. MS (ESI) mass calcd. for C$_{21}$H$_{25}$F$_3$N$_4$O$_2$, 422.2; m/z found 423.2 [M+H]$^+$. MP=153.6° C. The product is present as a mixture of conformers (ratio ca. 70:30) $^1$H NMR (300 MHz, DMSO) δ 8.34 (s, 0.3H), 7.97 (s, 0.7H), 7.65 (dd, J=8.9, 2.4 Hz, 0.3H), 7.59 (dd, J=8.9, 2.5 Hz, 0.7H), 7.39 (d, J=8.6 Hz, 0.3H), 7.27-7.12 (m, 2H), 6.96 (d, J=8.6 Hz, 0.7H), 6.75 (d, J=8.9 Hz, 0.3H), 6.69 (d, J=8.9 Hz, 0.7H), 4.85 (q, J=6.9 Hz, 0.3H), 4.48-4.33 (m, 0.7H), 4.11-3.72 (m, 3H), 3.59 (d, J=2.4 Hz, 0.7H), 3.22-3.08 (m, 0.3H), 3.07-2.96 (m, 0.3H), 2.96-2.82 (m, 0.7H), 2.38 (s, 0.9H), 2.10-1.54 (m, 6.1H), 1.32-1.22 (m, 6H).

Example 17

(±)-trans-(5-chloro-2-(2H-1,2,3-triazol-2-yl)phenyl)(2-methyl-3-((5-(trifluoromethyl)pyridin-2-yl)amino)piperidin-1-yl)methanone

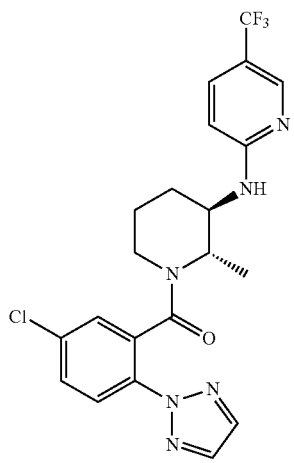 [SMILES: C[C@H]1[C@H](Nc2ccc(C(F)(F)F)cn2)CCCN1C(=O)c1cc(Cl)ccc1-n1nccn1]

Prepared analogous to Example 12 substituting intermediate A-4 with intermediate A-13. MS (ESI) mass calcd. for C$_{21}$H$_{20}$ClF$_3$N$_6$O, 464.2; m/z found 465.1 [M+H]$^+$. MP=224.4° C. (Mixture of 4 isomers, undefined ratio). $^1$H NMR (300 MHz, DMSO) δ 8.42-8.24 (m, 0.64H), 8.20 (s, 0.12H), 8.11 (d, J=3.7 Hz, 1.64H), 8.04 (s, 0.48H), 7.96 (dd, J=8.7, 5.0 Hz, 0.41H), 7.85-7.53 (m, 2.49H), 7.53-7.27 (m, 1.57H), 7.24 (s, 0.08H), 7.13 (d, J=2.4 Hz, 0.50H), 6.89-6.69 (m, 0.91H), 6.63 (s, 0.08H), 6.12 (s, 0.08H), 4.91 (d, J=6.7 Hz, 0.08H), 4.64 (d, J=7.2 Hz, 0.41H), 4.37 (d, J=13.0 Hz, 0.63H), 4.11 (s, 0.38H), 4.01 (s, 0.08H), 3.90 (d, J=18.5 Hz, 0.24H), 3.68 (dd, J=23.6, 6.5 Hz, 0.76H), 3.21 (d, J=16.3 Hz, 0.41H), 3.05-2.91 (m, 0.41H), 2.78 (t, J=11.7 Hz, 0.6H), 2.15-1.46 (m, 3.56H), 1.45-1.15 (m, 1.92H), 0.70 (d, J=6.9 Hz, 1.52H).

Example 18

(±)-trans-(2-methyl-3-((5-(trifluoromethyl)pyridin-2-yl)amino)piperidin-1-yl)(6-methyl-3-(2H-1,2,3-triazol-2-yl)pyridin-2-yl)methanone

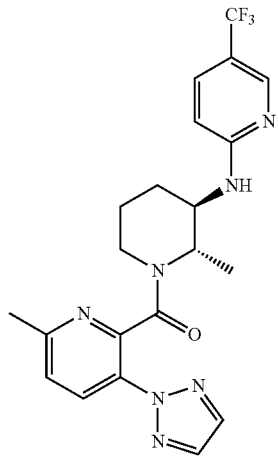 [SMILES: Cc1ccc(-n2nccn2)c(C(=O)N2CCC[C@@H](Nc3ccc(C(F)(F)F)cn3)[C@@H]2C)n1]

Prepared analogous to Example 12 substituting intermediate A-4 with intermediate A-22. MS (ESI) mass calcd. for $C_{21}H_{22}F_3N_7O$, 445.2; m/z found 446.0 [M+H]$^+$. MP=105.7° C. (Mixture of 4 isomers, undefined ratio). $^1$H NMR (300 MHz, CDCl$_3$) δ 8.39-8.22 (m, 1.15H), 8.17 (d, J=8.4 Hz, 0.74H), 8.05 (s, 0.33H), 7.92 (s, 1.23H), 7.64-7.51 (m, 0.23H), 7.45 (d, J=8.7 Hz, 0.74H), 7.38-7.29 (m, 1.15H), 6.96 (br s, 0.74H), 6.44 (d, J=8.8 Hz, 0.23H), 6.33 (br s, 0.23H), 6.17 (br s, 0.23H), 5.11 (q, J=7.2 Hz, 0.23H), 4.65 (br d, J=13.3 Hz, 0.74H), 4.13-3.85 (m, 1.35H), 3.49 (br s, 0.47H), 3.42-3.17 (m, 0.47H), 3.11-2.92 (m, 0.74H), 2.82 (s, 0.47H), 2.72-2.53 (m, 2.53H), 2.14-1.74 (m, 2.30H), 1.54-1.03 (m, 2.53H), 1.00-0.75 (m, 2.17H). The signal corresponding to the NH group was not observed.

Example 19

(±)-trans-(5-methoxy-2-(2H-1,2,3-triazol-2-yl)phenyl)(2-methyl-3-((5-(trifluoromethyl)pyridin-2-yl)amino)piperidin-1-yl)methanone

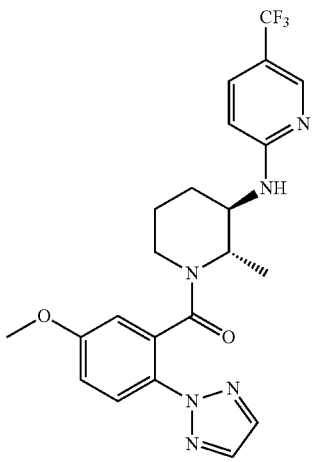 [SMILES: COc1ccc(-n2nccn2)c(C(=O)N2CCC[C@@H](Nc3ccc(C(F)(F)F)cn3)[C@@H]2C)c1]

Prepared analogous to Example 12 substituting intermediate A-4 with intermediate A-14. MS (ESI) mass calcd. for $C_{22}H_{23}F_3N_6O_2$, 460.2; m/z found 461.0 [M+H]$^+$. MP=170.8° C. (Mixture of 4 isomers, undefined ratio). $^1$H NMR (300 MHz, CDCl$_3$) δ 8.41-8.29 (m, 0.33H), 8.28-8.11 (m, 0.55H), 8.05 (s, 0.45H), 7.99 (d, J=9.0 Hz, 0.27H), 7.93 (s, 0.90H), 7.90-7.65 (m, 1.00H), 7.59 (dd, J=8.7, 2.2 Hz, 0.33H), 7.54-7.38 (m, 0.59H), 7.35 (dd, J=8.8, 2.3 Hz, 0.5H), 7.11-6.94 (m, 1.00H), 6.83 (d, J=2.7 Hz, 0.45H), 6.77 (d, J=2.8 Hz, 0.33H), 6.61 (d, J=2.7 Hz, 0.10H), 6.41 (t, J=9.1 Hz, 0.33H), 6.23 (d, J=8.7 Hz, 0.10H), 6.13 (d, J=8.8 Hz, 0.50H), 5.99 (br s, 0.27H), 5.26-5.09 (m, 0.37H), 5.07-4.90 (m, 0.20H), 4.68 (br d, J=13.5 Hz, 0.60H), 4.25-4.04 (m, 1.06H), 3.98 (s, 0.41H), 3.93-3.78 (m, 2.48H), 3.57 (s, 0.25H), 3.54-3.39 (m, 0.72H), 3.22 (td, J=13.4, 3.2 Hz, 0.39H), 2.93 (td, J=13.1, 3.0 Hz, 0.52H), 2.13-1.59 (m, 3.30H), 1.52 (d, J=6.9 Hz, 1.51H), 1.42 (d, J=7.1 Hz, 0.78H), 1.37-1.19 (m, 0.78H), 1.00-0.62 (m, 0.63H). The signal corresponding to the NH group was not observed.

Example 20

(±)-trans-(3-methyl-2-(2H-1,2,3-triazol-2-yl)phenyl)(2-methyl-3-((5-(trifluoromethyl)pyridin-2-yl)amino)piperidin-1-yl)methanone

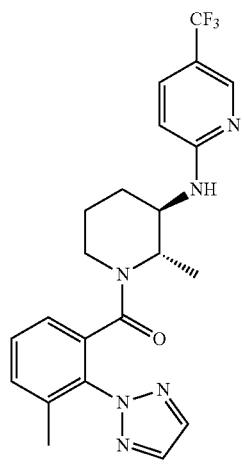

Prepared analogous to Example 12 substituting intermediate A-4 with intermediate A-15. MS (ESI) mass calcd. for $C_{22}H_{23}F_3N_6O$, 444.2; m/z found 445.2 [M+H]$^+$. MP=153.0. (Mixture of 4 isomers, undefined ratio). $^1$H NMR (300 MHz, CDCl$_3$) δ 8.41-8.31 (m, 0.19H), 8.26 (s, 0.56H), 8.07 (s, 0.19H), 7.98 (s, 1.09H), 7.90-7.70 (m, 0.76H), 7.64-7.52 (m, 0.19H), 7.52-7.33 (m, 2.15H), 7.25-7.09 (m, 0.75H), 6.76 (br d, J=26.3 Hz, 0.19H), 6.49 (d, J=8.8 Hz, 0.56H), 6.43 (d, J=9.0 Hz, 0.19H), 6.30 (d, J=8.8 Hz, 0.19H), 5.17 (br d, J=6.9 Hz, 0.19H), 5.00-4.76 (m, 0.19H), 4.53 (br d, J=13.4 Hz, 0.56H), 4.20-4.00 (m, 1.09H), 3.94 (br s, 0.19H), 3.64-3.55 (m, 0.19H), 3.51 (d, J=5.3 Hz, 0.35H), 3.40 (br d, J=14.7 Hz, 0.19H), 3.22 (s, 0.19H), 2.96 (s, 0.19H), 2.86 (td, J=13.2, 3.4 Hz, 0.66H), 2.32 (s, 1.75H), 2.28 (s, 0.35H), 2.22 (s, 0.19H), 2.13 (br s, 0.19H), 2.09-1.77 (m, 2.15H), 1.77-1.63 (m, 1.74H), 1.51 (d, J=7.0 Hz, 2.15H), 1.38 (d, J=7.1 Hz, 0.56H), 1.33-1.21 (m, 0.19H), 1.15 (d, J=6.1 Hz, 0.19H), 1.07 (d, J=6.9 Hz, 0.19H), 1.02-0.82 (m, 0.35H). The signal corresponding to the NH group was not observed.

Example 21

(±)-trans-(3-(2H-1,2,3-triazol-2-yl)pyridin-2-yl)(2-methyl-3-((5-(trifluoromethyl)pyridin-2-yl)amino)piperidin-1-yl)methanone

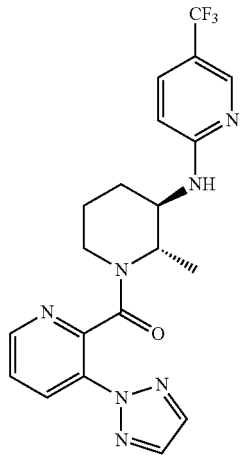 [SMILES: C[C@H]1[C@H](Nc2ccc(C(F)(F)F)cn2)CCCN1C(=O)c1ncccc1-n1nccn1]

Prepared analogous to Example 12 substituting intermediate A-4 with intermediate A-16. MS (ESI) mass calcd. for $C_{20}H_{20}F_3N_7O$, 431.2; m/z found 432.2 [M+H]$^+$. MP=79.6° C. (Mixture of 4 isomers, undefined ratio). $^1$H NMR (300 MHz, CDCl$_3$) δ 8.64 (dd, J=4.7, 1.3 Hz, 0.3H), 8.57 (d, J=3.6 Hz, 0.7H), 8.45 (d, J=8.4 Hz, 0.3H), 8.38 (s, 0.3H), 8.31 (d, J=8.2 Hz, 0.7H), 8.24 (s, 0.3H), 8.12 (s, 0.7H), 7.95 (s, 1.0H), 7.59 (d, J=8.4 Hz, 0.3H), 7.55-7.34 (m, 1.4H), 6.99 (br d, J=6.9 Hz, 0.7H), 6.43 (d, J=8.9 Hz, 0.3H), 6.32 (br s, 0.7H), 6.10 (br s, 0.3H), 5.15 (br d, J=7.2 Hz, 0.3H), 4.66 (br d, J=13.4 Hz, 0.7H), 4.20-3.83 (m, 0.9H), 3.49 (d, J=5.0 Hz, 0.7H), 3.44-3.26 (m, 0.7H), 3.14-2.94 (m, 0.7H), 2.13-1.76 (m, 2.7H), 1.75-1.61 (m, 1.20H), 1.48 (dd, J=6.9, 4.2 Hz, 2.5H), 0.99-0.93 (m, 0.3H), 0.82-0.76 (m, 0.3H). The signal corresponding to the NH group was not observed.

Example 22

(±)-trans-(2-methyl-3-((5-(trifluoromethyl)pyridin-2-yl)amino)piperidin-1-yl)(6-methyl-3-(oxazol-2-yl)pyridin-2-yl)methanone hydrochloride

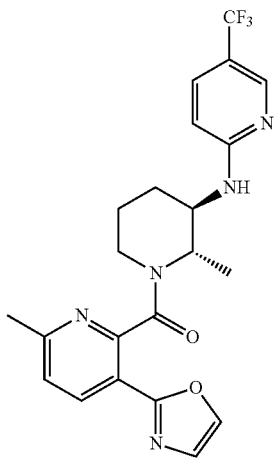 [SMILES: Cc1ccc(-c2ncco2)c(C(=O)N2CCC[C@@H](Nc3ccc(C(F)(F)F)cn3)[C@@H]2C)n1]

Prepared analogous to Example 12 substituting intermediate A-4 with intermediate A-18. MS (ESI) mass calcd. for $C_{22}H_{22}F_3N_5O_2$, 445.2; m/z found 446.2 [M+H]$^+$. (Mixture of 4 isomers, undefined ratio). $^1$H NMR (300 MHz, DMSO) δ 8.46 (s, 0.31H), 8.37 (d, J=6.2 Hz, 0.58H), 8.31 (s, 0.58H), 8.24-8.02 (m, 0.47H), 7.82 (d, J=7.4 Hz, 0.76H), 7.73-7.44 (m, 3.35H), 7.37 (d, J=8.2 Hz, 0.76H), 6.89 (d, J=9.0 Hz, 0.47H), 6.59 (br s, 0.72H), 4.94 (d, J=6.7 Hz, 0.58H), 4.51 (d, J=12.1 Hz, 0.76H), 3.86 (d, J=6.8 Hz, 0.66H), 3.76 (br s, 0.58H), 3.30-3.08 (m, 0.66H), 3.00 (t, J=11.7 Hz, 0.76H), 2.63 (s, 1.27H), 2.36 (s, 1.73H), 2.19-1.89 (m, 1.73H), 1.88-1.56 (m, 2.27H), 1.41 (d, J=6.6 Hz, 1.27H), 1.21 (d, J=6.5 Hz, 1.73H).

Example 23

(±)-trans-(2-methyl-3-((5-(trifluoromethyl)pyridin-2-yl)amino)piperidin-1-yl)(6-methyl-3-(pyrimidin-2-yl)pyridin-2-yl)methanone hydrochloride

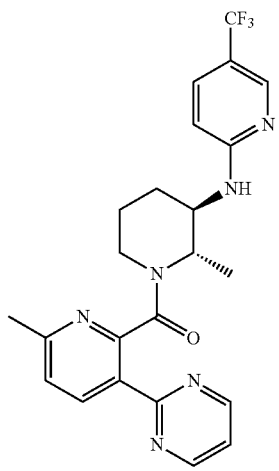 [SMILES: Cc1ccc(-c2ncccn2)c(C(=O)N2CCC[C@@H](Nc3ccc(C(F)(F)F)cn3)[C@@H]2C)n1]

Prepared analogous to Example 12 substituting intermediate A-4 with intermediate A-19. MS (ESI) mass calcd. for $C_{23}H_{23}F_3N_6O$, 456.2; m/z found 457.2 [M+H]$^+$. (Mixture of 4 isomers, undefined ratio). $^1$H NMR (300 MHz, DMSO) δ 9.00 (d, J=4.9 Hz, 1.90H), 8.86 (d, J=8.2 Hz, 0.45H), 8.45-8.36 (m, 1.00H), 8.53-8.08 (m, 0.67H), 8.21 (s, 0.55H), 7.85 (dd, J=27.3, 8.5 Hz, 1.33H), 7.69 (d, J=8.4 Hz, 0.55H), 7.60 (dt, J=11.9, 4.9 Hz, 1.00H), 7.44 (d, J=8.2 Hz, 0.55H), 7.22 (d, J=9.0 Hz, 0.45H), 6.62 (br s, 0.55H), 4.77 (br d, J=7.2 Hz, 0.67H), 4.46 (br d, J=13.3 Hz, 0.67H), 4.00-3.80 (m, 1.15H), 3.29 (br s, 0.78H), 2.99 (t, J=12.3 Hz, 0.78H), 2.81 (s, 1.40H), 2.44 (s, 1.60H), 2.17-1.73 (m, 3.18H), 1.66 (br d, J=12.3 Hz, 0.67H), 1.59-1.25 (m, 3.15H).

Example 24

(±)-trans-(5-fluoro-2-(2H-1,2,3-triazol-2-yl)phenyl)(2-methyl-3-((5-(trifluoromethyl)pyridin-2-yl)amino)piperidin-1-yl)methanone

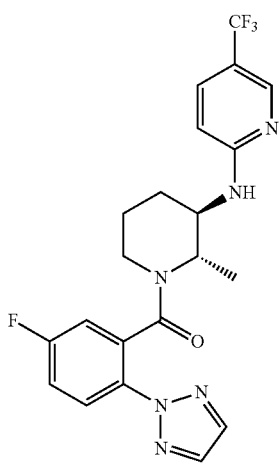 [SMILES: C[C@H]1[C@H](Nc2ccc(C(F)(F)F)cn2)CCCN1C(=O)c1cc(F)ccc1-n1nccn1]

Prepared analogous to Example 14 substituting intermediate A-11 with intermediate A-24. MS (ESI) mass calcd. for $C_{21}H_{20}F_4N_6O$, 448.2; m/z found 449.2 [M+H]$^+$. MP=168.1° C. The product is present as a mixture of conformers (ratio ca. 60:40) $^1$H NMR (300 MHz, DMSO) δ 8.32 (s, 0.4H), 8.08 (s, 1.2H), 8.07 (s, 0.8H), 8.00 (s, 0.6H), 7.94 (dd, J=9.0, 4.9 Hz, 0.4H), 7.77-7.56 (m, 2H), 7.54-7.28 (m, 1.6H), 7.10 (td, J=8.5, 2.9 Hz, 0.6H), 6.87-6.76 (m, 1.4H), 4.62 (q, J=7.0 Hz, 0.4H), 4.43-4.23 (m, 0.6H), 3.79-3.56 (m, 1.6H), 3.23 (d, J=15.9 Hz, 0.4H), 3.08-2.93 (m, 0.4H), 2.85-2.68 (m, 0.6H), 2.13-1.29 (m, 4H), 1.25 (d, J=7.0 Hz, 1.2H), 0.67 (d, J=6.9 Hz, 1.8H).

Example 25

((2S,3R)-2-methyl-3-((5-(trifluoromethyl)pyridin-2-yl)amino)piperidin-1-yl)(6-methyl-3-(oxazol-2-yl)pyridin-2-yl)methanone hydrochloride

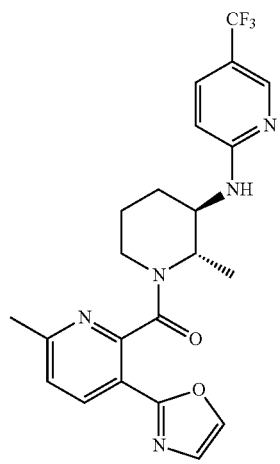 [SMILES: Cc1ccc(-c2ncco2)c(C(=O)N2CCC[C@@H](Nc3ccc(C(F)(F)F)cn3)[C@@H]2C)n1]

Prepared analogous to Example 14 substituting intermediate A-11 with intermediate A-18. MS (ESI) mass calcd. for $C_{22}H_{22}F_3N_5O_2$, 445.2; m/z found 446.2 [M+H]$^+$. The product is present as a mixture of conformers (ratio ca. 70:30) $^1$H NMR (300 MHz, CDCl$_3$) δ 8.36 (s, 0.3H), 8.29-8.20 (m, 1H), 8.14 (d, J=8.2 Hz, 0.7H), 7.81 (s, 1H), 7.65-7.49 (m, 0.6H), 7.41 (d, J=7.0 Hz, 0.7H), 7.36 (s, 0.7H), 7.32-7.22 (m, 1H), 7.12 (br s, 0.7H), 6.84 (br s, 0.3H), 6.46 (d, J=8.8 Hz, 0.3H), 6.24 (d, J=8.4 Hz, 0.7H), 5.20 (q, J=7.8 Hz, 0.3H), 4.82-4.64 (m, 0.7H), 4.12 (d, J=6.3 Hz, 0.3H), 4.02 (d, J=5.6 Hz, 0.7H), 3.76 (q, J=6.7 Hz, 0.7H), 3.36-3.14 (m, 0.6H), 3.11-2.94 (m, 0.7H), 2.63 (s, 0.9H), 2.60 (s, 2.1H), 2.09-1.52 (m, 4H), 1.49 (d, J=7.1 Hz, 0.9H), 1.43 (d, J=6.9 Hz, 2.1H).

Example 26

((2S,3R)-2-methyl-3-((5-(trifluoromethyl)pyridin-2-yl)amino)piperidin-1-yl)(5-methyl-3-(2H-1,2,3-triazol-2-yl)pyridin-2-yl)methanone

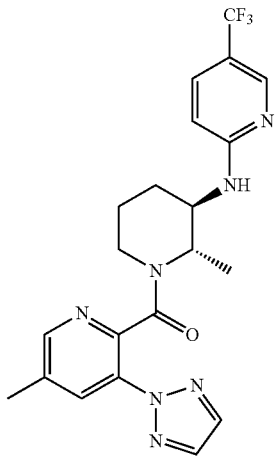

Prepared analogous to Example 14 substituting intermediate A-11 with intermediate A-21. MS (ESI) mass calcd. for $C_{21}H_{22}F_3N_7O$, 445.2; m/z found 446.2 [M+H]$^+$. MP=116.2° C. The product is present as a mixture of conformers (ratio ca. 70:30) $^1$H NMR (300 MHz, CDCl$_3$) δ 8.45 (s, 0.3H), 8.38 (s, 1.1H), 8.24 (s, 1.1H), 8.15-8.04 (m, 1.1H), 7.93 (s, 1.1H), 7.58 (dd, J=8.8, 2.1 Hz, 1.4H), 7.45 (d, J=7.1 Hz, 0.3H), 6.99 (d, J=7.2 Hz, 0.7H), 6.43 (d, J=8.8 Hz, 0.3H), 6.31 (d, J=8.4 Hz, 0.7H), 6.15 (d, J=7.7 Hz, 0.3H), 5.13 (q, J=6.7 Hz, 0.3H), 4.64 (d, J=12.6 Hz, 0.7H), 4.09-3.85 (m, 1.7H), 3.45-3.21 (m, 0.6H), 3.11-2.92 (m, 0.7H), 2.48 (s, 0.9H), 2.44 (s, 2.1H), 2.10-1.72 (m, 3.3H), 1.65-1.58 (m, 0.7H), 1.52-1.41 (m, 3H).

Example 27

((2S,3R)-2-methyl-3-((5-(trifluoromethyl)pyridin-2-yl)amino)piperidin-1-yl)(5-methyl-3-(pyrimidin-2-yl)pyridin-2-yl)methanone

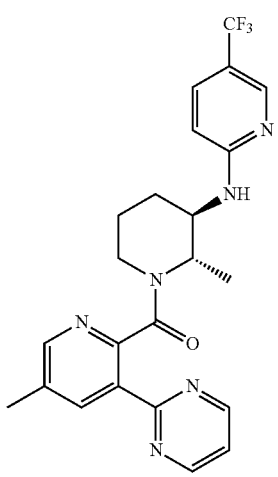 [SMILES: Cc1cnc(C(=O)N2CCC[C@@H](Nc3ccc(C(F)(F)F)cn3)[C@@H]2C)c(-c2ncccn2)c1]

Prepared analogous to Example 14 substituting intermediate A-11 with intermediate A-20. MS (ESI) mass calcd. for $C_{21}H_{22}F_3N_7O$, 445.2; m/z found 446.2 [M+H]$^+$. MP=111.4° C. The product is present as a mixture of conformers (ratio ca. 80:20) $^1$H NMR (300 MHz, CDCl$_3$) δ 8.93-8.74 (m, 2H), 8.59 (d, J=8.2 Hz, 0.2H), 8.38 (d, J=8.1 Hz, 0.8H), 8.28 (s, 0.2H), 8.20 (s, 0.8H), 7.52-7.13 (m, 2.8H), 6.48 (d, J=8.8 Hz, 0.4H), 6.17 (d, J=5.9 Hz, 0.8H), 5.06-4.88 (m, 0.2H), 4.62 (d, J=13.3 Hz, 0.8H), 4.12 (d, J=7.0 Hz, 0.2H), 4.04-3.79 (m, 1.8H), 3.32-3.11 (m, 0.2H), 3.08-2.86 (m, 0.8H), 2.60 (s, 0.6H), 2.57 (s, 2.4H), 2.10-1.54 (m, 4H), 1.50-1.41 (m, 3H).

Example 28

(±)-trans-(3-fluoro-2-methoxyphenyl)(2-methyl-3-((5-(trifluoromethyl)pyridin-2-yl)amino)piperidin-1-yl)methanone

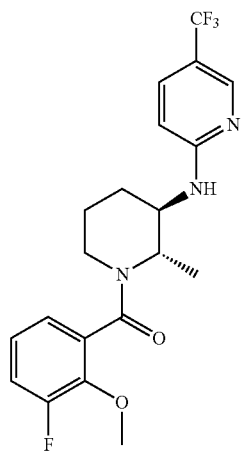 [SMILES: COc1c(F)cccc1C(=O)N1CCC[C@@H](Nc2ccc(C(F)(F)F)cn2)[C@@H]1C]

Prepared analogous to Example 42 substituting intermediate A-4 with 3-fluoro-2-methoxybenzoic acid and 5-bromo-2-chloropyridine with 2-chloro-5-(trifluoromethyl)pyridine. MS (ESI) mass calcd. for $C_{20}H_{21}F_4N_3O_2$, 411.2; m/z found 412.2 [M+H]$^+$. 1H NMR (CDCl$_3$): 8.35-8.05 (m, 1H), 7.76-7.39 (m, 1H), 7.17-5.95 (m, 4H), 5.26-4.63 (m, 1H), 4.29-2.75 (m, 6H), 2.17-1.56 (m, 4H), 1.48-1.23 (m, 3H).

Example 29

(±)-trans-(2-ethoxyphenyl)(2-methyl-3-((5-(trifluoromethyl)pyridin-2-yl)amino)piperidin-1-yl)methanone

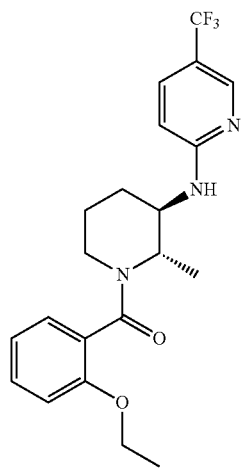

Prepared analogous to Example 42 substituting intermediate A-4 with 2-ethoxybenzoic acid and 5-bromo-2-chloropyridine with 2-chloro-5-(trifluoromethyl)pyridine. MS (ESI) mass calcd. for $C_{21}H_{24}F_3N_3O_2$, 407.2; m/z found 408.2 [M+H]$^+$. 1H NMR (CDCl$_3$): 8.32-8.04 (m, 1H), 7.85-7.27 (m, 2H), 7.21-6.23 (m, 4H), 5.25-2.83 (m, 5H), 2.07-1.24 (m, 11H).

Example 30

(±)-trans-(2-(2H-1,2,3-triazol-2-yl)phenyl)(3-((5-chloropyrimidin-2-yl)amino)-2-methylpiperidin-1-yl)methanone

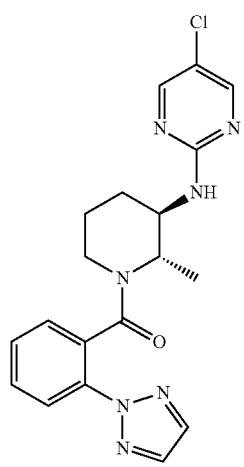

Step A: (±)-trans-tert-butyl-3-((5-chloropyrimidin-2-yl)amino)-2-methylpiperidine-1-carboxylate. To intermediate B-3 (300 mg, 1.4 mmol) in n-BuOH (5 mL) was added 2,5-dichloropyrimidine (210 mg, 1.4 mmol) and DIPEA (480 µL, 2.8 mmol). The reaction was then heated at 120° C. overnight. The reaction was allowed to cool to rt, diluted with H$_2$O and extracted with EtOAc. The combined organics were dried (MgSO$_4$). Silica gel chromatography (EtOAc in heptane) gave the title compound (237 mg, 43%). MS (ESI) mass calcd. for C$_{15}$H$_{23}$ClN$_4$O$_2$, 326.2, m/z found 327.0 [M+H]$^+$.

Step B. trans-(±)-5-chloro-N-(2-methylpiperidin-3-yl)pyrimidin-2-amine. Prepared analogous to Example 1 substituting (±)-tert-butyl-3-((4,6-dimethylpyrimidin-2-yl)amino)-2-methylpiperidine-1-carboxylate with the title compound from Step A.

Step C. (±)-trans-tert-butyl-3-((5-chloropyrimidin-2-yl)amino)-2-methylpiperidine-1-carboxylate. Prepared analogous to Example 12 substituting trans-(±)-2-methylpiperidin-3-yl)-5-(trifluoromethyl)pyridin-2-amine with the title compound from Step B. MS (ESI) mass calcd. for C$_{19}$H$_{20}$ClN$_7$O, 397.2; m/z found 398.2 [M+H]$^+$. MP=200.5° C. The product is present as a mixture of conformers (ratio ca. 60:40) $^1$H NMR (300 MHz, CDCl$_3$) δ 8.31-7.77 (m, 5H), 7.62-7.24 (m, 3.4H), 6.60 (d, J=8.4 Hz, 0.6H), 5.25 (q, J=6.9 Hz, 0.6H), 4.80-4.68 (m, 0.4H), 4.26-4.03 (m, 1H), 3.93 (d, J=7.4 Hz, 0.4H), 3.51 (dd, J=13.7, 3.9 Hz, 0.6H), 3.25 (td, J=13.4, 3.3 Hz, 0.6H), 3.08-2.84 (m, 0.4H), 1.96-1.59 (m, 4H), 1.50 (d, J=6.9 Hz, 1.2H), 1.44 (d, J=7.1 Hz, 1.8H).

Example 31

(±)-trans-(2-(2H-1,2,3-triazol-2-yl)phenyl)(2-methyl-3-((5-methylpyrimidin-2-yl)amino)piperidin-1-yl)methanone

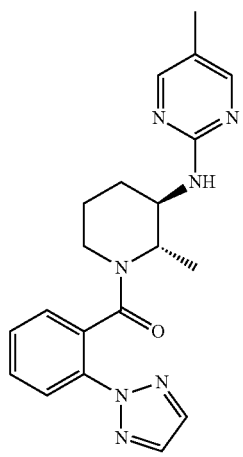 [SMILES: Cc1cnc(N[C@@H]2CCCN(C(=O)c3ccccc3-n3nccn3)[C@H]2C)nc1]

Prepared analogous to Example 30 substituting 2,5-dichloropyrimidine with 2-chloro-5-methylpyrimidine and n-BuOH with DMSO. MS (ESI) mass calcd. for C$_{20}$H$_{23}$N$_7$O, 377.2; m/z found 378.2 [M+H]$^+$. MP=153.0° C.

Example 32

(±)-trans-(2-(2H-1,2,3-triazol-2-yl)phenyl)(3-((5-chloropyridin-2-yl)amino)-2-methylpiperidin-1-yl)methanone

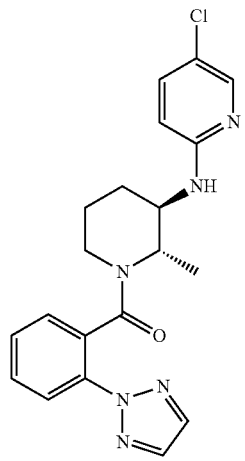

Step A: trans-(±)-tert-butyl-3-((5-chloropyridin-2-yl)amino)-2-methylpiperidine-1-carboxylate. To 5-chloro-2-iodopyridine (246 mg, 1 mmol) in THF 10 mL) was added Pd$_2$(dba)$_3$ (30 mg, 0.03 mmol), Xantphos (38 mg, 0.07 mmol) and sodium tert-butoxide (180 mg, 1.9 mmol). Then N$_2$ was bubbled through the solution for 10 min and intermediate B-3 (200 mg, 0.9 mmol) was added. The reaction was then heated at 90° C. overnight, cooled to rt and saturated NaHCO$_3$ (aq) was added followed by extraction with EtOAc. The combined organics were dried and purified via silica gel chromatography (EtOAc in heptane) to give the title compound (98 mg, 32%). MS (ESI) mass calcd. for C$_{16}$H$_{24}$ClN$_3$O$_2$, 325.2; m/z found 326.0 [M+H]$^+$.

Step B: trans-(±)-5-chloro-N-(2-methylpiperidin-3-yl)pyridin-2-amine. Prepared analogous to Example 1 substituting (±)-tert-butyl-3-((4,6-dimethylpyrimidin-2-yl)amino)-2-methylpiperidine-1-carboxylate with the title compound from Step A.

Step C: (±)-trans-(2-(2H-1,2,3-triazol-2-yl)phenyl)(3-((5-chloropyridin-2-yl)amino)-2-methylpiperidin-1-yl)methanone. Prepared analogous to Example 30 substituting trans-(±)-2-methylpiperidin-3-yl)-5-(trifluoromethyl)pyridin-2-amine with the title compound from Step B. MS (ESI) mass calcd. for C$_{20}$H$_{21}$ClN$_6$O, 396.2; m/z found 397.0 [M+H]$^+$. MP=128.0° C. The product is present as a mixture of conformers (12:13:35:40). $^1$H NMR (300 MHz, DMSO) 8.25 (d, J=12.3 Hz, 0.37H), 8.07 (s, 1.48H), 7.98 (d, J=2.6 Hz, 0.25H), 7.97-7.86 (m, 0.48H), 7.86-7.77 (m, 0.25H), 7.73 (d, J=8.1 Hz, 0.48H), 7.70-7.40 (m, 2.76H), 7.34 (t, J=7.1 Hz, 0.75H), 7.26 (d, J=11.5 Hz, 0.13H), 7.07 (d, J=6.5 Hz, 0.40H), 6.93 (d, J=6.8 Hz, 0.53H), 6.87 (d, J=7.7 Hz, 0.40H), 6.78 (t, J=7.1 Hz, 0.48H), 6.72 (d, J=9.0 Hz, 0.88H), 6.62 (d, J=9.1 Hz, 0.12H), 6.08 (d, J=9.0 Hz, 0.12H), 6.03 (d, J=7.9 Hz, 0.12H), 4.95-4.82 (m, 0.13H), 4.66 (q, J=7.5 Hz, 0.37H), 4.38 (br d, J=13.9 Hz, 0.41H), 4.01-3.89 (m, 0.25H), 3.89-3.77 (m, 0.40H), 3.70 (d, J=7.4 Hz, 0.48H), 3.19 (br d, J=14.4 Hz, 0.48H), 2.92 (br t, J=11.7 Hz, 0.48H), 2.84-2.65 (m, 1H), 2.13-1.47 (m, 4H), 1.43 (d, J=6.9 Hz, 0.36H), 1.31 (d, J=7.0 Hz, 0.39H), 1.24 (d, J=7.0 Hz, 1.05H), 0.77 (d, J=7.0 Hz, 1.20H).

Example 33

(±)-trans-(2-(2H-1,2,3-triazol-2-yl)phenyl)(2-methyl-3-((6-(trifluoromethyl)pyridazin-3-yl)amino)piperidin-1-yl)methanone hydrochloride

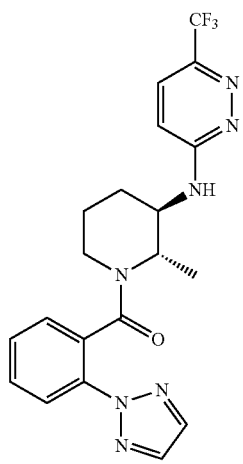 [SMILES: C[C@H]1[C@H](Nc2ccc(C(F)(F)F)nn2)CCCN1C(=O)c1ccccc1-n1nccn1]

Prepared analogous to Example 31 substituting 2-chloro-5-methylpyrimidine with 3-chloro-6-(trifluoromethyl)pyridazine. MS (ESI) mass calcd. for $C_{20}H_{20}F_3N_7O$, 431.2; m/z found 432.0 [M+H]$^+$. MP=167.0° C. (Mixture of 4 isomers, undefined ratio). $^1$H NMR (300 MHz, DMSO) δ 8.33-7.98 (m, J=25.2, 1.88H), 7.91 (d, J=8.0 Hz, 0.43H), 7.85-7.31 (m, 4.06H), 7.31-7.03 (m, 1.49H), 6.97 (d, J=6.5 Hz, 0.50H), 6.72 (t, J=7.2 Hz, 0.50H), 6.50 (s, 0.14H), 5.14-4.93 (m, 0.14H), 4.77 (q, J=7.0 Hz, 0.43H), 4.52-4.30 (m, 0.70H), 4.26-4.05 (m, 0.58H), 3.38-3.10 (m, 0.83H), 3.06-2.87 (m, 0.63H), 2.79 (t, J=11.8 Hz, 0.69H), 2.20-1.50 (m, 3.64H), 1.50-1.17 (m, 2.07H), 0.73 (d, J=6.9 Hz, 1.29H).

Example 34

(2-(2H-1,2,3-triazol-2-yl)phenyl)((2S,3R)-3-((5-fluoropyridin-2-yl)amino)-2-methylpiperidin-1-yl)methanone

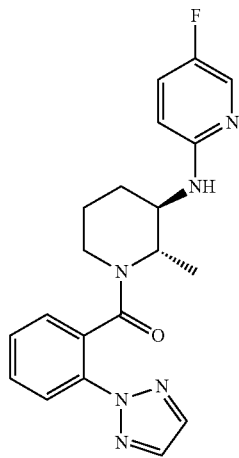 [SMILES: C[C@H]1[C@H](Nc2ccc(F)cn2)CCCN1C(=O)c1ccccc1-n1nccn1]

Prepared analogous to Example 32 substituting 5-chloro-2-iodopyridine with 5-fluoro-2-iodopyridine. MS (ESI) mass calcd. for $C_{20}H_{21}FN_6O$, 380.2; m/z found 381.2 [M+H]$^+$. MP=189.4° C. (Mixture of 4 isomers, undefined ratio). $^1$H NMR (300 MHz, DMSO) δ 8.25 (d, J=11.1 Hz, 0.44H), 8.15-7.99 (m, 1.77H), 7.90 (d, J=8.1 Hz, 0.52H), 7.84-7.42 (m, 4.24H), 7.35 (t, J=7.8 Hz, 0.65H), 7.12 (d, J=7.7 Hz, 0.71H), 7.06-6.91 (m, 0.51H), 6.91-6.77 (m, 0.78H), 6.76-6.67 (m, 0.16H), 6.21-6.07 (m, 0.22H), 4.93-4.76 (m, 0.35H), 4.66 (q, J=6.9 Hz, 0.61H), 4.38 (d, J=12.7 Hz, 0.83H), 3.30-3.11 (m, 0.85H), 3.03-2.85 (m, 0.86H), 2.84-2.71 (m, 0.5H), 2.12-1.47 (m, 3.52H), 1.48-1.14 (m, 2.50H), 0.79 (d, J=6.9 Hz, 0.98H).

Example 35

(±)-trans-(2-(2H-1,2,3-triazol-2-yl)phenyl)(2-methyl-3-((5-(trifluoromethyl)pyrimidin-2-yl)amino)piperidin-1-yl)methanone

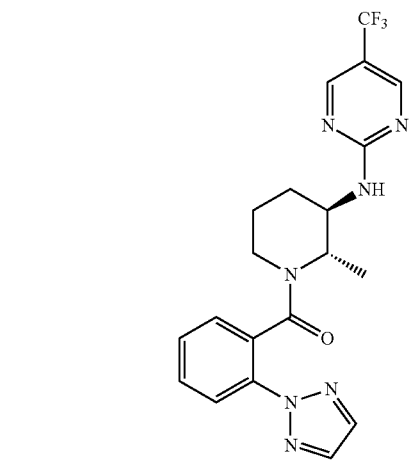 [SMILES: C[C@H]1[C@H](Nc2ncc(C(F)(F)F)cn2)CCCN1C(=O)c1ccccc1-n1nccn1]

Prepared analogous to Example 30 substituting 2,5-dichloropyrimidine with 2-chloro-5-(trifluoromethyl)pyrimidine. MS (ESI) mass calcd. for $C_{20}H_{20}F_3N_7O$, 431.2; m/z found 432.2 [M+H]$^+$. MP=204.4° C. (Mixture of 4 isomers, undefined ratio). $^1$H NMR (300 MHz, CDCl$_3$) δ 8.60-8.45 (m, 1.37H), 8.45-8.23 (m, 1.95H), 8.23-8.11 (m, 0.63H), 8.12-8.00 (m, 0.58H), 7.96 (d, J=7.3 Hz, 0.27H), 7.88 (d, J=8.3 Hz, 0.09H), 7.82 (d, J=6.5 Hz, 0.27H), 7.56 (td, J=7.9, 1.5 Hz, 0.89H), 7.51-7.33 (m, 1.45H), 7.30 (d, J=1.4 Hz, 0.78H), 7.07 (dd, J=7.7, 1.3 Hz, 0.08H), 6.97 (t, J=10.4 Hz, 0.56H), 6.81 (t, J=7.5 Hz, 0.08H), 5.88 (d, J=7.3 Hz, 0.08H), 5.72 (d, J=6.2 Hz, 0.08H), 5.28 (q, J=6.9 Hz, 0.48H), 5.05 (d, J=7.1 Hz, 0.08H), 4.76 (d, J=13.6 Hz, 0.38H), 4.40-4.24 (m, 0.48H), 4.14 (q, J=7.1 Hz, 0.38H), 4.04 (d, J=7.5 Hz, 0.22H), 3.97-3.83 (m, 0.08H), 3.68 (s, 0.08H), 3.53 (dd, J=15.5, 4.7 Hz, 0.7H), 3.27 (td, J=13.4, 3.3 Hz, 0.58H), 3.14-2.76 (m, 0.38H), 2.16-1.21 (m, 6.56H), 1.15 (d, J=6.1 Hz, 0.08H), 1.05-0.93 (m, 0.08H), 0.93-0.82 (m, 0.12H), 0.73 (d, J=7.0 Hz, 0.16H).

Example 36

(±)-trans-(2-(2H-1,2,3-triazol-2-yl)phenyl)(2-methyl-3-(pyridin-2-ylamino)piperidin-1-yl)methanone

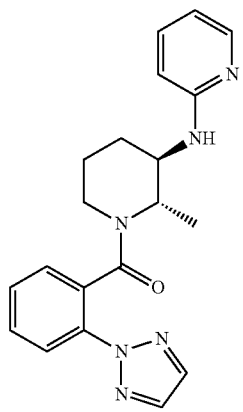 [SMILES: C[C@H]1[C@H](Nc2ccccn2)CCCN1C(=O)c1ccccc1-n1nccn1]

Prepared analogous to Example 32 substituting 5-chloro-2-iodopyridine with 2-iodopyridine. MS (ESI) mass calcd. for $C_{20}H_{22}N_6O$, 362.2; m/z found 363.2 [M+H]$^+$. MP=277.1° C. (Mixture of 4 isomers, undefined ratio). $^1$H NMR (300 MHz, DMSO) δ 8.99-8.49 (m, 0.83H), 8.40 (d, J=5.3 Hz, 0.15H), 8.22 (br s, 0.32H), 8.18-7.73 (m, 4.79H), 7.70-7.43 (m, 1.78H), 7.42-7.03 (m, 1.68H), 7.03-6.77 (m, 1.25H), 6.77-6.67 (m, 0.10H), 6.67-6.51 (m, 0.10H), 4.92-4.77 (m, 0.15H), 4.68 (q, J=6.8 Hz, 0.60H), 4.43 (br d, J=13.9 Hz, 0.42H), 4.06 (br s, 0.60H), 3.92 (br s, 0.32H), 3.86-3.67 (m, 0.60H), 3.24 (br s, 0.29H), 2.99 (t, J=11.9 Hz, 0.60H), 2.83 (t, J=11.5 Hz, 0.42H), 2.24-1.54 (m, 3.04H), 1.54-1.12 (m, 3.13H), 0.88 (d, J=6.6 Hz, 0.83H).

Example 37

(±)-trans-(2-(2H-1,2,3-triazol-2-yl)phenyl)(2-methyl-3-((5-methylpyridin-2-yl)amino)piperidin-1-yl)methanone

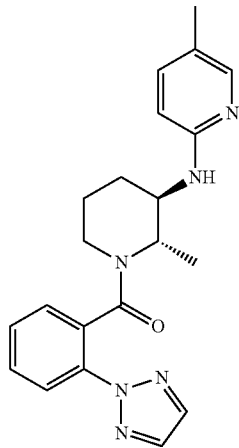 [SMILES: Cc1ccc(N[C@@H]2CCCN(C(=O)c3ccccc3-n3nccn3)[C@H]2C)nc1]

Prepared analogous to Example 32 substituting 5-chloro-2-iodopyridine with 2-chloro-5-methylpyridine. MS (ESI) mass calcd. for $C_{21}H_{24}N_6O$, 376.2; m/z found 377.2 [M+H]$^+$.
MP=148.0° C. (Mixture of 4 isomers, undefined ratio). $^1$H NMR (300 MHz, DMSO) δ 8.66 (d, J=8.0 Hz, 0.64H), 8.57 (br s, 0.34H), 8.25 (d, J=8.1 Hz, 0.41H), 8.14 (d, J=9.9 Hz, 1.66H), 8.05-7.76 (m, 3.39H), 7.76-7.52 (m, 1.66H), 7.45 (t, J=8.2 Hz, 0.34H), 7.35 (d, J=9.7 Hz, 0.64H), 7.28 (d, J=7.1 Hz, 0.34H), 7.23-7.13 (m, 0.16H), 6.99 (t, J=7.5 Hz, 0.34H), 6.60 (br s, 0.08H), 4.86 (br s, 0.16H), 4.72 (q, J=6.9 Hz, 0.64H), 4.47 (br d, J=12.9 Hz, 0.41H), 4.07 (br s, 0.64H), 3.95 (br s, 0.34H), 3.76 (br s, 0.64H), 3.27 (br s, 0.11H), 3.01 (dd, J=21.0, 8.4 Hz, 0.64H), 2.92-2.81 (m, 0.34H), 2.74 (s, 0.41H), 2.72-2.67 (m, 0.08H), 2.25 (s, 2.59H), 2.19-1.57 (m, 3.30H), 1.56-1.40 (m, 1.14H), 1.37 (d, J=7.0 Hz, 1.57H), 1.29 (s, 0.16H), 0.90 (d, J=6.8 Hz, 0.83H).

Example 38

(±)-trans-(2-(2H-1,2,3-triazol-2-yl)phenyl)(2-methyl-3-((5-(trifluoromethyl)pyrazin-2-yl)amino)piperidin-1-yl)methanone

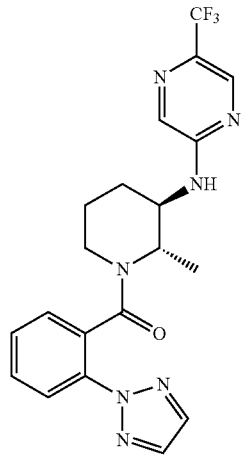 [SMILES: C[C@H]1[C@H](Nc2cnc(C(F)(F)F)cn2)CCCN1C(=O)c1ccccc1-n1nccn1]

Prepared analogous to Example 31 substituting 2-chloro-5-methylpyrimidine with 2-chloro-5-(trifluoromethyl)pyrazine and DIPEA with $K_2CO_3$. MS (ESI) mass calcd. for $C_{20}H_{20}F_3N_7O$, 431.2; m/z found 432.2 [M+H]$^+$. $^1$H NMR (300 MHz, DMSO) δ 8.42 (br s, 0.5H), 8.27-8.17 (m, 1.09H), 8.15 (s, 0.26H), 8.10 (s, 1.31H), 8.08 (s, 0.62H), 8.06-7.99 (m, 0.62H), 7.99-7.91 (m, 0.62H), 7.90 (s, 0.26H), 7.80-7.39 (m, 2.14H), 7.27 (t, J=7.1 Hz, 0.50H), 7.11 (s, 0.09H), 7.07 (d, J=7.7 Hz, 0.45H), 6.94 (s, 0.09H), 6.66 (t, J=7.6 Hz, 0.45H), 4.72 (q, J=6.6 Hz, 0.50H), 4.41 (br d, J=12.7 Hz, 0.70H), 4.04 (br s, 0.50H), 3.98-3.90 (m, 0.45H), 3.31-3.27 (m, 0.28H), 3.18 (br s, 0.62H), 3.03-2.91 (m, 0.50H), 2.84-2.76 (m, 0.45H), 2.31-2.25 (m, 0.26H), 2.15-1.84 (m, 1.81H), 1.84-1.67 (m, 1.09H), 1.67-1.49 (m, 1.09H), 1.39 (d, J=7.2 Hz, 0.62H), 1.32 (s, 0.09H), 1.27 (d, J=7.0 Hz, 0.95H), 0.66 (d, J=6.9 Hz, 1.09H).

Example 39

(±)-trans-(2-(2H-1,2,3-triazol-2-yl)phenyl)(2-methyl-3-(quinazolin-2-ylamino)piperidin-1-yl)methanone

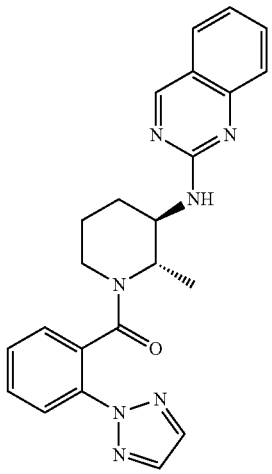 [SMILES: C[C@H]1[C@H](Nc2ncc3ccccc3n2)CCCN1C(=O)c1ccccc1-n1nccn1]

Prepared analogous to Example 30 substituting 2,5-dichloropyrimidine with 2-chloroquinazoline. MS (ESI) mass calcd. for $C_{23}H_{23}N_7O$, 413.2; m/z found 414.2 [M+H]⁺ (Mixture of 4 isomers, undefined ratio). ¹H NMR (300 MHz, CDCl₃) δ 9.02 (s, 0.44H), 8.83 (s, 0.15H), 8.35 (s, 0.61H), 8.14 (d, J=8.1 Hz, 0.44H), 8.08 (s, 0.28H), 8.00 (d, J=7.6 Hz, 0.33H), 7.91 (d, J=7.9 Hz, 0.33H), 7.86-7.10 (m, 7.45H), 7.10-6.94 (m, 0.23H), 6.82 (br s, 0.15H), 6.64 (d, J=8.0 Hz, 0.44H), 6.30 (br s, 0.15H), 5.77 (br s, 0.15H), 5.54 (br s, 0.15H), 5.29 (br d, J=5.5 Hz, 0.61H), 5.18-5.03 (m, 0.15H), 4.84-4.61 (m, 0.33H), 4.41 (d, J=7.9 Hz, 0.44H), 4.30 (br s, 0.15H), 4.25-3.97 (m, 0.61H), 3.91-3.68 (m, 0.15H), 3.50 (d, J=10.1 Hz, 0.44H), 3.25 (t, J=11.9 Hz, 0.49H), 3.09-2.69 (m, 0.39H), 2.39-1.81 (m, 1.13H), 1.81-1.56 (m, 1.30H), 1.52 (d, J=6.8 Hz, 0.80H), 1.44 (dd, J=13.1, 6.7 Hz, 1.94H), 1.02-0.62 (m, 1.83H). The signal corresponding to the NH group was not observed.

Example 40

(±)-trans-(2-(2H-1,2,3-triazol-2-yl)phenyl)(3-((5-fluoropyrimidin-2-yl)amino)-2-methylpiperidin-1-yl)methanone

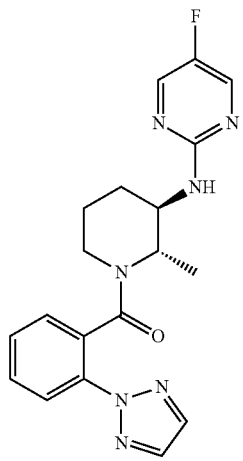 [SMILES: C[C@H]1[C@H](Nc2ncc(F)cn2)CCCN1C(=O)c1ccccc1-n1nccn1]

Prepared analogous to Example 31 substituting 2-chloro-5-methylpyrimidine with 2-chloro-5-fluoropyrimidine. MS (ESI) mass calcd. for $C_{19}H_{20}FN_7O$, 381.2; m/z found 382.1 [M+H]⁺. (Mixture of 4 isomers, undefined ratio). ¹H NMR (300 MHz, DMSO) δ 8.48 (s, 0.47H), 8.39 (d, J=7.6 Hz, 1.01H), 8.24 (s, 0.61H), 8.17 (s, 0.47H), 8.07 (d, J=3.7 Hz, 1.01H), 8.02 (d, J=8.4 Hz, 0.37H), 7.88 (d, J=7.0 Hz, 0.47H), 7.73 (d, J=7.8 Hz, 0.58H), 7.69-7.28 (m, 2.90H), 7.00 (d, J=6.4 Hz, 0.37H), 6.83 (t, J=7.1 Hz, 0.37H), 6.42 (d, J=8.5 Hz, 0.37H), 4.94 (dd, J=13.8, 7.1 Hz, 0.37H), 4.68 (dd, J=13.4, 6.2 Hz, 0.37H), 4.44 (d, J=12.4 Hz, 0.20H), 4.34 (d, J=11.9 Hz, 0.37H), 4.04 (d, J=8.5 Hz, 0.37H), 3.94 (t, J=10.0 Hz, 0.37H), 3.77 (dd, J=14.2, 7.0 Hz, 0.37H), 3.47-3.38 (m, 0.47H), 3.20 (d, J=13.7 Hz, 0.37H), 3.01-2.82 (m, 0.37H), 2.82-2.67 (m, 0.37H), 2.12-1.79 (m, 1.74H), 1.76-1.47 (m, 1.55H), 1.44 (d, J=6.9 Hz, 0.52H), 1.35 (d, J=7.2 Hz, 0.86H), 1.33-1.26 (m, 0.61H), 1.23 (d, J=7.0 Hz, 0.86H), 0.77 (d, J=7.0 Hz, 0.86H).

Example 41

(±)-trans-(2-(2H-1,2,3-triazol-2-yl)phenyl)(3-(benzo[d]oxazol-2-ylamino)-2-methylpiperidin-1-yl methanone

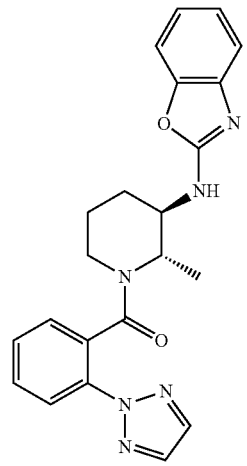 [SMILES: C[C@H]1[C@H](Nc2nc3ccccc3o2)CCCN1C(=O)c1ccccc1-n1nccn1]

Step A: (±)-tert-butyl 3-(benzo[d]oxazol-2-ylamino)-2-methylpiperidine-1-carboxylate. To intermediate B-3 (1.4 g, 6.6 mmol) in 1,4-dioxane (20 mL) was added DIPEA (2.3 mL, 13.2 mmol) and 2-(methylsulfinyl)benzo[d]oxazole (2.4 g, 13.2 mmol). After heating at 80° C. for 4 h, the mixture was cooled to rt and saturated NaHCO3 (aq) was added. The aqueous layer was extracted with EtOAc (3x). The combined organics were dried (MgSO₄). Purification via silica gel chromatography (0-50% EtOAc in hexanes) gave the title compound (1.7 g, 77%).

Step B: (±)-N-(-2-methylpiperidin-3-yl)benzo[d]oxazol-2-amine. Prepared analogous to Example 1 substituting (±)-tert-butyl-3-((4,6-dimethylpyrimidin-2-yl)amino)-2-methylpiperidine-1-carboxylate with the title compound from step A.

Step C: (±)-trans-(2-(2H-1,2,3-triazol-2-yl)phenyl)(3-(benzo[d]oxazol-2-ylamino)-2-methylpiperidin-1-yl)methanone. Prepared analogous to Example 30 substituting trans-(±)-5-chloro-N-(2-methylpiperidin-3-yl)pyrimidin-2-amine with the title compound from step B. MS (ESI) mass calcd. for $C_{22}H_{22}N_6O_2$, 402.2; m/z found 403.2 [M+H]⁺. (Mixture of 4 isomers, undefined ratio). ¹H NMR (300 MHz, DMSO) δ 8.03 (dd, J=12.9, 10.4 Hz, 0.82H), 7.91 (d, J=6.3 Hz, 0.36H), 7.84 (d, J=2.8 Hz, 1.27H), 7.81-7.70 (m, 0.36H), 7.66 (d, J=7.8 Hz, 0.46H), 7.59-7.47 (m, 0.82H), 7.47-7.23 (m, 1.79H), 7.24-7.08 (m, 1.27H), 7.08-6.95 (m, 0.61H), 6.95-6.65 (m, 2.88H), 6.16 (t, J=7.8 Hz, 0.36H), 4.90-4.76 (m, 0.36H), 4.57 (q, J=7.1 Hz, 0.46H), 4.25-4.06 (m, 0.46H), 3.91-3.78 (m, 0.36H), 3.75-3.56 (m, 0.82H), 3.56-3.44 (m, 0.36H), 3.32-3.19 (m, 0.36H), 2.97 (br d, J=14.4 Hz, 0.36H), 2.82-2.63 (m, 0.46H), 2.06-2.00 (m, 0.18H), 1.91-1.18 (m, 4.56H), 1.18-1.08 (m, 0.82H), 0.80 (d, J=6.1 Hz, 0.36H), 0.58 (d, J=6.9 Hz, 1.08H).

Example 42

(±)-trans-(2-(2H-1,2,3-triazol-2-yl)phenyl)(3-((5-bromopyridin-2-yl)amino)-2-methylpiperidin-1-yl)methanone

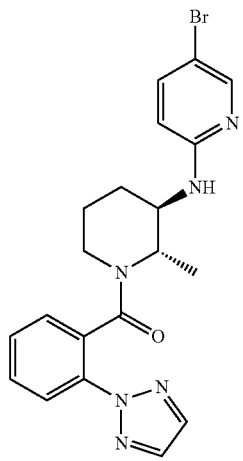

Step A: (±)-trans-tert-butyl 3-((5-bromopyridin-2-yl)amino)-2-methylpiperidine-1-carboxylate. Intermediate B-3 (1.6 g, 7.5 mmol), 5-bromo-2-fluoropyridine (2.9 g, 15 mmol) and $K_2CO_3$ (4.1 g, 30 mmol) were heated in NMP (50 mL) at 100° C. for 8 h. The reaction was allowed to cool to rt then concentrated and purified via silica gel chromatography (50% EtOAc in petroleum ethers).

Step B: (±)-trans-5-bromo-N-(2-methylpiperidin-3-yl)pyridin-2-amine.
To the title compound from step A in DCM (10 mL) was added TFA (1 mL). After 1 h, the reaction was concentrated to give the title compound that was used without further purification.

Step C: (±)-trans-(2-(2H-1,2,3-triazol-2-yl)phenyl)(3-((5-bromopyridin-2-yl)amino)-2-methylpiperidin-1-yl)methanone. The title compound from Step B (50 mg), DIPEA (1 mL), intermediate A-4 (100 mg) and HATU (200 mg) were stirred in THF at rt for 3 h. Upon completion of the reaction, purification was performed using preparative HPLC to give the title compound (20 mg, 55% yield). MS (ESI) mass calcd. for $C_{20}H_{21}BrN_6O$, 440.2; m/z found 441.1 [M+H]$^+$. $^1$H NMR (CDCl$_3$): 8.11-7.26 (m, 8H), 7.11-5.91 (m, 1H), 5.19-4.55 (m, 1H), 4.26-2.68 (m, 3H), 2.11-0.71 (m, 7H).

Example 43

(±)-trans-(3-((5-bromopyridin-2-yl)amino)-2-methylpiperidin-1-yl)(3-fluoro-2-methoxyphenyl)methanone

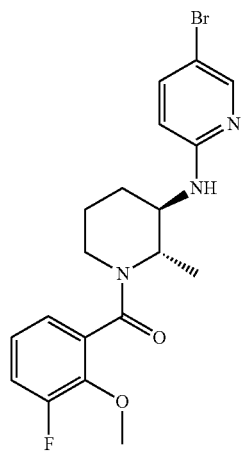

Prepared analogous to Example 42 substituting intermediate A-4 with 3-fluoro-2-methoxybenzoic acid. MS (ESI) mass calcd. for $C_{19}H_{21}BrFN_3O_2$, 421.2; m/z found 422.1 [M+H]$^+$. $^1$H NMR (CDCl$_3$): 8.03-7.50 (m, 2H), 7.33-6.09 (m, 4H), 5.24-4.61 (m, 1H), 4.02-3.33 (m, 5H), 3.30-2.84 (m, 1H), 2.24-1.16 (m, 7H).

Example 44

(±)-trans-(3-(5-bromopyridin-2-yl)amino)-2-methylpiperidin-1-yl)(2-ethoxyphenyl)methanone

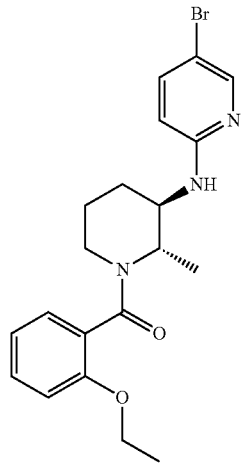

Prepared analogous to Example 42 substituting intermediate A-4 with 2-ethoxybenzoic acid. MS (ESI) mass calcd. for $C_{20}H_{24}BrN_3O_2$, 417.2; m/z found 418.1 [M+H]$^+$. 1H NMR (CDCl$_3$): 7.93-6.19 (m, 7H), 5.20-4.52 (m, 1H), 4.32-3.87 (m, 2H), 3.81-2.83 (m, 3H), 2.22-1.76 (m, 3H), 1.52-1.21 (m, 7H).

Example 45

(±)-trans-(2-(2H-1,2,3-triazol-2-yl)phenyl)(3-((5-chlorobenzo[d]oxazol-2-yl)amino)-2-methylpiperidin-1-yl)methanone

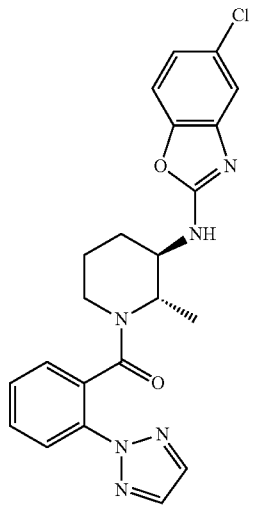 [SMILES: C[C@H]1[C@H](Nc2nc3cc(Cl)ccc3o2)CCCN1C(=O)c1ccccc1-n1nccn1]

Prepared analogous to Example 42 substituting 5-bromo-2-fluoropyridine with 2,5-dichlorobenzo[d]oxazole. MS (ESI) mass calcd. for $C_{22}H_{21}ClN_6O_2$, 436.2; m/z found 437.2 [M+H]$^+$. 1H NMR (CDCl$_3$): 11.55 (s, 1H), 8.14-7.71 (m, 4H), 7.60-7.28 (m, 4H), 7.23-6.98 (m, 1H), 5.42-4.67 (m, 1H), 4.27-3.94 (m, 1H), 3.50-3.45 (m, 1H), 3.07-2.94 (m, 1H), 2.18-1.80 (m, 3H), 1.7-1.39 (m, 4H).

Example 46

(±)-trans-(3-((5-chlorobenzo[d]oxazol-2-yl)amino)-2-methylpiperidin-1-yl)(2-ethoxyphenyl)methanone

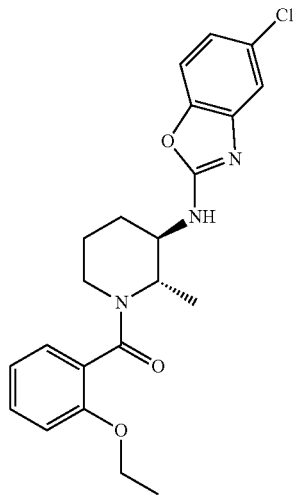 [SMILES: CCOc1ccccc1C(=O)N1CCC[C@@H](Nc2nc3cc(Cl)ccc3o2)[C@@H]1C]

Prepared analogous to Example 45 substituting intermediate A-4 with 2-ethoxybenzoic acid. MS (ESI) mass calcd. for $C_{22}H_{24}ClN_3O_3$, 413.2; m/z found 414.2 [M+H]$^+$. $^1$H NMR (CDCl3): 7.47-6.19 (m, 7H), 5.85-4.57 (m, 1H), 4.57-2.68 (m, 5H), 2.25-0.99 (m, 10H).

Example 47

(±)-trans-(3-((5-chlorobenzo[d]oxazol-2-yl)amino)-2-methylpiperidin-1-yl)(3-fluoro-2-methoxyphenyl)methanone

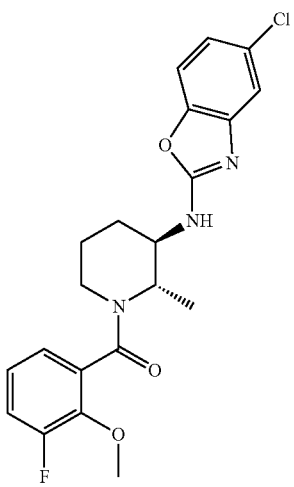 [SMILES: COc1c(F)cccc1C(=O)N1CCC[C@@H](Nc2nc3cc(Cl)ccc3o2)[C@@H]1C]

Prepared analogous to Example 45 substituting intermediate A-4 with 3-fluoro-2-methoxybenzoic acid. MS (ESI) mass calcd. for $C_{21}H_{21}ClFN_3O_3$, 417.2; m/z found 418.1 [M+H]$^+$. 1H NMR (CDCl$_3$): 7.37-7.25 (m, 1H), 7.23-6.52 (m, 5H), 5.26-4.62 (m, 1H), 4.24-3.85 (m, 3H), 3.83-3.60 (m, 1H), 3.41-3.09 (m, 1H), 2.97-2.88 (m, 1H), 2.32-1.57 (m, 4H), 1.56-1.05 (m, 3H).

Example 48

(±)-trans-(2-(2H-1,2,3-triazol-2-yl)phenyl)(2-methyl-3-(quinoxalin-2-ylamino)piperidin-1-yl)methanone

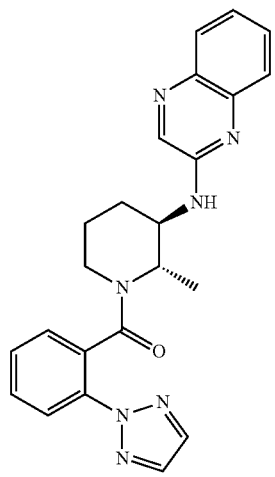 [SMILES: C[C@H]1[C@H](Nc2cnc3ccccc3n2)CCCN1C(=O)c1ccccc1-n1nccn1]

Prepared analogous to Example 42 substituting 5-bromo-2-fluoropyridine with 2-chloroquinoxaline. MS (ESI) mass calcd. for $C_{23}H_{23}N_7O$, 413.2; m/z found 414.2 [M+H]$^+$. 1H NMR (CDCl3): 8.40-7.95 (m, 2H), 7.95-7.70 (m, 3H), 7.70-7.26 (m, 6H), 5.36-4.56 (m, 1H), 4.42-2.77 (m, 3H), 2.16-0.68 (m, 7H).

Example 49

(±)-trans-(2-ethoxyphenyl)(2-methyl-3-(quinoxalin-2-ylamino)piperidin-1-yl)methanone

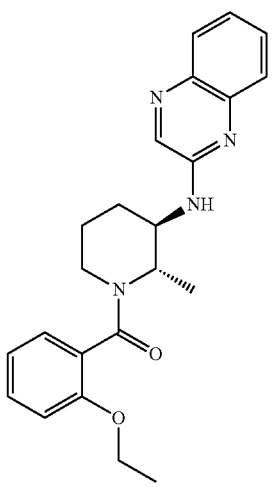 [SMILES: CCOc1ccccc1C(=O)N1CCC[C@@H](Nc2cnc3ccccc3n2)[C@@H]1C]

Prepared analogous to Example 48 substituting intermediate A-4 with 2-ethoxybenzoic acid. MS (ESI) mass calcd. for $C_{23}H_{26}N_4O_2$, 390.2; m/z found 391.2 [M+H]$^+$. 1H NMR (CDCl3): 8.72-8.36 (m, 1H), 7.98-7.29 (m, 5H), 7.24-6.57 (m, 3H), 5.27-2.90 (m, 6H), 2.13-1.76 (m, 3H), 1.62-1.30 (m, 7H).

Example 50

(±)-trans-(3-fluoro-2-methoxyphenyl)(2-methyl-3-(quinoxalin-2-ylamino)piperidin-1-yl)methanone

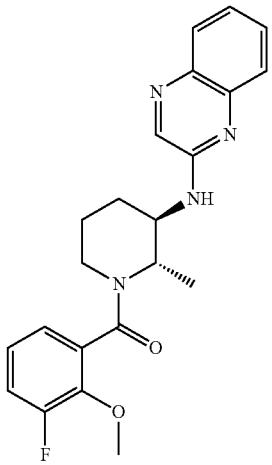 [SMILES: COc1c(F)cccc1C(=O)N1CCC[C@@H](Nc2cnc3ccccc3n2)[C@@H]1C]

Prepared analogous to Example 48 substituting intermediate A-4 with 3-fluoro-2-methoxybenzoic acid. MS (ESI) mass calcd. for $C_{22}H_{23}FN_4O_2$, 394.2; m/z found 395.2 [M+H]$^+$. 1H NMR (CDCl3): 8.75-8.26 (m, 1H), 7.96 (d, J=8.5 Hz, 1H), 7.84 (t, J=9.2 Hz, 1H), 7.71 (t, J=7.6 Hz, 1H), 7.55 (t, J=7.7 Hz, 1H), 7.37-6.08 (m, 3H), 5.32-4.60 (m, 1H), 4.31-3.80 (m, 4H), 3.77-2.91 (m, 2H), 2.29-1.51 (m, 4H), 1.51-1.29 (m, 3H).

Example 51

(±)-trans-(2-(2H-1,2,3-triazol-2-yl)phenyl)(2-methyl-3-((4-phenylpyrimidin-2-yl)amino)piperidin-1-yl)methanone

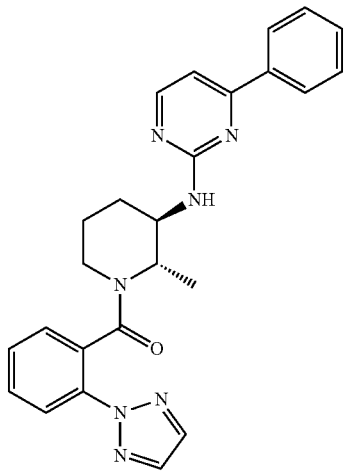 [SMILES: C[C@H]1[C@H](Nc2nccc(-c3ccccc3)n2)CCCN1C(=O)c1ccccc1-n1nccn1]

Prepared analogous to Example 42 substituting 5-bromo-2-fluoropyridine with 2-chloro-4-phenylpyrimidine. MS (ESI) mass calcd. for $C_{25}H_{25}N_7O$, 439.2; m/z found 440.2 [M+H]$^+$.

Example 52

(±)-trans-(3-fluoro-2-methoxyphenyl)(2-methyl-3-((4-phenylpyrimidin-2-yl)amino)piperidin-1-yl)methanone

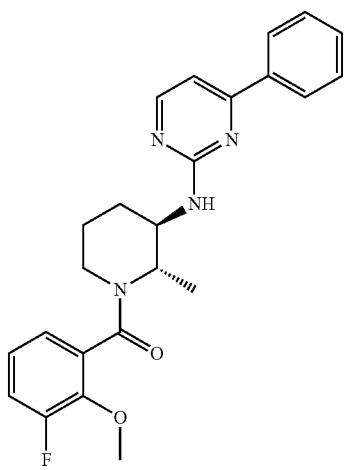 [SMILES: COc1c(F)cccc1C(=O)N1CCC[C@@H](Nc2nccc(-c3ccccc3)n2)[C@@H]1C]

Prepared analogous to Example 51 substituting intermediate A-4 with 3-fluoro-2-methoxybenzoic acid. MS (ESI) mass calcd. for $C_{24}H_{25}FN_4O_2$, 420.2; m/z found 421.2

[M+H]+. 1H NMR (CDCl3): 10.31-9.49 (m, 1H), 8.18-8.09 (m, 2H), 7.81-6.43 (m, 8H), 5.57-4.67 (m, 1H), 4.60-4.13 (m, 1H), 4.13-2.77 (m, 5H), 2.38-1.88 (m, 3H), 1.88-1.09 (m, 4H).

Example 53

(±)-trans-(2-ethoxyphenyl)(2-methyl-3-((4-phenylpyrimidin-2-yl)amino)piperidin-1-yl)methanone

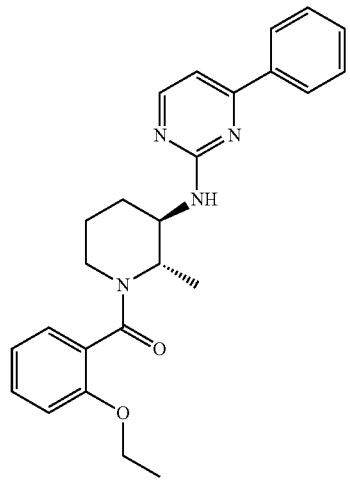 [SMILES: CCOc1ccccc1C(=O)N1CCC[C@@H](Nc2nccc(-c3ccccc3)n2)[C@@H]1C]

Prepared analogous to Example 51 substituting intermediate A-4 with 2-ethoxybenzoic acid. MS (ESI) mass calcd. for $C_{25}H_{28}N_4O_2$, 416.2; m/z found 417.2 [M+H]+. 1H NMR (CDCl3): 10.37-9.49 (m, 1H), 8.29-6.29 (m, 11H), 5.58-4.61 (m, 1H), 4.61-4.25 (m, 1H), 4.25-2.84 (m, 4H), 2.22-1.89 (m, 3H), 1.80-1.07 (m, 7H).

Example 54

(±)-cis-(3-fluoro-2-methoxyphenyl)(2-methyl-3-((5-(trifluoromethyl)pyridin-2-yl)amino)piperidin-1-yl)methanone

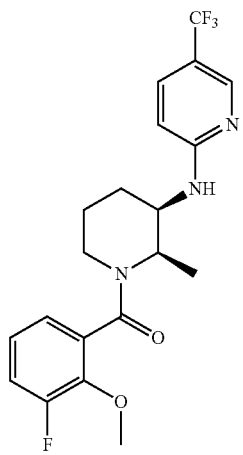 [SMILES: COc1c(F)cccc1C(=O)N1CCC[C@@H](Nc2ccc(C(F)(F)F)cn2)[C@H]1C]

Prepared analogous to Example 28 substituting intermediate B-3 for intermediate B-6. MS (ESI) mass calcd. for $C_{20}H_{21}F_4N_3O_2$, 411.2; m/z found 412.1 [M+H]+. 1H NMR (CDCl3): 8.38-7.38 (m, 2H), 7.23-5.71 (m, 4H), 5.68-3.74 (m, 6H), 3.35-2.78 (m, 1H), 2.03-1.39 (m, 4H), 1.36-1.02 (m, 3H).

Example 55

(±)-cis-(2-ethoxyphenyl)(2-methyl-3-((5-(trifluoromethyl)pyridin-2-yl)amino)piperidin-1-yl)methanone

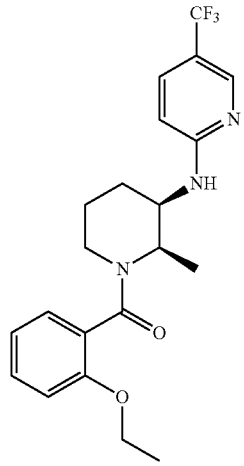

Prepared analogous to Example 54 substituting 3-fluoro-2-methoxybenzoic acid with 2-ethoxybenzoic acid. MS (ESI) mass calcd. for $C_{21}H_{24}F_3N_3O_2$, 407.2; m/z found 408.1 [M+H]+. 1H NMR (CDCl3): 8.37-7.27 (m, 3H), 7.25-6.18 (m, 4H), 6.01-3.98 (m, 4H), 3.97-2.68 (m, 2H), 1.95-1.65 (m, 3H), 1.59-1.32 (m, 4H), 1.29-0.98 (m, 3H).

Example 56

(±)-cis-(2-(2H-1,2,3-triazol-2-yl)phenyl)(2-methyl-3-((5-(trifluoromethyl)pyridin-2-yl)amino)piperidin-1-yl)methanone

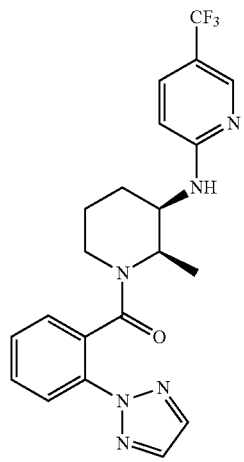 [SMILES: C[C@@H]1[C@H](Nc2ccc(C(F)(F)F)cn2)CCCN1C(=O)c1ccccc1-n1nccn1]

Prepared analogous to Example 54 substituting 3-fluoro-2-methoxybenzoic acid with intermediate A-4. MS (ESI)

mass calcd. for $C_{21}H_{21}F_3N_6O$, 430.2; m/z found 431.2 [M+H]$^+$. 1H NMR (CDCl$_3$): 8.14-7.72 (m, 4H), 7.64-7.30 (m, 3H), 7.24-6.41 (m, 2H), 5.32-2.70 (m, 4H), 2.06-1.35 (m, 4H), 1.33-1.16 (m, 3H).

Example 57

(±)-cis-(2-(2H-1,2,3-triazol-2-yl)phenyl)(3-((5-bromopyridin-2-yl)amino)-2-methylpiperidin-1-yl)methanone

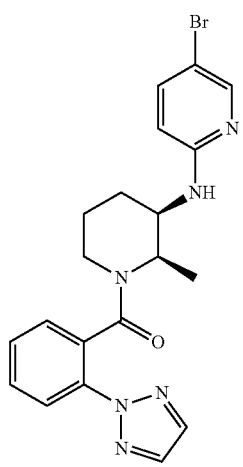 [SMILES: C[C@@H]1[C@H](Nc2ccc(Br)cn2)CCCN1C(=O)c1ccccc1-n1nccn1]

Prepared analogous to Example 42 substituting Intermediate B-3 with Intermediate B-6. MS (ESI) mass calcd. for $C_{20}H_{21}BrN_6O$, 440.2; m/z found 441.1 [M+H]$^+$. 1H NMR (CDCl3): 9.69 (brs, 1H), 8.10-7.67 (m, 4H), 7.65-7.38 (m, 3H), 7.36-6.01 (m, 2H), 5.35-4.43 (m, 1H), 4.03-2.60 (m, 3H), 2.03-1.77 (m, 2H), 1.76-0.76 (m, 5H).

Example 58

(±)-cis-(3-(5-bromopyridin-2-yl)amino)-2-methylpiperidin-1-yl)(3-fluoro-2-methoxyphenyl)methanone

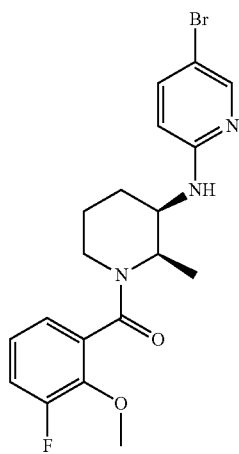 [SMILES: COc1c(F)cccc1C(=O)N1CCC[C@@H](Nc2ccc(Br)cn2)[C@H]1C]

Prepared analogous to Example 57 substituting intermediate A-4 with 3-fluoro-2-methoxybenzoic acid. MS (ESI) mass calcd. for $C_{19}H_{21}BrFN_3O_2$, 421.2; m/z found 421.9 [M+H]$^+$. 1H NMR (CDCl$_3$): 8.10-7.27 (m, 2H), 7.23-6.72 (m, 3H), 6.71-5.94 (m, 1H), 5.41-4.52 (m, 1H), 4.19-3.53 (m, 4H), 3.35-2.77 (m, 3H), 2.08-0.99 (m, 7H).

Example 59

(±)-cis-(3-(5-bromopyridin-2-yl)amino)-2-methylpiperidin-1-yl)(2-ethoxyphenyl)methanone

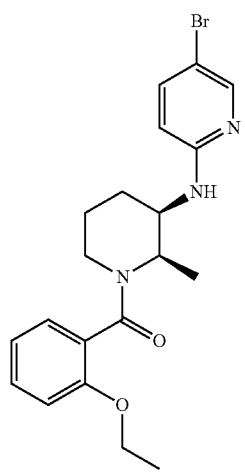

Prepared analogous to Example 57 substituting intermediate A-4 with 2-ethoxybenzoic acid. MS (ESI) mass calcd. for $C_{20}H_{24}BrN_3O_2$, 417.2; m/z found 418.0 [M+H]$^+$. 1H NMR (CDCl$_3$): 8.01-7.29 (m, 3H), 7.24-6.81 (m, 3H), 6.51-5.76 (m, 1H), 5.36-4.64 (m, 1H), 4.35-3.78 (m, 3H), 3.77-2.76 (m, 2H), 2.11-0.83 (m, 10H).

Example 60

(±)-cis-((2-(2H-1,2,3-triazol-2-yl)phenyl)(3-((5-chlorobenzo[d]oxazol-2-yl)amino)-2-methylpiperidin-1-yl)methanone

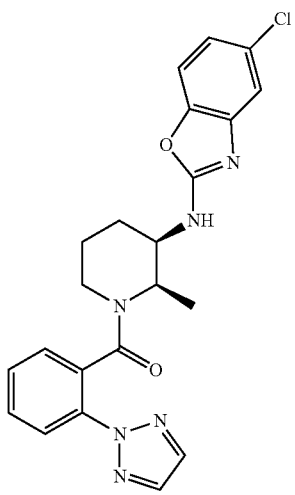 [SMILES: C[C@@H]1[C@H](Nc2nc3cc(Cl)ccc3o2)CCCN1C(=O)c1ccccc1-n1nccn1]

Prepared analogous to Example 45 substituting intermediate B-3 with intermediate B-6. MS (ESI) mass calcd. for $C_{22}H_{21}ClN_6O_2$, 436.2; m/z found 437.1 [M+H]$^+$. 1H NMR (CDCl3): 11.37-10.92 (m, 1H), 8.21-7.97 (m, 1H), 7.90-7.88 (m, 1H), 7.81-7.80 (m, 1H), 7.61-7.27 (m, 5H), 7.24-7.10 (m, 1H), 5.47-4.04 (m, 1H), 4.01-3.46 (m, 1H), 3.41-2.74 (m, 2H), 2.06-0.96 (m, 7H).

Example 61

(±)-cis-(3-((5-chlorobenzo[d]oxazol-2-yl)amino)-2-methylpiperidin-1-yl)(2-ethoxyphenyl)methanone

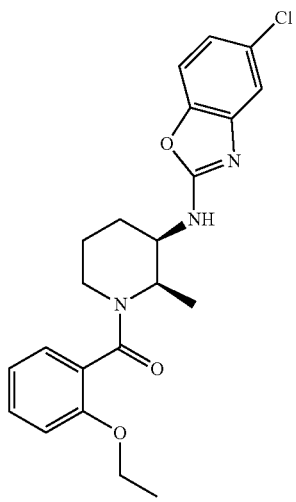 [SMILES: CCOc1ccccc1C(=O)N1CCC[C@@H](Nc2nc3cc(Cl)ccc3o2)[C@H]1C]

Prepared analogous to Example 60 substituting intermediate A-4 with 2-ethoxybenzoic acid. MS (ESI) mass calcd. for $C_{22}H_{24}ClN_3O_3$, 413.2; m/z found 414.0 [M+H]$^+$. 1H NMR (CDCl3): 7.42-7.27 (m, 3H), 7.21-6.84 (m, 4H), 5.39-4.70 (m, 1H), 4.27-3.68 (m, 4H), 3.41-2.74 (m, 1H), 2.07-1.61 (m, 3H), 1.60-1.04 (m, 7H).

Example 62

(±)-cis-(3-((5-chlorobenzo[d]oxazol-2-yl)amino)-2-methylpiperidin-1-yl)(3-fluoro-2-methoxyphenyl)methanone

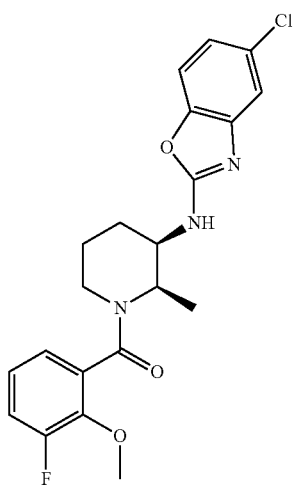 [SMILES: COc1c(F)cccc1C(=O)N1CCC[C@@H](Nc2nc3cc(Cl)ccc3o2)[C@H]1C]

Prepared analogous to Example 60 substituting intermediate A-4 with 3-fluoro-2-methoxybenzoic acid. MS (ESI) mass calcd. for $C_{21}H_{21}ClFN_3O_3$, 417.2; m/z found 417.9 [M+H]$^+$. 1H NMR (CDCl3): 7.35-6.88 (m, 6H), 5.54-3.57 (m, 5H), 3.39-2.72 (m, 3H), 2.12-1.37 (m, 4H), 1.33-1.00 (m, 3H).

Example 63

(±)-cis-(2-(2H-1,2,3-triazol-2-yl)phenyl)(2-methyl-3-(quinoxalin-2-ylamino)piperidin-1-yl)methanone

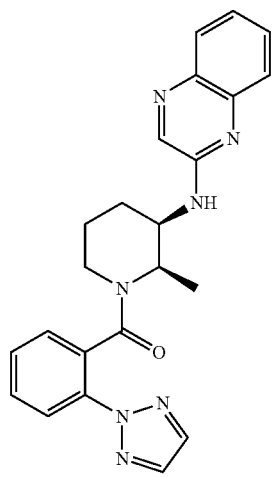 [SMILES: C[C@@H]1[C@H](Nc2cnc3ccccc3n2)CCCN1C(=O)c1ccccc1-n1nccn1]

Prepared analogous to Example 48 substituting intermediate B-3 with intermediate B-6. MS (ESI) mass calcd. for $C_{23}H_{23}N_7O$, 413.2; m/z found 414.2 [M+H]$^+$. 1H NMR (CDCl3): 11.03 (s, 1H), 8.97-8.37 (m, 1H), 8.14-7.28 (m, 10H), 5.41-3.90 (m, 2H), 3.74-2.57 (m, 2H), 2.20-1.82 (m, 2H), 1.80-0.85 (m, 5H).

Example 64

(±)-cis-(3-fluoro-2-methoxyphenyl)(2-methyl-3-(quinoxalin-2-ylamino)piperidin-1-yl)methanone

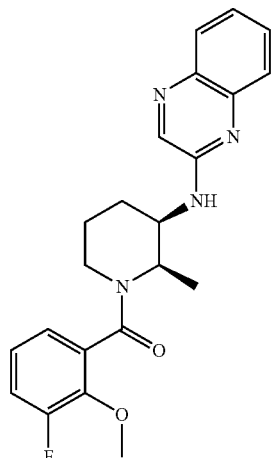

Prepared analogous to Example 63 substituting intermediate A-4 with 3-fluoro-2-methoxybenzoic acid. MS (ESI) mass calcd. for $C_{22}H_{23}FN_4O_2$, 394.2; m/z found 395.2 [M+H]$^+$. 1H NMR (CDCl3): 8.96-8.11 (m, 1H), 8.08-7.64

(m, 3H), 7.55 (s, 1H), 7.22-6.85 (m, 3H), 5.45-4.59 (m, 1H), 4.41-2.79 (m, 6H), 2.30-1.06 (m, 7H).

Example 65

(±)-cis-(2-ethoxyphenyl)(2-methyl-3-(quinoxalin-2-ylamino)piperidin-1-yl)methanone

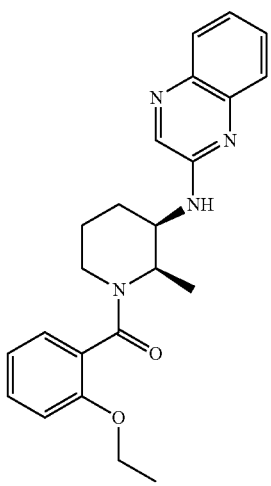 [SMILES: CCOc1ccccc1C(=O)N1CCC[C@@H](Nc2cnc3ccccc3n2)[C@H]1C]

Prepared analogous to Example 63 substituting intermediate A-4 with 2-ethoxybenzoic acid. MS (ESI) mass calcd. for $C_{23}H_{26}N_4O_2$, 390.2; m/z found 391.2 [M+H]$^+$. 1H NMR (CDCl3): 8.96-8.35 (m, 1H), 8.01-7.29 (m, 5H), 7.25-6.59 (m, 3H), 5.43-5.16 (m, 1H), 4.81-2.64 (m, 5H), 2.26-1.71 (m, 3H), 1.71-1.12 (m, 7H).

Example 66

(±)-cis-(2-(2H-1,2,3-triazol-2-yl)phenyl)(2-methyl-3-((4-phenylpyrimidin-2-yl)amino)piperidin-1-yl)methanone

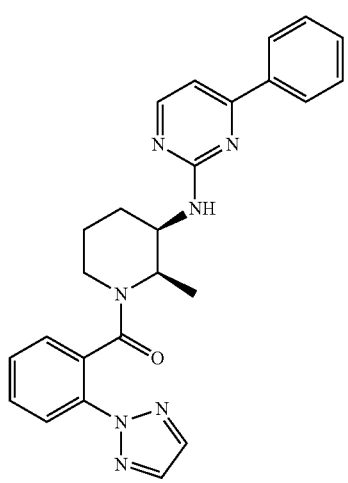 [SMILES: C[C@@H]1[C@H](Nc2nccc(-c3ccccc3)n2)CCCN1C(=O)c1ccccc1-n1nccn1]

Prepared analogous to Example 51 substituting intermediate B-3 with intermediate B-6. MS (ESI) mass calcd. for $C_{25}H_{25}N_7O$, 439.2; m/z found 440.2 [M+H]$^+$. 1H NMR (CDCl3): 9.88-9.51 (m, 1H), 8.35-7.93 (m, 3H), 7.92-7.27 (m, 8H), 7.24-5.46 (m, 2H), 4.98-3.88 (m, 2H), 3.49-2.73 (m, 2H), 2.09-0.84 (m, 7H).

Example 67

(±)-cis-(3-fluoro-2-methoxyphenyl)(2-methyl-3-((4-phenylpyrimidin-2-yl)amino)piperidin-1-yl)methanone

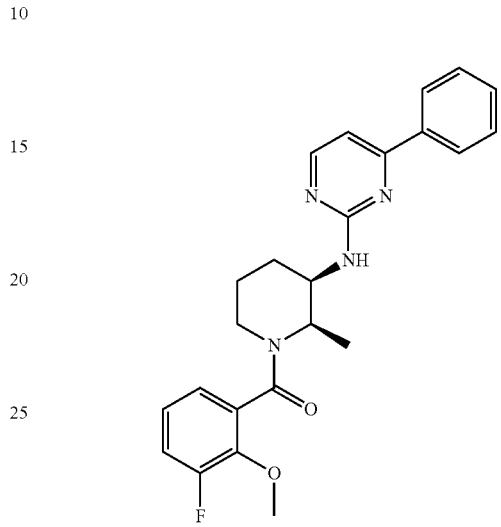

Prepared analogous to Example 66 substituting intermediate A-4 with 3-fluoro-2-methoxybenzoic acid. MS (ESI) mass calcd. for $C_{24}H_{25}FN_4O_2$, 420.2; m/z found 421.2 [M+H]$^+$. 1H NMR (CDCl$_3$): 10.18-9.91 (m, 1H), 8.42-7.48 (m, 6H), 7.24-5.53 (m, 4H), 4.76-3.81 (m, 5H), 3.79-2.77 (m, 2H), 2.13-1.41 (m, 4H), 1.38-0.97 (m, 3H).

Example 68

(±)-cis-(2-ethoxyphenyl)(2-methyl-3-((4-phenylpyrimidin-2-yl)amino)piperidin-1-yl)methanone

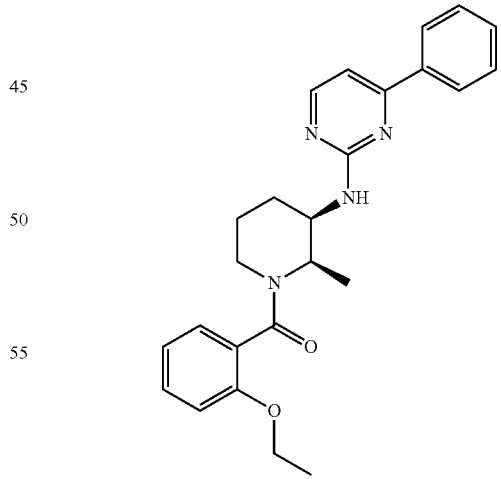

Prepared analogous to Example 66 substituting intermediate A-4 with 2-ethoxybenzoic acid. MS (ESI) mass calcd. for $C_{25}H_{28}N_4O_2$, 416.2; m/z found 417.2 [M+H]$^+$. 1H NMR (CDCl3): 9.34 (s, 1H), 8.32-7.89 (m, 3H), 7.74-7.46 (m, 3H), 7.37-7.31 (m, 1H), 7.23-6.73 (m, 3H), 6.29-5.49 (m, 1H), 4.82-3.76 (m, 4H), 3.41-2.76 (m, 2H), 1.99-1.63 (m, 3H), 1.61-1.10 (m, 7H).

Example 69

(6-methyl-2-(2H-1,2,3-triazol-2-yl)pyridin-3-yl)((2S,3R)-2-methyl-3-((5-(trifluoromethyl)pyrimidin-2-yl)amino)piperidin-1-yl)methanone

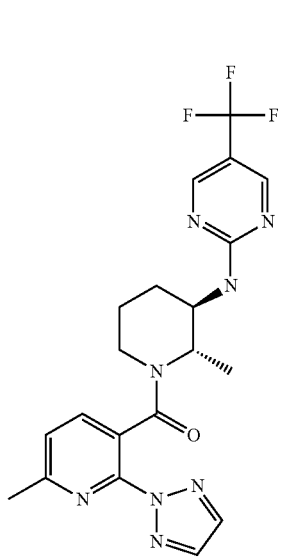

Step A: (2S,3R)-tert-butyl 2-methyl-3-((5-(trifluoromethyl)pyrimidin-2-yl)amino)piperidine-1-carboxylate. A solution of intermediate B-4 (1 g), 2-chloro-5-(trifluoromethyl)pyrimidine (850 mg) and DIPEA (1.6 mL) in n-BuOH (15 mL) was heated to 100° C. for 1 h. The mixture was diluted with H$_2$O and extracted with EtOAc. The combined organics were dried (MgSO$_4$). Purification via silica gel chromatography (0-30% EtOAc in heptane) gave the title compound (1.5 g, 89%). MS (ESI) mass calcd. for C$_{16}$H$_{23}$F$_3$N$_4$O$_2$, 360.4; m/z found 305.1 [M−55]$^+$.

Step B: N-((2S,3R)-2-methylpiperidin-3-yl)-5-(trifluoromethyl)pyrimidin-2-amine. To the title compound of step A (1.5 g) in DCM (12 mL) was added TFA (4 mL). After 1 h, the reaction was diluted with saturated Na$_2$CO$_3$ (aq) and extracted with DCM. The organic layers were dried (MgSO4) and concentrated to give the title compound (1.03 g) that was used without further purification.

Step C: (6-methyl-2-(2H-1,2,3-triazol-2-yl)pyridin-3-yl)((2S,3R)-2-methyl-3-((5-(trifluoromethyl)pyrimidin-2-yl)amino)piperidin-1-yl)methanone. To a solution of the title compound from Step B (100 mg), intermediate A-8 (118 mg) and DIPEA (0.2 mL) in DMF (5 mL) was added HBTU (218 mg). After 1 h, H$_2$O and EtOAc were added. The organic layer was dried (MgSO$_4$). Purification via silica gel chromatography (0-30% EtOAc in heptane) gave the title compound (86 mg, 47%). MS (ESI) mass calcd. for C$_{20}$H$_{21}$F$_3$N$_8$O, 446.2; m/z found 447.2 [M+H]$^+$. MP=245.2° C. (Mixture of 4 isomers, undefined ratio). $^1$H NMR (300 MHz, CDCl$_3$) δ 8.52 (br d, J=11.5 Hz, 1.51H), 8.35 (s, 1.27H), 8.18 (br s, 0.10H), 8.09 (s, 0.46H), 7.87 (d, J=5.3 Hz, 0.46H), 7.80 (d, J=7.7 Hz, 0.10H), 7.74-7.49 (m, 0.87H), 7.43-7.14 (m, 1.73H), 6.87 (d, J=8.3 Hz, 0.46H), 6.61 (d, J=7.7 Hz, 0.10H), 5.85 (d, J=7.0 Hz, 0.10H), 5.69 (d, J=5.5 Hz, 0.10H), 5.34-5.16 (m, 0.46H), 5.01 (q, J=6.6 Hz, 0.10H), 4.73 (br d, J=14.3 Hz, 0.30H), 4.29 (br d, J=6.5 Hz, 0.46H), 4.19-3.95 (m, 0.46H), 3.83 (br d, J=7.0 Hz, 0.15H), 3.65 (br s, 0.15H), 3.47 (dd, J=13.7, 4.2 Hz, 0.46H), 3.26 (td, J=13.4, 3.1 Hz, 0.60H), 3.05-2.83 (m, 0.46H), 2.80 (s, 0.26H), 2.78-2.64 (m, 2.16H), 2.61 (s, 0.52H), 2.52 (s, 0.26H), 1.95-1.81 (m, 1.73H), 1.80-1.70 (m, 0.26H), 1.71-1.54 (m, 1.13H), 1.53-1.19 (m, 3.37H), 1.08 (dd, J=14.4, 6.7 Hz, 0.10H), 1.00-0.84 (m, 0.15H), 0.74 (d, J=6.9 Hz, 0.26H).

Example 70

(6-methyl-2-(1H-1,2,3-triazol-1-yl)pyridin-3-yl)((2S,3R)-2-methyl-3-((5-(trifluoromethyl)pyrimidin-2-yl)amino)piperidin-1-yl)methanone

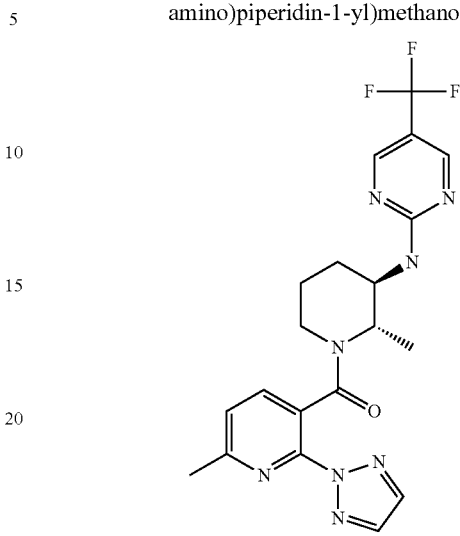

Prepared analogous to Example 69 substituting intermediate A-8 with intermediate A-9. MS (ESI) mass calcd. for C$_{20}$H$_{21}$F$_3$N$_8$O, 446.2; m/z found 447.2[M+H]$^+$. MP=181.6° C. (Mixture of 4 isomers, undefined ratio). $^1$H NMR (300 MHz, CDCl$_3$) δ 8.66-8.15 (m, 2.14H), 7.90 (d, J=10.8 Hz, 0.45H), 7.83-7.67 (m, 0.68H), 7.60 (dd, J=7.7, 2.6 Hz, 0.45H), 7.41-7.14 (m, 1.53H), 6.79 (d, J=8.6 Hz, 0.26H), 6.61 (d, J=7.8 Hz, 0.16H), 5.82 (dd, J=26.8, 6.6 Hz, 0.33H), 5.17 (q, J=6.8 Hz, 0.33H), 5.05-4.86 (m, 0.26H), 4.71 (t, J=15.1 Hz, 0.33H), 4.35 (br d, J=7.7 Hz, 0.45H), 4.25-4.00 (m, 0.78H), 3.87 (q, J=6.9 Hz, 0.26H), 3.73 (br s, 0.26H), 3.54-3.37 (m, 0.33H), 3.36-3.05 (m, 0.62H), 3.03-2.75 (m, 0.45H), 2.62 (s, 1.14H), 2.59 (s, 0.76H), 2.46 (s, 0.50H), 2.18-1.83 (m, 1.62H), 1.81-1.55 (m, 1.41H), 1.53-0.79 (m, 4.57H). The signal corresponding to the NH group was not observed.

Example 71

(4-methyl-2-(2H-1,2,3-triazol-2-yl)phenyl)((2S,3R)-2-methyl-3-((5-(trifluoromethyl)pyrimidin-2-yl)amino)piperidin-1-yl)methanone

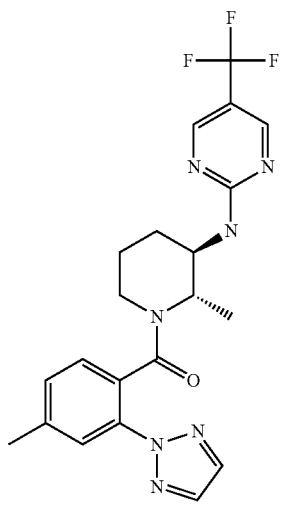 [SMILES: Cc1ccc(C(=O)N2CCC[C@@H](Nc3ncc(C(F)(F)F)cn3)[C@@H]2C)c(-n2nccn2)c1]

Prepared analogous to Example 69 substituting intermediate A-8 with intermediate A-11. MS (ESI) mass calcd. for $C_{21}H_{22}F_3N_7O$, 445.2; m/z found 446.2 [M+H]$^+$. The product is present as a mixture of conformers (ratio ca. 60:40) $^1$H NMR (300 MHz, CDCl$_3$) δ 8.51 (d, J=10.7 Hz, 1.4H), 8.40-8.28 (m, 0.9H), 8.25 (s, 1.2H), 8.00 (s, 0.6H), 7.96 (s, 0.6H), 7.86-7.71 (m, 0.9H), 7.24-7.11 (m, 1.8H), 7.02-6.88 (m, 0.6H), 5.24 (q, J=7.1 Hz, 0.6H), 4.73 (d, J=13.1 Hz, 0.4H), 4.33-4.23 (m, 0.6H), 4.14 (q, J=6.6 Hz, 0.4H), 4.00 (d, J=6.6 Hz, 0.4H), 3.59-3.48 (m, 0.6H), 3.31-3.13 (m, 0.6H), 3.01-2.88 (m, 0.4H), 2.46 (s, 1.8H), 2.43 (s, 1.2H), 2.07-1.53 (m, 4H), 1.48 (d, J=6.9 Hz, 1.2H), 1.42 (d, J=7.1 Hz, 1.8H).

Example 72

((2S,3R)-2-methyl-3-((5-(trifluoromethyl)pyrazin-2-yl)amino)piperidin-1-yl)(5-methyl-3-(2H-1,2,3-triazol-2-yl)pyridin-2-yl)methanone

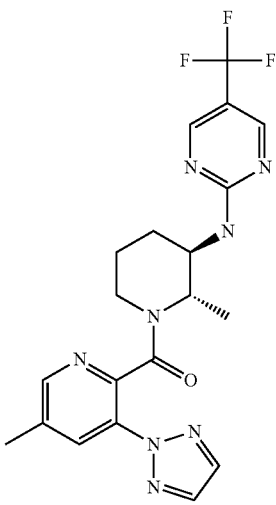

Step A: (2S,3R)-tert-butyl 2-methyl-3-((5-(trifluoromethyl)pyrazin-2-yl)amino)piperidine-1-carboxylate. To 2-chloro-5-(trifluoromethyl)pyrazine (326 μL) in DMSO (8 mL) was added intermediate B-4 (600 mg) and K$_2$CO$_3$ (658 mg). The reaction was heated in a microwave reactor at 120° C. for 5 min. The mixture was diluted with saturated NaHCO$_3$ (aq) and extracted with DCM. The combined organics were washed with brine and dried (MgSO$_4$). Purification via silica gel chromatography (0-16% EtOAc in heptane) gave the title compound (459 mg, 46%). MS (ESI) mass calcd. for $C_{16}H_{23}F_3N_4O_2$, 360.4; m/z found 305.1 [M−55]$^+$.

Step B: N-((2S,3R)-2-methylpiperidin-3-yl)-5-(trifluoromethyl)pyrazin-2-amine. Prepared analogous to example 69 Step B substituting the title compound of Step A example 69 with the title compound of Step A. MS (ESI) mass calcd. for $C_{11}H_{15}F_3N_4$, 260.2; m/z found 261 [M+H]$^+$.

Step C: ((2S,3R)-2-methyl-3-((5-(trifluoromethyl)pyrazin-2-yl)amino)piperidin-1-yl)(5-methyl-3-(2H-1,2,3-triazol-2-yl)pyridin-2-yl)methanone. Prepared analogous to example 69 substituting intermediate A-8 with intermediate A-21. MS (ESI) mass calcd. for $C_{20}H_{21}F_3N_8O$, 446.2; m/z found 447 [M+H]$^+$. The product is present as a mixture of conformers (ratio ca. 70:30) $^1$H NMR (300 MHz, CDCl$_3$) 8.46 (s, 0.3H), 8.39 (s, 0.7H), 8.34 (s, 0.3H), 8.25 (s, 0.3H), 8.22 (s, 0.7H), 8.13 (s, 0.7H), 8.03-7.76 (m, 3H), 7.48 (d, J=6.6 Hz, 0.7H), 6.47 (d, J=7.9 Hz, 0.3H), 5.20-5.05 (m, 0.3H), 4.72-4.58 (m, 0.7H), 4.16 (br s, 0.3H), 4.08-3.87 (m, 1.7H), 3.43-3.25 (m, 0.3H), 3.12-2.95 (m, 0.7H), 2.49 (s, 0.9H), 2.46 (s, 2.1H), 2.08-1.63 (m, 4H), 1.50-1.47 (m, 3H).

Example 73

((2S,3R)-3-(benzo[d]oxazol-2-ylamino)-2-methylpiperidin-1-yl)(5-methyl-3-(2H-1,2,3-triazol-2-yl)pyridin-2-yl)methanone

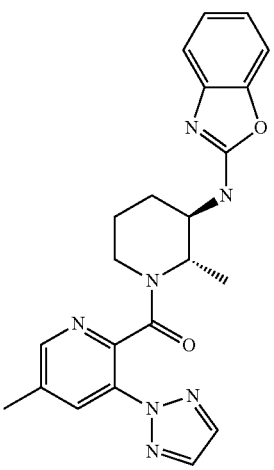 [SMILES: Cc1cnc(C(=O)N2CCC[C@@H](Nc3nc4ccccc4o3)[C@@H]2C)c(-n2nccn2)c1]

Prepared analogous to example 41 substituting intermediate B-3 with intermediate B-4 and intermediate A-4 with intermediate A-21. MS (ESI) mass calcd. for $C_{22}H_{23}N_7O_2$, 417.2; m/z found 418.2 [M+H]$^+$. MP=112.9° C. The product is present as a mixture of conformers (ratio ca. 60:40) $^1$H NMR (300 MHz, CDCl$_3$) δ 8.46 (s, 0.4H), 8.42 (s, 0.6H), 8.29 (s, 0.4H), 8.18 (s, 0.6H), 8.09 (s, 0.8H), 7.99 (s, 1.2H), 7.72 (d, J=7.1 Hz, 0.6H), 7.38 (d, J=7.8 Hz, 0.4H), 7.33-7.27 (m, 1H), 7.23-6.95 (m, 2.6H), 6.64 (d, J=8.8 Hz, 0.4H), 5.34-5.16 (m, 0.4H), 4.66 (d, J=12.2 Hz, 0.6H), 4.26-4.2 (m, 0.4H), 4.03 (q, J=6.8 Hz, 0.6H), 3.92 (d, J=6.7 Hz, 0.6H), 3.50-3.34 (m, 0.8H), 3.12-2.94 (m, 0.6H), 2.49 (s, 1.2H), 2.43 (s, 1.8H), 2.30-1.62 (m, 4H), 1.54-1.45 (m, 3H).

Example 74

(6-methyl-2-(2H-1,2,3-triazol-2-yl)pyridin-3-yl)((2S,3R)-2-methyl-3-((5-(trifluoromethyl)pyrazin-2-yl)amino)piperidin-1-yl)methanone

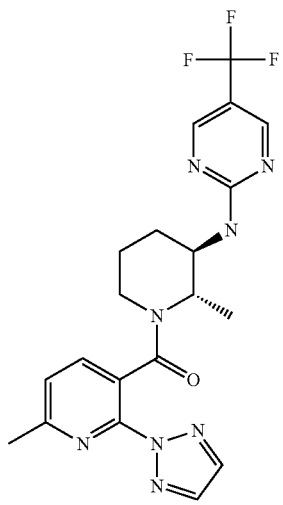

Prepared analogous to example 72 substituting intermediate A-21 with intermediate A-8. MS (ESI) mass calcd. for $C_{20}H_{21}F_3N_8O$, 446.2; m/z found 447 [M+H]$^+$. MP=172.8° C. (Mixture of 4 isomers, undefined ratio). $^1$H NMR (300 MHz, CDCl$_3$) δ 8.37 (br s, 0.21H), 8.32 (s, 0.11H), 8.21 (s, 0.40H), 8.15-7.97 (m, 1.26H), 7.97-7.84 (m, 0.66H), 7.78 (d, J=7.7 Hz, 0.14H), 7.74-7.53 (m, 1.46H), 7.40-7.14 (m, 1.35H), 6.54 (d, J=7.8 Hz, 0.11H), 6.18 (br s, 0.30H), 5.47 (s, 0.14H), 5.28-5.09 (m, 0.39H), 5.08-4.90 (m, 0.18H), 4.70 (br d, J=13.3 Hz, 0.66H), 4.22-3.94 (m, 1.59H), 3.80 (br s, 0.21H), 3.64 (br s, 0.21H), 3.55-3.39 (m, 0.30H), 3.38-3.17 (m, 0.40H), 3.05-2.90 (m, 0.66H), 2.89-2.79 (m, 0.18H), 2.71 (s, J=3.7 Hz, 0.92H), 2.70 (s, 1.04H), 2.26-1.12 (m, 6.39H), 0.88 (t, J=6.8 Hz, 0.40H), 0.69 (d, J=6.9 Hz, 0.21H). The signal corresponding to the NH group was not observed.

Example 75

((2S,3R)-3-(benzo[d]oxazol-2-ylamino)-2-methylpiperidin-1-yl)(6-methyl-2-(2H-1,2,3-triazol-2-yl)pyridin-3-yl)methanone

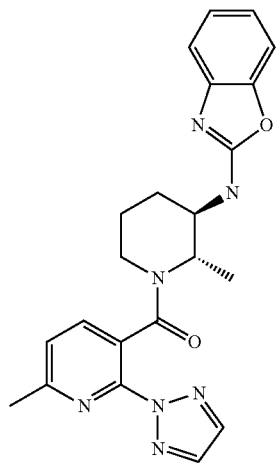 [SMILES: Cc1ccc(C(=O)N2CCC[C@@H](Nc3nc4ccccc4o3)[C@@H]2C)c(-n2nccn2)n1]

Prepared analogous to example 73 substituting intermediate A-21 with intermediate A-8. MS (ESI) mass calcd. for $C_{22}H_{23}N_7O_2$, 417.2; m/z found 418.2 [M+H]$^+$. MP=136.3° C. The product is present as a mixture of conformers (ratio ca. 50:50) $^1$H NMR (300 MHz, CDCl$_3$) δ 8.25 (s, 1H), 8.09 (s, 1H), 7.69-7.52 (m, 1H), 7.42-6.91 (m, 5.5H), 6.44 (d, J=8.6 Hz, 0.5H), 5.39-5.22 (m, 0.5H), 4.81-4.63 (m, 0.5H), 4.27-3.91 (m, 1.5H), 3.54-3.40 (m, 0.5H), 3.39-3.22 (m, 0.5H), 3.06-2.83 (m, 0.5H), 2.72 (s, 1.5H), 2.67 (s, 1.5H), 2.24-1.64 (m, 4H), 1.51 (d, J=7.0 Hz, 1.5H), 1.45 (d, J=7.2 Hz, 1.5H).

Example 76

((2S,3R)-3-(benzo[d]oxazol-2-ylamino)-2-methylpiperidin-1-yl)(6-methyl-2-(1H-1,2,3-triazol-1-yl)pyridin-3-yl)methanone

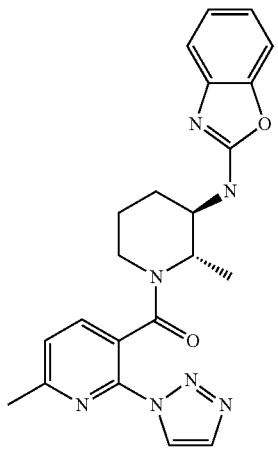 [SMILES: Cc1ccc(C(=O)N2CCC[C@@H](Nc3nc4ccccc4o3)[C@@H]2C)c(-n2ccnn2)n1]

Prepared analogous to example 73 substituting intermediate A-21 with intermediate A-9. MS (ESI) mass calcd. for $C_{22}H_{23}N_7O_2$, 417.2; m/z found 418.2 [M+H]$^+$. MP=206.3° C. The product is present as a mixture of conformers (ratio ca. 50:50) $^1$H NMR (300 MHz, CDCl$_3$) δ 8.60 (s, 0.5H), 8.41 (s, 0.5H), 7.94 (s, 1H), 7.66-7.50 (m, 1H), 7.40-6.87 (m, 5.5H), 6.55 (d, J=9.5 Hz, 0.5H), 5.28-5.17 (m, 0.5H), 4.79-4.68 (m, 0.5H), 4.34-4.22 (m, 0.5H), 4.22-4.11 (m, 0.5H), 4.10-3.94 (m, 0.5H), 3.73-3.39 (m, 0.5H), 3.37-3.23 (m, 0.5H), 3.04-2.89 (m, 0.5H), 2.63 (s, 1.5H), 2.56 (s, 1.5H), 2.15-1.70 (m, 4H), 1.50 (d, J=7.0 Hz, 1.5H), 1.44 (d, J=7.0 Hz, 1.5H).

Example 77

((2S,3R)-3-((5-chloropyridin-2-yl)amino)-2-methylpiperidin-1-yl)(5-methyl-3-(oxazol-2-yl)pyridin-2-yl)methanone

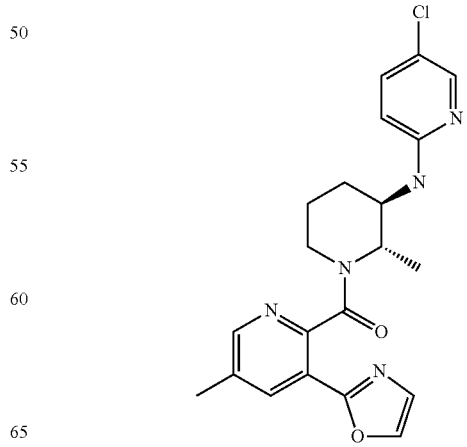

Prepared analogous to example 32 substituting intermediate B-3 with intermediate B-4 and intermediate A-4 with intermediate A-17. MS (ESI) mass calcd. for $C_{21}H_{22}ClN_5O_2$, 411.1; m/z found 412.1 [M+H]$^+$. MP=206.3° C. The product is present as a mixture of conformers (ratio ca. 70:30) $^1$H NMR (300 MHz, CDCl$_3$) δ 8.46 (s, 0.3H), 8.38 (s, 0.7H), 8.24 (s, 0.3H), 8.13-8.02 (m, 1.7H), 7.96-7.89 (m, 2H), 7.36 (dd, J=8.9, 2.6 Hz, 0.3H), 7.23 (dd, J=8.9, 2.5 Hz, 0.7H), 6.56 (d, J=7.2 Hz, 0.7H), 6.36 (d, J=8.9 Hz, 0.3H), 6.22 (d, J=8.8 Hz, 0.7H), 5.72 (d, J=7.2 Hz, 0.3H), 5.17-5.03 (m, 0.3H), 4.69-4.56 (m, 0.7H), 3.99-3.81 (m, 1.6H), 3.32 (q, J=13.8 Hz, 0.7H), 3.11-2.87 (m, 0.7H), 2.48 (s, 0.9H), 2.45 (s, 2.1H), 2.08-1.73 (m, 3H), 1.69-1.61 (m, 1H), 1.51-1.39 (m, 3H).

Example 78

((2S,3R)-2-methyl-3-((5-(trifluoromethyl)pyrimidin-2-yl)amino)piperidin-1-yl)(6-methyl-3-(pyrimidin-2-yl)pyridin-2-yl)methanone

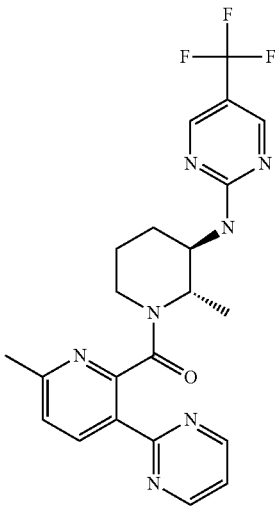 [SMILES: Cc1ccc(-c2ncccn2)c(C(=O)N2CCC[C@@H](Nc3ncc(C(F)(F)F)cn3)[C@@H]2C)n1]

Prepared analogous to Example 69 substituting intermediate A-8 with intermediate A-19. MS (ESI) mass calcd. for $C_{22}H_{22}F_3N_7O$, 457.2; m/z found 458.2 [M+H]$^+$. MP=116.9° C.

Example 79

(4-methyl-2-(2H-1,2,3-triazol-2-yl)phenyl)((2S,3R)-2-methyl-3-((5-(trifluoromethyl)pyrazin-2-yl)amino)piperidin-1-yl)methanone

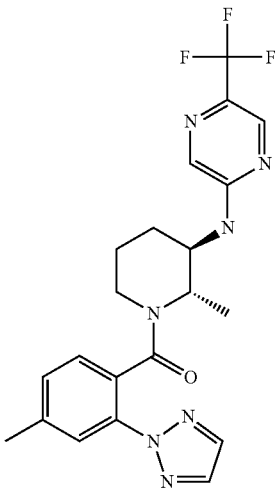 [SMILES: Cc1ccc(C(=O)N2CCC[C@@H](Nc3cnc(C(F)(F)F)cn3)[C@@H]2C)c(-n2nccn2)c1]

Prepared analogous to example 72 substituting intermediate A-21 with intermediate A-11. MS (ESI) mass calcd. for $C_{21}H_{22}F_3N_7O$, 445.2; m/z found 446.2 [M+H]$^+$. MP=116.2° C.

Example 80

((2S,3R)-3-((5-bromopyridin-2-yl)amino)-2-methylpiperidin-1-yl)(5-methyl-3-(oxazol-2-yl)pyridin-2-yl)methanone

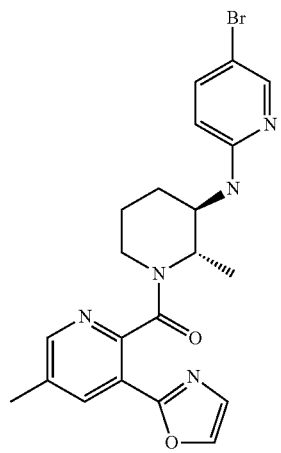 [SMILES: Cc1cnc(C(=O)N2CCC[C@@H](Nc3ccc(Br)cn3)[C@@H]2C)c(-c2ncco2)c1]

Prepared analogous to example 42 substituting intermediate B-3 with intermediate B-4 and intermediate A-4 with intermediate A-17. MS (ESI) mass calcd. for $C_{21}H_{22}BrN_5O_2$, 455.1; m/z found 457 [M+H]$^+$. MP=135.6° C.

Example 81

((2S,3R)-3-(benzo[d]oxazol-2-ylamino)-2-methylpiperidin-1-yl)(6-methyl-3-(pyrimidin-2-yl)pyridin-2-yl)methanone

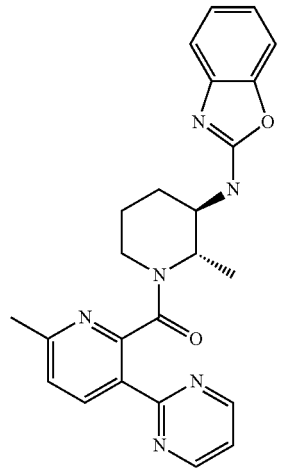 [SMILES: Cc1ccc(-c2ncccn2)c(C(=O)N2CCC[C@@H](Nc3nc4ccccc4o3)[C@@H]2C)n1]

85

Prepared analogous to example 73 substituting intermediate A-21 with intermediate A-19. MS (ESI) mass calcd. for $C_{24}H_{24}N_6O_2$, 428.2; m/z found 429.2 [M+H]$^+$. MP=143.9° C.

Example 82

(4-methoxy-2-(2H-1,2,3-triazol-2-yl)phenyl)((2S,3R)-2-methyl-3-((5-(trifluoromethyl)pyrazin-2-yl)amino)piperidin-1-yl)methanone

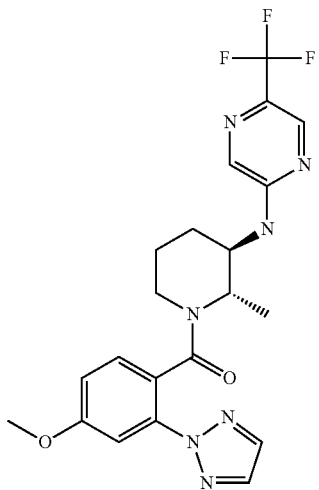 [SMILES: COc1ccc(C(=O)N2CCC[C@@H](Nc3cnc(C(F)(F)F)cn3)[C@@H]2C)c(-n2nccn2)c1]

Prepared analogous to example 72 substituting intermediate A-21 with intermediate A-10. MS (ESI) mass calcd. for $C_{21}H_{22}F_3N_7O_2$, 461.2; m/z found 462.2 [M+H]$^+$. MP=112.7° C.

Example 83

((2S,3R)-2-methyl-3-((5-(trifluoromethyl)pyrazin-2-yl)amino)piperidin-1-yl)(5-methyl-3-(oxazol-2-yl)pyridin-2-yl)methanone

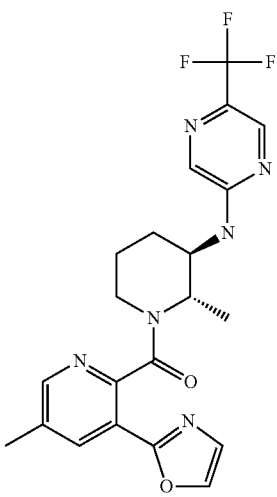 [SMILES: Cc1cnc(C(=O)N2CCC[C@@H](Nc3cnc(C(F)(F)F)cn3)[C@@H]2C)c(-c2ncco2)c1]

86

Prepared analogous to example 72 substituting intermediate A-21 with intermediate A-17. MS (ESI) mass calcd. for $C_{21}H_{21}F_3N_6O_2$, 446.2; m/z found 447.2 [M+H]$^+$. MP=122.9° C.

Example 84

((2S,3R)-2-methyl-3-((5-(trifluoromethyl)pyrazin-2-yl)amino)piperidin-1-yl)(6-methyl-3-(pyrimidin-2-yl)pyridin-2-yl)methanone

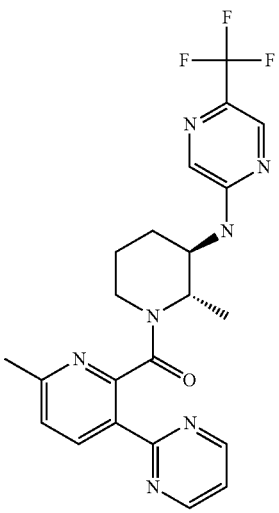 [SMILES: Cc1ccc(-c2ncccn2)c(C(=O)N2CCC[C@@H](Nc3cnc(C(F)(F)F)cn3)[C@@H]2C)n1]

Prepared analogous to example 72 substituting intermediate A-21 with intermediate A-19. MS (ESI) mass calcd. for $C_{22}H_{22}F_3N_7O$, 457.2; m/z found 458.2 [M+H]$^+$. MP=120.6° C.

Example 85

(2-(2H-1,2,3-triazol-2-yl)phenyl)((2S,3R)-2-methyl-3-((5-(trifluoromethyl)pyrazin-2-yl)amino)piperidin-1-yl)methanone

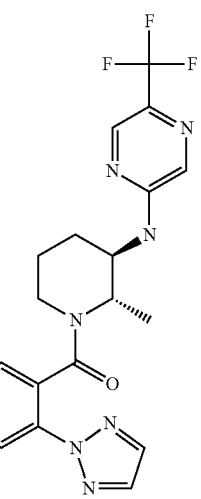

Prepared analogous to example 72 substituting intermediate A-21 with intermediate A-4. MS (ESI) mass calcd. for $C_{20}H_{20}F_3N_7O$, 431.2; m/z found 432 [M+H]$^+$. MP=202.4° C.

Example 86

((2S,3R)-3-((5-chloropyrazin-2-yl)amino)-2-methylpiperidin-1-yl)(5-methyl-3-(oxazol-2-yl)pyridin-2-yl)methanone

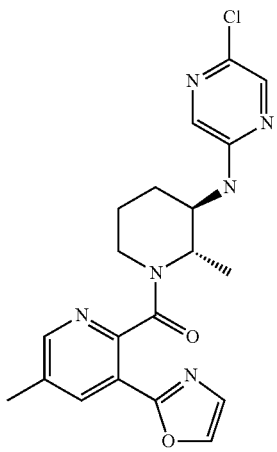 [SMILES: Cc1cnc(C(=O)N2CCC[C@@H](Nc3cnc(Cl)cn3)[C@@H]2C)c(-c2ncco2)c1]

Prepared analogous to example 77 substituting 5-chloro-2-iodopyridine with 2-chloro-5-iodopyrazine. MS (ESI) mass calcd. for $C_{20}H_{21}ClN_6O_2$, 412.1; m/z found 413.1 [M+H]$^+$.

Example 87

((2S,3R)-2-methyl-3-((5-(trifluoromethyl)pyridin-2-yl)amino)piperidin-1-yl)(6-methyl-3-(2H-1,2,3-triazol-2-yl)pyridin-2-yl)methanone

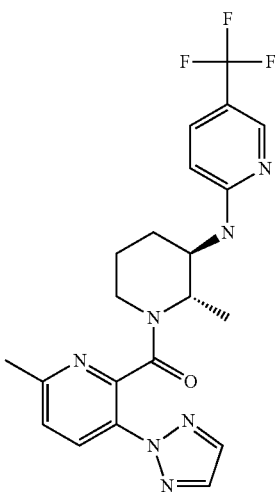 [SMILES: Cc1ccc(-n2nccn2)c(C(=O)N2CCC[C@@H](Nc3ccc(C(F)(F)F)cn3)[C@@H]2C)n1]

Prepared analogous to example 12 substituting intermediate B-3 with intermediate B-4 and intermediate A-4 with intermediate A-22. MS (ESI) mass calcd. for $C_{21}H_{22}F_3N_7O$, 445.2; m/z found 446 [M+H]$^+$.

Example 88

((2S,3R)-3-(benzo[d]oxazol-2-ylamino)-2-methylpiperidin-1-yl)(5-methyl-3-(oxazol-2-yl)pyridin-2-yl)methanone

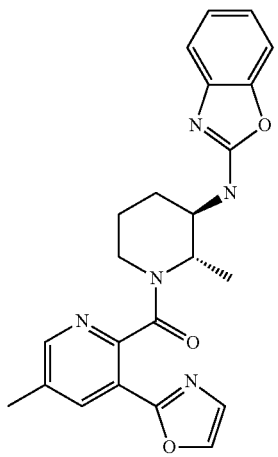 [SMILES: Cc1cnc(C(=O)N2CCC[C@@H](Nc3nc4ccccc4o3)[C@@H]2C)c(-c2ncco2)c1]

Prepared analogous to example 73 substituting intermediate A-21 with intermediate A-17. MS (ESI) mass calcd. for $C_{23}H_{23}N_5O_3$, 417.2; m/z found 418.2 [M+H]$^+$. MP=196.8° C.

Example 89

(5-methoxy-2-(2H-1,2,3-triazol-2-yl)phenyl)((2S,3R)-2-methyl-3-((5-(trifluoromethyl)pyrimidin-2-yl)amino)piperidin-1-yl)methanone

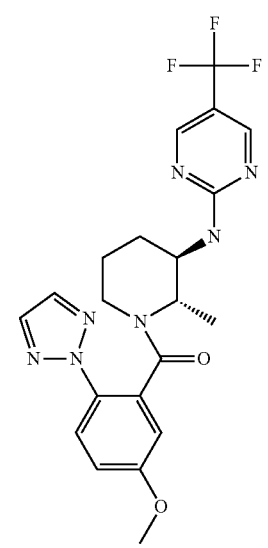 [SMILES: COc1ccc(-n2nccn2)c(C(=O)N2CCC[C@@H](Nc3ncc(C(F)(F)F)cn3)[C@@H]2C)c1]

Prepared analogous to Example 69 substituting intermediate A-8 with intermediate A-14. MS (ESI) mass calcd. for $C_{21}H_{22}F_3N_7O_2$, 461.2; m/z found 462.2 [M+H]+.

Example 90

(5-fluoro-2-(2H-1,2,3-triazol-2-yl)phenyl)((2S,3R)-2-methyl-3-((5-(trifluoromethyl)pyrazin-2-yl)amino)piperidin-1-yl)methanone

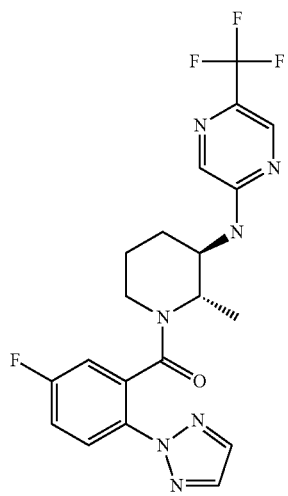 [SMILES: C[C@H]1[C@H](Nc2cnc(C(F)(F)F)cn2)CCCN1C(=O)c1cc(F)ccc1-n1nccn1]

Prepared analogous to Example 72 substituting intermediate A-21 with intermediate A-24. MS (ESI) mass calcd. for $C_{20}H_{19}F_4N_7O$, 449.2; m/z found 450 [M+H]+. MP=106.2° C.

Example 91

((2S,3R)-3-((5-chloropyrimidin-2-yl)amino)-2-methylpiperidin-1-yl)(4-methyl-2-(2H-1,2,3-triazol-2-yl)phenyl)methanone

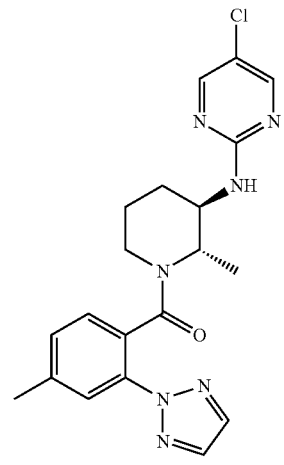

Prepared analogous to Example 30 substituting intermediate B-3 with intermediate B-4 and intermediate A-4 with intermediate A-11. MS (ESI) mass calcd. for $C_{20}H_{22}ClN_7O$, 411.2; m/z found 412.2 [M+H]+. MP=166.3° C.

Example 92

((2S,3R)-3-((5-bromopyridin-2-yl)amino)-2-methylpiperidin-1-yl)(5-methyl-3-(2H-1,2,3-triazol-2-yl)pyridin-2-yl)methanone

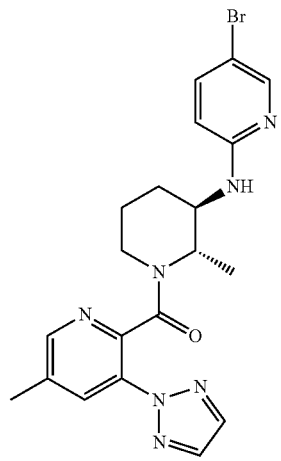 [SMILES: Cc1cnc(C(=O)N2CCC[C@@H](Nc3ccc(Br)cn3)[C@@H]2C)c(-n2nccn2)c1]

Prepared analogous to example 42 substituting intermediate B-3 with intermediate B-4 and intermediate A-4 with intermediate A-21. MS (ESI) mass calcd. for $C_{20}H_{22}BrN_7O$, 455.2; m/z found 457 [M+H]+.

Example 93

(6-methyl-2-(1H-1,2,3-triazol-1-yl)pyridin-3-yl)((2S,3R)-2-methyl-3-((5-(trifluoromethyl)pyridin-2-yl)amino)piperidin-1-yl)methanone

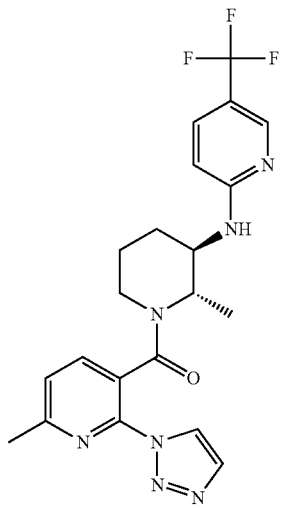

Prepared analogous to Example 87 substituting intermediate A-22 with intermediate A-9. MS (ESI) mass calcd. for $C_{21}H_{22}F_3N_7O$, 445.2; m/z found 446.2[M+H]$^+$. MP=159.8° C.

Example 94

((2S,3R)-2-methyl-3-((5-(trifluoromethyl)pyrimidin-2-yl)amino)piperidin-1-yl)(5-methyl-3-(2H-1,2,3-triazol-2-yl)pyridin-2-yl)methanone

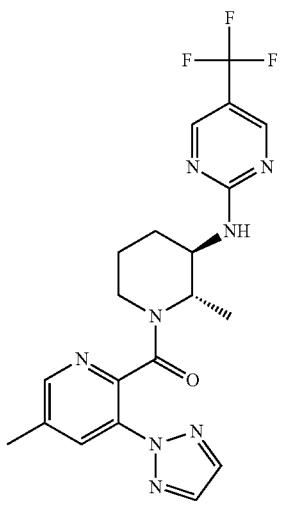 [SMILES: Cc1cnc(C(=O)N2CCC[C@@H](Nc3ncc(C(F)(F)F)cn3)[C@@H]2C)c(-n2nccn2)c1]

Prepared analogous to Example 69 substituting intermediate A-8 with intermediate A-21. MS (ESI) mass calcd. for $C_{20}H_{21}F_3N_8O$, 446.2; m/z found 447 [M+H]$^+$. MP=101.2° C.

Example 95

(4-methoxy-2-(2H-1,2,3-triazol-2-yl)phenyl)((2S,3R)-2-methyl-3-((5-(trifluoromethyl)pyrimidin-2-yl)amino)piperidin-1-yl)methanone

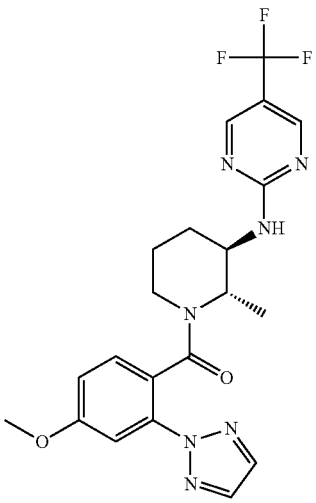

Prepared analogous to Example 69 substituting intermediate A-8 with intermediate A-10. MS (ESI) mass calcd. for $C_{21}H_{22}F_3N_7O_2$, 461.2; m/z found 462.2 [M+H]$^+$. The product is present as a mixture of conformers (ratio ca. 60:40) $^1$H NMR (300 MHz, CDCl$_3$) δ 8.51 (d, J=10.0 Hz, 1.4H), 8.37 (d, J=10.3 Hz, 0.6H), 8.25 (s, 1.4H), 8.00 (s, 0.4H), 7.78 (d, J=4.4 Hz, 0.4H), 7.67 (d, J=2.3 Hz, 0.6H), 7.46 (d, J=2.3 Hz, 0.4H), 7.24 (d, J=9.3 Hz, 0.6H), 7.17 (d, J=8.5 Hz, 0.6H), 7.03-6.85 (m, 1.6H), 5.24 (q, J=6.7 Hz, 0.6H), 4.72 (d, J=13.2 Hz, 0.4H), 4.27 (d, J=6.7 Hz, 0.6H), 4.22-4.08 (m, 0.4H), 4.01 (d, J=6.4 Hz, 0.4H), 3.91 (s, 1.8H), 3.87 (s, 1.2H), 3.55 (dd, J=13.6, 3.7 Hz, 0.6H), 3.23 (td, J=13.4, 3.0 Hz, 0.6H), 2.99-2.90 (m, 0.4H), 2.09-1.52 (m, 4H), 1.48 (d, J=6.9 Hz, 1.2H), 1.42 (d, J=7.1 Hz, 1.8H).

Example 96

(6-methyl-2-(1H-1,2,3-triazol-1-yl)pyridin-3-yl)((2S,3R)-2-methyl-3-((5-(trifluoromethyl)pyrazin-2-yl)amino)piperidin-1-yl)methanone

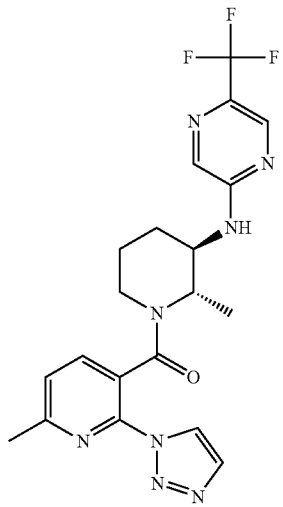

Prepared analogous to Example 72 substituting intermediate A-21 with intermediate A-9. MS (ESI) mass calcd. for $C_{20}H_{21}F_3N_8O$, 446.2; m/z found [M+H]$^+$. MP=149.6° C.

Example 97

(4-methoxy-2-(2H-1,2,3-triazol-2-yl)phenyl)((2S,3R)-2-methyl-3-((5-(trifluoromethyl)pyridin-2-yl)amino)piperidin-1-yl)methanone

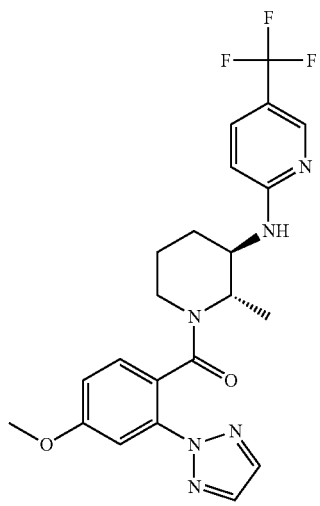

Prepared analogous to Example 87 substituting intermediate A-22 with intermediate A-10. MS (ESI) mass calcd. for $C_{22}H_{23}F_3N_6O_2$, 460.2; m/z found [M+H]$^+$.

Example 98

(6-methyl-2-(2H-1,2,3-triazol-2-yl)pyridin-3-yl)((2S,3R)-2-methyl-3-((5-(trifluoromethyl)pyridin-2-yl)amino)piperidin-1-yl)methanone

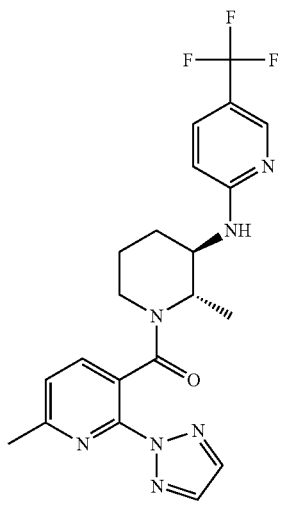 [SMILES: Cc1ccc(C(=O)N2CCC[C@@H](Nc3ccc(C(F)(F)F)cn3)[C@@H]2C)c(-n2nccn2)n1]

Prepared analogous to Example 87 substituting intermediate A-22 with intermediate A-8. MS (ESI) mass calcd. for $C_{21}H_{22}F_3N_7O$, 445.2; m/z found 446 [M+H]$^+$.

Example 99

((2S,3R)-3-((5-chloropyridin-2-yl)amino)-2-methylpiperidin-1-yl)(4-methyl-2-(2H-1,2,3-triazol-2-yl)phenyl)methanone

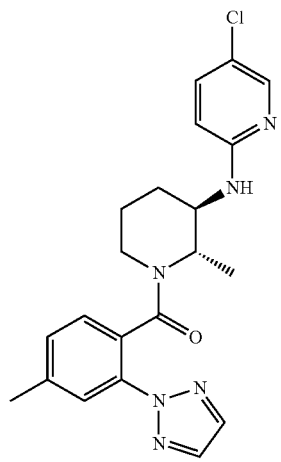

Prepared analogous to Example 32 substituting intermediate B-3 with intermediate B-4 and intermediate A-4 with intermediate A-11. MS (ESI) mass calcd. for $C_{21}H_{23}ClN_6O$, 410.2; m/z found 411.2 [M+H]$^+$.

Example 100

(2-(2H-1,2,3-triazol-2-yl)phenyl)((2S,3R)-3-((5-chloropyridin-2-yl)amino)-2-methylpiperidin-1-yl)methanone

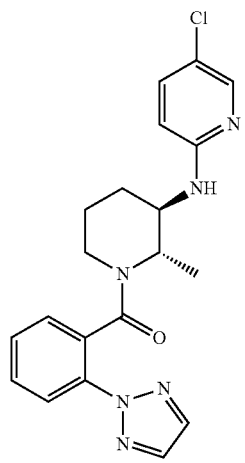

Prepared analogous to Example 32 substituting intermediate B-3 with intermediate B-4. MS (ESI) mass calcd. for $C_{20}H_{21}ClN_6O$, 396.1; m/z found 397 [M+H]$^+$. MP=140.1° C.

Example 101

((2S,3R)-2-methyl-3-((5-(trifluoromethyl)pyrimidin-2-yl)oxy)piperidin-1-yl)(5-methyl-3-(2H-1,2,3-triazol-2-yl)pyridin-2-yl)methanone

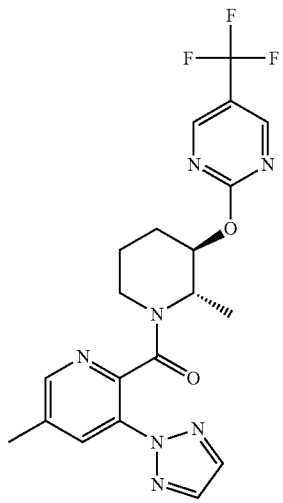

Step A: (2S,3R)-tert-butyl 2-methyl-3-((5-(trifluoromethyl)pyrimidin-2-yl)oxy)piperidine-1-carboxylate. To (2S,3R)-tert-butyl 3-hydroxy-2-methylpiperidine-1-carboxylate (670 mg, prepared according to J. Org. Chem. 2008, 73, 2898) in THF (15 mL) at 0° C. was added NaH (60 wt %, 188 mg).

After 15 min, 2-chloro-5-(trifluoromethyl)pyrimidine (570 mg) was added and the reaction allowed to proceed at rt overnight. The reaction was diluted with H2O and extracted with DCM. The organic layers were dried (MgSO4). Purification via silica gel chromatography (0-40% EtOAc in heptane) gave the title compound (813 mg, 72%).

Step B: 2-(((2S,3R)-2-methylpiperidin-3-yl)oxy)-5-(trifluoromethyl)pyrimidine. To the title compound of step A (813 mg) in DCM (6 mL) was added TFA (2 mL). After 1 h, the reaction was diluted with saturated Na$_2$CO$_3$ (aq) and extracted with DCM. The organic layers were dried (MgSO$_4$) and concentrated to give the title compound (452 mg) that was used without further purification.

Step C: ((2S,3R)-2-methyl-3-((5-(trifluoromethyl)pyrimidin-2-yl)oxy)piperidin-1-yl)(5-methyl-3-(2H-1,2,3-triazol-2-yl)pyridin-2-yl)methanone. To a solution of the title compound from Step B (100 mg), intermediate A-21 (118 mg) and DIPEA (0.2 mL) in DMF (5 mL) was added HBTU (218 mg). After 1 h, H$_2$O and EtOAc were added. The organic layer was dried (MgSO$_4$). Purification via prep HPLC gave the title compound (62 mg, 36%). MS (ESI) mass calcd. for C$_{20}$H$_{20}$F$_3$N$_7$O$_2$, 447.2; m/z found 448.2 [M+H]$^+$. MP=214.9° C.

Example 102

(4-methyl-2-(2H-1,2,3-triazol-2-yl)phenyl)((2S,3R)-2-methyl-3-((5-(trifluoromethyl)pyrimidin-2-yl)oxy)piperidin-1-yl)methanone

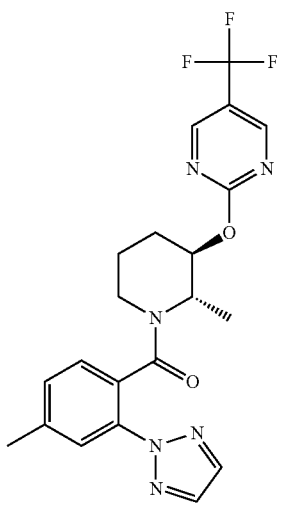

Prepared analogous to Example 101 substituting intermediate A-21 with intermediate A-11. MS (ESI) mass calcd. for C$_{21}$H$_{21}$F$_3$N$_6$O$_2$, 446.2; m/z found 447.2 [M+H]$^+$. MP=163.7° C.

Example 103

(2-(2H-1,2,3-triazol-2-yl)phenyl)((2S,3R)-2-methyl-3-((5-(trifluoromethyl)pyrimidin-2-yl)oxy)piperidin-1-yl)methanone

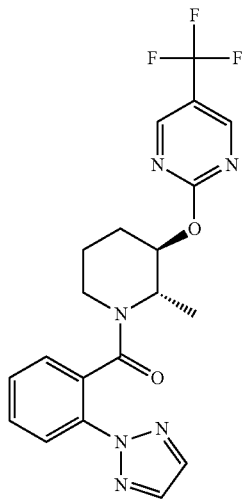 [SMILES: C[C@H]1[C@H](Oc2ncc(C(F)(F)F)cn2)CCCN1C(=O)c1ccccc1-n1nccn1]

Prepared analogous to Example 101 substituting intermediate A-21 with intermediate A-4. MS (ESI) mass calcd. for C$_{20}$H$_{19}$F$_3$N$_6$O$_2$, 432.2; m/z found 433 [M+H]$^+$.

Example 104

((2S,3R)-2-methyl-3-((5-(trifluoromethyl)pyrimidin-2-yl)oxy)piperidin-1-yl)(6-methyl-3-(2H-1,2,3-triazol-2-yl)pyridin-2-yl)methanone

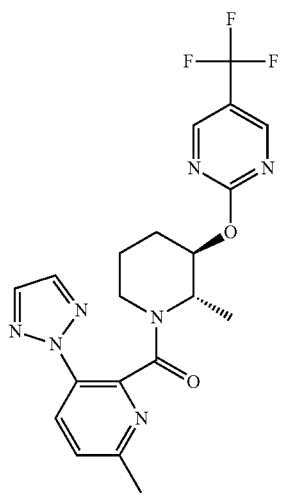

Prepared analogous to Example 101 substituting intermediate A-21 with intermediate A-22. MS (ESI) mass calcd. for $C_{20}H_{20}F_3N_7O_2$, 447.2; m/z found 448 [M+H]$^+$. MP=161.5° C.

Example 105

((2S,3R)-2-methyl-3-((5-(trifluoromethyl)pyrazin-2-yl)oxy)piperidin-1-yl)(5-methyl-3-(2H-1,2,3-triazol-2-yl)pyridin-2-yl)methanone

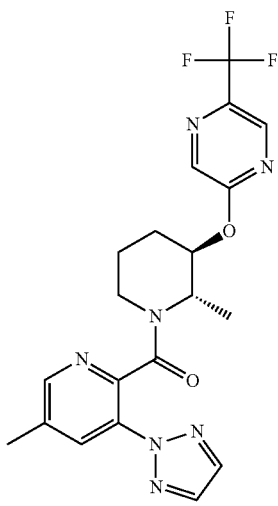 [SMILES: Cc1cnc(C(=O)N2CCC[C@@H](Oc3cnc(C(F)(F)F)cn3)[C@@H]2C)c(-n2nccn2)c1]

Prepared analogous to Example 101 substituting 2-chloro-5-(trifluoromethyl)pyrimidine with 2-chloro-5-(trifluoromethyl)pyrazine. MS (ESI) mass calcd. for $C_{20}H_{20}F_3N_7O_2$, 447.2; m/z found 448 [M+H]$^+$. MP=149.7° C.

Example 106

(2-(2H-1,2,3-triazol-2-yl)phenyl)((2S,3R)-2-methyl-3-((5-(trifluoromethyl)pyrazin-2-yl)oxy)piperidin-1-yl)methanone

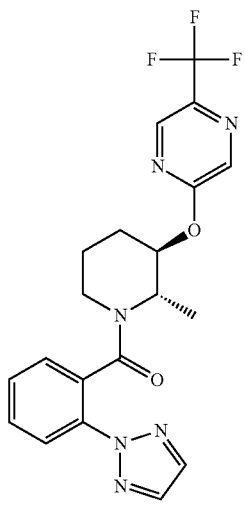

Prepared analogous to Example 105 substituting intermediate A-21 with intermediate A-4. MS (ESI) mass calcd. for $C_{20}H_{19}F_3N_6O_2$, 432.2; m/z found 433.2 [M+H]$^+$. MP=111.2° C.

Example 107

((2S,3R)-2-methyl-3-((5-(trifluoromethyl)pyrazin-2-yl)oxy)piperidin-1-yl)(6-methyl-3-(2H-1,2,3-triazol-2-yl)pyridin-2-yl)methanone

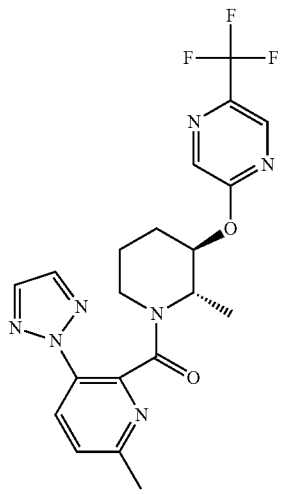 [SMILES: Cc1ccc(-n2nccn2)c(C(=O)N2CCC[C@@H](Oc3cnc(C(F)(F)F)cn3)[C@@H]2C)n1]

Prepared analogous to Example 105 substituting intermediate A-21 with intermediate A-22. MS (ESI) mass calcd. for $C_{20}H_{20}F_3N_7O_2$, 447.2; m/z found 448 [M+H]$^+$. MP=161.5° C.

Example 108

((2S,3R)-2-methyl-3-((5-(trifluoromethyl)pyridin-2-yl)oxy)piperidin-1-yl)(6-methyl-3-(2H-1,2,3-triazol-2-yl)pyridin-2-yl)methanone

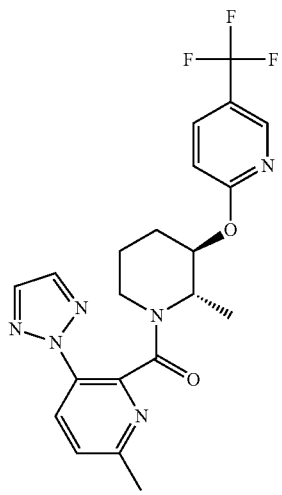

Prepared analogous to Example 101 substituting 2-chloro-5-(trifluoromethyl)pyrimidine with 2-chloro-5-(trifluoromethyl)pyridine and intermediate A-21 with intermediate A-22. MS (ESI) mass calcd. for $C_{21}H_{21}F_3N_6O_2$, 446.2; m/z found [M+H]+.

Example 109

(±)-trans-(2-methyl-3-((5-(trifluoromethyl)pyridin-2-yl)oxy)piperidin-1-yl)(6-methyl-3-(2H-1,2,3-triazol-2-yl)pyridin-2-yl)methanone

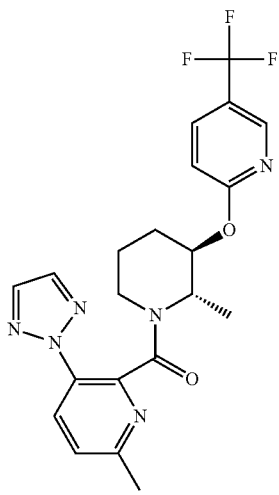

Prepared analogous to Example 108 using (±)-trans-tert-butyl 3-hydroxy-2-methylpiperidine-1-carboxylate. MS (ESI) mass calcd. for $C_{21}H_{21}F_3N_6O_2$, 446.2; m/z found 447.2 [M+H]+. MP=161.3° C.

Example 110

(2-(2H-1,2,3-triazol-2-yl)phenyl)((2S,3R)-2-methyl-3-((5-(trifluoromethyl)pyridin-2-yl)oxy)piperidin-1-yl)methanone

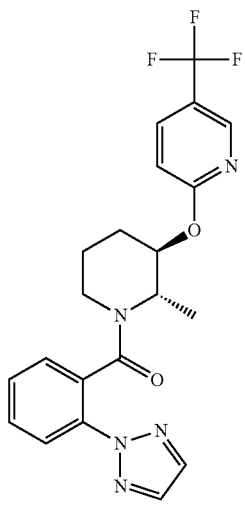

Prepared analogous to Example 108 substituting intermediate A-22 with intermediate A-4. MS (ESI) mass calcd. for $C_{21}H_{20}F_3N_5O_2$, 431.2; m/z found 432.2 [M+H]+. MP=159.7° C.

Example 111

((2S,3R)-2-methyl-3-((5-(trifluoromethyl)pyridin-2-yl)oxy)piperidin-1-yl)(5-methyl-3-(2H-1,2,3-triazol-2-yl)pyridin-2-yl)methanone

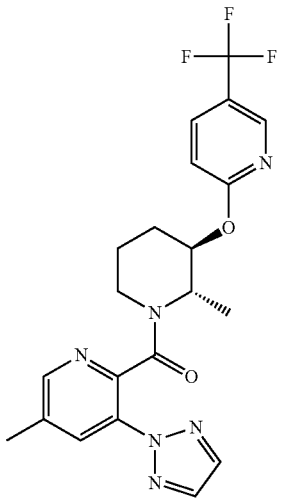

Prepared analogous to Example 108 substituting intermediate A-22 with intermediate A-21. MP=281.7° C.

Example 112

(4-methyl-2-(2H-1,2,3-triazol-2-yl)phenyl)((2S,3R)-2-methyl-3-((5-(trifluoromethyl)pyridin-2-yl)oxy)piperidin-1-yl)methanone

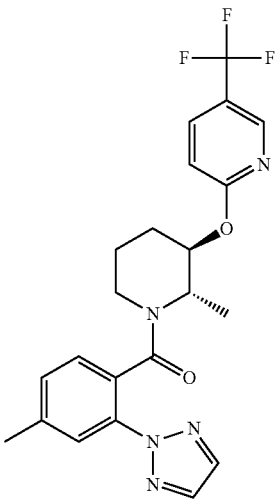

Prepared analogous to example 108 substituting intermediate A-22 with intermediate A-11. MS (ESI) mass calcd. for $C_{21}H_{21}F_3N_6O_2$, 446.2; m/z found 447 [M+H]+. MP=167.1° C.

Example 113

(4-methyl-2-(2H-1,2,3-triazol-2-yl)phenyl)((2S,3R)-2-methyl-3-((5-(trifluoromethyl)pyrazin-2-yl)oxy)piperidin-1-yl)methanone

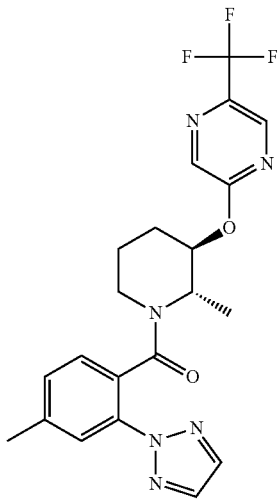

Prepared analogous to Example 105 substituting intermediate A-21 with intermediate A-11. MS (ESI) mass calcd. for $C_{21}H_{21}F_3N_6O_2$, 446.2; m/z found 447 [M+H]$^+$. MP=167.1° C.

The following compounds are also within the scope of the invention. They can be prepared using methods known in the art, in combination with the experimental details and schemes provided herein.

Example 114

(3-fluoro-2-(pyrimidin-2-yl)phenyl)((2S,3R)-3-((5-fluoropyridin-2-yl)oxy)-2-methylpiperidin-1-yl)methanone

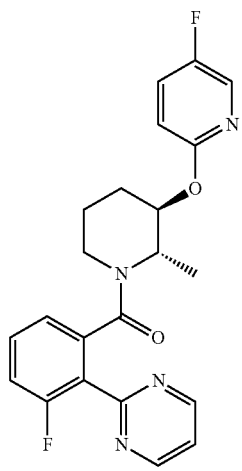

Example 115

(3-fluoro-2-(pyrimidin-2-yl)phenyl)((2S,3R)-3-((5-fluoropyrimidin-2-yl)oxy)-2-methylpiperidin-1-yl)methanone

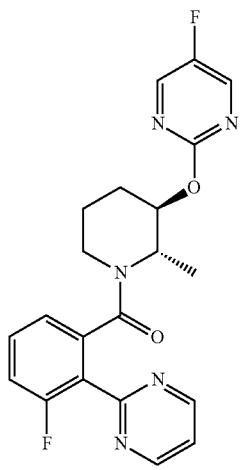

Example 116

(3-fluoro-2-(pyrimidin-2-yl)phenyl)((2S,3R)-2-methyl-3-((5-(trifluoromethyl)pyridin-2-yl)oxy)piperidin-1-yl)methanone

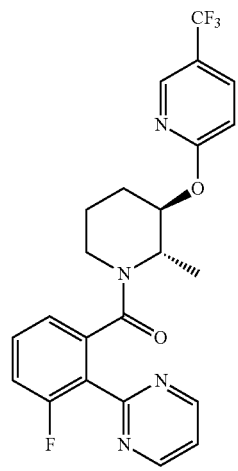 [SMILES: C[C@H]1[C@H](Oc2ccc(C(F)(F)F)cn2)CCCN1C(=O)c1cccc(F)c1-c1ncccn1]

Example 117

(3-fluoro-2-(pyrimidin-2-yl)phenyl)((2S,3R)-2-methyl-3-((5-(trifluoromethyl)pyrimidin-2-yl)oxy)piperidin-1-yl)methanone

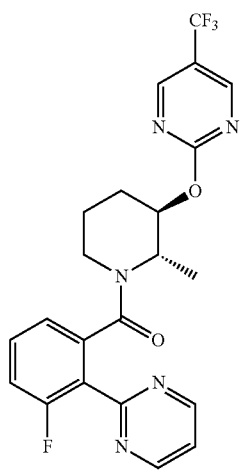

Example 119

((2S,3R)-3-(benzo[d]oxazol-2-yloxy)-2-methylpiperidin-1-yl)(3-fluoro-2-(pyrimidin-2-yl)phenyl)methanone

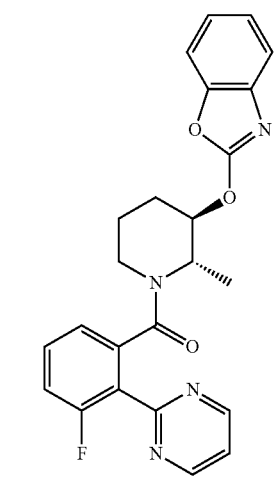

Example 118

(3-fluoro-2-(pyrimidin-2-yl)phenyl)((2S,3R)-2-methyl-3-((5-(trifluoromethyl)pyrazin-2-yl)oxy)piperidin-1-yl)methanone

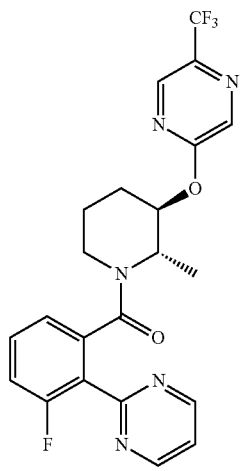 [SMILES: C[C@H]1[C@H](Oc2cnc(C(F)(F)F)cn2)CCCN1C(=O)c1cccc(F)c1-c1ncccn1]

Example 120

((2S,3R)-3-(benzo[d]oxazol-2-yloxy)-2-methylpiperidin-1-yl)(3-fluoro-2-(2H-1,2,3-triazol-2-yl)phenyl)methanone

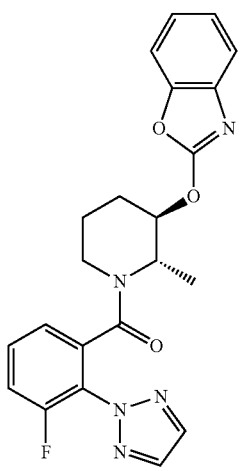 [SMILES: C[C@H]1[C@H](Oc2nc3ccccc3o2)CCCN1C(=O)c1cccc(F)c1-n1nccn1]

105

Example 121

(3-fluoro-2-(2H-1,2,3-triazol-2-yl)phenyl)((2S,3R)-3-((5-fluoropyridin-2-yl)oxy)-2-methylpiperidin-1-yl)methanone

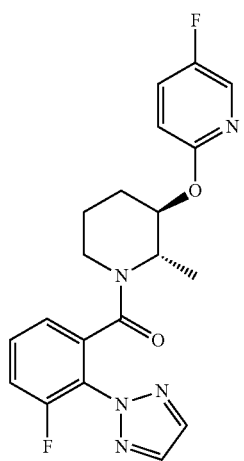 [SMILES: C[C@H]1[C@H](Oc2ccc(F)cn2)CCCN1C(=O)c1cccc(F)c1-n1nccn1]

Example 122

(3-fluoro-2-(2H-1,2,3-triazol-2-yl)phenyl)((2S,3R)-3-((5-fluoropyrimidin-2-yl)oxy)-2-methylpiperidin-1-yl)methanone

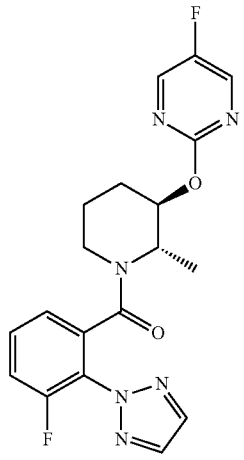

106

Example 123

(3-fluoro-2-(2H-1,2,3-triazol-2-yl)phenyl)((2S,3R)-2-methyl-3-((5-(trifluoromethyl)pyrimidin-2-yl)oxy)piperidin-1-yl)methanone

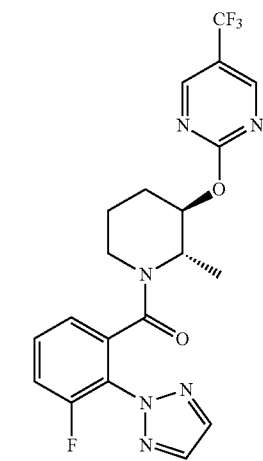

Example 124

(3-fluoro-2-(2H-1,2,3-triazol-2-yl)phenyl)((2S,3R)-2-methyl-3-((5-(trifluoromethyl)pyridin-2-yl)oxy)piperidin-1-yl)methanone

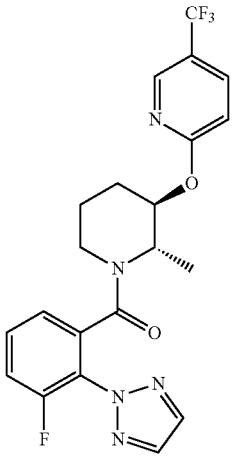 [SMILES: C[C@H]1[C@H](Oc2ccc(C(F)(F)F)cn2)CCCN1C(=O)c1cccc(F)c1-n1nccn1]

Example 125

(3-fluoro-2-(2H-1,2,3-triazol-2-yl)phenyl)((2S,3R)-2-methyl-3-((5-(trifluoromethyl)pyrazin-2-yl)oxy)piperidin-1-yl)methanone

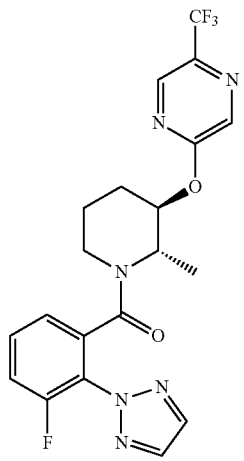 [SMILES: C[C@H]1[C@H](Oc2cnc(C(F)(F)F)cn2)CCCN1C(=O)c1cccc(F)c1-n1nccn1]

Example 126

((2S,3R)-3-(benzo[d]oxazol-2-yloxy)-2-methylpiperidin-1-yl)(3-fluoro-2-(2H-1,2,3-triazol-2-yl)phenyl)methanone

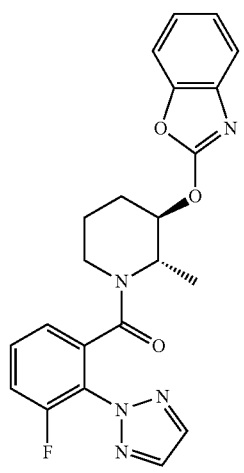 [SMILES: C[C@H]1[C@H](Oc2nc3ccccc3o2)CCCN1C(=O)c1cccc(F)c1-n1nccn1]

Example 127

((2S,3R)-3-(benzo[d]oxazol-2-yloxy)-2-methylpiperidin-1-yl)(2-fluoro-6-(2H-1,2,3-triazol-2-yl)phenyl)methanone

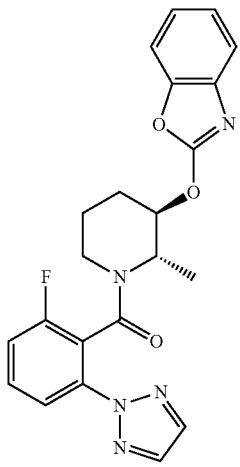 [SMILES: C[C@H]1[C@H](Oc2nc3ccccc3o2)CCCN1C(=O)c1c(F)cccc1-n1nccn1]

Example 128

(2-fluoro-6-(2H-1,2,3-triazol-2-yl)phenyl)((2S,3R)-3-((5-fluoropyridin-2-yl)oxy)-2-methylpiperidin-1-yl)methanone

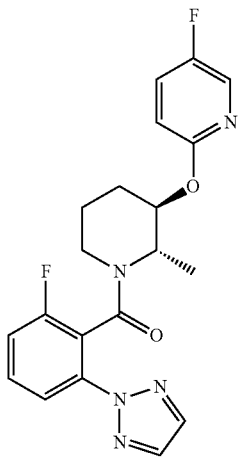

Example 129

(2-fluoro-6-(2H-1,2,3-triazol-2-yl)phenyl)((2S,3R)-3-((5-fluoropyrimidin-2-yl)oxy)-2-methylpiperidin-1-yl)methanone

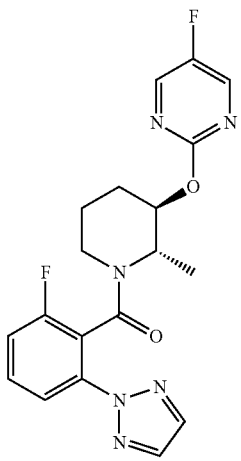 [SMILES: C[C@H]1[C@H](Oc2ncc(F)cn2)CCCN1C(=O)c1c(F)cccc1-n1nccn1]

Example 130

(2-fluoro-6-(2H-1,2,3-triazol-2-yl)phenyl)((2S,3R)-2-methyl-3-((5-(trifluoromethyl)pyrimidin-2-yl)oxy)piperidin-1-yl)methanone

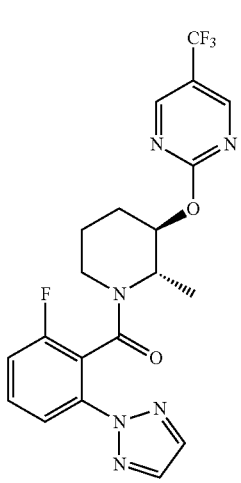 [SMILES: C[C@H]1[C@H](Oc2ncc(C(F)(F)F)cn2)CCCN1C(=O)c1c(F)cccc1-n1nccn1]

Example 131

(2-fluoro-6-(2H-1,2,3-triazol-2-yl)phenyl)((2S,3R)-2-methyl-3-((5-(trifluoromethyl)pyridin-2-yl)oxy)piperidin-1-yl)methanone

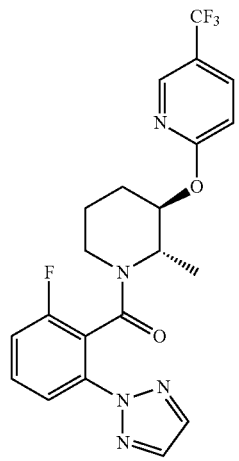 [SMILES: C[C@H]1[C@H](Oc2ccc(C(F)(F)F)cn2)CCCN1C(=O)c1c(F)cccc1-n1nccn1]

Example 132

(2-fluoro-6-(2H-1,2,3-triazol-2-yl)phenyl)((2S,3R)-2-methyl-3-((5-(trifluoromethyl)pyrazin-2-yl)oxy)piperidin-1-yl)methanone

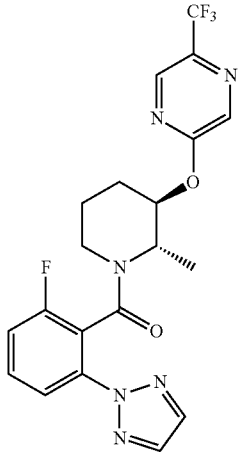

111

Example 133

(2-fluoro-6-(pyrimidin-2-yl)phenyl)((2S,3R)-2-methyl-3-((5-(trifluoromethyl)pyrazin-2-yl)oxy)piperidin-1-yl)methanone

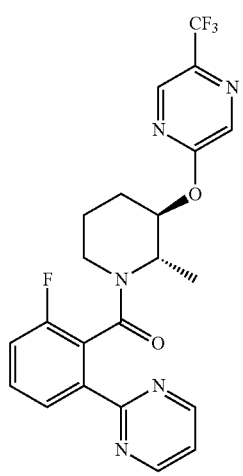 [SMILES: C[C@H]1[C@H](Oc2cnc(C(F)(F)F)cn2)CCCN1C(=O)c1c(F)cccc1-c1ncccn1]

Example 134

(2-fluoro-6-(pyrimidin-2-yl)phenyl)((2S,3R)-2-methyl-3-((5-(trifluoromethyl)pyridin-2-yl)oxy)piperidin-1-yl)methanone

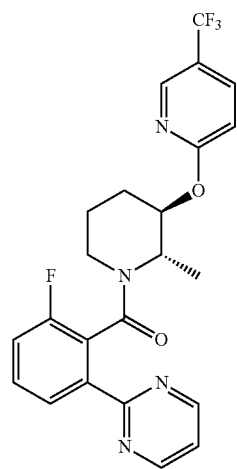 [SMILES: C[C@H]1[C@H](Oc2ccc(C(F)(F)F)cn2)CCCN1C(=O)c1c(F)cccc1-c1ncccn1]

112

Example 135

(2-fluoro-6-(pyrimidin-2-yl)phenyl)((2S,3R)-2-methyl-3-((5-(trifluoromethyl)pyrimidin-2-yl)oxy)piperidin-1-yl)methanone

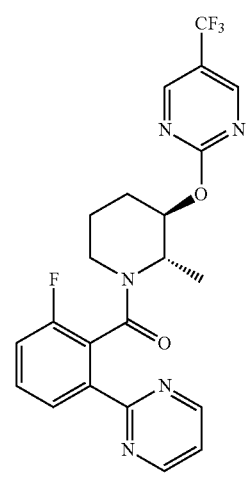

Example 136

(2-fluoro-6-(pyrimidin-2-yl)phenyl)((2S,3R)-3-((5-fluoropyrimidin-2-yl)oxy)-2-methylpiperidin-1-yl)methanone

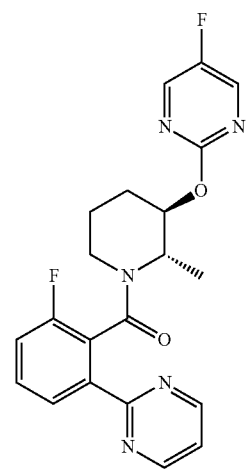

Example 137

(2-fluoro-6-(pyrimidin-2-yl)phenyl)((2S,3R)-3-((5-fluoropyridin-2-yl)oxy)-2-methylpiperidin-1-yl)methanone

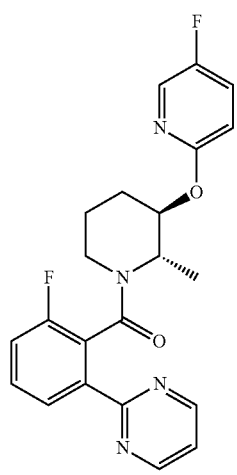 [SMILES: C[C@H]1[C@H](Oc2ccc(F)cn2)CCCN1C(=O)c1c(F)cccc1-c1ncccn1]

Example 138

(5-fluoro-2-(pyrimidin-2-yl)phenyl)((2S,3R)-2-methyl-3-((5-(trifluoromethyl)pyridin-2-yl)oxy)piperidin-1-yl)methanone

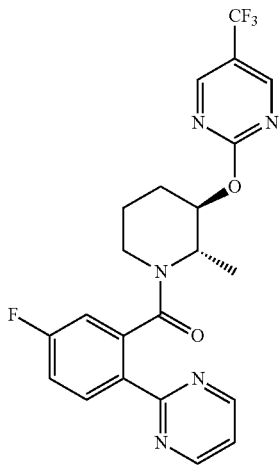 [SMILES: C[C@H]1[C@H](Oc2ncc(C(F)(F)F)cn2)CCCN1C(=O)c1cc(F)ccc1-c1ncccn1]

Example 139

(4-fluoro-2-(pyrimidin-2-yl)phenyl)((2S,3R)-2-methyl-3-((5-(trifluoromethyl)pyridin-2-yl)oxy)piperidin-1-yl)methanone

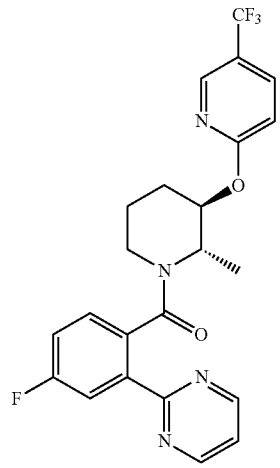 [SMILES: C[C@H]1[C@H](Oc2ccc(C(F)(F)F)cn2)CCCN1C(=O)c1ccc(F)cc1-c1ncccn1]

Example 140

(4-fluoro-2-(pyrimidin-2-yl)phenyl)((2S,3R)-2-methyl-3-((5-(trifluoromethyl)pyridin-2-yl)oxy)piperidin-1-yl)methanone

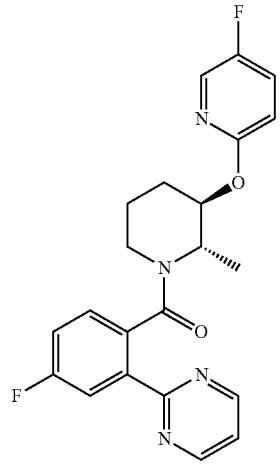 [SMILES: C[C@H]1[C@H](Oc2ccc(F)cn2)CCCN1C(=O)c1ccc(F)cc1-c1ncccn1]

115

Example 141

(4-fluoro-2-(pyrimidin-2-yl)phenyl)((2S,3R)-3-((5-fluoropyridin-2-yl)oxy)-2-methylpiperidin-1-yl)methanone

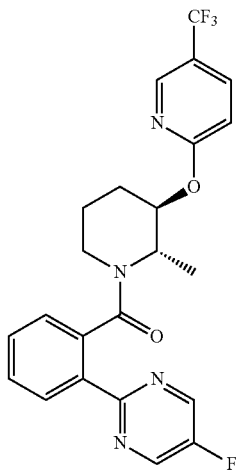

Example 142

(3-fluoro-2-(5-fluoropyrimidin-2-yl)phenyl)((2S,3R)-2-methyl-3-((5-(trifluoromethyl)pyridin-2-yl)oxy)piperidin-1-yl)methanone

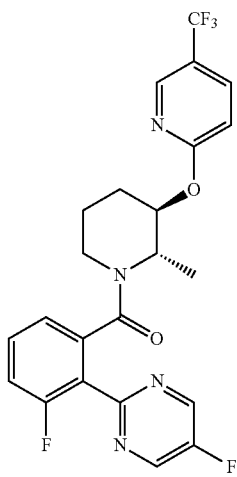

116

Example 143

((2S,3R)-2-methyl-3-((5-(trifluoromethyl)pyridin-2-yl)oxy)piperidin-1-yl)(2-(pyrimidin-2-yl)phenyl)methanone

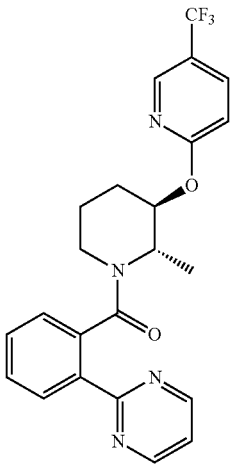 [SMILES: C[C@H]1[C@H](Oc2ccc(C(F)(F)F)cn2)CCCN1C(=O)c1ccccc1-c1ncccn1]

Example 144

(2-(3-methyl-1,2,4-oxadiazol-5-yl)phenyl)((2S,3R)-2-methyl-3-((5-(trifluoromethyl)pyridin-2-yl)amino)piperidin-1-yl)methanone

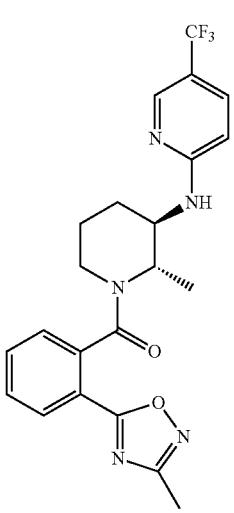 [SMILES: Cc1noc(-c2ccccc2C(=O)N2CCC[C@@H](Nc3ccc(C(F)(F)F)cn3)[C@@H]2C)n1]

Example 145

(4-fluoro-2-(3-methyl-1,2,4-oxadiazol-5-yl)phenyl)((2S,3R)-2-methyl-3-((5-(trifluoromethyl)pyridin-2-yl)amino)piperidin-1-yl)methanone

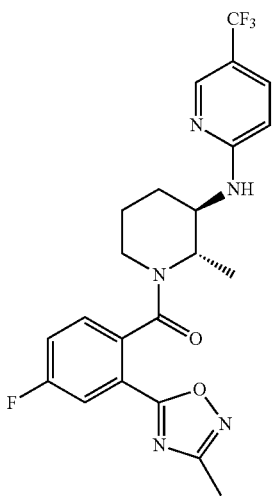 [SMILES: Cc1noc(-c2cc(F)ccc2C(=O)N2CCC[C@@H](Nc3ccc(C(F)(F)F)cn3)[C@@H]2C)n1]

Example 146

(3-fluoro-2-(3-methyl-1,2,4-oxadiazol-5-yl)phenyl)((2S,3R)-2-methyl-3-((5-(trifluoromethyl)pyrazin-2-yl)amino)piperidin-1-yl)methanone

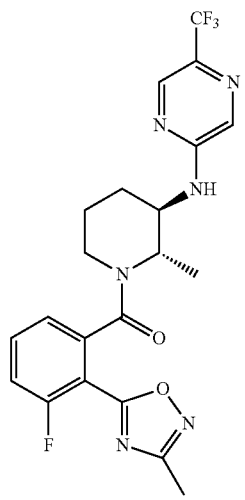

Assays:

The in vitro affinity of the compounds of the invention for the rat/human orexin 1 and human orexin 2 receptors was determined by competitive radioligand binding using [$^3$H](1-(5-(2-fluoro-phenyl)-2-methyl-thiazol-4-yl)-1-((S)-2-(5-phenyl-(1,3,4)oxadiazol-2-ylmethyl)-pyrrolidin-1-yl)-methanone)(Langmead et al., 2004) and [$^3$H]EMPA (n-ethyl-2[96-methoxy-pyridin-3-yl)-(toluene-2-sulfonyl)-amino]-N-pyridin-3-ylmethyl acetamide), respectively (Langmead et al., 2004, British Journal of Pharmacology 141:340-346; Malherbe et al., 2004, British Journal of Pharmacology 156: 1326-41).

The in vitro functional antagonism of the compounds on the human orexin 1 and orexin 2 receptors was determined using fluorometric imaging plate reader (FLIPR) based calcium assays.

Rat and Human Orexin 1 Receptor Radioligand Binding Studies

Human Embryonic Kidney 293 cells (HEK293) stably expressing rat orexin 1 receptor (Genebank accession number NM_001525) or Chinese ovary cells (CHO) stably expressing human orexin 1 receptor (Genebank accession number NM_001526) were grown to confluency in DMEM (Hyclone, cat #SH30022), 10% FBS, 1× Pen/Strep, 1× sodium pyruvate, 10 mM HEPES, 600 g/mL G418 and DMEM/F12 (Gibco, Cat #11039), 10% FBS, 1× Pen/Strep, 600 g/mL G418 media, respectively on 150 cm$^2$ tissue culture plates, washed with 5 mM EDTA in PBS (HyClone Dulbecco's Phoshpate Buffered Saline 1× with Calcium and Magnesium, Cat #SH30264.01, hereafter referred to simply as PBS) and scraped into 50 ml tubes. After centrifugation (2K×G, 5 min at 4° C.), the supernatant was aspirated and the pellets frozen and stored at −80° C. Cells were resuspended in PBS in the presence of 1 tablet of protease inhibitor cocktail (Roche, Cat. #11836145001) per 50 mL. Each cell pellet from a 15 cm plate was resuspended in 10 mL, stored on ice, and homogenized for 45 sec prior to addition to the reactions. Competition binding experiments in 96 well polypropylene plates were performed using [$^3$H]-(1-(5-(2-fluoro-phenyl)-2-methyl-thiazol-4-yl)-1-((S)-2-(5-phenyl-(1,3,4)oxadiazol-2-yl-methyl)-pyrrolidin-1-yl)-methanone) (Moraveck Corporation, specific activity=35.3 Ci/mmol), diluted to a 10 nM concentration in PBS (4 nM final). Compounds were solubilized in 100% DMSO (Acros Organics, Cat. #61042-1000) and tested over a range of 7 concentrations (from 0.1 nM to 10 μM). The final concentration of DMSO in the reactions is equal to or less than 0.1%. Total and nonspecific binding was determined in the absence and presence of 10 μM almorexant. The total volume of each reaction is 200 μL (20 μL of diluted compounds, 80 μL of [3H]-(1-(5-(2-fluoro-phenyl)-2-methyl-thiazol-4-yl)-1-((S)-2-(5-phenyl-(1,3,4)oxadiazol-2-yl-methyl)-pyrrolidin-1-yl)-methanone) diluted in PBS and 100 μL of the cell suspension). Reactions were run for 60 min at room temperature and terminated by filtration through GF/C filter plates (PerkinElmer, Cat. #6005174) presoaked in 0.3% polyethylenimine using the cell harvester (PerkinElmer Filtermate). The plates were washed 3 times by aspirating 30 ml PBS through the plates. Plates were dried in 55° C. oven for 60 min, scintillation fluid was added, and the radioactivity was counted on a Topcount (Packard).

IC$_{50}$ values (i.e. concentration of unlabelled compound required to compete for 50% of specific binding to the radioligand) was calculated using the GraphPad Prism software (GraphPad Prism Software Inc., San Diego, Calif.) with a fit to a sigmoidal dose-response curve. Apparent Ki values were calculated as $K_i=IC_{50}/(1+C/K_d)$, where C is concentration of radioligand and $K_d$=4 nM for rat orexin 1 receptor and 6 nM for human orexin 1 receptor.

Human Orexin 2 Receptor Radioligand Binding Studies

HEK293 stably expressing human orexin 2 receptor (Genebank accession number NM_001526) were grown to confluency in DMEM (Hyclone, cat #SH30022), 10% FBS, 1× Pen/Strep, 1× NaPyruvate, 10 mM HEPES, 600 ug/ml G418 media on 150 cm$^2$ tissue culture plates, washed with 5 mM EDTA in PBS (HyClone Dulbecco's Phoshpate Buffered Saline 1× with Calcium and Magnesium, Cat #SH30264.01, hereafter referred to simply as PBS) and scraped into 50 ml tubes. After centrifugation (2K×G, 5 min at 4° C.), the supernatant was aspirated and the pellets frozen and stored at −80° C. Cells were resuspended in PBS in the presence of 1 tablet of protease inhibitor cocktail (Roche, Cat. #11836145001) per 50 mL. Each cell pellet from a 15 cm plate was resuspended in 10 mL, stored on ice, and homogenized for 45 sec just prior to addition to the reactions. Competition binding experiments in 96 well polypropylene plates were performed using [$^3$H]-EMPA (Moraveck Corporation, specific activity=29.6 Ci/mmol), diluted to a 5 nM concentration in PBS (2 nM final concentration). Compounds were solubilized in 100% DMSO (Acros Organics, Cat. #61042-1000) and tested over a range of 7 concentration (from 0.1 nM to 10 μM). The final concentration of DMSO in the reactions is equal to or less than 0.1%. Total and nonspecific binding was determined in the absence and presence of 10 M almorexant. The total volume of each reaction is 200 μL (20 μL of diluted compounds, 80 μL of [$^3$H]-EMPA diluted in PBS and 100 μL of the cell suspension).

Reactions were run for 60 min at room temperature and terminated by filtration through GF/C filter plates (PerkinElmer, Cat. #6005174) presoaked in 0.3% polyethylenimine using the cell harvester (PerkinElmer Filtermate). The plates were washed 3 times by aspirating 30 ml PBS through the plates. Plates were dried in 55° C. oven for 60 min, scintillation fluid was added, and the radioactivity was counted on a Topcount (Packard).

$IC_{50}$ values (i.e. concentration of unlabelled compound required to compete for 50% of specific binding to the radioligand) was calculated using the GraphPad Prism software (GraphPad Prism Software Inc., San Diego, Calif.) with a fit to a sigmoidal dose-response curve. Apparent Ki values were calculated as $K_i=IC_{50}/(1+C/K_d)$, where C is concentration of radioligand and $K_d=2$ nM.

Human Orexin 1 Receptor Ca$^{2+}$ Mobilization Assay

CHO cells stably transfected with the human orexin 1 receptor (Genebank accession number NM_001526) were grown to confluency in DMEM/F12, 10% FBS, 1× pen-strep, 400 g/ml G418. Cells were seeded on to 384-well Packard viewplates at a density of 10,000 cells/well and incubated overnight at 37° C., 5% CO$_2$. The cells were dye-loaded with BD Calcium Assay kit (BD, cat #640178) in HBSS (Gibco, cat#14025-092) with 2.5 mM probenecid and incubated at 37° C., 5% CO$_2$ for 45 min. Cells were pre-incubated with compounds (diluted in DMEM/F-12) for 15-30 minutes before agonist (orexin A, 10 nM) stimulation. Ligand-induced Ca$^{2+}$ release was measured using a Fluorometric Imaging Plate Reader (FLIPR, Molecular Devices, Sunnyvale, Calif.). Functional responses were measured as peak fluorescence intensity minus basal. The concentration of agonist that produced a half-maximal response is represented by the EC$_{50}$ value. Antagonistic potency values were converted to apparent pK$_B$ values using a modified Cheng-Prusoff correction. Apparent pK$_B$=−log IC$_{50}$/1+[conc agonist/EC$_{50}$]. Data are expressed as mean±S.E.M.

Human Orexin 2 Receptor Ca$^{2+}$ Mobilization Assay

PFSK-1 cells endogenously expressing the human orexin 2 receptor were grown to confluency in RPMI1640 (Hyclone, cat#30027.02), 10% FBS, 1× pen-strep. Cells were seeded on to 384-well Packard viewplates at a density of 5,000 cells/well and incubated overnight at 37° C., 5% CO2. The cells were dye-loaded with BD Calcium Assay kit (BD, cat #640178) in HBSS (Gibco, cat#14025-092) with 2.5 mM probenecid and incubated at 37° C., 5% CO$_2$ for 45 min. Cells were pre-incubated with compounds (diluted in DMEM/F-12) for 15-30 minutes before agonist (orexin B, 100 nM) stimulation. Ligand-induced Ca$^{2+}$ release was measured using a Fluorometric Imaging Plate Reader (FLIPR, Molecular Devices, Sunnyvale, Calif.). Functional responses were measured as peak fluorescence intensity minus basal. The concentration of agonist that produced a half-maximal response is represented by the EC$_{50}$ value. Antagonistic potency values were converted to apparent pK$_B$ values using a modified Cheng-Prusoff correction. Apparent pK$_B$=−log IC$_{50}$/1+[conc agonist/EC$_{50}$]. Data are expressed as mean±S.E.M.

Preferred compounds of the invention are set forth in the table below. Orexin receptor activity of certain compounds of the invention is also set forth in the below table.

| Ex. | Structure | rOX1 $K_i$ (nm) | hOX1 $K_i$ (nm) | hOX2 $K_i$ (nm) | Compound Name |
|---|---|---|---|---|---|
| 1 | 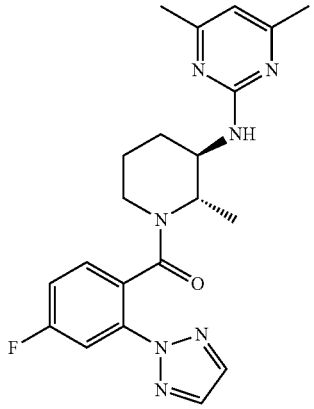 [SMILES: Cc1cc(C)nc(N[C@@H]2CCCN(C(=O)c3ccc(F)cc3-n3nccn3)[C@H]2C)n1] | | 1034 | 290 | (±)-trans-(3-((4,6-dimethylpyrimidin-2-yl)amino)-2-methylpiperidin-1-yl)(4-fluoro-2-(2H-1,2,3-triazol-2-yl)phenyl)methanone |

-continued

| Ex. | Structure | rOX1 $K_i$ (nm) | hOX1 $K_i$ (nm) | hOX2 $K_i$ (nm) | Compound Name |
|---|---|---|---|---|---|
| 2 | 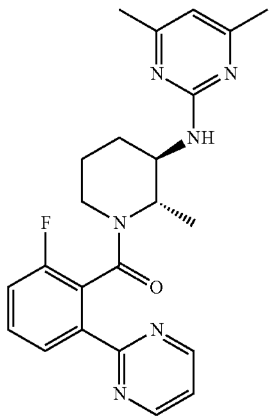 [SMILES: Cc1cc(C)nc(N[C@@H]2CCCN(C(=O)c3c(F)cccc3-c3ncccn3)[C@H]2C)n1] | | 400 | 217 | (±)-trans-(3-((4,6-dimethylpyrimidin-2-yl)amino)-2-methylpiperidin-1-yl)(2-fluoro-6-(pyrimidin-2-yl)phenyl)methanone |
| 3 | 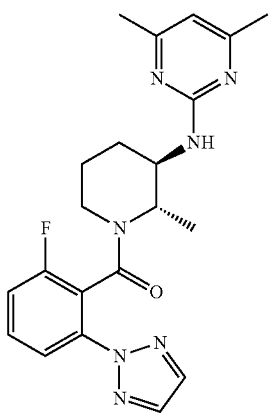 [SMILES: Cc1cc(C)nc(N[C@@H]2CCCN(C(=O)c3c(F)cccc3-n3nccn3)[C@H]2C)n1] | | 1065 | 260 | (±)-trans-(3-((4,6-dimethylpyrimidin-2-yl)amino)-2-methylpiperidin-1-yl)(2-fluoro-6-(2H-1,2,3-triazol-2-yl)phenyl)methanone |
| 4 | 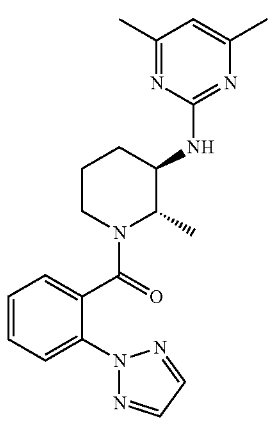 [SMILES: Cc1cc(C)nc(N[C@@H]2CCCN(C(=O)c3ccccc3-n3nccn3)[C@H]2C)n1] | | 78 | 40 | (±)-trans-(2-(2H-1,2,3-triazol-2-yl)phenyl)(3-((4,6-dimethylpyrimidin-2-yl)amino)-2-methylpiperidin-1-yl)methanone |

-continued

| Ex. | Structure | rOX1 K$_i$ (nm) | hOX1 K$_i$ (nm) | hOX2 K$_i$ (nm) | Compound Name |
|---|---|---|---|---|---|
| 5 | 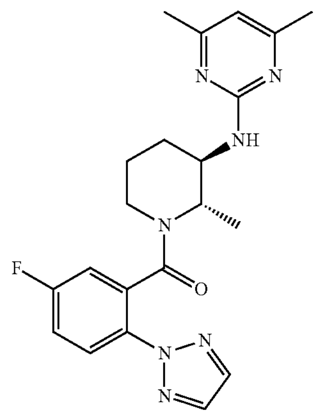 [SMILES: Cc1cc(C)nc(N[C@@H]2CCCN(C(=O)c3cc(F)ccc3-n3nccn3)[C@H]2C)n1] | | 560 | 116 | (±)-trans-(3-((4,6-dimethylpyrimidin-2-yl)amino)-2-methylpiperidin-1-yl)(5-fluoro-2-(2H-1,2,3-triazol-2-yl)phenyl)methanone |
| 6 | 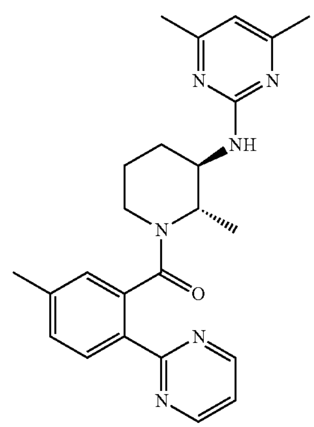 | 25 | 40 | 25 | (±)-trans-(3-((4,6-dimethylpyrimidin-2-yl)amino)-2-methylpiperidin-1-yl)(5-methyl-2-(pyrimidin-2-yl)phenyl)methanone |
| 7 | 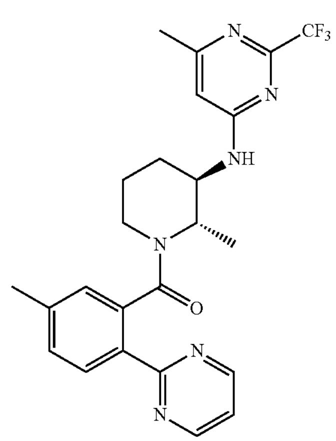 [SMILES: Cc1ccc(-c2ncccn2)c(C(=O)N2CCC[C@@H](Nc3cc(C)nc(C(F)(F)F)n3)[C@@H]2C)c1] | | 126 | 228 | (±)-trans-(5-methyl-2-(pyrimidin-2-yl)phenyl)(2-methyl-3-((6-methyl-2-(trifluoromethyl)pyrimidin-4-yl)amino)piperidin-1-yl)methanone |

-continued

| Ex. | Structure | rOX1 K$_i$ (nm) | hOX1 K$_i$ (nm) | hOX2 K$_i$ (nm) | Compound Name |
|---|---|---|---|---|---|
| 8 | 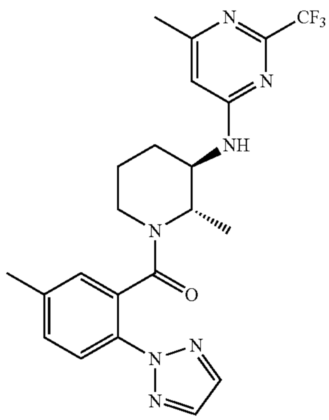 [SMILES: Cc1ccc(-n2nccn2)c(C(=O)N2CCC[C@@H](Nc3cc(C)nc(C(F)(F)F)n3)[C@@H]2C)c1] | | 462 | 587 | (±)-trans-(5-methyl-2-(2H-1,2,3-triazol-2-yl)phenyl)(2-methyl-3-((6-methyl-2-(trifluoromethyl)pyrimidin-4-yl)amino)piperidin-1-yl)methanone |
| 9 | 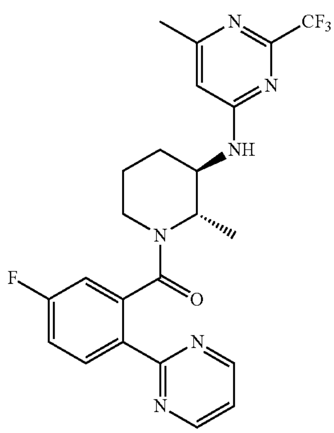 [SMILES: Cc1cc(N[C@@H]2CCCN(C(=O)c3cc(F)ccc3-c3ncccn3)[C@H]2C)nc(C(F)(F)F)n1] | | 6708 | 2054 | (±)-trans-(5-fluoro-2-(pyrimidin-2-yl)phenyl)(2-methyl-3-((6-methyl-2-(trifluoromethyl)pyrimidin-4-yl)amino)piperidin-1-yl)methanone |
| 10 | 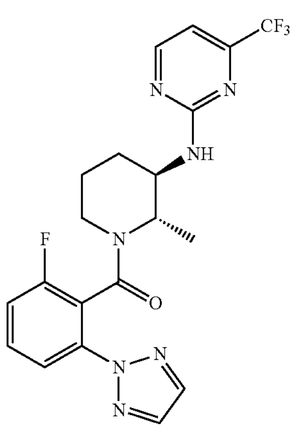 [SMILES: C[C@H]1[C@H](Nc2nccc(C(F)(F)F)n2)CCCN1C(=O)c1c(F)cccc1-n1nccn1] | | 315 | 144 | (±)-trans-(2-fluoro-6-(2H-1,2,3-triazol-2-yl)phenyl)(2-methyl-3-((4-(trifluoromethyl)pyrimidin-2-yl)amino)piperidin-1-yl)methanone |

-continued

| Ex. | Structure | rOX1 K$_i$ (nm) | hOX1 K$_i$ (nm) | hOX2 K$_i$ (nm) | Compound Name |
|---|---|---|---|---|---|
| 11 | 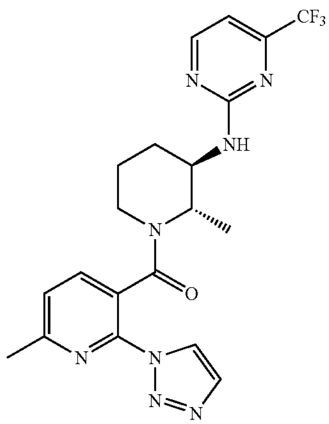 [SMILES: Cc1ccc(C(=O)N2CCC[C@@H](Nc3nccc(C(F)(F)F)n3)[C@@H]2C)c(-n2ccnn2)n1] | | 8999 | 634 | (±)-trans-(6-methyl-2-(1H-1,2,3-triazol-1-yl)pyridin-3-yl)(2-methyl-3-((4-(trifluoromethyl)pyrimidin-2-yl)amino)piperidin-1-yl)methanone |
| 12 | 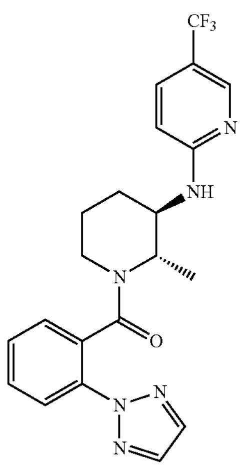 | 14 | 11 | 332 | (±)-trans-(2-(2H-1,2,3-triazol-2-yl)phenyl)(2-methyl-3-((5-(trifluoromethyl)pyridin-2-yl)amino)piperidin-1-yl)methanone |
| 13 | 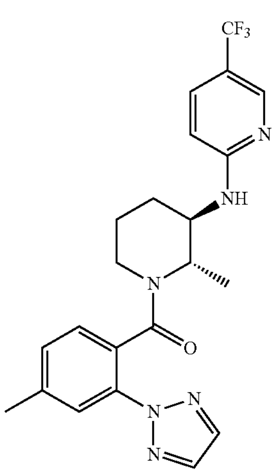 [SMILES: Cc1ccc(C(=O)N2CCC[C@@H](Nc3ccc(C(F)(F)F)cn3)[C@@H]2C)c(-n2nccn2)c1] | 15 | 9 | 920 | (±)-trans-(4-methyl-2-(2H-1,2,3-triazol-2-yl)phenyl)(2-methyl-3-((5-(trifluoromethyl)pyridin-2-yl)amino)piperidin-1-yl)methanone |

-continued

| Ex. | Structure | rOX1 $K_i$ (nm) | hOX1 $K_i$ (nm) | hOX2 $K_i$ (nm) | Compound Name |
|---|---|---|---|---|---|
| 14 | 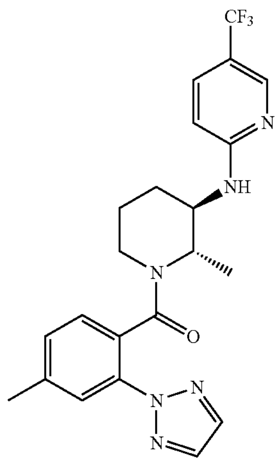 [SMILES: Cc1ccc(C(=O)N2CCC[C@@H](Nc3ccc(C(F)(F)F)cn3)[C@@H]2C)c(-n2nccn2)c1] | 9 | 7 | 681 | (4-methyl-2-(2H-1,2,3-triazol-2-yl)phenyl)((2S,3R)-2-methyl-3-((5-(trifluoromethyl)pyridin-2-yl)amino)piperidin-1-yl)methanone |
| 15 | 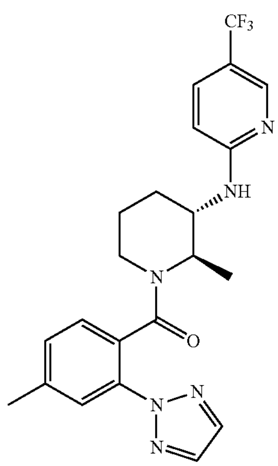 [SMILES: Cc1ccc(C(=O)N2CCC[C@H](Nc3ccc(C(F)(F)F)cn3)[C@H]2C)c(-n2nccn2)c1] | 8200 | | >10000 | (4-methyl-2-(2H-1,2,3-triazol-2-yl)phenyl)((2R,3S)-2-methyl-3-((5-(trifluoromethyl)pyridin-2-yl)amino)piperidin-1-yl)methanone |
| 16 | 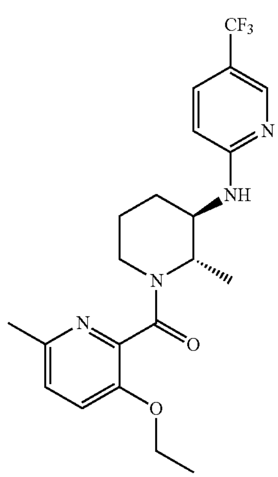 [SMILES: CCOc1ccc(C)nc1C(=O)N1CCC[C@@H](Nc2ccc(C(F)(F)F)cn2)[C@@H]1C] | 35 | 38 | 680 | (±)-trans-(3-ethoxy-6-methylpyridin-2-yl)(2-methyl-3-((5-(trifluoromethyl)pyridin-2-yl)amino)piperidin-1-yl)methanone |

| Ex. | Structure | rOX1 K$_i$ (nm) | hOX1 K$_i$ (nm) | hOX2 K$_i$ (nm) | Compound Name |
|---|---|---|---|---|---|
| 17 | 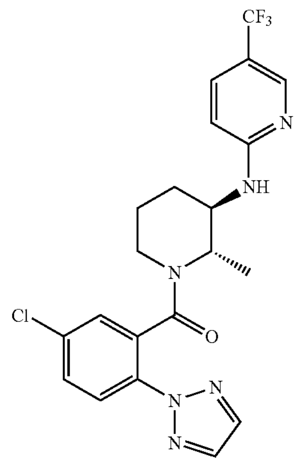 [SMILES: C[C@H]1[C@H](Nc2ccc(C(F)(F)F)cn2)CCCN1C(=O)c1cc(Cl)ccc1-n1nccn1] | 11 | 8 | 221 | (±)-trans-(5-chloro-2-(2H-1,2,3-triazol-2-yl)phenyl)(2-methyl-3-((5-(trifluoromethyl)pyridin-2-yl)amino)piperidin-1-yl)methanone |
| 18 | 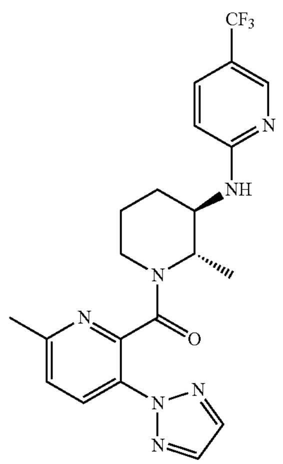 [SMILES: Cc1ccc(-n2nccn2)c(C(=O)N2CCC[C@@H](Nc3ccc(C(F)(F)F)cn3)[C@@H]2C)n1] | 13 | 10 | 272 | (±)-trans-(2-methyl-3-((5-(trifluoromethyl)pyridin-2-yl)amino)piperidin-1-yl)(6-methyl-3-(2H-1,2,3-triazol-2-yl)pyridin-2-yl)methanone |
| 19 | 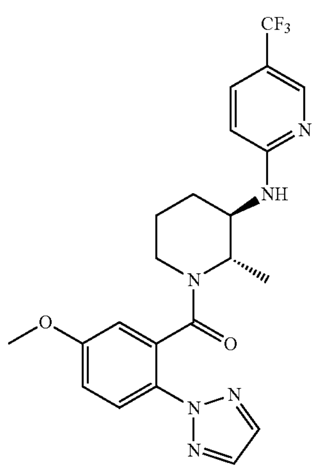 [SMILES: COc1ccc(-n2nccn2)c(C(=O)N2CCC[C@@H](Nc3ccc(C(F)(F)F)cn3)[C@@H]2C)c1] | 10 | 10 | 238 | (±)-trans-(5-methoxy-2-(2H-1,2,3-triazol-2-yl)phenyl)(2-methyl-3-((5-(trifluoromethyl)pyridin-2-yl)amino)piperidin-1-yl)methanone |

-continued

| Ex. | Structure | rOX1 K$_i$ (nm) | hOX1 K$_i$ (nm) | hOX2 K$_i$ (nm) | Compound Name |
|---|---|---|---|---|---|
| 20 | 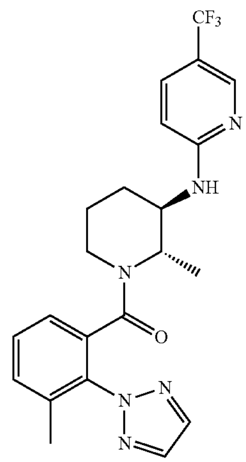 [SMILES: Cc1cccc(C(=O)N2CCC[C@@H](Nc3ccc(C(F)(F)F)cn3)[C@@H]2C)c1-n1nccn1] | 14 | 8 | 150 | (±)-trans-(3-methyl-2-(2H-1,2,3-triazol-2-yl)phenyl)(2-methyl-3-((5-(trifluoromethyl)pyridin-2-yl)amino)piperidin-1-yl)methanone |
| 21 | 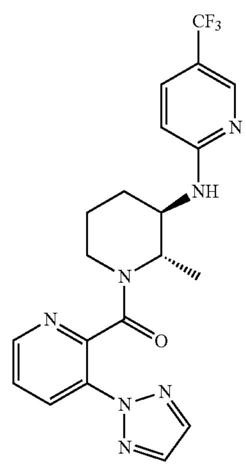 [SMILES: C[C@H]1[C@H](Nc2ccc(C(F)(F)F)cn2)CCCN1C(=O)c1ncccc1-n1nccn1] | 19 | 25 | 595 | (±)-trans-(3-(2H-1,2,3-triazol-2-yl)pyridin-2-yl)(2-methyl-3-((5-(trifluoromethyl)pyridin-2-yl)amino)piperidin-1-yl)methanone |
| 22 | 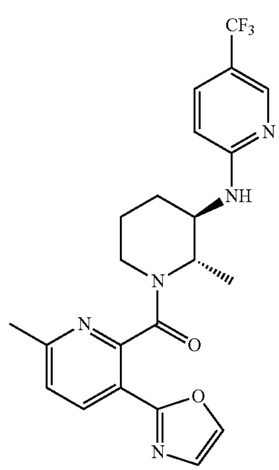 [SMILES: Cc1ccc(-c2ncco2)c(C(=O)N2CCC[C@@H](Nc3ccc(C(F)(F)F)cn3)[C@@H]2C)n1] | 33 | 19 | 422 | (±)-trans-(2-methyl-3-((5-(trifluoromethyl)pyridin-2-yl)amino)piperidin-1-yl)(6-methyl-3-(oxazol-2-yl)pyridin-2-yl)methanone |

-continued

| Ex. | Structure | rOX1 K$_i$ (nm) | hOX1 K$_i$ (nm) | hOX2 K$_i$ (nm) | Compound Name |
|---|---|---|---|---|---|
| 23 | 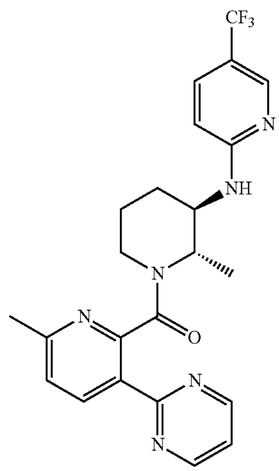 [SMILES: Cc1ccc(-c2ncccn2)c(C(=O)N2CCC[C@@H](Nc3ccc(C(F)(F)F)cn3)[C@@H]2C)n1] | 36 | 23 | 208 | (±)-trans-(2-methyl-3-((5-(trifluoromethyl)pyridin-2-yl)amino)piperidin-1-yl)(6-methyl-3-(pyrimidin-2-yl)pyridin-2-yl)methanone |
| 24 | 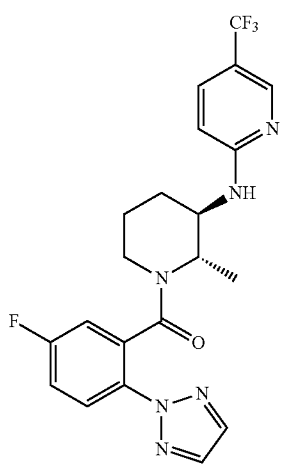 [SMILES: C[C@H]1[C@H](Nc2ccc(C(F)(F)F)cn2)CCCN1C(=O)c1cc(F)ccc1-n1nccn1] | 8 | 16 | 324 | (±)-trans-(5-fluoro-2-(2H-1,2,3-triazol-2-yl)phenyl)(2-methyl-3-((5-(trifluoromethyl)pyridin-2-yl)amino)piperidin-1-yl)methanone |
| 25 | 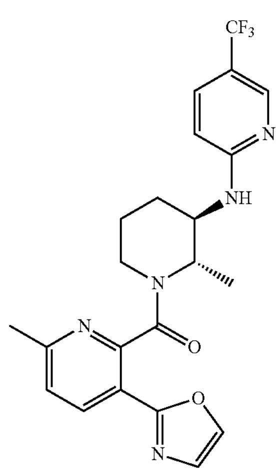 [SMILES: Cc1ccc(-c2ncco2)c(C(=O)N2CCC[C@@H](Nc3ccc(C(F)(F)F)cn3)[C@@H]2C)n1] | 11 | 19 | 190 | ((2S,3R)-2-methyl-3-((5-(trifluoromethyl)pyridin-2-yl)amino)piperidin-1-yl)(6-methyl-3-(oxazol-2-yl)pyridin-2-yl)methanone |

-continued

| Ex. | Structure | rOX1 K$_i$ (nm) | hOX1 K$_i$ (nm) | hOX2 K$_i$ (nm) | Compound Name |
|---|---|---|---|---|---|
| 26 | 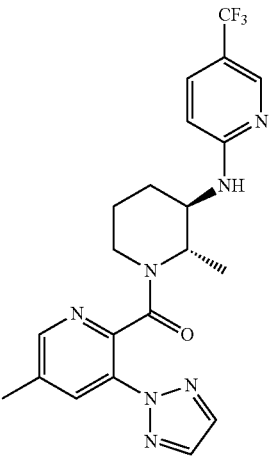 | 11 | 14 | 2035 | ((2S,3R)-2-methyl-3-((5-(trifluoromethyl)pyridin-2-yl)amino)piperidin-1-yl)(5-methyl-3-(2H-1,2,3-triazol-2-yl)pyridin-2-yl)methanone |
| 27 | 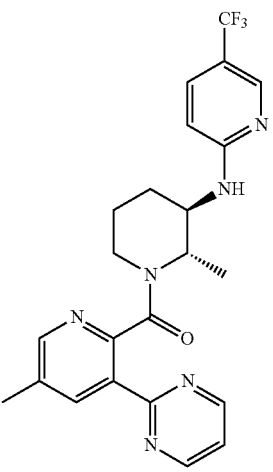 [SMILES: Cc1cnc(C(=O)N2CCC[C@@H](Nc3ccc(C(F)(F)F)cn3)[C@@H]2C)c(-c2ncccn2)c1] | 19 | 26 | 91 | ((2S,3R)-2-methyl-3-((5-(trifluoromethyl)pyridin-2-yl)amino)piperidin-1-yl)(5-methyl-3-(pyrimidin-2-yl)pyridin-2-yl)methanone |
| 28 | 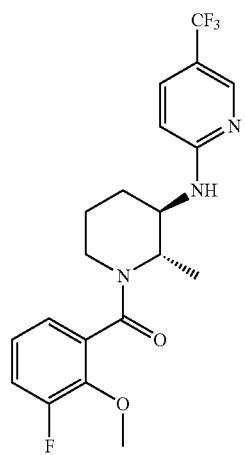 [SMILES: COc1c(F)cccc1C(=O)N1CCC[C@@H](Nc2ccc(C(F)(F)F)cn2)[C@@H]1C] | 496 | | 3900 | (±)-trans-(3-fluoro-2-methoxyphenyl)(2-methyl-3-((5-(trifluoromethyl)pyridin-2-yl)amino)piperidin-1-yl)methanone |

| Ex. | Structure | rOX1 $K_i$ (nm) | hOX1 $K_i$ (nm) | hOX2 $K_i$ (nm) | Compound Name |
|---|---|---|---|---|---|
| 29 | 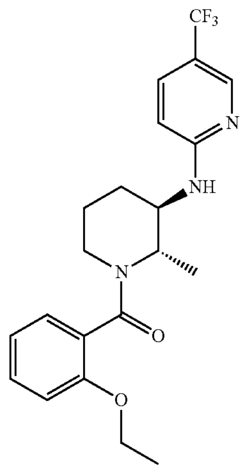 | 97 | 90 | 1400 | (±)-trans-(2-ethoxyphenyl)(2-methyl-3-((5-(trifluoromethyl)pyridin-2-yl)amino)piperidin-1-yl)methanone |
| 30 | 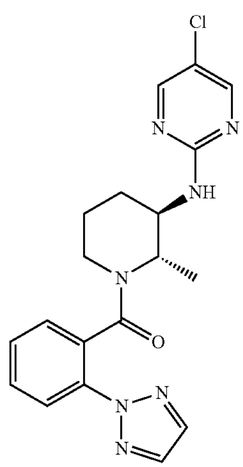 [SMILES: C[C@H]1[C@H](Nc2ncc(Cl)cn2)CCCN1C(=O)c1ccccc1-n1nccn1] | 55 | 54 | 656 | (±)-trans-(2-(2H-1,2,3-triazol-2-yl)phenyl)(3-((5-chloropyrimidin-2-yl)amino)-2-methylpiperidin-1-yl)methanone |
| 31 | 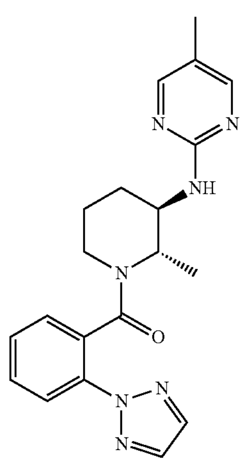 [SMILES: Cc1cnc(N[C@@H]2CCCN(C(=O)c3ccccc3-n3nccn3)[C@H]2C)nc1] | 131 | 120 | 508 | (±)-trans-(2-(2H-1,2,3-triazol-2-yl)phenyl)(2-methyl-3-((5-methylpyrimidin-2-yl)amino)piperidin-1-yl)methanone |

-continued

| Ex. | Structure | rOX1 K$_i$ (nm) | hOX1 K$_i$ (nm) | hOX2 K$_i$ (nm) | Compound Name |
|---|---|---|---|---|---|
| 32 | 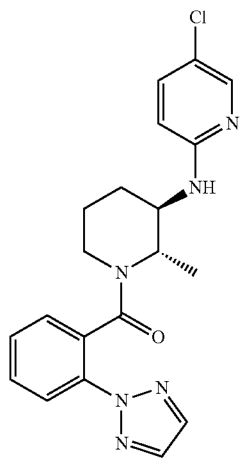 | 34 | 12 | 286 | (±)-trans-(2-(2H-1,2,3-triazol-2-yl)phenyl)(3-((5-chloropyridin-2-yl)amino)-2-methylpiperidin-1-yl)methanone |
| 33 | 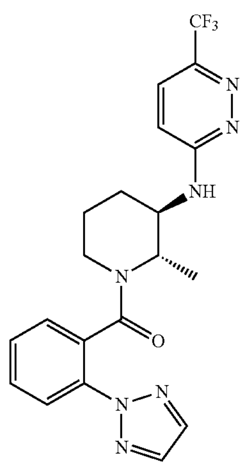 [SMILES: C[C@H]1[C@H](Nc2ccc(C(F)(F)F)nn2)CCCN1C(=O)c1ccccc1-n1nccn1] | 199 | 160 | 4800 | (±)-trans-(2-(2H-1,2,3-triazol-2-yl)phenyl)(2-methyl-3-((6-(trifluoromethyl)pyridazin-3-yl)amino)piperidin-1-yl)methanone |
| 34 | 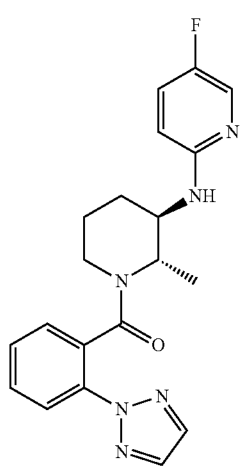 | 355 | | 700 | (2-(2H-1,2,3-triazol-2-yl)phenyl)((2S,3R)-3-((5-fluoropyridin-2-yl)amino)-2-methylpiperidin-1-yl)methanone |

| Ex. | Structure | rOX1 $K_i$ (nm) | hOX1 $K_i$ (nm) | hOX2 $K_i$ (nm) | Compound Name |
|---|---|---|---|---|---|
| 35 | 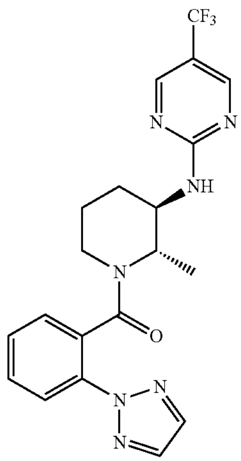 | 20 | 29 | 738 | (±)-trans-(2-(2H-1,2,3-triazol-2-yl)phenyl)(2-methyl-3-((5-(trifluoromethyl)pyrimidin-2-yl)amino)piperidin-1-yl)methanone |
| 36 | 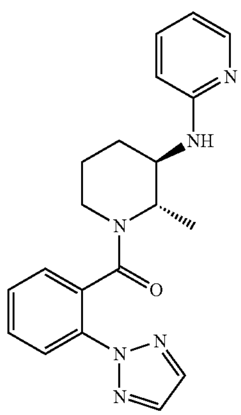 [SMILES: C[C@H]1[C@H](Nc2ccccn2)CCCN1C(=O)c1ccccc1-n1nccn1] | | 690 | 1500 | (±)-trans-(2-(2H-1,2,3-triazol-2-yl)phenyl)(2-methyl-3-(pyridin-2-ylamino)piperidin-1-yl)methanone |
| 37 | 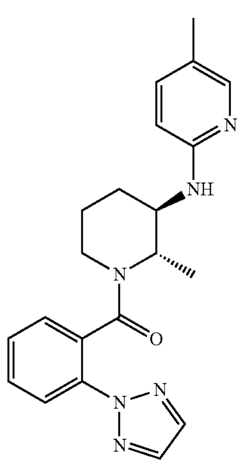 [SMILES: Cc1ccc(N[C@@H]2CCCN(C(=O)c3ccccc3-n3nccn3)[C@H]2C)nc1] | 76 | 71 | 824 | (±)-trans-(2-(2H-1,2,3-triazol-2-yl)phenyl)(2-methyl-3-((5-methylpyridin-2-yl)amino)piperidin-1-yl)methanone |

| Ex. | Structure | rOX1 K$_i$ (nm) | hOX1 K$_i$ (nm) | hOX2 K$_i$ (nm) | Compound Name |
|---|---|---|---|---|---|
| 38 | 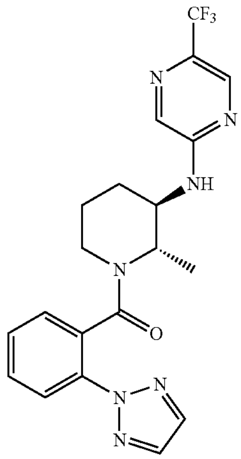 [SMILES: C[C@H]1[C@H](Nc2cnc(C(F)(F)F)cn2)CCCN1C(=O)c1ccccc1-n1nccn1] | 18 | 25 | 529 | (±)-trans-(2-(2H-1,2,3-triazol-2-yl)phenyl)(2-methyl-3-((5-(trifluoromethyl)pyrazin-2-yl)amino)piperidin-1-yl)methanone |
| 39 | 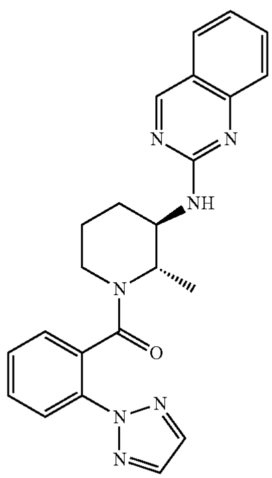 [SMILES: C[C@H]1[C@H](Nc2ncc3ccccc3n2)CCCN1C(=O)c1ccccc1-n1nccn1] | 32 | 12 | 189 | (±)-trans-(2-(2H-1,2,3-triazol-2-yl)phenyl)(2-methyl-3-(quinazolin-2-ylamino)piperidin-1-yl)methanone |
| 40 | 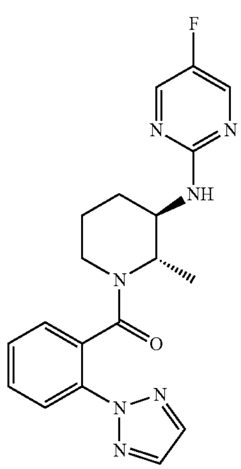 [SMILES: C[C@H]1[C@H](Nc2ncc(F)cn2)CCCN1C(=O)c1ccccc1-n1nccn1] | | 870 | 822 | (±)-trans-(2-(2H-1,2,3-triazol-2-yl)phenyl)(3-((5-fluoropyrimidin-2-yl)amino)-2-methylpiperidin-1-yl)methanone |

-continued

| Ex. | Structure | rOX1 $K_i$ (nm) | hOX1 $K_i$ (nm) | hOX2 $K_i$ (nm) | Compound Name |
|---|---|---|---|---|---|
| 41 | 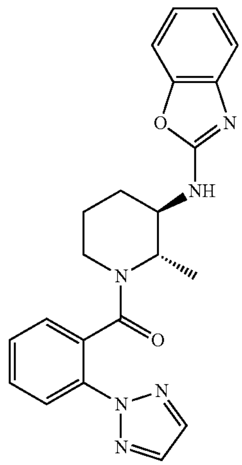 [SMILES: C[C@H]1[C@H](Nc2nc3ccccc3o2)CCCN1C(=O)c1ccccc1-n1nccn1] | 9 | 9 | 284 | (±)-trans-(2-(2H-1,2,3-triazol-2-yl)phenyl)(3-(benzo[d]oxazol-2-ylamino)-2-methylpiperidin-1-yl)methanone |
| 42 | 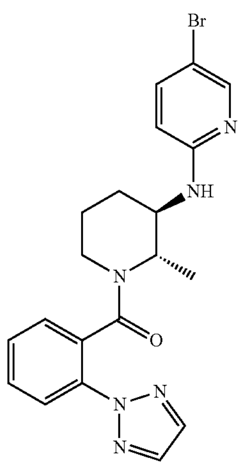 | 11 | 10 | 410 | (±)-trans-(2-(2H-1,2,3-triazol-2-yl)phenyl)(3-((5-bromopyridin-2-yl)amino)-2-methylpiperidin-1-yl)methanone |
| 43 | 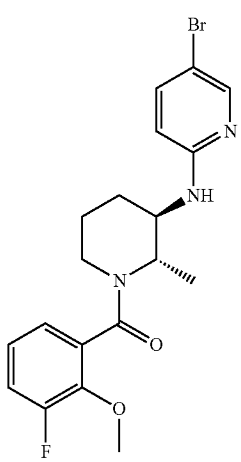 [SMILES: COc1c(F)cccc1C(=O)N1CCC[C@@H](Nc2ccc(Br)cn2)[C@@H]1C] | | 715 | 4600 | (±)-trans-(3-((5-bromopyridin-2-yl)amino)-2-methylpiperidin-1-yl)(3-fluoro-2-methoxyphenyl)methanone |

-continued

| Ex. | Structure | rOX1 $K_i$ (nm) | hOX1 $K_i$ (nm) | hOX2 $K_i$ (nm) | Compound Name |
|---|---|---|---|---|---|
| 44 | 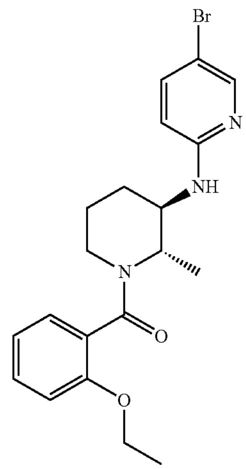 [SMILES: CCOc1ccccc1C(=O)N1CCC[C@@H](Nc2ccc(Br)cn2)[C@@H]1C] | 82 | 72 | 1600 | (±)-trans-(3-(5-bromopyridin-2-yl)amino)-2-methylpiperidin-1-yl)(2-ethoxyphenyl)methanone |
| 45 | 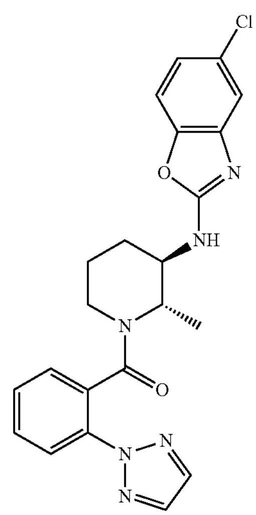 [SMILES: C[C@H]1[C@H](Nc2nc3cc(Cl)ccc3o2)CCCN1C(=O)c1ccccc1-n1nccn1] | 28 | 26 | 281 | (±)-trans-(2-(2H-1,2,3-triazol-2-yl)phenyl)(3-((5-chlorobenzo[d]oxazol-2-yl)amino)-2-methylpiperidin-1-yl)methanone |
| 46 | 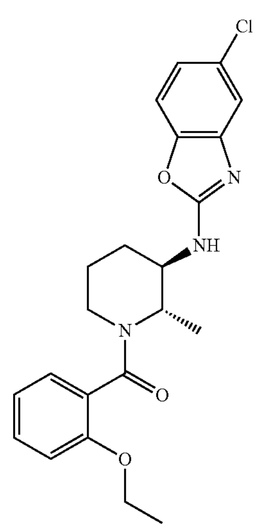 [SMILES: CCOc1ccccc1C(=O)N1CCC[C@@H](Nc2nc3cc(Cl)ccc3o2)[C@@H]1C] | 185 | 153 | 489 | (±)-trans-(3-((5-chlorobenzo[d]oxazol-2-yl)amino)-2-methylpiperidin-1-yl)(2-ethoxyphenyl)methanone |

-continued

| Ex. | Structure | rOX1 K$_i$ (nm) | hOX1 K$_i$ (nm) | hOX2 K$_i$ (nm) | Compound Name |
|---|---|---|---|---|---|
| 47 | 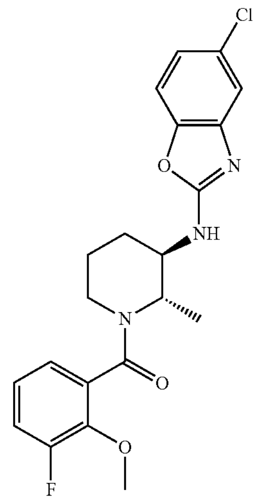 [SMILES: COc1c(F)cccc1C(=O)N1CCC[C@@H](Nc2nc3cc(Cl)ccc3o2)[C@@H]1C] | 373 | | 1300 | (±)-trans-(3-((5-chlorobenzo[d]oxazol-2-yl)amino)-2-methylpiperidin-1-yl)(3-fluoro-2-methoxyphenyl)methanone |
| 48 | 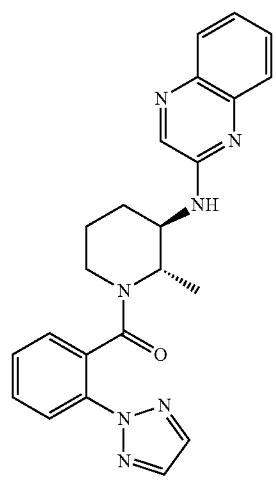 [SMILES: C[C@H]1[C@H](Nc2cnc3ccccc3n2)CCCN1C(=O)c1ccccc1-n1nccn1] | 14 | 11 | 96 | (±)-trans-(2-(2H-1,2,3-triazol-2-yl)phenyl)(2-methyl-3-(quinoxalin-2-ylamino)piperidin-1-yl)methanone |
| 49 | 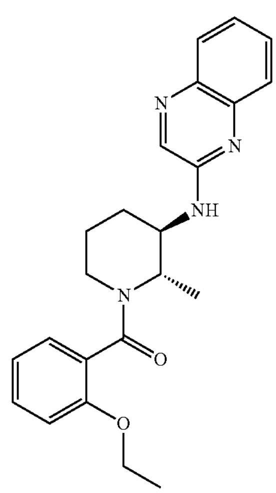 [SMILES: CCOc1ccccc1C(=O)N1CCC[C@@H](Nc2cnc3ccccc3n2)[C@@H]1C] | 95 | 70 | 89 | (±)-trans-((2-ethoxyphenyl)(2-methyl-3-(quinoxalin-2-ylamino)piperidin-1-yl)methanone |

-continued

| Ex. | Structure | rOX1 $K_i$ (nm) | hOX1 $K_i$ (nm) | hOX2 $K_i$ (nm) | Compound Name |
|---|---|---|---|---|---|
| 50 | 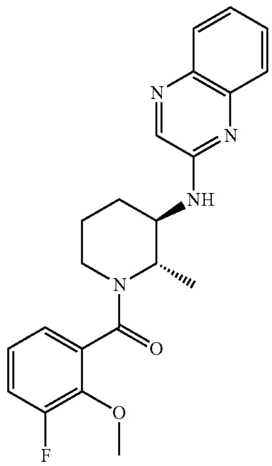 [SMILES: COc1c(F)cccc1C(=O)N1CCC[C@@H](Nc2cnc3ccccc3n2)[C@@H]1C] | | 396 | 353 | (±)-trans-(3-fluoro-2-methoxyphenyl)(2-methyl-3-(quinoxalin-2-ylamino)piperidin-1-yl)methanone |
| 51 | 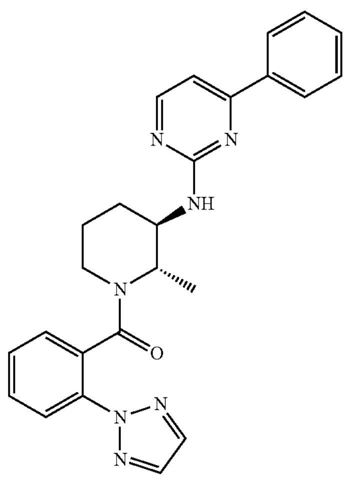 [SMILES: C[C@H]1[C@H](Nc2nccc(-c3ccccc3)n2)CCCN1C(=O)c1ccccc1-n1nccn1] | | 341 | 2100 | (±)-trans-(2-(2H-1,2,3-triazol-2-yl)phenyl)(2-methyl-3-((4-phenylpyrimidin-2-yl)amino)piperidin-1-yl)methanone |
| 52 | 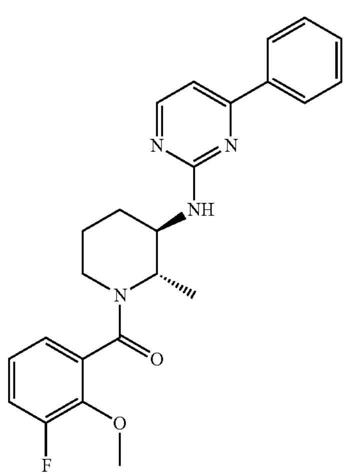 [SMILES: COc1c(F)cccc1C(=O)N1CCC[C@@H](Nc2nccc(-c3ccccc3)n2)[C@@H]1C] | | 6200 | 2700 | (±)-trans-(3-fluoro-2-methoxyphenyl)(2-methyl-3-((4-phenylpyrimidin-2-yl)amino)piperidin-1-yl)methanone |

-continued

| Ex. | Structure | rOX1 K$_i$ (nm) | hOX1 K$_i$ (nm) | hOX2 K$_i$ (nm) | Compound Name |
|---|---|---|---|---|---|
| 53 | 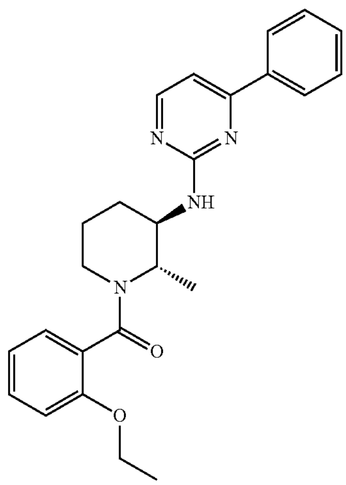 [SMILES: CCOc1ccccc1C(=O)N1CCC[C@@H](Nc2nccc(-c3ccccc3)n2)[C@@H]1C] | 715 | | 58 | (±)-trans-(2-ethoxyphenyl)(2-methyl-3-((4-phenylpyrimidin-2-yl)amino)piperidin-1-yl)methanone |
| 54 | 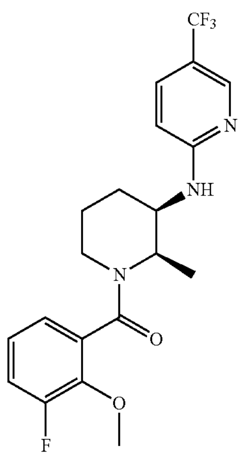 [SMILES: COc1c(F)cccc1C(=O)N1CCC[C@@H](Nc2ccc(C(F)(F)F)cn2)[C@H]1C] | 4500 | | >10000 | (±)-cis-(3-fluoro-2-methoxyphenyl)(2-methyl-3-((5-(trifluoromethyl)pyridin-2-yl)amino)piperidin-1-yl)methanone |
| 55 | 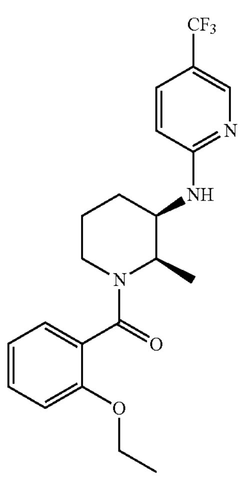 | 1200 | | >10000 | (±)-cis-(2-ethoxyphenyl)(2-methyl-3-((5-(trifluoromethyl)pyridin-2-yl)amino)piperidin-1-yl)methanone |

-continued

| Ex. | Structure | rOX1 $K_i$ (nm) | hOX1 $K_i$ (nm) | hOX2 $K_i$ (nm) | Compound Name |
|---|---|---|---|---|---|
| 56 | 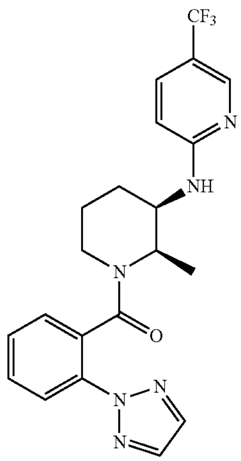 [SMILES: C[C@@H]1[C@H](Nc2ccc(C(F)(F)F)cn2)CCCN1C(=O)c1ccccc1-n1nccn1] | 128 | 112 | 3600 | (±)-cis-(2-(2H-1,2,3-triazol-2-yl)phenyl)(2-methyl-3-((5-(trifluoromethyl)pyridin-2-yl)amino)piperidin-1-yl)methanone |
| 57 | 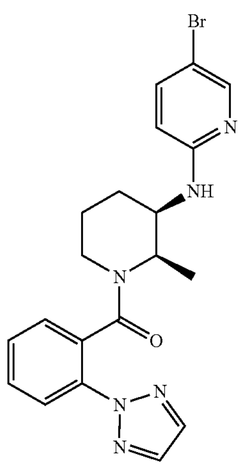 [SMILES: C[C@@H]1[C@H](Nc2ccc(Br)cn2)CCCN1C(=O)c1ccccc1-n1nccn1] | 720 | | >10000 | (±)-cis-(2-(2H-1,2,3-triazol-2-yl)phenyl)(3-((5-bromopyridin-2-yl)amino)-2-methylpiperidin-1-yl)methanone |
| 58 | 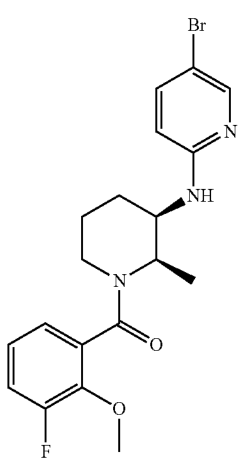 [SMILES: COc1c(F)cccc1C(=O)N1CCC[C@@H](Nc2ccc(Br)cn2)[C@H]1C] | >10000 | | >10000 | (±)-cis-(3-(5-bromopyridin-2-yl)amino)-2-methylpiperidin-1-yl)(3-fluoro-2-methoxyphenyl)methanone |

-continued

| Ex. | Structure | rOX1 K$_i$ (nm) | hOX1 K$_i$ (nm) | hOX2 K$_i$ (nm) | Compound Name |
|---|---|---|---|---|---|
| 59 | 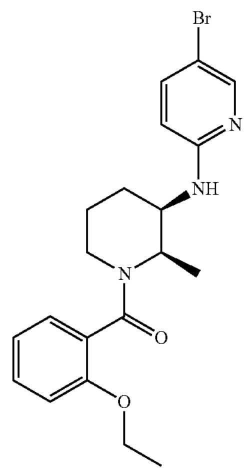 [SMILES: CCOc1ccccc1C(=O)N1CCC[C@@H](Nc2ccc(Br)cn2)[C@H]1C] | 1800 | | >10000 | (±)-cis-(3-(5-bromopyridin-2-yl)amino)-2-methylpiperidin-1-yl)(2-ethoxyphenyl)methanone |
| 60 | 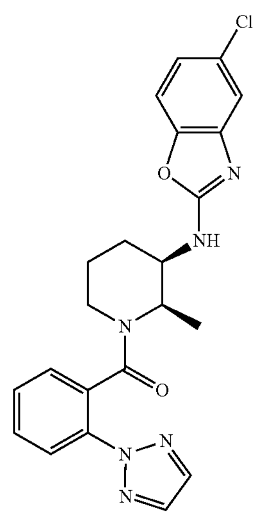 [SMILES: C[C@@H]1[C@H](Nc2nc3cc(Cl)ccc3o2)CCCN1C(=O)c1ccccc1-n1nccn1] | >10000 | | >10000 | (±)-cis-((2-(2H-1,2,3-triazol-2-yl)phenyl)(3-((5-chlorobenzo[d]oxazol-2-yl)amino)-2-methylpiperidin-1-yl)methanone |
| 61 | 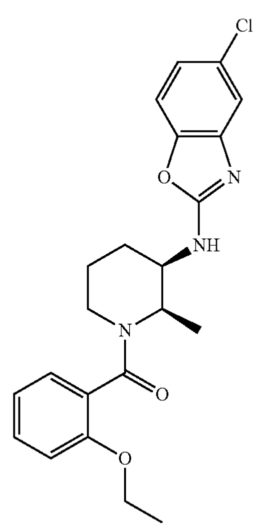 [SMILES: CCOc1ccccc1C(=O)N1CCC[C@@H](Nc2nc3cc(Cl)ccc3o2)[C@H]1C] | 1100 | | 2500 | (±)-cis-(3-((5-chlorobenzo[d]oxazol-2-yl)amino)-2-methylpiperidin-1-yl)(2-ethoxyphenyl)methanone |

-continued

| Ex. | Structure | rOX1 K$_i$ (nm) | hOX1 K$_i$ (nm) | hOX2 K$_i$ (nm) | Compound Name |
|---|---|---|---|---|---|
| 62 | 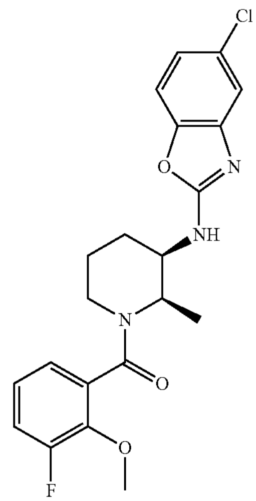 [SMILES: COc1c(F)cccc1C(=O)N1CCC[C@@H](Nc2nc3cc(Cl)ccc3o2)[C@H]1C] | | 1800 | 5700 | (±)-cis-(3-((5-chlorobenzo[d]oxazol-2-yl)amino)-2-methylpiperidin-1-yl)(3-fluoro-2-methoxyphenyl)methanone |
| 63 | 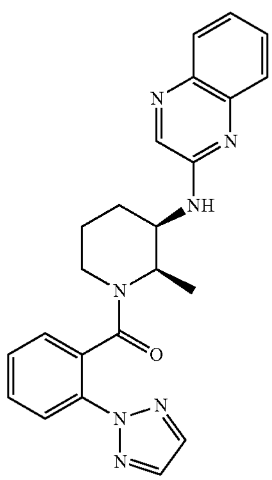 [SMILES: C[C@@H]1[C@H](Nc2cnc3ccccc3n2)CCCN1C(=O)c1ccccc1-n1nccn1] | | 3300 | >10000 | (±)-cis-(2-(2H-1,2,3-triazol-2-yl)phenyl)(2-methyl-3-(quinoxalin-2-ylamino)piperidin-1-yl)methanone |
| 64 | 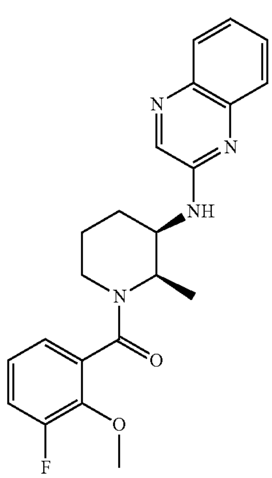 [SMILES: COc1c(F)cccc1C(=O)N1CCC[C@@H](Nc2cnc3ccccc3n2)[C@H]1C] | | 1100 | 1300 | (±)-cis-(3-fluoro-2-methoxyphenyl)(2-methyl-3-(quinoxalin-2-ylamino)piperidin-1-yl)methanone |

-continued

| Ex. | Structure | rOX1 K$_i$(nm) | hOX1 K$_i$(nm) | hOX2 K$_i$(nm) | Compound Name |
|---|---|---|---|---|---|
| 65 | 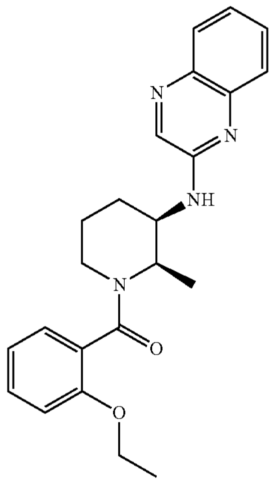 [SMILES: CCOc1ccccc1C(=O)N1CCC[C@@H](Nc2cnc3ccccc3n2)[C@H]1C] | | 314 | 295 | (±)-cis-(2-ethoxyphenyl)(2-methyl-3-(quinoxalin-2-ylamino)piperidin-1-yl)methanone |
| 66 | 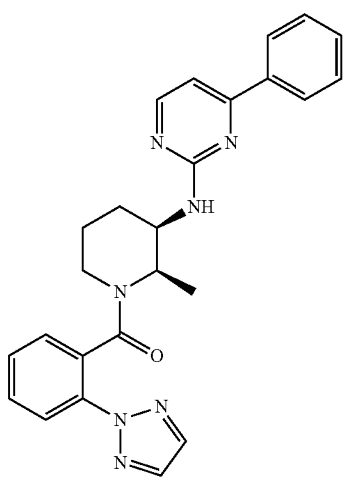 [SMILES: C[C@@H]1[C@H](Nc2nccc(-c3ccccc3)n2)CCCN1C(=O)c1ccccc1-n1nccn1] | | 570 | 1800 | (±)-cis-(2-(2H-1,2,3-triazol-2-yl)phenyl)(2-methyl-3-((4-phenylpyrimidin-2-yl)amino)piperidin-1-yl)methanone |
| 67 | 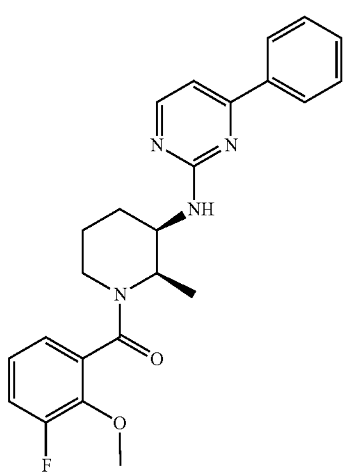 [SMILES: COc1c(F)cccc1C(=O)N1CCC[C@@H](Nc2nccc(-c3ccccc3)n2)[C@H]1C] | | 840 | >10000 | (±)-cis-(3-fluoro-2-methoxyphenyl)(2-methyl-3-((4-phenylpyrimidin-2-yl)amino)piperidin-1-yl)methanone |

-continued

| Ex. | Structure | rOX1 K$_i$ (nm) | hOX1 K$_i$ (nm) | hOX2 K$_i$ (nm) | Compound Name |
|---|---|---|---|---|---|
| 68 | 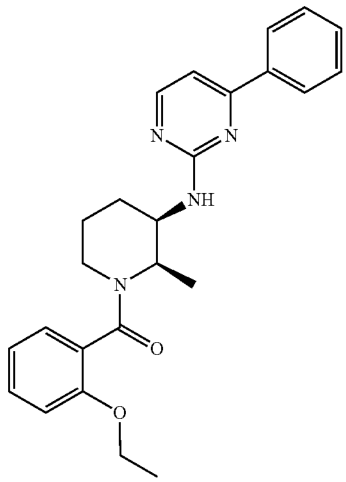 [SMILES: CCOc1ccccc1C(=O)N1CCC[C@@H](Nc2nccc(-c3ccccc3)n2)[C@H]1C] | 1400 | | >10000 | (±)-cis-(2-ethoxyphenyl)(2-methyl-3-((4-phenylpyrimidin-2-yl)amino)piperidin-1-yl)methanone |
| 69 | 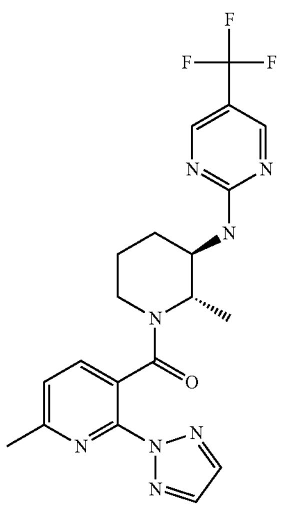 | 70 | 112 | >10000 | (6-methyl-2-(2H-1,2,3-triazol-2-yl)pyridin-3-yl)((2S,3R)-2-methyl-3-((5-(trifluoromethyl)pyrimidin-2-yl)amino)piperidin-1-yl)methanone |
| 70 | 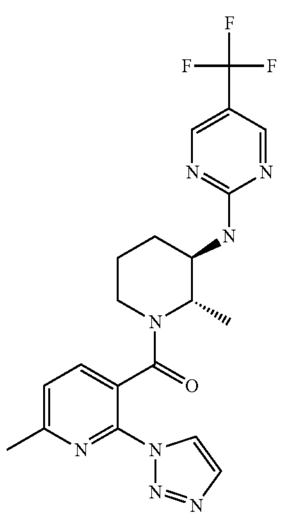 [SMILES: Cc1ccc(C(=O)N2CCC[C@@H](Nc3ncc(C(F)(F)F)cn3)[C@@H]2C)c(-n2ccnn2)n1] | 170 | 165 | 7501 | (6-methyl-2-1H-1,2,3-triazol-1-yl)pyridin-3-yl)((2S,3R)-2-methyl-3-((5-(trifluoromethyl)pyrimidin-2-yl)amino)piperidin-1-yl)methanone |

-continued

| Ex. | Structure | rOX1 K$_i$ (nm) | hOX1 K$_i$ (nm) | hOX2 K$_i$ (nm) | Compound Name |
|---|---|---|---|---|---|
| 71 | 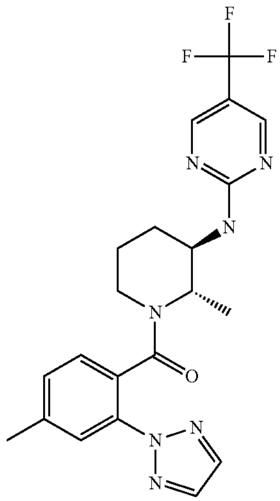 | 10 | 12 | 1500 | (4-methyl-2-(2H-1,2,3-triazol-2-yl)phenyl)((2S,3R)-2-methyl-3-((5-(trifluoromethyl)pyrimidin-2-yl)amino)piperidin-1-yl)methanone |
| 72 | 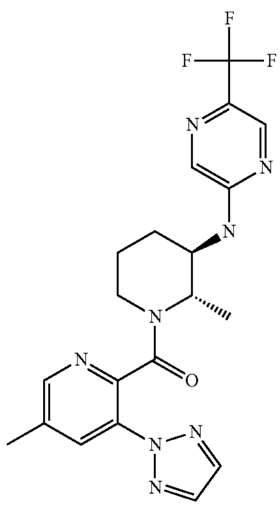 | 24 | 33 | 4025 | ((2S,3R)-2-methyl-3-((5-(trifluoromethyl)pyrazin-2-yl)amino)piperidin-1-yl)(5-methyl-3-(2H-1,2,3-triazol-2-yl)pyridin-2-yl)methanone |
| 73 | 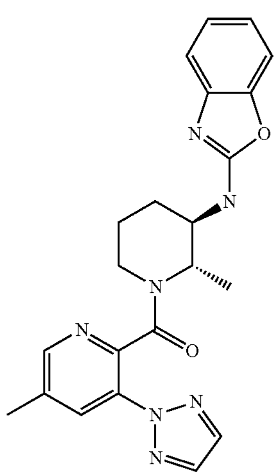 | 7 | 21 | 1889 | ((2S,3R)-3-(benzo[d]oxazol-2-ylamino)-2-methylpiperidin-1-yl)(5-methyl-3-(2H-1,2,3-triazol-2-yl)pyridin-2-yl)methanone |

-continued

| Ex. | Structure | rOX1 K$_i$ (nm) | hOX1 K$_i$ (nm) | hOX2 K$_i$ (nm) | Compound Name |
|---|---|---|---|---|---|
| 74 | 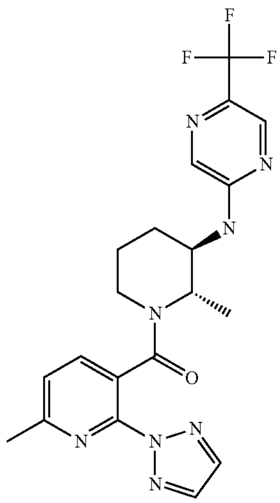 | 40 | 52 | >10000 | (6-methyl-2-2H-1,2,3-triazol-2-yl)pyridin-3-yl)((2S,3R)-2-methyl-3-((5-(trifluoromethyl)pyrazin-2-yl)amino)piperidin-1-yl)methanone |
| 75 | 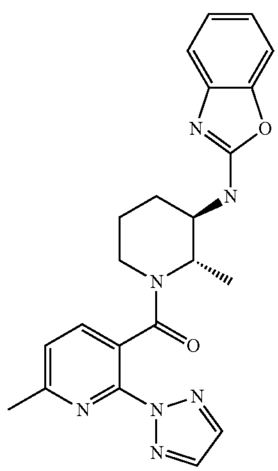 | 23 | 40 | 9499 | ((2S,3R)-3-(benzo[d]oxazol-2-ylamino)-2-methylpiperidin-1-yl)(6-methyl-2-(2H-1,2,3-triazol-2-yl)pyridin-3-yl)methanone |
| 76 | 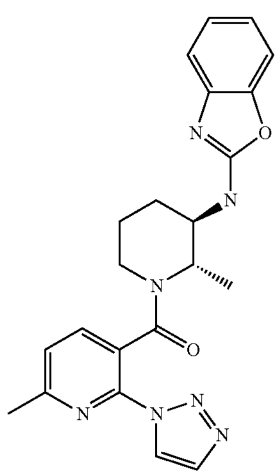 | 54 | 62 | 1300 | ((2S,3R)-3-(benzo[d]oxazol-2-ylamino)-2-methylpiperidin-1-yl)(6-methyl-2-(1H-1,2,3-triazol-1-yl)pyridin-3-yl)methanone |

-continued

| Ex. | Structure | rOX1 K$_i$ (nm) | hOX1 K$_i$ (nm) | hOX2 K$_i$ (nm) | Compound Name |
|---|---|---|---|---|---|
| 77 | 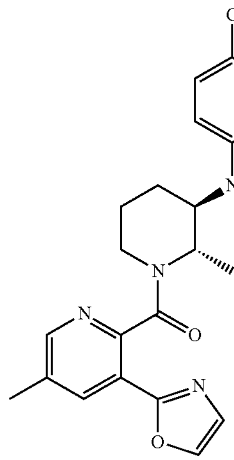 | 36 | 55 | 4018 | ((2S,3R)-3-((5-chloropyridin-2-yl)amino)-2-methylpiperidin-1-yl)(5-methyl-3-(oxazol-2-yl)pyridin-2-yl)methanone |
| 78 | 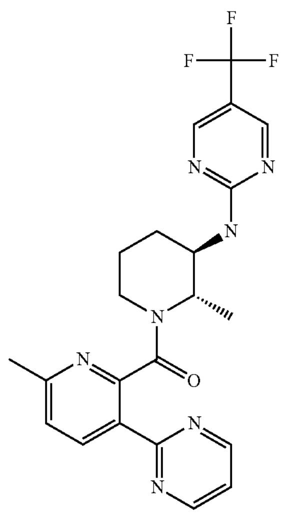 | 30 | 57 | 436 | ((2S,3R)-2-methyl-3-((5-(trifluoromethyl)pyrimidin-2-yl)amino)piperidin-1-yl)(6-methyl-3-(pyrimidin-2-yl)pyridin-2-yl)methanone |
| 79 | 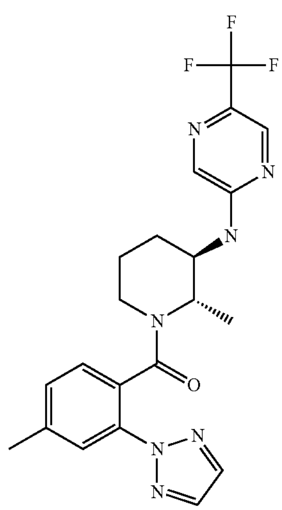 | 8 | 7 | 1300 | (4-methyl-2-(2H-1,2,3-triazol-2-yl)phenyl)((2S,3R)-2-methyl-3-((5-(trifluoromethyl)pyrazin-2-yl)amino)piperidin-1-yl)methanone |

-continued

| Ex. | Structure | rOX1 K$_i$ (nm) | hOX1 K$_i$ (nm) | hOX2 K$_i$ (nm) | Compound Name |
|---|---|---|---|---|---|
| 80 | 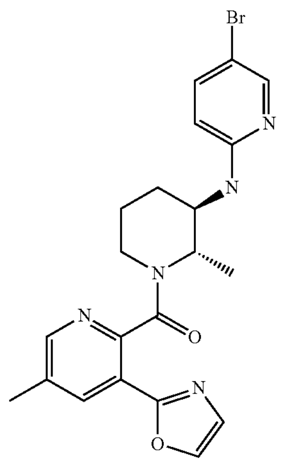 | 29 | 24 | 4900 | ((2S,3R)-3-((5-bromopyridin-2-yl)amino)-2-methylpiperidin-1-yl)(5-methyl-3-(oxazol-2-yl)pyridin-2-yl)methanone |
| 81 | 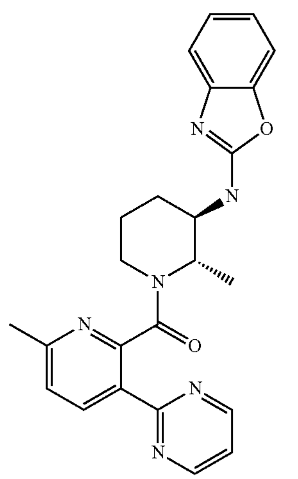 [SMILES: Cc1ccc(-c2ncccn2)c(C(=O)N2CCC[C@@H](Nc3nc4ccccc4o3)[C@@H]2C)n1] | 14 | 23 | 100 | ((2S,3R)-3-(benzo[d]oxazol-2-ylamino)-2-methylpiperidin-1-yl)(6-methyl-3-(pyrimidin-2-yl)pyridin-2-yl)methanone |
| 82 | 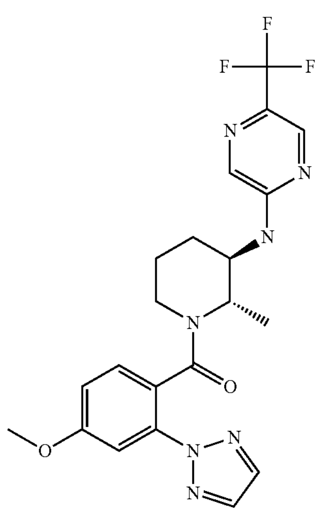 [SMILES: COc1ccc(C(=O)N2CCC[C@@H](Nc3cnc(C(F)(F)F)cn3)[C@@H]2C)c(-n2nccn2)c1] | 53 | 58 | 6400 | (4-methoxy-2-(2H-1,2,3-triazol-2-yl)phenyl)((2S,3R)-2-methyl-3-((5-(trifluoromethyl)pyrazin-2-yl)amino)piperidin-1-yl)methanone |

| Ex. | Structure | rOX1 K$_i$ (nm) | hOX1 K$_i$ (nm) | hOX2 K$_i$ (nm) | Compound Name |
|---|---|---|---|---|---|
| 83 | 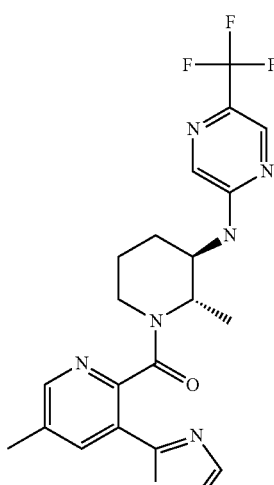 | 57 | 53 | 7000 | ((2S,3R)-2-methyl-3-((5-(trifluoromethyl)pyrazin-2-yl)amino)piperidin-1-yl)(5-methyl-3-(oxazol-2-yl)pyridin-2-yl)methanone |
| 84 | 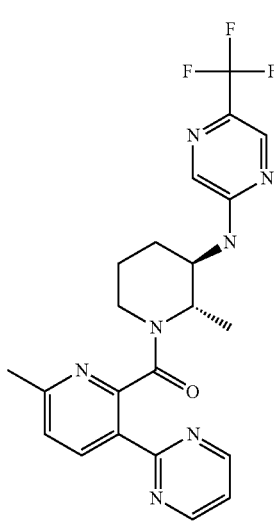 | 23 | 28 | 173 | ((2S,3R)-2-methyl-3-((5-(trifluoromethyl)pyrazin-2-yl)amino)piperidin-1-yl)(6-methyl-3-(pyrimidin-2-yl)pyridin-2-yl)methanone |
| 85 | 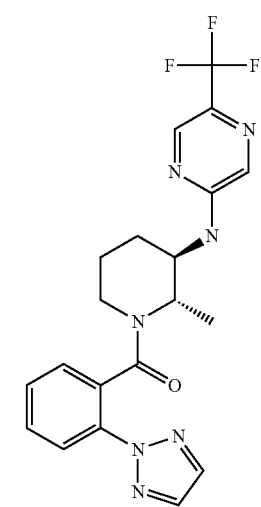 [SMILES: C[C@H]1[C@H](Nc2cnc(C(F)(F)F)cn2)CCCN1C(=O)c1ccccc1-n1nccn1] | 8 | 10 | 210 | (2-(2H-1,2,3-triazol-2-yl)phenyl)((2S,3R)-2-methyl-3-((5-(trifluoromethyl)pyrazin-2-yl)amino)piperidin-1-yl)methanone |

-continued

| Ex. | Structure | rOX1 K$_i$ (nm) | hOX1 K$_i$ (nm) | hOX2 K$_i$ (nm) | Compound Name |
|---|---|---|---|---|---|
| 86 | 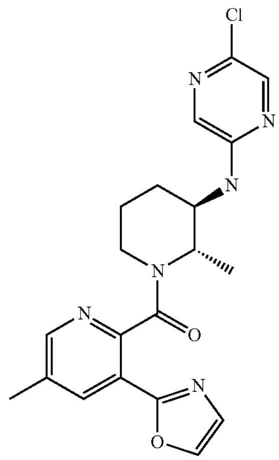 | 213 | 249 | >10000 | ((2S,3R)-3-((5-chloropyrazin-2-yl)amino)-2-methylpiperidin-1-yl)(5-methyl-3-(oxazol-2-yl)pyridin-2-yl)methanone |
| 87 | 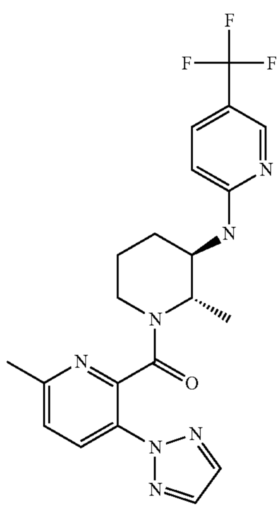 [SMILES: Cc1ccc(-n2nccn2)c(C(=O)N2CCC[C@@H](Nc3ccc(C(F)(F)F)cn3)[C@@H]2C)n1] | 7 | 12 | 154 | ((2S,3R)-2-methyl-3-((5-(trifluoromethyl)pyridin-2-yl)amino)piperidin-1-yl)(6-methyl-3-(2H-1,2,3-triazol-2-yl)pyridin-2-yl)methanone |
| 88 | 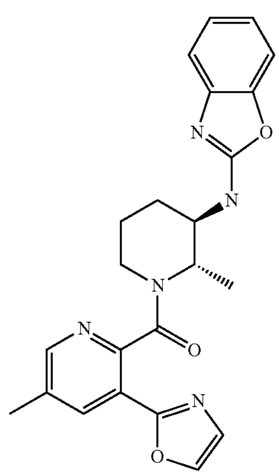 [SMILES: Cc1cnc(C(=O)N2CCC[C@@H](Nc3nc4ccccc4o3)[C@@H]2C)c(-c2ncco2)c1] | 13 | 25 | 3300 | ((2S,3R)-3-(benzo[d]oxazol-2-ylamino)-2-methylpiperidin-1-yl)(5-methyl-3-(oxazol-2-yl)pyridin-2-yl)methanone |

-continued
| Ex. | Structure | rOX1 K$_i$ (nm) | hOX1 K$_i$ (nm) | hOX2 K$_i$ (nm) | Compound Name |
|---|---|---|---|---|---|
| 89 | 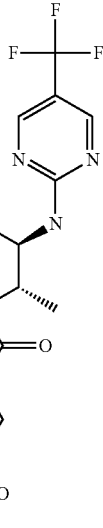 | 14 | 10 | 371 | (5-methoxy-2-(2H-1,2,3-triazol-2-yl)phenyl)((2S,3R)-2-methyl-3-((5-(trifluoromethyl)pyrimidin-2-yl)amino)piperidin-1-yl)methanone |
| 90 | 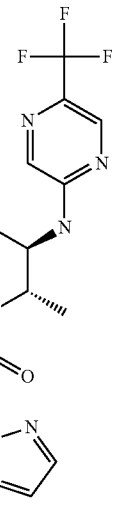 | 20 | 19 | 486 | (5-fluoro-2-(2H-1,2,3-triazol-2-yl)phenyl)((2S,3R)-2-methyl-3-((5-(trifluoromethyl)pyrazin-2-yl)amino)piperidin-1-yl)methanone |
| 91 | 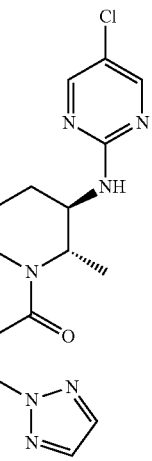 | 32 | 48 | 2100 | ((2S,3R)-3-((5-chloropyrimidin-2-yl)amino)-2-methylpiperidin-1-yl)(4-methyl-2-(2H-1,2,3-triazol-2-yl)phenyl)methanone |

-continued

| Ex. | Structure | rOX1 $K_i$ (nm) | hOX1 $K_i$ (nm) | hOX2 $K_i$ (nm) | Compound Name |
|---|---|---|---|---|---|
| 92 | 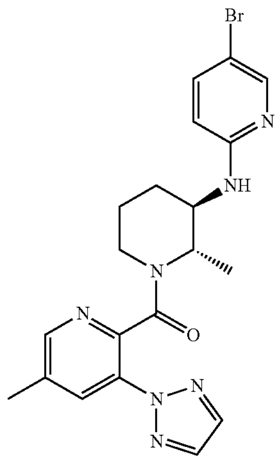 | 19 | 18 | 4200 | ((2S,3R)-3-((5-bromopyridin-2-yl)amino)-2-methylpiperidin-1-yl)(5-methyl-3-(2H-1,2,3-triazol-2-yl)pyridin-2-yl)methanone |
| 93 | 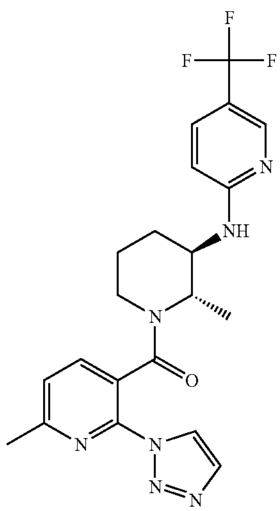 | 52 | 38 | 2700 | (6-methyl-2-(1H-1,2,3-triazol-1-yl)pyridin-3-yl)((2S,3R)-2-methyl-3-((5-(trifluoromethyl)pyridin-2-yl)amino)piperidin-1-yl)methanone |
| 94 | 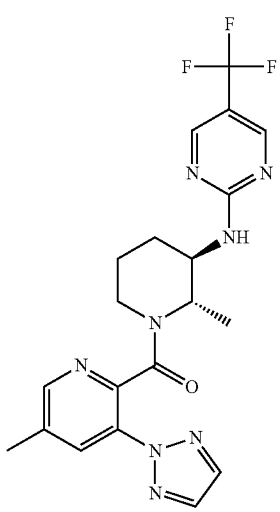 | 38 | 25 | >10000 | ((2S,3R)-2-methyl-3-((5-(trifluoromethyl)pyrimidin-2-yl)amino)piperidin-1-yl)(5-methyl-3-(2H-1,2,3-triazol-2-yl)pyridin-2-yl)methanone |

-continued

| Ex. | Structure | rOX1 K$_i$ (nm) | hOX1 K$_i$ (nm) | hOX2 K$_i$ (nm) | Compound Name |
|---|---|---|---|---|---|
| 95 | 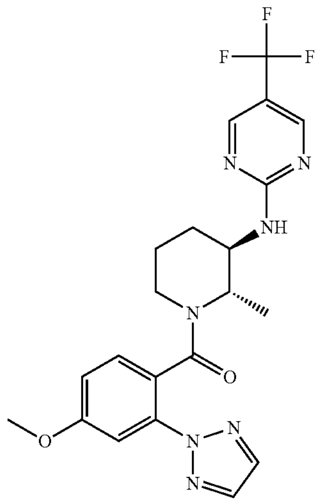 [SMILES: COc1ccc(C(=O)N2CCC[C@@H](Nc3ncc(C(F)(F)F)cn3)[C@@H]2C)c(-n2nccn2)c1] | 81 | 103 | >10000 | (4-methoxy-2-(2H-1,2,3-triazol-2-yl)phenyl)((2S,3R)-methyl-3-((5-(trifluoromethyl)pyrimidin-2-yl)amino)piperidin-1-yl)methanone |
| 96 | 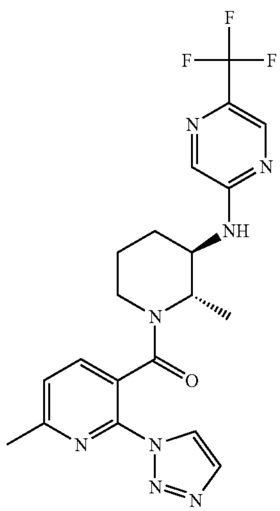 | 81 | 47 | 3900 | (6-methyl-2-(1H-1,2,3-triazol-1-yl)pyridin-3-yl)((2S,3R)-2-methyl-3-((5-(trifluororoethyl)pyrazin-2-yl)amino)piperidin-1-yl)methanone |
| 97 | 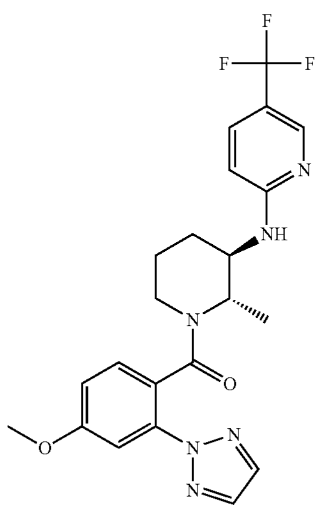 | 44 | 32 | 6100 | (4-methoxy-2-(2H-1,2,3-triazol-2-yl)phenyl)((2S,3R)-2-methyl-3-((5-(trifluoromethyl)pyridin-2-yl)amino)piperidin-1-yl)methanone |

| Ex. | Structure | rOX1 K_i (nm) | hOX1 K_i (nm) | hOX2 K_i (nm) | Compound Name |
|---|---|---|---|---|---|
| 98 | 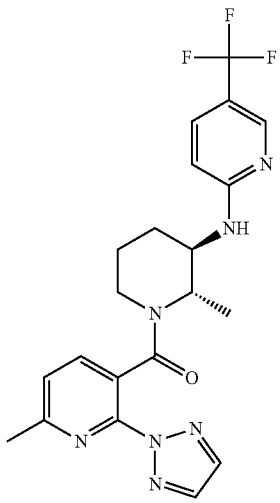 | 26 | 12 | >10000 | (6-methyl-2-(2H-1,2,3-triazol-2-yl)pyridin-3-yl)((2S,3R)-2-methyl-3-((5-(trifluoromethyl)pyridin-2-yl)amino)piperidin-1-yl)methanone |
| 99 | 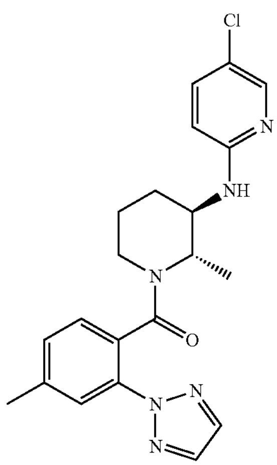 | 23 | 15 | 1400 | ((2S,3R)-3-((5-chloropyridin-2-yl)amino)-2-methylpiperidin-1-yl)(4-methyl-2-(2H-1,2,3-triazol-2-yl)phenyl)methanone |
| 100 | 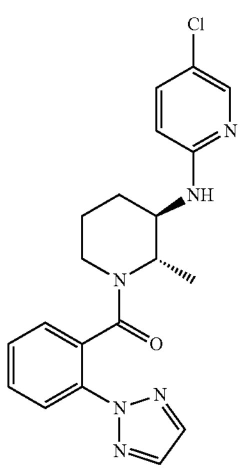 | 8 | 12 | 207 | (2-(2H-1,2,3-triazol-2-yl)phenyl)((2S,3R)-3-((5-chloropyridin-2-yl)amino)-2-methylpiperidin-1-yl)methanone |

-continued

| Ex. | Structure | rOX1 K$_i$ (nm) | hOX1 K$_i$ (nm) | hOX2 K$_i$ (nm) | Compound Name |
|---|---|---|---|---|---|
| 101 | 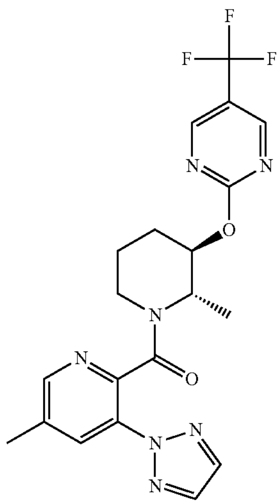 | 215 | 446 | >10000 | ((2S,3R)-2-methyl-3-((5-(trifluoromethyl)pyrimidin-2-yl)oxy)piperidin-1-yl)(5-methyl-3-(2H-1,2,3-triazol-2-yl)pyridin-2-yl)methanone |
| 102 | 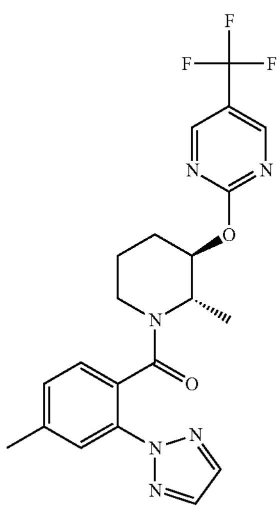 | 28 | 25 | 5200 | (4-methyl-2-(2H-1,2,3-triazol-2-yl)phenyl)((2S,3R)-2-methyl-3-((5-(trifluoromethyl)pyrimidin-2-yl)oxy)piperidin-1-yl)methanone |
| 103 | 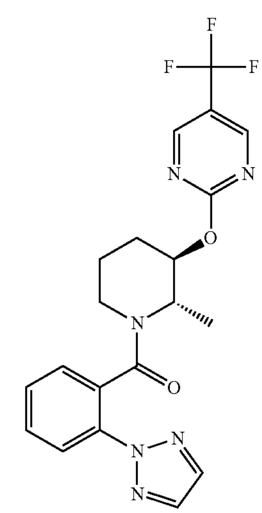 [SMILES: C[C@H]1[C@H](Oc2ncc(C(F)(F)F)cn2)CCCN1C(=O)c1ccccc1-n1nccn1] | 44 | 97 | 2300 | (2-(2H-1,2,3-triazol-2-yl)phenyl)((2S,3R)-2-methyl-3-((5-(trifluoromethyl)pyrimidin-2-yl)oxy)piperidin-1-yl)methanone |

-continued

| Ex. | Structure | rOX1 K$_i$ (nm) | hOX1 K$_i$ (nm) | hOX2 K$_i$ (nm) | Compound Name |
|---|---|---|---|---|---|
| 104 | 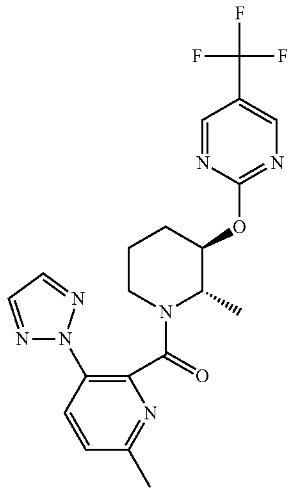 [SMILES: Cc1ccc(-n2nccn2)c(C(=O)N2CCC[C@@H](Oc3ncc(C(F)(F)F)cn3)[C@@H]2C)n1] | 119 | 173 | >10000 | ((2S,3R)-2-methyl-3-((5-(trifluoromethyl)pyrimidin-2-yl)oxy)piperidin-1-yl)(6-methyl-3-(2H-1,2,3-triazol-2-yl)pyridin-2-yl)methanone |
| 105 | 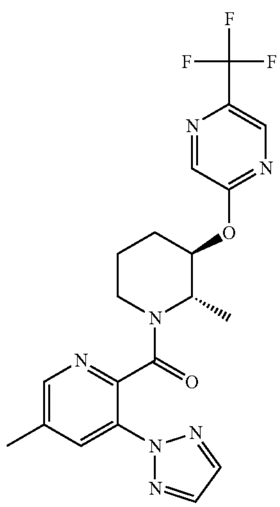 | | | | ((2S,3R)-2-methyl-3-((5-(trifluoromethyl)pyrazin-2-yl)oxy)piperidin-1-yl)(5-methyl-3-(2H-1,2,3-triazol-yl)pyridin-2-yl)methanone |
| 106 | 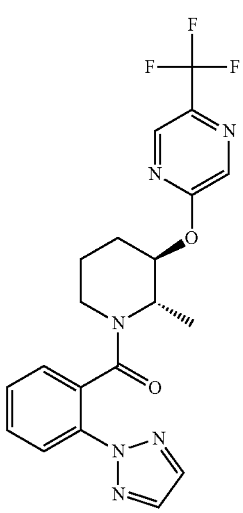 [SMILES: C[C@H]1[C@H](Oc2cnc(C(F)(F)F)cn2)CCCN1C(=O)c1ccccc1-n1nccn1] | | | | (2-(2H-1,2,3-triazol-2-yl)phenyl)((2S,3R)-2-methyl-3-((5-(trifluoromethyl)pyrazin-2-yl)oxy)piperidin-1-yl)methanone |

-continued

| Ex. | Structure | rOX1 K$_i$ (nm) | hOX1 K$_i$ (nm) | hOX2 K$_i$ (nm) | Compound Name |
|---|---|---|---|---|---|
| 107 | 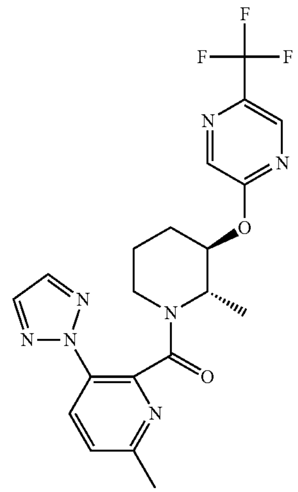 [SMILES: Cc1ccc(-n2nccn2)c(C(=O)N2CCC[C@@H](Oc3cnc(C(F)(F)F)cn3)[C@@H]2C)n1] | | | | ((2S,3R)-2-methyl-3-((5-(trifluoromethyl)pyrazin-2-yl)oxy)piperidin-1-yl)(6-methyl-3-(2H-1,2,3-triazol-2-yl)pyridin-2-yl)methanone |
| 108 | 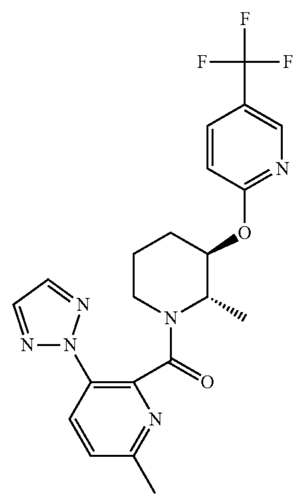 [SMILES: Cc1ccc(-n2nccn2)c(C(=O)N2CCC[C@@H](Oc3ccc(C(F)(F)F)cn3)[C@@H]2C)n1] | | | | ((2S,3R)-2-methyl-3-((5-(trifluoromethyl)pyridin-2-yl)oxy)piperidin-1-yl)(6-methyl-3-(2H-1,2,3-triazol-2-yl)pyridin-2-yl)methanone |
| 109 | 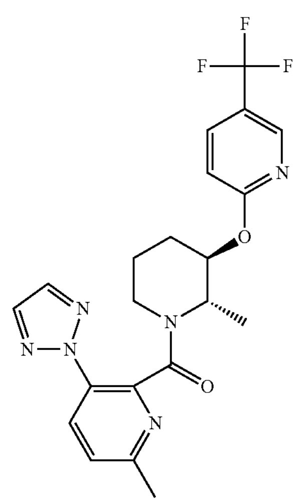 [SMILES: Cc1ccc(-n2nccn2)c(C(=O)N2CCC[C@@H](Oc3ccc(C(F)(F)F)cn3)[C@@H]2C)n1] | | | | (±)-trans-(2-methyl-3-((5-(trifluoromethyl)pyridin-2-yl)oxy)piperidin-1-yl)(6-methyl-3-(2H-1,2,3-triazol-2-yl)pyridin-2-yl)methanone |

-continued

| Ex. | Structure | rOX1 K$_i$(nm) | hOX1 K$_i$(nm) | hOX2 K$_i$(nm) | Compound Name |
|---|---|---|---|---|---|
| 110 | 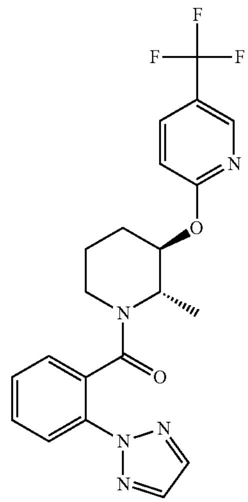 [SMILES: C[C@H]1[C@H](Oc2ccc(C(F)(F)F)cn2)CCCN1C(=O)c1ccccc1-n1nccn1] | | | | (2-(2H-1,2,3-triazol-2-yl)phenyl)((2S,3R)-2-methyl-3-((5-(trifluoromethyl)pyridin-2-yl)oxy)piperidin-1-yl)methanone |
| 111 | 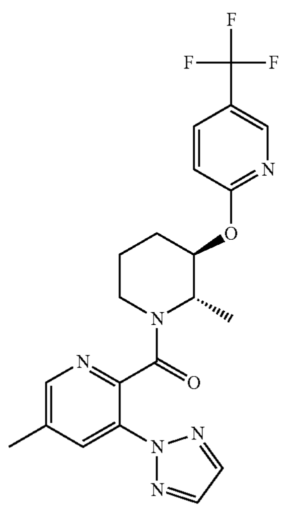 | | | | ((2S,3R)-2-methyl-3-((5-(trifluoromethyl)pyridin-2-yl)oxy)piperidin-1-yl)(5-methyl-3-(2H-1,2,3-triazol-2-yl)pyridin-2-yl)methanone |
| 112 | 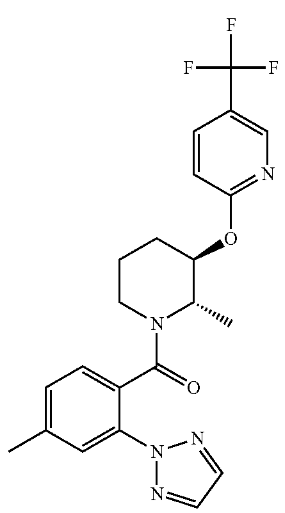 | 8 | 12 | 562 | (4-methyl-2-(2H-1,2,3-triazol-2-yl)phenyl)((2S,3R)-2-methyl-3-((5-(trifluoromethyl)pyridin-2-yl)oxy)piperidin-1-yl)methanone |

| Ex. | Structure | rOX1 K<sub>i</sub> (nm) | hOX1 K<sub>i</sub> (nm) | hOX2 K<sub>i</sub> (nm) | Compound Name |
|---|---|---|---|---|---|
| 113 | 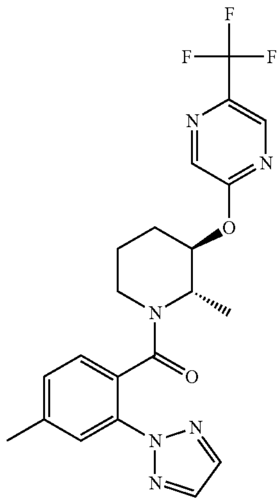 | | | | (4-methyl-2-(2H-1,2,3-triazol-2-yl)phenyl)((2S,3R)-2-methyl-3-((5-(trifluoromethyl)pyrazin-2-yl)oxy)piperidin-1-yl)methanone |
| 114 | 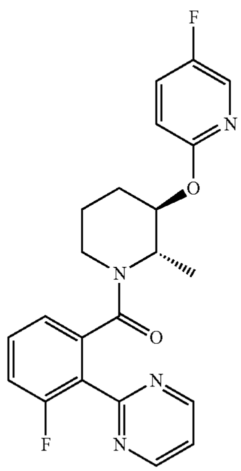 | | | | (3-fluoro-2-(pyrimidin-2-yl)phenyl)((2S,3R)-3-((5-fluoropyridin-2-yl)oxy)-2-methylpiperidin-1-yl)methanone |
| 115 | 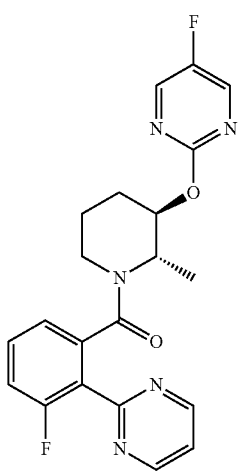 | | | | (3-fluoro-2-(pyrimidin-2-yl)phenyl)((2S,3R)-3-((5-fluoropyrimidin-2-yl)oxy)-2-methylpiperidin-1-yl)methanone |

| Ex. | Structure | rOX1 K$_i$ (nm) | hOX1 K$_i$ (nm) | hOX2 K$_i$ (nm) | Compound Name |
|---|---|---|---|---|---|
| 116 | 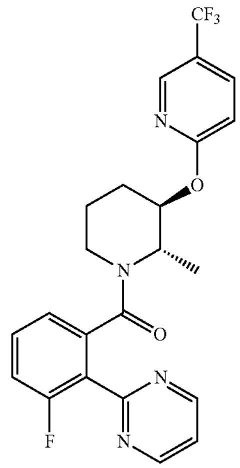 [SMILES: C[C@H]1[C@H](Oc2ccc(C(F)(F)F)cn2)CCCN1C(=O)c1cccc(F)c1-c1ncccn1] | | | | (3-fluoro-2-(pyrimidin-2-yl)phenyl)((2S,3R)-2-methyl-3-((5-(trifluoromethyl)pyridin-2-yl)oxy)piperidin-1-yl)methanone |
| 117 | 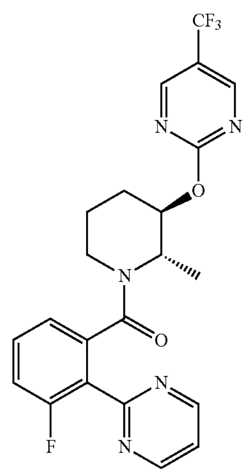 | | | | (3-fluoro-2-(pyrimidin-2-yl)phenyl)((2S,3R)-2-methyl-3-((5-(trifluoromethyl)pyrimidin-2-yl)oxy)piperidin-1-yl)methanone |
| 118 | 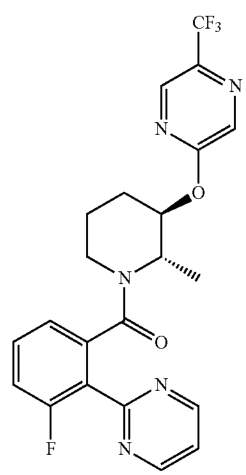 | | | | (3-fluoro-2-(pyrimidin-2-yl)phenyl)((2S,3R)-2-methyl-3-((5-(trifluoromethyl)pyrazin-2-yl)oxy)piperidin-1-yl)methanone |

| Ex. | Structure | rOX1 K<sub>i</sub> (nm) | hOX1 K<sub>i</sub> (nm) | hOX2 K<sub>i</sub> (nm) | Compound Name |
|---|---|---|---|---|---|
| 119 | 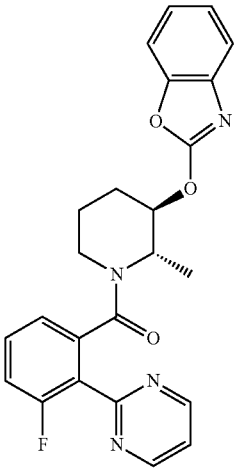 | | | | ((2S,3R)-3-(benzo[d]oxazol-2-yloxy)-2-methylpiperidin-1-yl)(3-fluoro-2-(pyrimidin-2-yl)phenyl)methanone |
| 120 | 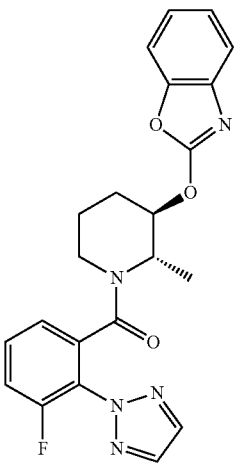 [SMILES: C[C@H]1[C@H](Oc2nc3ccccc3o2)CCCN1C(=O)c1cccc(F)c1-n1nccn1] | | | | ((2S,3R)-3-(benzo[d]oxazol-2-yloxy)-2-methylpiperidin-1-yl)(3-fluoro-2-(2H-1,2,3-triazol-2-yl)phenyl)methanone |
| 121 | 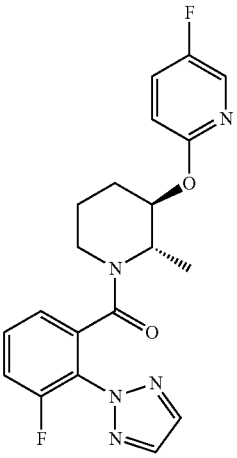 | | | | (3-fluoro-2-(2H-1,2,3-triazol-2-yl)phenyl)((2S,3R)-3-((5-fluoropyridin-2-yl)oxy)-2-methylpiperidin-1-yl)methanone |

-continued

| Ex. | Structure | rOX1 K_i (nm) | hOX1 K_i (nm) | hOX2 K_i (nm) | Compound Name |
|---|---|---|---|---|---|
| 122 | 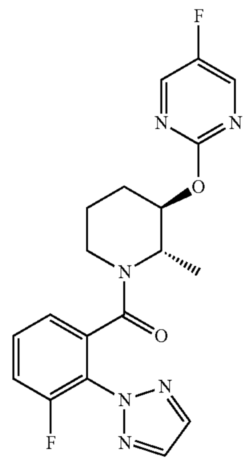 | | | | (3-fluoro-2-(2H-1,2,3-triazol-2-yl)phenyl)((2S,3R)-3-((5-fluoropyrimidin-2-yl)oxy)-2-methylpiperidin-1-yl)methanone |
| 123 | 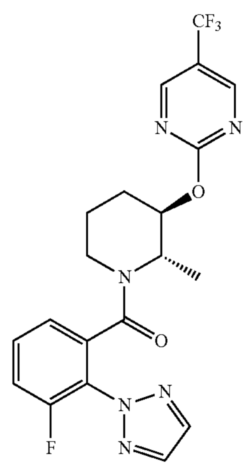 | | | | (3-fluoro-2-(2H-1,2,3-triazol-2-yl)phenyl)((2S,3R)-2-methyl-3-((5-(trifluoromethyl)pyrimidin-2-yl)oxy)piperidin-1-yl)methanone |
| 124 | 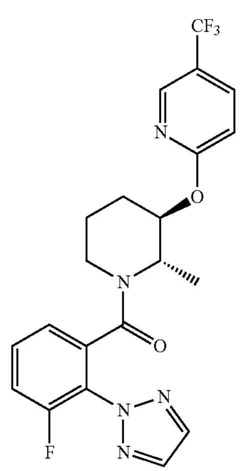 [SMILES: C[C@H]1[C@H](Oc2ccc(C(F)(F)F)cn2)CCCN1C(=O)c1cccc(F)c1-n1nccn1] | | | | (3-fluoro-2-(2H-1,2,3-triazol-2-yl)phenyl)((2S,3R)-2-methyl-3-((5-(trifluoromethyl)pyridin-2-yl)oxy)piperidin-1-yl)methanone |

-continued

| Ex. | Structure | rOX1 K_i (nm) | hOX1 K_i (nm) | hOX2 K_i (nm) | Compound Name |
|---|---|---|---|---|---|
| 125 | 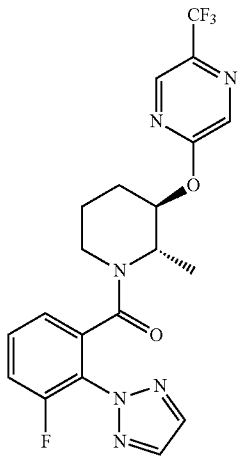 | | | | (3-fluoro-2-(2H-1,2,3-triazol-2-yl)phenyl)((2S,3R)-2-methyl-3-((5-(trifluoromethyl)pyrazin-2-yl)oxy)piperidin-1-yl)methanone |
| 126 | 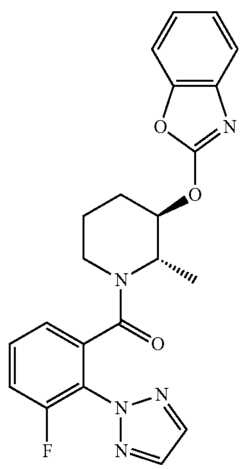 [SMILES: C[C@H]1[C@H](Oc2nc3ccccc3o2)CCCN1C(=O)c1cccc(F)c1-n1nccn1] | | | | ((2S,3R)-3-(benzo[d]oxazol-2-yloxy)-2-methylpiperidin-1-yl)(3-fluoro-2-(2H-1,2,3-triazol-2-yl)phenyl)methanone |
| 127 | 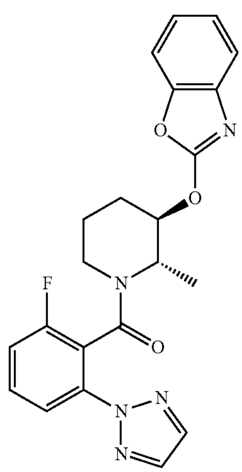 [SMILES: C[C@H]1[C@H](Oc2nc3ccccc3o2)CCCN1C(=O)c1c(F)cccc1-n1nccn1] | | | | ((2S,3R)-3-(benzo[d]oxazol-2-yloxy)-2-methylpiperidin-1-yl)(2-fluoro-6-(2H-1,2,3-triazol-2-yl)phenyl)methanone |

-continued

| Ex. | Structure | rOX1 K$_i$ (nm) | hOX1 K$_i$ (nm) | hOX2 K$_i$ (nm) | Compound Name |
|---|---|---|---|---|---|
| 128 | 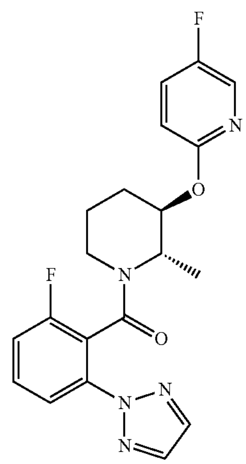 [SMILES: C[C@H]1[C@H](Oc2ccc(F)cn2)CCCN1C(=O)c1c(F)cccc1-n1nccn1] | | | | (2-fluoro-6-(2H-1,2,3-triazol-2-yl)phenyl)((2S,3R)-3-((5-fluoropyridin-2-yl)oxy)-2-methylpiperidin-1-yl)methanone |
| 129 | 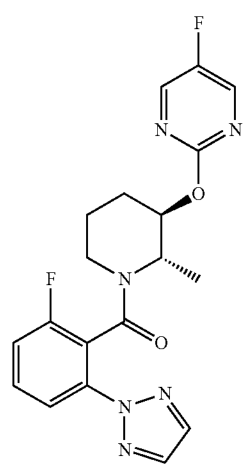 [SMILES: C[C@H]1[C@H](Oc2ncc(F)cn2)CCCN1C(=O)c1c(F)cccc1-n1nccn1] | | | | (2-fluoro-6-(2H-1,2,3-triazol-2-yl)phenyl)((2S,3R)-3-((5-fluoropyrimidin-2-yl)oxy)-2-methylpiperidin-1-yl)methanone |
| 130 | 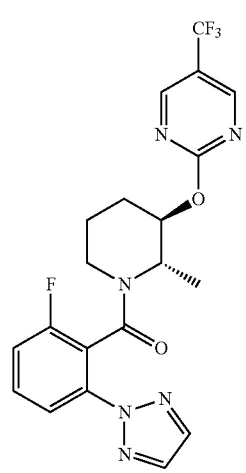 [SMILES: C[C@H]1[C@H](Oc2ncc(C(F)(F)F)cn2)CCCN1C(=O)c1c(F)cccc1-n1nccn1] | | | | (2-fluoro-6-(2H-1,2,3-triazol-2-yl)phenyl)((2S,3R)-2-methyl-3-((5-(trifluoromethyl)pyrimidin-2-yl)oxy)piperidin-1-yl)methanone |

| Ex. | Structure | rOX1 K$_i$ (nm) | hOX1 K$_i$ (nm) | hOX2 K$_i$ (nm) | Compound Name |
|---|---|---|---|---|---|
| 131 | 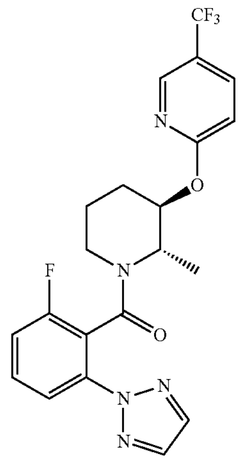 [SMILES: C[C@H]1[C@H](Oc2ccc(C(F)(F)F)cn2)CCCN1C(=O)c1c(F)cccc1-n1nccn1] | | | | (2-fluoro-6-(2H-1,2,3-triazol-2-yl)phenyl)((2S,3R)-2-methyl-3-((5-(trifluoromethyl)pyridin-2-yl)oxy)piperidin-1-yl)methanone |
| 132 | 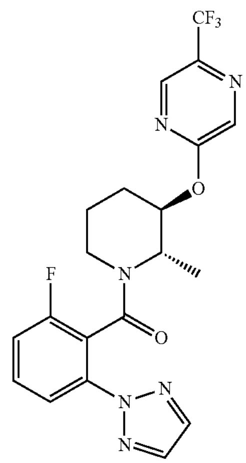 [SMILES: C[C@H]1[C@H](Oc2cnc(C(F)(F)F)cn2)CCCN1C(=O)c1c(F)cccc1-n1nccn1] | | | | (2-fluoro-6-(2H-1,2,3-triazol-2-yl)phenyl)((2S,3R)-2-methyl-3-((5-(trifluoromethyl)pyrazin-2-yl)oxy)piperidin-1-yl)methanone |
| 133 | 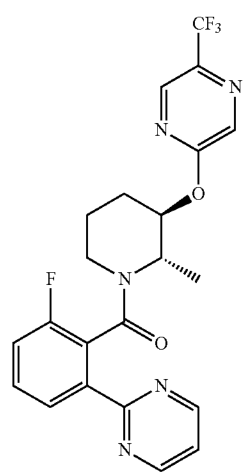 [SMILES: C[C@H]1[C@H](Oc2cnc(C(F)(F)F)cn2)CCCN1C(=O)c1c(F)cccc1-c1ncccn1] | | | | (2-fluoro-6-(pyrimidin-2-yl)phenyl)((2S,3R)-2-methyl-3-((5-(trifluoromethyl)pyrazin-2-yl)oxy)piperidin-1-yl)methanone |

-continued

| Ex. | Structure | rOX1 K$_i$ (nm) | hOX1 K$_i$ (nm) | hOX2 K$_i$ (nm) | Compound Name |
|---|---|---|---|---|---|
| 134 | 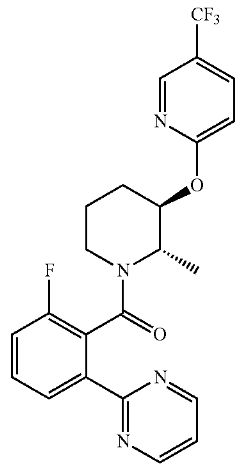 [SMILES: C[C@H]1[C@H](Oc2ccc(C(F)(F)F)cn2)CCCN1C(=O)c1c(F)cccc1-c1ncccn1] | | | | (2-fluoro-6-(pyrimidin-2-yl)phenyl)((2S,3R)-2-methyl-3-((5-(trifluoromethyl)pyridin-2-yl)oxy)piperidin-1-yl)methanone |
| 135 | 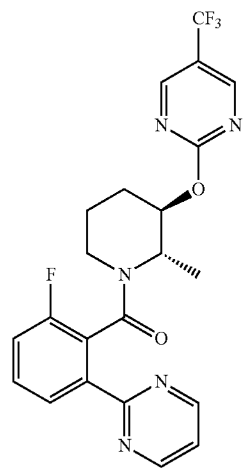 | | | | (2-fluoro-6-(pyrimidin-2-yl)phenyl)((2S,3R)-2-methyl-3-((5-trifluoromethyl)pyrimidin-2-yl)oxy)piperidin-1-yl)methanone |
| 136 | 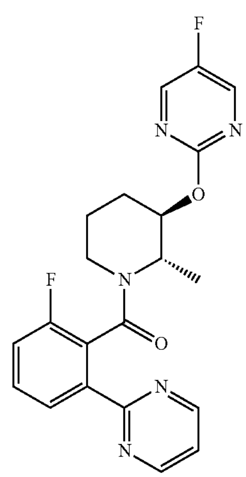 [SMILES: C[C@H]1[C@H](Oc2ncc(F)cn2)CCCN1C(=O)c1c(F)cccc1-c1ncccn1] | | | | (2-fluoro-6-(pyrimidin-2-yl)phenyl)((2S,3R)-3-((5-fluoropyrimidin-2-yl)oxy)-2-methylpiperidin-1-yl)methanone |

| Ex. | Structure | rOX1 K$_i$ (nm) | hOX1 K$_i$ (nm) | hOX2 K$_i$ (nm) | Compound Name |
|---|---|---|---|---|---|
| 137 | 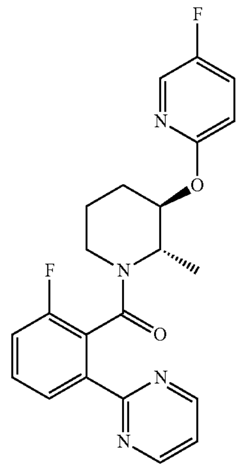 [SMILES: C[C@H]1[C@H](Oc2ccc(F)cn2)CCCN1C(=O)c1c(F)cccc1-c1ncccn1] | | | | (2-fluoro-6-(pyrimidin-2-yl)phenyl)((2S,3R)-3-((5-fluoropyridin-2-yl)oxy)-2-methylpiperidin-1-yl)methanone |
| 138 | 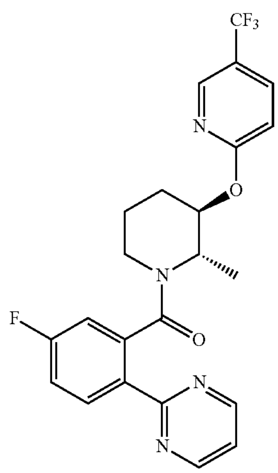 [SMILES: C[C@H]1[C@H](Oc2ccc(C(F)(F)F)cn2)CCCN1C(=O)c1cc(F)ccc1-c1ncccn1] | | | | (5-fluoro-2-(pyrimidin-2-yl)phenyl)((2S,3R)-2-methyl-3-((5-(trifluoromethyl)pyridin-2-yl)oxy)piperidin-1-yl)methanone |
| 139 | 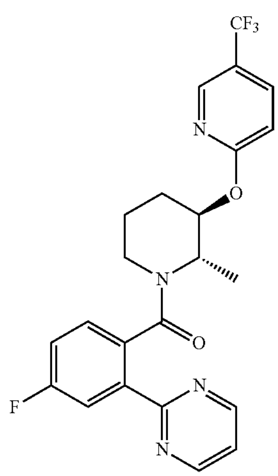 | | | | (4-fluoro-2-(pyrimidin-2-yl)phenyl)((2S,3R)-2-methyl-3-((5-(trifluoromethyl)pyridin-2-yl)oxy)piperidin-1-yl)methanone |

-continued

| Ex. | Structure | rOX1 K<sub>i</sub> (nm) | hOX1 K<sub>i</sub> (nm) | hOX2 K<sub>i</sub> (nm) | Compound Name |
|---|---|---|---|---|---|
| 140 | 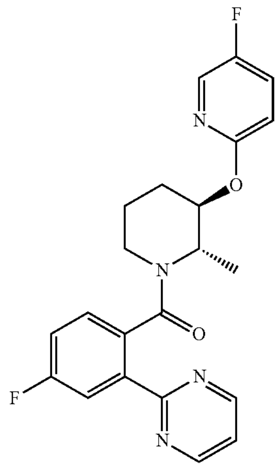 [SMILES: C[C@H]1[C@H](Oc2ccc(F)cn2)CCCN1C(=O)c1ccc(F)cc1-c1ncccn1] | | | | (4-fluoro-2-(pyrimidin-2-yl)phenyl)((2S,3R)-2-methyl-3-((5-(trifluoromethyl)pyridin-2-yl)oxy)piperidin-1-yl)methanone |
| 141 | 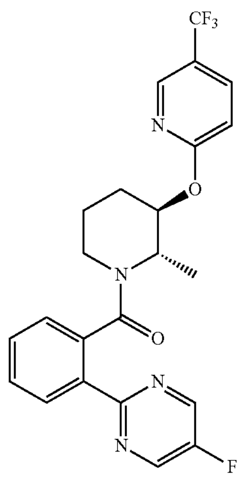 [SMILES: C[C@H]1[C@H](Oc2ccc(C(F)(F)F)cn2)CCCN1C(=O)c1ccccc1-c1ncc(F)cn1] | | | | (4-fluoro-2-(pyrimidin-2-yl)phenyl)((2S,3R)-3-((5-fluoropyridin-2-yl)oxy)-2-methylpiperidin-1-yl)methanone |
| 142 | 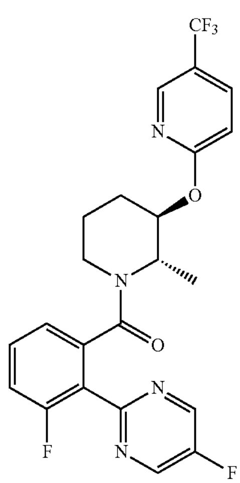 [SMILES: C[C@H]1[C@H](Oc2ccc(C(F)(F)F)cn2)CCCN1C(=O)c1cccc(F)c1-c1ncc(F)cn1] | | | | (3-fluoro-2-(5-fluoropyrimidin-2-yl)phenyl)((2S,3R)-2-methyl-3-((5-(trifluoromethyl)pyridin-2-yl)oxy)piperidin-1-yl)methanone |

| Ex. | Structure | rOX1 K$_i$ (nm) | hOX1 K$_i$ (nm) | hOX2 K$_i$ (nm) | Compound Name |
|---|---|---|---|---|---|
| 143 | 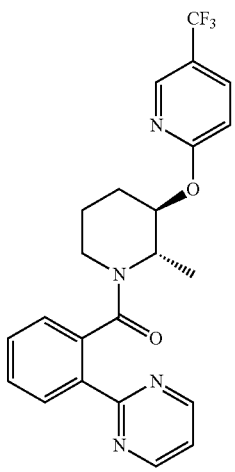 [SMILES: C[C@H]1[C@H](Oc2ccc(C(F)(F)F)cn2)CCCN1C(=O)c1ccccc1-c1ncccn1] | | | | ((2S,3R)-2-methyl-3-((5-(trifluoromethyl)pyridin-2-yl)oxy)piperidin-1-yl)(2-(pyrimidin-2-yl)phenyl)methanone |
| 144 | 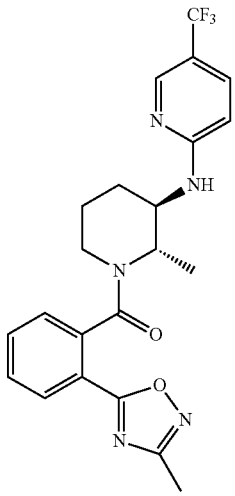 [SMILES: Cc1noc(-c2ccccc2C(=O)N2CCC[C@@H](Nc3ccc(C(F)(F)F)cn3)[C@@H]2C)n1] | | | | (2-(3-methyl-1,2,4-oxadiazol-5-yl)phenyl)((2S,3R)-2-methyl-3-((5-(trifluoromethyl)pyridin-2-yl)amino)piperidin-1-yl)methanone |
| 145 | 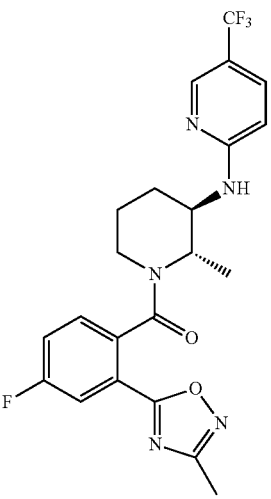 | | | | (4-fluoro-2-(3-methyl-1,2,4-oxadiazol-5-yl)phenyl)((2S,3R)-2-methyl-3-((5-(trifluoromethyl)pyridin-2-yl)amino)piperidin-1-yl)methanone |

| Ex. | Structure | rOX1 $K_i$ (nm) | hOX1 $K_i$ (nm) | hOX2 $K_i$ (nm) | Compound Name |
|---|---|---|---|---|---|
| 146 | 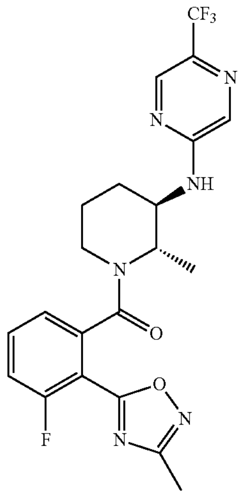 [SMILES: Cc1noc(-c2c(F)cccc2C(=O)N2CCC[C@@H](Nc3cnc(C(F)(F)F)cn3)[C@@H]2C)n1] | | | | (3-fluoro-2-(3-methyl-1,2,4-oxadiazol-5-yl)phenyl)((2S,3R)-2-methyl-3-((5-(trifluoromethyl)pyrazin-2-yl)amino)piperidin-1-yl)methanone |

What is claimed:

1. A compound of Formula I:

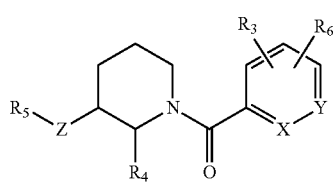

or an enantiomer or diastereomer thereof;
or a pharmaceutically acceptable salt thereof;
wherein
X is $CR_1$ or N;
Y is $CR_2$ or N;
Z is NH or O;
$R_1$ is alkoxy, triazolyl, oxazolyl, isoxazolyl, oxadiazolyl, or pyrimidinyl
$R_2$ is H, alkyl, or halo;
$R_3$ is H, alkyl, alkoxy, halo, triazolyl, oxazolyl, or pyrimidinyl;
$R_4$ is alkyl;
$R_5$ is pyridyl; benzoxazolyl; pyrimidinyl; pyridazinyl; quinoxalinyl; pyrazinyl; or quinazolinyl;
  wherein the pyridyl; benzoxazolyl; pyrimidinyl; pyridazinyl; quinoxalinyl; pyrazinyl; or quinazolinyl is optionally substituted with one or two substituents independently selected from the group consisting of alkyl, halo, or phenyl; and
$R_6$ is H or alkyl.
2. The compound of claim 1, wherein Z is NH.
3. The compound of claim 1 wherein Z is O.
4. The compound of claim 1, wherein $R_4$ is $C_{1-3}$alkyl.
5. The compound of claim 4, wherein $R_4$ is methyl.
6. The compound of claim 1, wherein X is $CR_1$ and Y is $CR_2$.
7. The compound of claim 1, wherein X is N and Y is $CR_2$.
8. The compound of claim 1, wherein X is $CR_1$ and Y is N.
9. The compound of claim 1, wherein X and Y are each N.
10. The compound of claim 1 or claim 8, wherein $R_1$ is alkoxy, triazolyl, or pyrimidinyl.
11. The compound of claim 10, wherein $R_1$ is alkoxy.
12. The compound of claim 10, wherein $R_1$ is triazolyl.
13. The compound of claim 10, wherein $R_1$ is pyrimidinyl.
14. The compound of claim 13, wherein the pyrimidinyl is halo-pyrimidinyl.
15. The compound of claim 1 or claim 8, wherein $R_1$ is oxazolyl, isoxazolyl, or oxadiazolyl.
16. The compound of claim 15, wherein oxadiazolyl is methyl-oxadiazolyl.
17. The compound of claim 1, wherein $R_2$ is H.
18. The compound of claim 1, wherein $R_2$ is halo.
19. The compound of claim 18, wherein halo is F, Cl, or Br.
20. The compound of claim 1, wherein $R_2$ is alkyl.
21. The compound of claim 20, wherein alkyl is —$CH_3$.
22. The compound of any one of the preceding claims, wherein $R_3$ is alkyl, alkoxy, halo, triazolyl, oxazolyl, or pyrimidinyl.
23. The compound of claim 22, wherein $R_3$ is alkyl.
24. The compound of claim 23, wherein alkyl is trihaloalkyl.
25. The compound of claim 23, wherein alkyl is —$CH_3$.
26. The compound of claim 22, wherein $R_3$ is alkoxy.
27. The compound of claim 22, wherein $R_3$ is halo.
28. The compound of claim 22, wherein $R_3$ is triazolyl.
29. The compound of claim 22, wherein $R_3$ is oxazolyl.
30. The compound of claim 22, wherein $R_3$ is pyrimidinyl.
31. The compound of claim 1, wherein $R_5$ is pyridyl, optionally substituted with one or two substituents independently selected from the group consisting of alkyl, halo, or phenyl.
32. The compound of claim 31, wherein alkyl is trihaloalkyl.
33. The compound of claim 31, wherein alkyl is —$CH_3$.
34. The compound of claim 1 wherein $R_5$ is benzoxazolyl, optionally substituted with one or two substituents independently selected from the group consisting of alkyl, halo, or phenyl.
35. The compound of claim 34, wherein alkyl is trihaloalkyl.

36. The compound of claim 34, wherein alkyl is —CH$_3$.

37. The compound of claim 1, wherein R$_5$ is pyrimidinyl, optionally substituted with one or two substituents independently selected from the group consisting of alkyl, halo, or phenyl.

38. The compound of claim 37, wherein alkyl is trihaloalkyl.

39. The compound of claim 37, wherein alkyl is —CH$_3$.

40. The compound of claim 1, wherein R$_5$ is pyridazinyl, optionally substituted with one or two substituents independently selected from the group consisting of alkyl, halo, or phenyl.

41. The compound of claim 40, wherein alkyl is trihaloalkyl.

42. The compound of claim 40, wherein alkyl is —CH$_3$.

43. The compound of claim 1, wherein R$_5$ is quinoxalinyl, optionally substituted with one or two substituents independently selected from the group consisting of alkyl, halo, or phenyl.

44. The compound of claim 43, wherein alkyl is trihaloalkyl.

45. The compound of claim 43, wherein alkyl is —CH$_3$.

46. The compound of claim 1, wherein R$_5$ is pyrazinyl, optionally substituted with one or two substituents independently selected from the group consisting of alkyl, halo, or phenyl.

47. The compound of claim 46, wherein alkyl is trihaloalkyl.

48. The compound of claim 46, wherein alkyl is —CH$_3$.

49. The compound of claim 1, wherein R$_5$ is quinazolinyl, optionally substituted with one or two substituents independently selected from the group consisting of alkyl, halo, or phenyl.

50. The compound of claim 49, wherein alkyl is trihaloalkyl.

51. The compound of claim 49, wherein alkyl is —CH$_3$.

52. The compound of claim 1, wherein R$_6$ is H.

53. The compound of claim 1, wherein R$_6$ is alkyl.

54. A compound selected from the group consisting of

| Ex. | Structure | Compound Name |
|-----|-----------|---------------|
| 1 | | (±)-trans-(3-((4,6-dimethylpyrimidin-2-yl)amino)-2-methylpiperidin-1-yl)(4-fluoro-2-(2H-1,2,3-triazol-2-yl)phenyl)methanone |
| 2 | 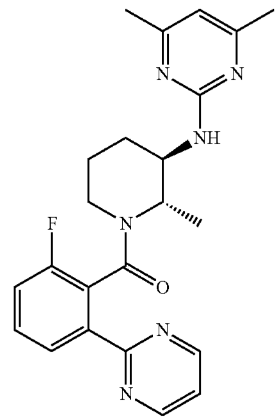 [SMILES: Cc1cc(C)nc(N[C@@H]2CCCN(C(=O)c3c(F)cccc3-c3ncccn3)[C@H]2C)n1] | (±)-trans-(3-((4,6-dimethylpyrimidin-2-yl)amino)-2-methylpiperidin-1-yl)(2-fluoro-6-(pyrimidin-2-yl)phenyl)methanone |
| 3 | 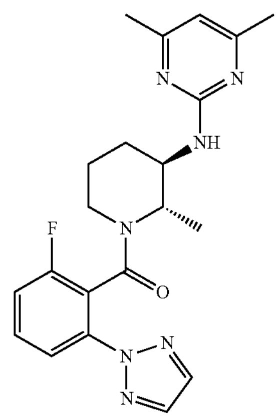 [SMILES: Cc1cc(C)nc(N[C@@H]2CCCN(C(=O)c3c(F)cccc3-n3nccn3)[C@H]2C)n1] | (±)-trans-(3-((4,6-dimethylpyrimidin-2-yl)amino)-2-methylpiperidin-1-yl)(2-fluoro-6-(2H-1,2,3-triazol-2-yl)phenyl)methanone |
| 4 | 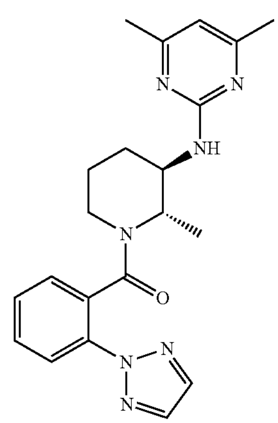 [SMILES: Cc1cc(C)nc(N[C@@H]2CCCN(C(=O)c3ccccc3-n3nccn3)[C@H]2C)n1] | (±)-trans-(2-((2H-1,2,3-triazol-2-yl)phenyl)(3-((4,6-dimethylpyrimidin-2-yl)amino)-2-methylpiperidin-1-yl)methanone |

| Ex. | Structure | Compound Name |
|---|---|---|
| 5 | 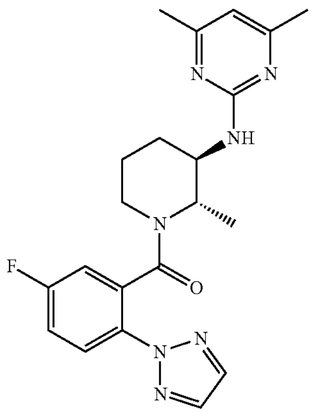 [SMILES: Cc1cc(C)nc(N[C@@H]2CCCN(C(=O)c3cc(F)ccc3-n3nccn3)[C@H]2C)n1] | (±)-trans-(3-((4,6-dimethylpyrimidin-2-yl)amino)-2-methylpiperidin-1-yl)(5-fluoro-2-(2H-1,2,3-triazol-2-yl)phenyl)methanone |
| 6 | 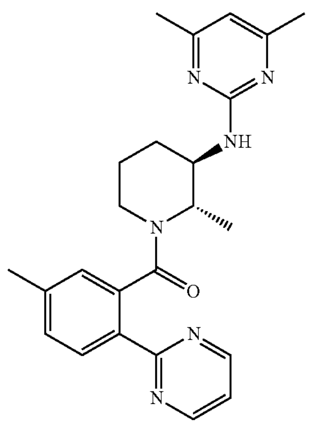 | (±)-trans-(3-((4,6-dimethylpyrimidin-2-yl)amino)-2-methylpiperidin-1-yl)(5-methyl-2-(pyrimidin-2-yl)phenyl)methanone |
| 7 | 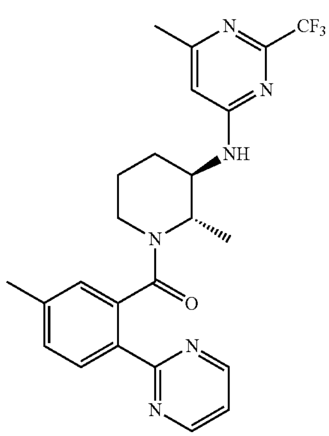 [SMILES: Cc1ccc(-c2ncccn2)c(C(=O)N2CCC[C@@H](Nc3cc(C)nc(C(F)(F)F)n3)[C@@H]2C)c1] | (±)-trans-(5-methyl-2-(pyrimidin-2-yl)phenyl)(2-methyl-3-((6-methyl-2-(trifluoromethyl)pyrimidin-4-yl)amino)piperidin-1-yl)methanone |
| 8 | 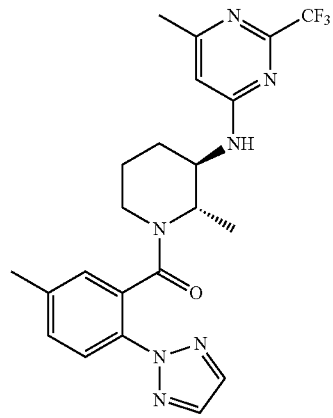 [SMILES: Cc1ccc(-n2nccn2)c(C(=O)N2CCC[C@@H](Nc3cc(C)nc(C(F)(F)F)n3)[C@@H]2C)c1] | (±)-trans-(5-methyl-2-(2H-1,2,3-triazol-2-yl)phenyl)(2-methyl-3-((6-methyl-2-(trifluoromethyl)pyrimidin-4-yl)amino)piperidin-1-yl)methanone |
| 9 | 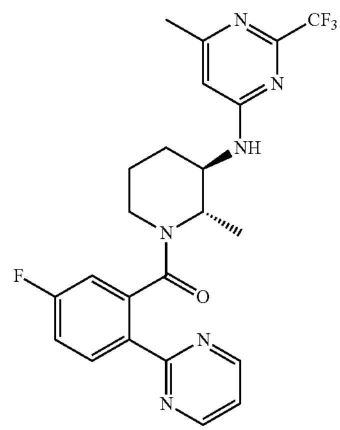 [SMILES: Cc1cc(N[C@@H]2CCCN(C(=O)c3cc(F)ccc3-c3ncccn3)[C@H]2C)nc(C(F)(F)F)n1] | (±)-trans-(5-fluoro-2-(pyrimidin-2-yl)phenyl)(2-methyl-3-((6-methyl-2-(trifluoromethyl)pyrimidin-4-yl)amino)piperidin-1-yl)methanone |
| 10 | 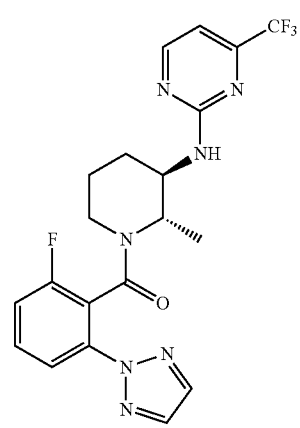 [SMILES: C[C@H]1[C@H](Nc2nccc(C(F)(F)F)n2)CCCN1C(=O)c1c(F)cccc1-n1nccn1] | (±)-trans-(2-fluoro-6-(2H-1,2,3-triazol-2-yl)phenyl)(2-methyl-3-((4-(trifluoromethyl)pyrimidin-2-yl)amino)piperidin-1-yl)methanone |

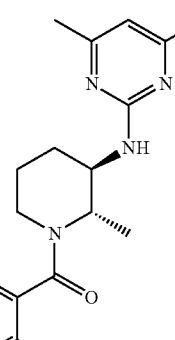

-continued

| Ex. | Structure | Compound Name |
|---|---|---|
| 11 | 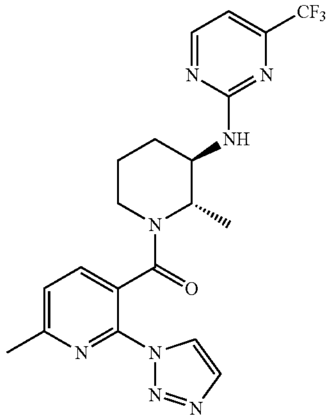 [SMILES: Cc1ccc(C(=O)N2CCC[C@@H](Nc3nccc(C(F)(F)F)n3)[C@@H]2C)c(-n2ccnn2)n1] | (±)-trans-(6-methyl-2-(1H-1,2,3-triazol-1-yl)pyridin-3-yl)(2-methyl-3-((4-(trifluoromethyl)pyrimidin-2-yl)amino)piperidin-1-yl)methanone |
| 12 | 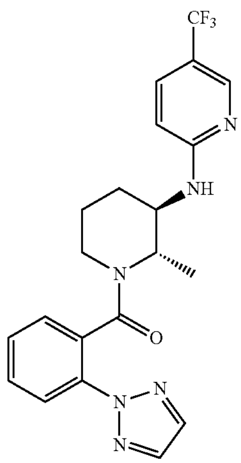 | (±)-trans-(2-(2H-1,2,3-triazol-2-yl)phenyl)(2-methyl-3-((5-(trifluoromethyl)pyridin-2-yl)amino)piperidin-1-yl)methanone |
| 13 | 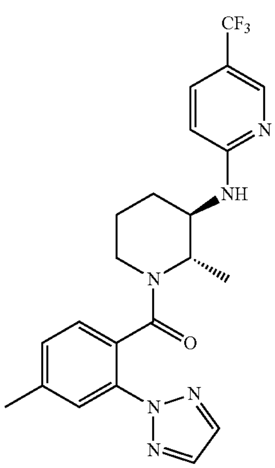 | (±)-trans-(4-methyl-2-(2H-1,2,3-triazol-2-yl)phenyl)(2-methyl-3-((5-(trifluoromethyl)pyridin-2-yl)amino)piperidin-1-yl)methanone |
| 14 | | (4-methyl-2-(2H-1,2,3-triazol-2-yl)phenyl)((2S,3R)-2-methyl-3-((5-(trifluoromethyl)pyridin-2-yl)amino)piperidin-1-yl)methanone |
| 15 | | (4-methyl-2-(2H-1,2,3-triazol-2-yl)phenyl)((2R,3S)-2-methyl-3-((5-(trifluoromethyl)pyridin-2-yl)amino)piperidin-1-yl)methanone |
| 16 | | (±)-trans-(3-ethoxy-6-methylpyridin-2-yl)(2-methyl-3-((5-(trifluoromethyl)pyridin-2-yl)amino)piperidin-1-yl)methanone |

| Ex. | Structure | Compound Name |
|---|---|---|
| 17 | 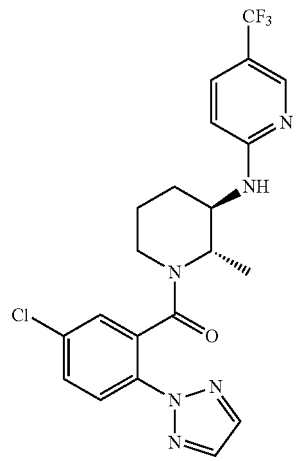 [SMILES: C[C@H]1[C@H](Nc2ccc(C(F)(F)F)cn2)CCCN1C(=O)c1cc(Cl)ccc1-n1nccn1] | (±)-trans-(5-chloro-2-(2H-1,2,3-triazol-2-yl)phenyl)(2-methyl-3-((5-(trifluoromethyl)pyridin-2-yl)amino)piperidin-1-yl)methanone |
| 18 | 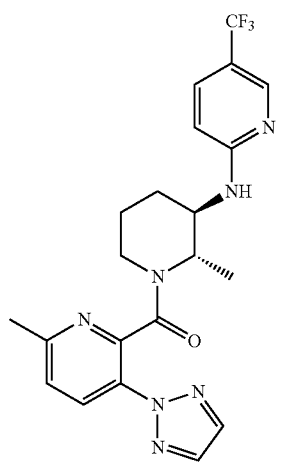 [SMILES: Cc1ccc(-n2nccn2)c(C(=O)N2CCC[C@@H](Nc3ccc(C(F)(F)F)cn3)[C@@H]2C)n1] | (±)-trans-(2-methyl-3-((5-(trifluoromethyl)pyridin-2-yl)amino)piperidin-1-yl)(6-methyl-3-(2H-1,2,3-triazol-2-yl)pyridin-2-yl)methanone |
| 19 | 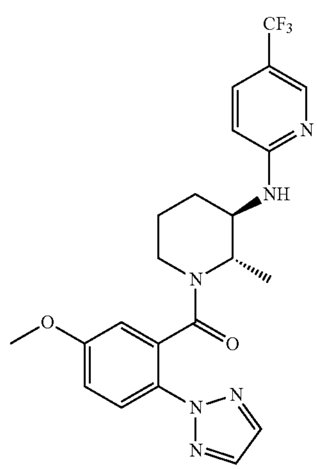 [SMILES: COc1ccc(-n2nccn2)c(C(=O)N2CCC[C@@H](Nc3ccc(C(F)(F)F)cn3)[C@@H]2C)c1] | (±)-trans-(5-methoxy-2-(2H-1,2,3-triazol-2-yl)phenyl)(2-methyl-3-((5-(trifluoromethyl)pyridin-2-yl)amino)piperidin-1-yl)methanone |
| 20 | | (±)-trans-(3-methyl-2-(2H-1,2,3-triazol-2-yl)phenyl)(2-methyl-3-((5-(trifluoromethyl)pyridin-2-yl)amino)piperidin-1-yl)methanone |
| 21 | | (±)-trans-(3-(2H-1,2,3-triazol-2-yl)pyridin-2-yl)(2-methyl-((5-(trifluoromethyl)pyridin-2-yl)amino)piperidin-1-yl)methanone |
| 22 | | (±)-trans-(2-methyl-3-((5-(trifluoromethyl)pyridin-2-yl)amino)piperidin-1-yl)(6-methyl-3-(oxazol-2-yl)pyridin-2-yl)methanone |

| Ex. | Structure | Compound Name |
|---|---|---|
| 23 | 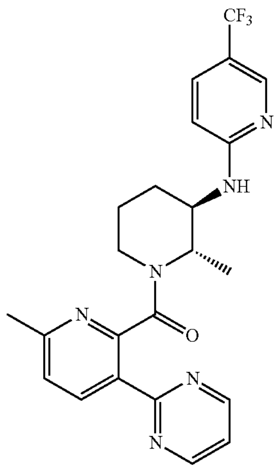 [SMILES: Cc1ccc(-c2ncccn2)c(C(=O)N2CCC[C@@H](Nc3ccc(C(F)(F)F)cn3)[C@@H]2C)n1] | (±)-trans-(2-methyl-3-((5-(trifluoromethyl)pyridin-2-yl)amino)piperidin-1-yl)(6-methyl-3-(pyrimidin-2-yl)pyridin-2-yl)methanone |
| 24 | 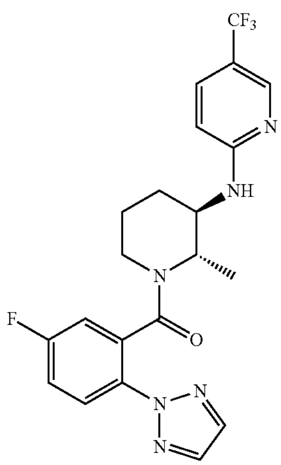 [SMILES: C[C@H]1[C@H](Nc2ccc(C(F)(F)F)cn2)CCCN1C(=O)c1cc(F)ccc1-n1nccn1] | (±)-trans-(5-fluoro-2-(2H-1,2,3-triazol-2-yl)phenyl)(2-methyl-3-((5-(trifluoromethyl)pyridin-2-yl)amino)piperidin-1-yl)methanone |
| 25 | 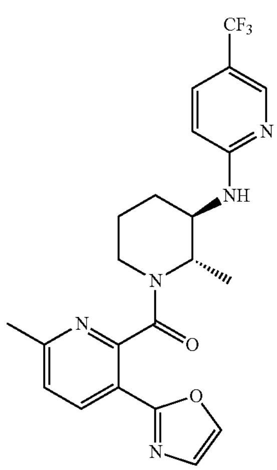 [SMILES: Cc1ccc(-c2ncco2)c(C(=O)N2CCC[C@@H](Nc3ccc(C(F)(F)F)cn3)[C@@H]2C)n1] | ((2S,3R)-2-methyl-3-((5-(trifluoromethyl)pyridin-2-yl)amino)piperidin-1-yl)(6-methyl-3-(oxazol-2-yl)pyridin-2-yl)methanone |
| 26 | 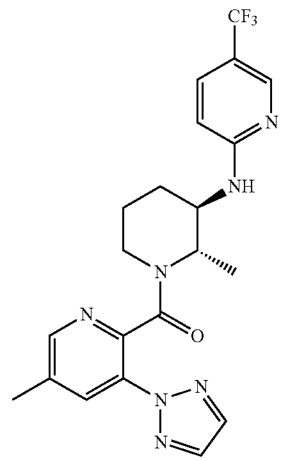 | ((2S,3R)-2-methyl-3-((5-(trifluoromethyl)pyridin-2-yl)amino)piperidin-1-yl)(5-methyl-3-(2H-1,2,3-triazol-2-yl)pyridin-2-yl)methanone |
| 27 | 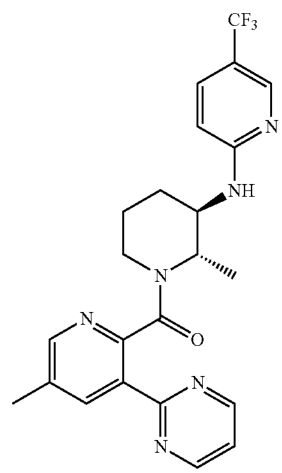 [SMILES: Cc1cnc(C(=O)N2CCC[C@@H](Nc3ccc(C(F)(F)F)cn3)[C@@H]2C)c(-c2ncccn2)c1] | ((2S,3R)-2-methyl-3-((5-(trifluoromethyl)pyridin-2-yl)amino)piperidin-1-yl)(5-methyl-3-(pyrimidin-2-yl)pyridin-2-yl)methanone |
| 28 | 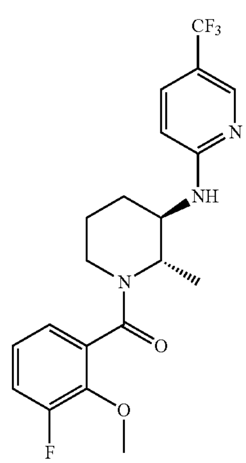 [SMILES: COc1c(F)cccc1C(=O)N1CCC[C@@H](Nc2ccc(C(F)(F)F)cn2)[C@@H]1C] | (±)-trans-(3-fluoro-2-methoxyphenyl)(2-methyl-3-((5-(trifluoromethyl)pyridin-2-yl)amino)piperidin-1-yl)methanone |

-continued

| Ex. | Structure | Compound Name |
|---|---|---|
| 29 | 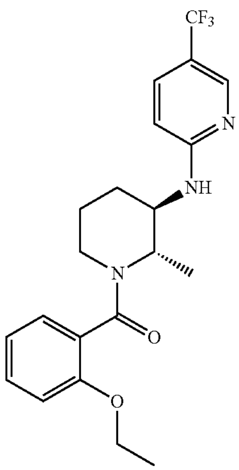 | (±)-trans-(2-ethoxyphenyl)(2-methyl-3-((5-(trifluoromethyl)pyridin-2-yl)amino)piperidin-1-yl)methanone |
| 30 | 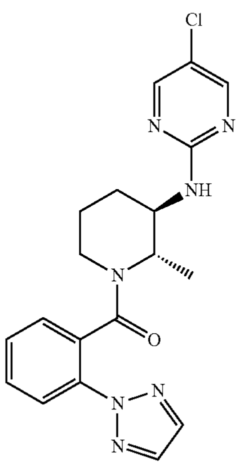 | (±)-trans-(2-(2H-1,2,3-triazol-2-yl)phenyl)(3-((5-chloropyrimidin-2-yl)amino)-2-methylpiperidin-1-yl)methanone |
| 31 | 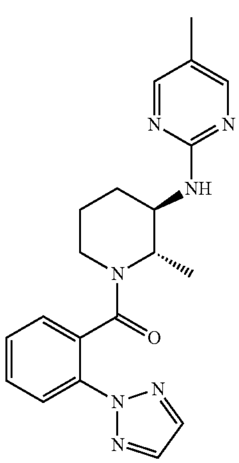 [SMILES: Cc1cnc(N[C@@H]2CCCN(C(=O)c3ccccc3-n3nccn3)[C@H]2C)nc1] | (±)-trans-(2-(2H-1,2,3-triazol-2-yl)phenyl)(2-methyl-3-((5-methylpyrimidin-2-yl)amino)piperidin-1-yl)methanone |
| 32 | | (±)-trans-(2-(2H-1,2,3-triazol-2-yl)phenyl)(3-((5-chloropyridin-2-yl)amino)-2-methylpiperidin-1-yl)methanone |
| 33 | | (±)-trans-(2-(2H-1,2,3-triazol-2-yl)phenyl)(2-methyl-3-((6-(trifluoromethyl)pyridazin-3-yl)amino)piperidin-1-yl)methanone |
| 34 | | (2-(2H-1,2,3-triazol-2-yl)phenyl)((2S,3R)-3-((5-fluoropyridin-2-yl)amino)-methyl-piperidin-1-yl)methanone |

| Ex. | Structure | Compound Name |
|---|---|---|
| 35 | 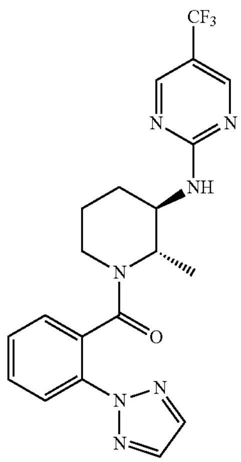 | (±)-trans-(2-(2H-1,2,3-triazol-2-yl)phenyl)(2-methyl-3-((5-(trifluoromethyl)pyrimidin-2-yl)amino)piperidin-1-yl)methanone |
| 36 | 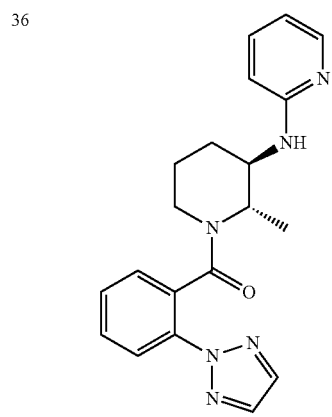 | (±)-trans-(2-(2H-1,2,3-triazol-2-yl)phenyl)(2-methyl-3-(pyridin-2-ylamino)piperidin-1-yl)methanone |
| 37 | 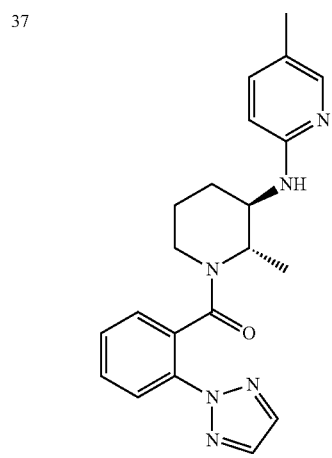 | (±)-trans-(2-(2H-1,2,3-triazol-2-yl)phenyl)(2-methyl-3-((5-methyl-pyridin-2-yl)amino)piperidin-1-yl)methanone |
| 38 | | (±)-trans-(2-(2H-1,2,3-triazol-2-yl)phenyl)(2-methyl-3-((5-(trifluoromethyl)pyrazin-2-yl)amino)piperidin-1-yl)methanone |
| 39 | | (±)-trans-(2-(2H-1,2,3-triazol-2-yl)phenyl)(2-methyl-3-(quinazolin-2-ylamino)piperidin-1-yl)methanone |
| 40 | | (±)-trans-(2-(2H-1,2,3-triazol-2-yl)phenyl)(3-((5-fluoropyrimidin-2-yl)amino)-2-methylpiperidin-1-yl)methanone |

| Ex. | Structure | Compound Name |
|---|---|---|
| 41 | 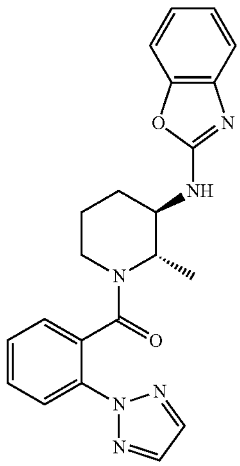 [SMILES: C[C@H]1[C@H](Nc2nc3ccccc3o2)CCCN1C(=O)c1ccccc1-n1nccn1] | (±)-trans-(2-(2H-1,2,3-triazol-2-yl)phenyl)(3-(benzo[d]oxazol-2-ylamino)-2-methylpiperidin-1-yl)methanone |
| 42 | 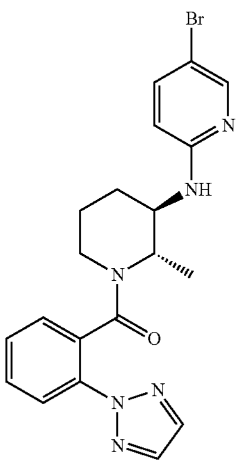 | (±)-trans-(2-(2H-1,2,3-triazol-2-yl)phenyl)(3-((5-bromopyridin-2-yl)amino)-2-methylpiperidin-1-yl)methanone |
| 43 | 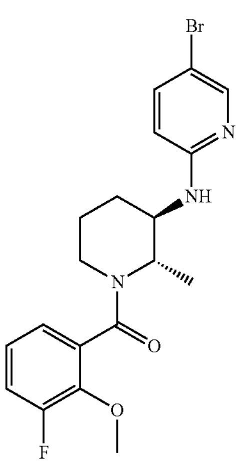 [SMILES: COc1c(F)cccc1C(=O)N1CCC[C@@H](Nc2ccc(Br)cn2)[C@@H]1C] | (±)-trans-(3-((5-bromopyridin-2-yl)amino)-2-methylpiperidin-1-yl)(3-fluoro-2-methoxyphenyl)methanone |
| 44 | 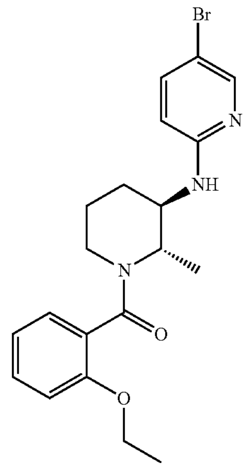 [SMILES: CCOc1ccccc1C(=O)N1CCC[C@@H](Nc2ccc(Br)cn2)[C@@H]1C] | (±)-trans-(3-(5-bromopyridin-2-yl)amino)-2-methyl-piperidin-1-yl)(2-ethoxyphenyl)methanone |
| 45 | 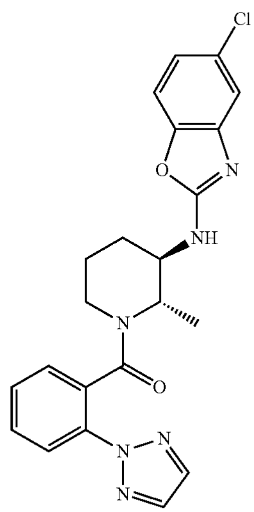 [SMILES: C[C@H]1[C@H](Nc2nc3cc(Cl)ccc3o2)CCCN1C(=O)c1ccccc1-n1nccn1] | (±)-trans-(2-(2H-1,2,3-triazol-2-yl)phenyl)(3-((5-chlorobenzo[d]oxazol-2-yl)amino)-2-methyl-piperidin-1-yl)methanone |
| 46 | 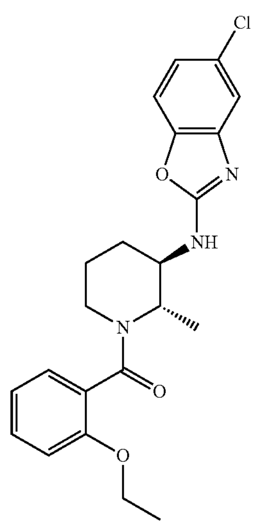 [SMILES: CCOc1ccccc1C(=O)N1CCC[C@@H](Nc2nc3cc(Cl)ccc3o2)[C@@H]1C] | (±)-trans-(3-((5-chlorobenzo[d]oxazol-2-yl)amino)-2-methylpiperidin-1-yl)(2-ethoxyphenyl)methanone |

-continued

| Ex. | Structure | Compound Name |
|---|---|---|
| 47 | 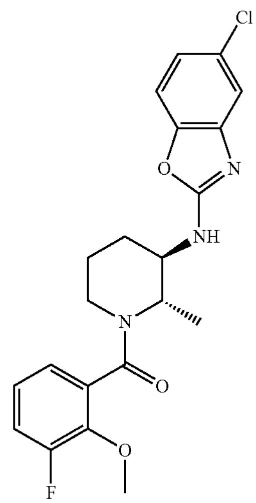 [SMILES: COc1c(F)cccc1C(=O)N1CCC[C@@H](Nc2nc3cc(Cl)ccc3o2)[C@@H]1C] | (±)-trans-(3-((5-chlorobenzo[d]oxazol-2-yl)amino)-2-methyl-piperidin-yl)(3-fluoro-2-methoxy-phenyl)methanone |
| 48 | 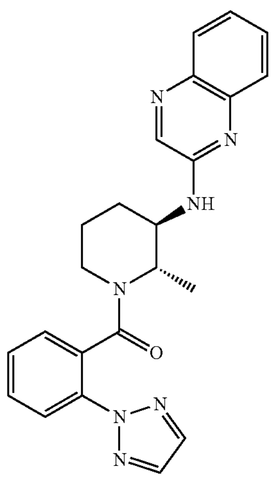 [SMILES: C[C@H]1[C@H](Nc2cnc3ccccc3n2)CCCN1C(=O)c1ccccc1-n1nccn1] | (±)-trans-(2-(2H-1,2,3-triazol-2-yl)phenyl)(2-methyl-3-(quinoxalin-2-ylamino)piperidin-1-yl)methanone |
| 49 | 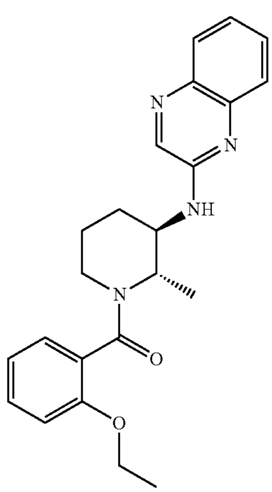 [SMILES: CCOc1ccccc1C(=O)N1CCC[C@@H](Nc2cnc3ccccc3n2)[C@@H]1C] | (±)-trans-((2-ethoxyphenyl)(2-methyl-3-(quinoxalin-2-ylamino)piperidin-1-yl)methanone |

-continued

| Ex. | Structure | Compound Name |
|---|---|---|
| 50 | | (±)-trans-(3-fluoro-2-methoxyphenyl)(2-methyl-3-(quinoxalin-2-ylamino)piperidin-1-yl)methanone |
| 51 | | (±)-trans-(2-(2H-1,2,3-triazol-2-yl)phenyl)(2-methyl-3-((4-phenyl-pyrimidin-2-yl)amino)piperidin-1-yl)methanone |
| 52 | | (±)-trans-(3-fluoro-2-methoxyphenyl)(2-methyl-3-((4-phenylpyrimidin-2-yl)amino)piperidin-1-yl)methanone |

-continued

| Ex. | Structure | Compound Name |
|---|---|---|
| 53 | 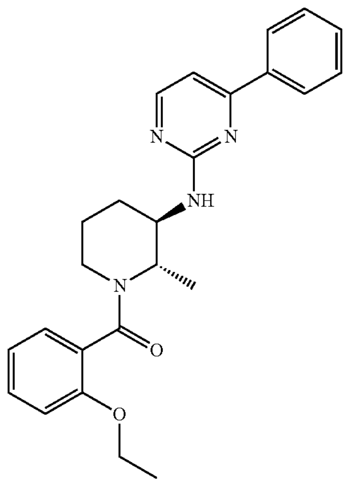 [SMILES: CCOc1ccccc1C(=O)N1CCC[C@@H](Nc2nccc(-c3ccccc3)n2)[C@@H]1C] | (±)-trans-(2-ethoxyphenyl)(2-methyl-3-((4-phenyl-pyrimidin-2-yl)amino)piperidin-1-yl)methanone |
| 54 | 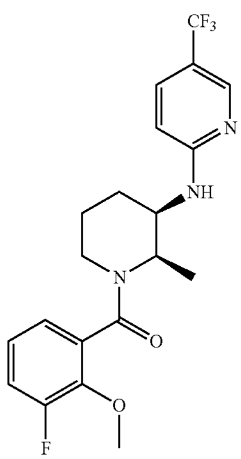 [SMILES: COc1c(F)cccc1C(=O)N1CCC[C@@H](Nc2ccc(C(F)(F)F)cn2)[C@H]1C] | (±)-cis-(3-fluoro-2-methoxyphenyl)(2-methyl-3-((5-(trifluoromethyl)pyridin-2-yl)amino)piperidin-1-yl)methanone |
| 55 | 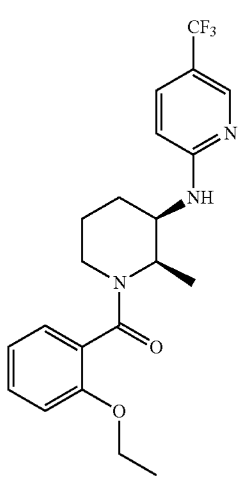 | (±)-cis-(2-ethoxy-phenyl)(2-methyl-3-((5-(trifluoro-methyl)pyridin-2-yl)amino)piperidin-1-yl)methanone |
| 56 | 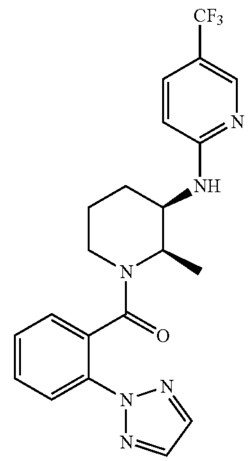 | (±)-cis-(2-(2H-1,2,3-triazol-2-yl)phenyl)(2-methyl-3-((5-(trifluoromethyl)pyridin-2-yl)amino)piperidin-1-yl)methanone |
| 57 | 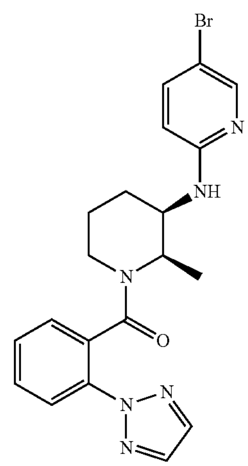 [SMILES: C[C@@H]1[C@H](Nc2ccc(Br)cn2)CCCN1C(=O)c1ccccc1-n1nccn1] | (±)-cis-(2-(2H-1,2,3-triazol-2-yl)phenyl)(3-((5-bromopyridin-2-yl)amino)-2-methylpiperidin-1-yl)methanone |
| 58 | 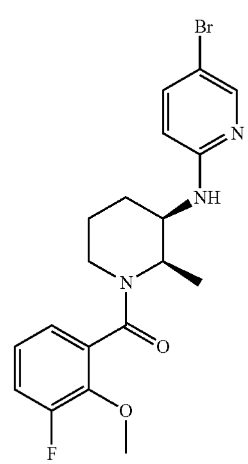 [SMILES: COc1c(F)cccc1C(=O)N1CCC[C@@H](Nc2ccc(Br)cn2)[C@H]1C] | (±)-cis-(3-((5-bromopyridin-2-yl)amino)-2-methyl-piperidin-1-yl)(3-fluoro-2-methoxy-phenyl)methanone |

| Ex. | Structure | Compound Name |
|---|---|---|
| 59 | 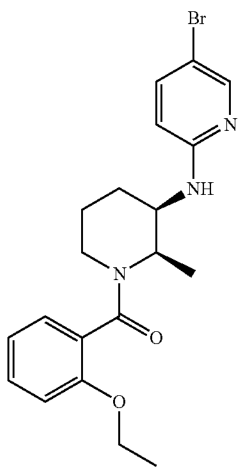 [SMILES: CCOc1ccccc1C(=O)N1CCC[C@@H](Nc2ccc(Br)cn2)[C@H]1C] | (±)-cis-(3-(5-bromopyridin-2-yl)amino)-2-methylpiperidin-1-yl)(2-ethoxyphenyl)methanone |
| 60 | 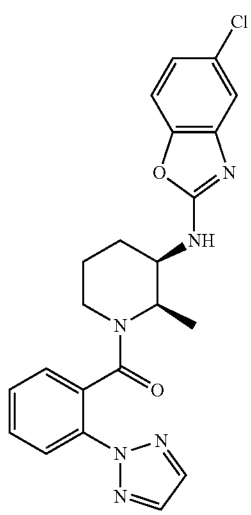 [SMILES: C[C@@H]1[C@H](Nc2nc3cc(Cl)ccc3o2)CCCN1C(=O)c1ccccc1-n1nccn1] | (±)-cis-((2-(2H-1,2,3-triazol-2-yl)phenyl)(3-((5-chlorobenzo[d]oxazol-2-yl)amino)-2-methylpiperidin-1-yl)methanone |
| 61 | 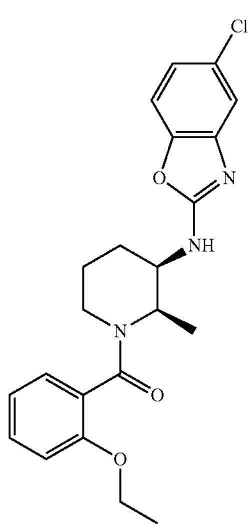 [SMILES: CCOc1ccccc1C(=O)N1CCC[C@@H](Nc2nc3cc(Cl)ccc3o2)[C@H]1C] | (±)-cis-(3-((5-chlorobenzo[d]oxazol-2-yl)amino)-2-methylpiperidin-1-yl)(2-ethoxyphenyl)methanone |
| 62 | | (±)-cis-(3-((5-chlorobenzo[d]oxazol-2-yl)amino)-2-methylpiperidin-1-yl)(3-fluoro-2-methoxyphenyl)methanone |
| 63 | | (±)-cis-(2-(2H-1,2,3-triazol-2-yl)phenyl)(2-methyl-3-(quinoxalin-2-ylamino)piperidin-1-yl)methanone |
| 64 | | (±)-cis-(3-fluoro-2-methoxyphenyl)(2-methyl-3-(quinoxalin-2-ylamino)piperidin-1-yl)methanone |

| Ex. | Structure | Compound Name |
|---|---|---|
| 65 | 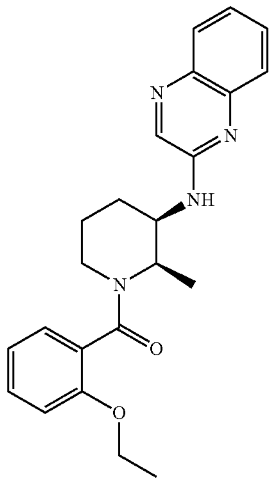 [SMILES: CCOc1ccccc1C(=O)N1CCC[C@@H](Nc2cnc3ccccc3n2)[C@H]1C] | (±)-cis-(2-ethoxy-phenyl)(2-methyl-3-(quinoxalin-2-ylamino)piperidin-1-yl)methanone |
| 66 | 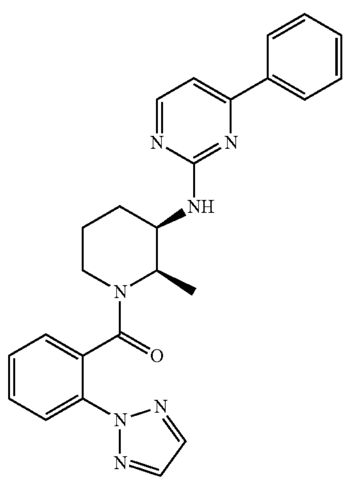 [SMILES: C[C@@H]1[C@H](Nc2nccc(-c3ccccc3)n2)CCCN1C(=O)c1ccccc1-n1nccn1] | (±)-cis-(2-(2H-1,2,3-triazol-2-yl)phenyl)(2-methyl-3-((4-phenyl-pyrimidin-2-yl)amino)piperidin-1-yl)methanone |
| 67 | 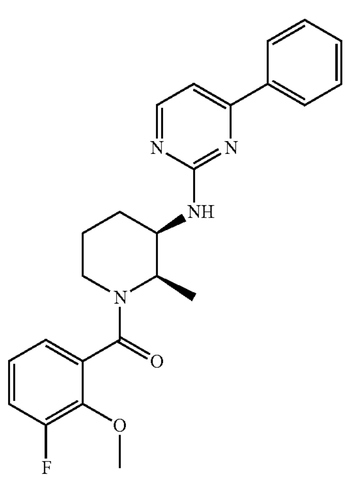 [SMILES: COc1c(F)cccc1C(=O)N1CCC[C@@H](Nc2nccc(-c3ccccc3)n2)[C@H]1C] | (±)-cis-(3-fluoro-2-methoxyphenyl)(2-methyl-3-((4-phenylpyrimidin-2-yl)amino)piperidin-1-yl)methanone |
| 68 | | (±)-cis-(2-ethoxy-phenyl)(2-methyl-3-((4-phenyl-pyrimidin-2-yl)amino)piperidin-1-yl)methanone |
| 69 | | (6-methyl-2-(2H-1,2,3-triazol-2-yl)pyridin-3-yl)((2S,3R)-2-methyl-3-((5-(trifluoro-methyl)pyrimidin-2-yl)amino)piperidin-1-yl)methanone |
| 70 | | (6-methyl-2-(1H-1,2,3-triazol-1-yl)pyridin-3-yl)(2S,3R)-2-methyl-3-((5-(trifluoromethyl)pyrimidin-2-yl)amino)piperidin-1-yl)methanone |

| Ex. | Structure | Compound Name |
|---|---|---|
| 71 | 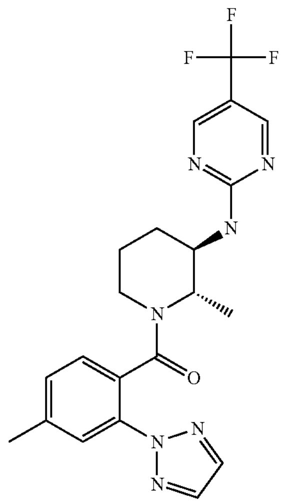 | (4-methyl-2-(2H-1,2,3-triazol-2-yl)phenyl)(2S,3R)-2-methyl-3-((5-(trifluoromethyl)pyrimidin-2-yl)amino)piperidin-1-yl)methanone |
| 72 | 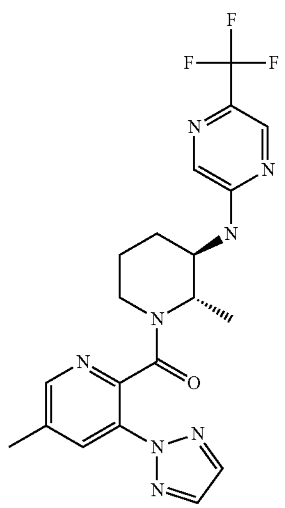 | ((2S,3R)-2-methyl-3-((5-(trifluoromethyl)pyrazin-2-yl)amino)piperidin-1-yl)(5-methyl-3-(2H-1,2,3-triazol-2-yl)pyridin-2-yl)methanone |
| 73 | 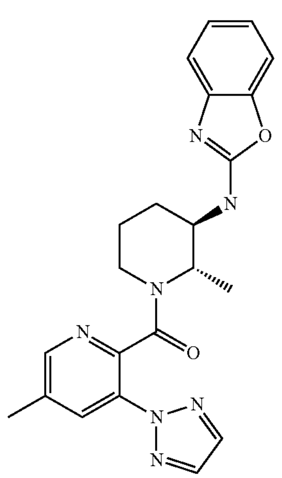 [SMILES: Cc1cnc(C(=O)N2CCC[C@@H](Nc3nc4ccccc4o3)[C@@H]2C)c(-n2nccn2)c1] | ((2S,3R)-3-(benzo[d]oxazol-2-ylamino)-2-methylpiperidin-1-yl)(5-methyl-3-(2H-1,2,3-triazol-2-yl)pyridin-2-yl)methanone |
| 74 | | (6-methyl-2-(2H-1,2,3-triazol-2-yl)pyridin-3-yl)(2S,3R)-2-methyl-3-((5-(trifluoromethyl)pyrazin-2-yl)amino)piperidin-1-yl)methanone |
| 75 | | ((2S,3R)-3-(benzo[d]oxazol-2-ylamino)-2-methyl-piperidin-1-yl)(6-methyl-2-(2H-1,2,3-triazol-2-yl)pyridin-3-yl)methanone |
| 76 | | ((2S,3R)-3-(benzo[d]oxazol-2-ylamino)-2-methyl-piperidin-1-yl)(6-methyl-2-(1H-1,2,3-triazol-1-yl)pyridin-3-yl)methanone |

| Ex. | Structure | Compound Name |
|---|---|---|
| 77 | 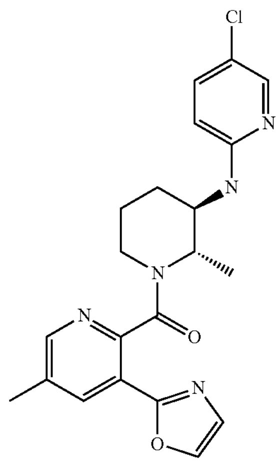 [SMILES: Cc1cnc(C(=O)N2CCC[C@@H](Nc3ccc(Cl)cn3)[C@@H]2C)c(-c2ncco2)c1] | ((2S,3R)-3-((5-chloropyridin-2-yl)amino)-2-methyl-piperidin-1-yl)(5-methyl-3-(oxazol-2-yl)pyridin-2-yl)methanone |
| 78 | 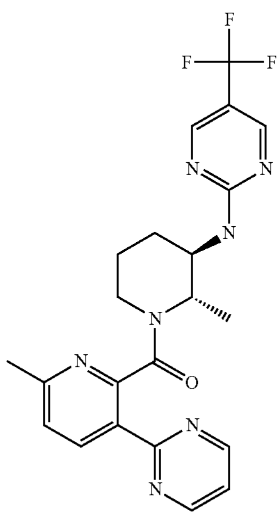 | ((2S,3R)-2-methyl-3-((5-(trifluoro-methyl)pyrimidin-2-yl)amino)piperidin-1-yl)(6-methyl-3-(pyrimidin-2-yl)pyridin-2-yl)methanone |
| 79 | 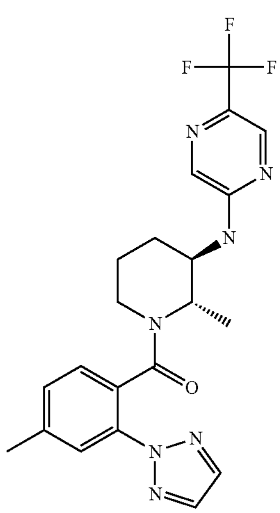 [SMILES: Cc1ccc(C(=O)N2CCC[C@@H](Nc3cnc(C(F)(F)F)cn3)[C@@H]2C)c(-n2nccn2)c1] | (4-methyl-2-(2H-1,2,3-triazol-2-yl)phenyl)(2S,3R)-2-methyl-3-((5-(trifluoromethyl)pyrazin-2-yl)amino)piperidin-1-yl)methanone |
| 80 | | ((2S,3R)-3-((5-bromopyridin-2-yl)amino)-2-methyl-piperidin-1-yl)(5-methyl-3-(oxazol-2-yl)pyridin-2-yl)methanone |
| 81 | | ((2S,3R)-3-(benzo[d]oxazol-2-ylamino)-2-methylpiperidin-1-yl)(6-methyl-3-(pyrimidin-2-yl)pyridin-2-yl)methanone |
| 82 | | (4-methoxy-2-(2H-1,2,3-triazol-2-yl)phenyl)((2S,3R)-2-methyl-3-((5-(trifluoro-methyl)pyrazin-2-yl)amino)piperidin-1-yl)methanone |

| Ex. | Structure | Compound Name |
|---|---|---|
| 83 | 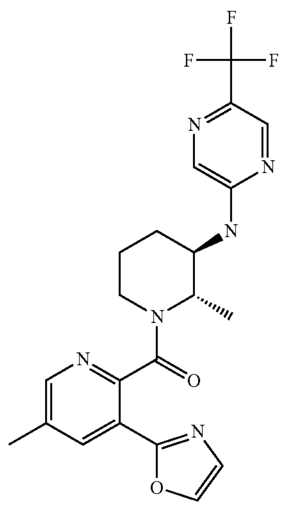 [SMILES: Cc1cnc(C(=O)N2CCC[C@@H](Nc3cnc(C(F)(F)F)cn3)[C@@H]2C)c(-c2ncco2)c1] | ((2S,3R)-2-methyl-3-((5-(trifluoromethyl)pyrazin-2-yl)amino)piperidin-1-yl)(5-methyl-3-(oxazol-2-yl)pyridin-2-yl)methanone |
| 84 | 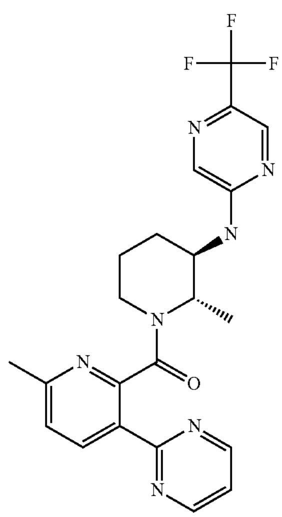 | ((2S,3R)-2-methyl-3-((5-(trifluoromethyl)pyrazin-2-yl)amino)piperidin-1-yl)(6-methyl-3-(pyrimidin-2-yl)pyridin-2-yl)methanone |
| 85 | 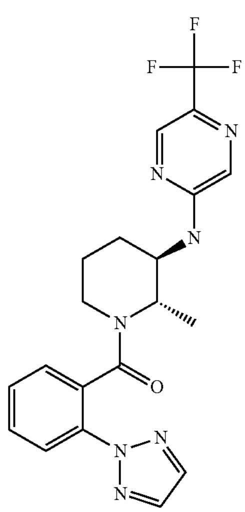 [SMILES: C[C@H]1[C@H](Nc2cnc(C(F)(F)F)cn2)CCCN1C(=O)c1ccccc1-n1nccn1] | (2-(2H-1,2,3-triazol-2-yl)phenyl)((2S,3R)-2-methyl-3-((5-(trifluoromethyl)pyrazin-2-yl)amino)piperidin-1-yl)methanone |
| 86 | 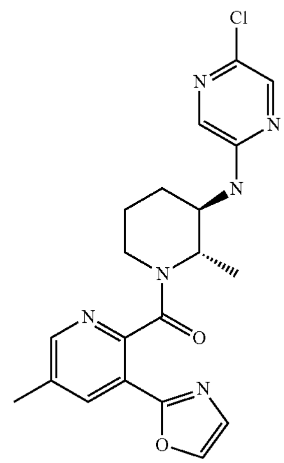 [SMILES: Cc1cnc(C(=O)N2CCC[C@@H](Nc3cnc(Cl)cn3)[C@@H]2C)c(-c2ncco2)c1] | ((2S,3R)-3-((5-chloropyrazin-2-yl)amino)-2-methylpiperidin-1-yl)(5-methyl-3-(oxazol-2-yl)pyridin-2-yl)methanone |
| 87 | 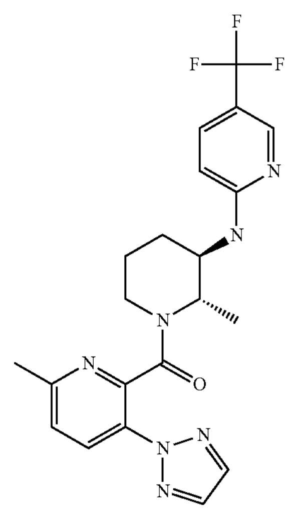 [SMILES: Cc1ccc(-n2nccn2)c(C(=O)N2CCC[C@@H](Nc3ccc(C(F)(F)F)cn3)[C@@H]2C)n1] | ((2S,3R)-2-methyl-3-((5-(trifluoromethyl)pyridin-2-yl)amino)piperidin-1-yl)(6-methyl-3-(2H-1,2,3-triazol-2-yl)pyridin-2-yl)methanone |
| 88 | 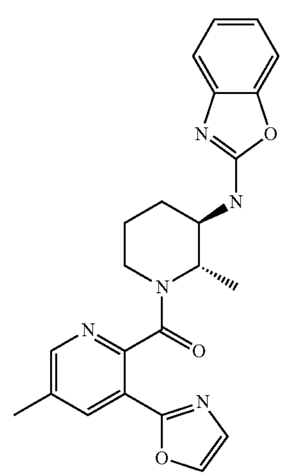 [SMILES: Cc1cnc(C(=O)N2CCC[C@@H](Nc3nc4ccccc4o3)[C@@H]2C)c(-c2ncco2)c1] | ((2S,3R)-3-(benzo[d]oxazol-2-ylamino)-2-methylpiperidin-1-yl)(5-methyl-3-(oxazol-2-yl)pyridin-2-yl)methanone |

| Ex. | Structure | Compound Name |
|---|---|---|
| 89 | 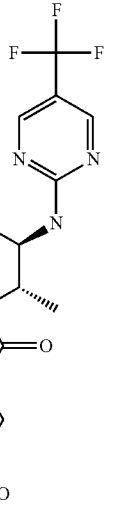 | (5-methoxy-2-(2H-1,2,3-triazol-2-yl)phenyl)((2S,3R)-2-methyl-3-((5-(trifluoromethyl)pyrimidin-2-yl)amino)piperidin-1-yl)methanone |
| 90 | 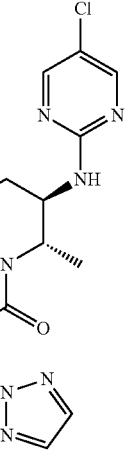 | (5-fluoro-2-(2H-1,2,3-triazol-2-yl)phenyl)((2S,3R)-2-methyl-3-((5-(trifluoromethyl)pyrazin-2-yl)amino)piperidin-1-yl)methanone |
| 91 | 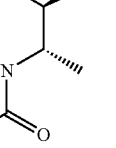 | ((2S,3R)-3-((5-chloropyrimidin-2-yl)amino)-2-methylpiperidin-1-yl)(4-methyl-2-(2H-1,2,3-triazol-2-yl)phenyl)methanone |
| 92 | 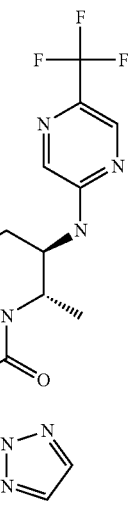 | ((2S,3R)-3-((5-bromopyridin-2-yl)amino)-2-methylpiperidin-1-yl)(5-methyl-3-(2H-1,2,3-triazol-2-yl)pyridin-2-yl)methanone |
| 93 | 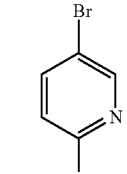 | (6-methyl-2-(1H-1,2,3-triazol-1-yl)pyridin-3-yl)((2S,3R)-2-methyl-3-((5-(trifluoromethyl)pyridin-2-yl)amino)piperidin-1-yl)methanone |
| 94 | 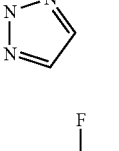 | ((2S,3R)-2-methyl-3-((5-(trifluoromethyl)pyrimidin-2-yl)amino)piperidin-1-yl)(5-methyl-3-(2H-1,2,3-triazol-2-yl)pyridin-2-yl)methanone |

| Ex. | Structure | Compound Name |
|---|---|---|
| 95 | 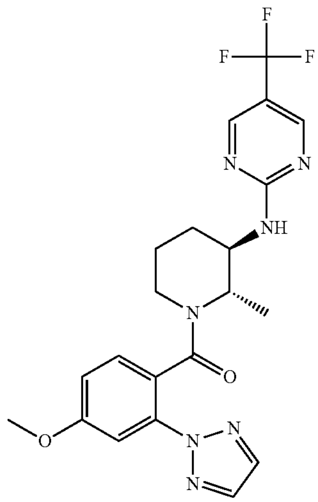 | (4-methoxy-2-(2H-1,2,3-triazol-2-yl)phenyl)((2S,3R)-2-methyl-3-((5-(trifluoromethyl)pyrimidin-2-yl)amino)piperidin-1-yl)methanone |
| 96 | 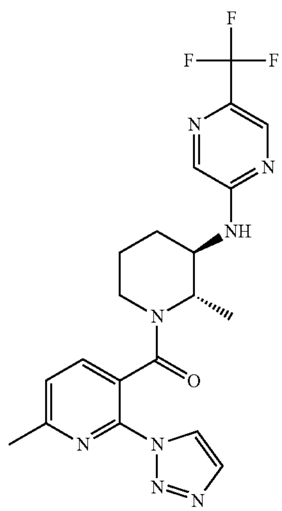 | (6-methyl-2-(1H-1,2,3-triazol-1-yl)pyridin-3-yl)((2S,3R)-2-methyl-3-((5-(trifluoromethyl)pyrazin-2-yl)amino)piperidin-1-yl)methanone |
| 97 | 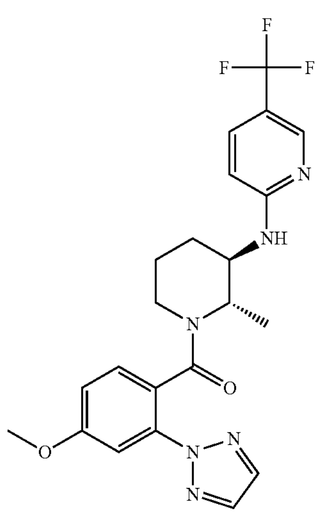 | (4-methoxy-2-(2H-1,2,3-triazol-2-yl)phenyl)((2S,3R)-2-methyl-3-((5-(trifluoromethyl)pyridin-2-yl)amino)piperidin-1-yl)methanone |
| 98 | | (6-methyl-2-(2H-1,2,3-triazol-2-yl)pyridin-3-yl)((2S,3R)-2-methyl-3-((5-(trifluoromethyl)pyridin-2-yl)amino)piperidin-1-yl)methanone |
| 99 | | ((2S,3R)-3-((5-chloropyridin-2-yl)amino)-2-methylpiperidin-1-yl)(4-methyl-2-(2H-1,2,3-triazol-2-yl)phenyl)methanone |
| 100 | | (2-(2H-1,2,3-triazol-2-yl)phenyl)((2S,3R)-3-((5-chloropyridin-2-yl)amino)methylpiperidin-1-yl)methanone |

-continued

| Ex. | Structure | Compound Name |
|---|---|---|
| 101 | 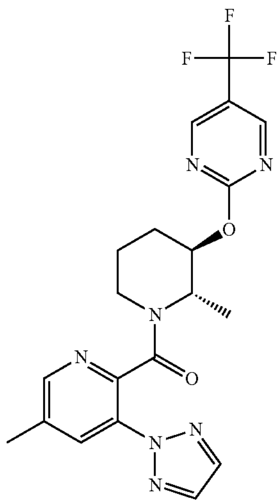 | ((2S,3R)-2-methyl-3-((5-(trifluoromethyl)pyrimidin-2-yl)oxy)piperidin-1-yl)(5-methyl-3-(2H-1,2,3-triazol-2-yl)pyridin-2-yl)methanone |
| 102 | 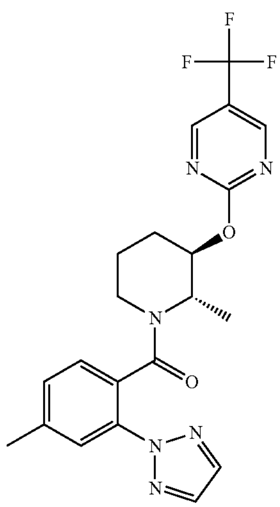 | (4-methyl-2-(2H-1,2,3-triazol-2-yl)phenyl)((2S,3R)-2-methyl-3-((5-(trifluoromethyl)pyrimidin-2-yl)oxy)piperidin-1-yl)methanone |
| 103 | 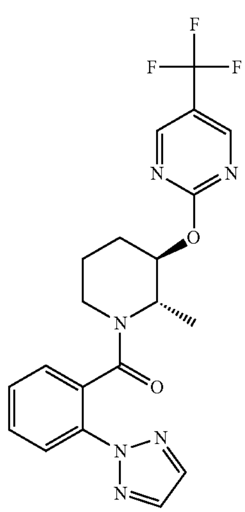 [SMILES: C[C@H]1[C@H](Oc2ncc(C(F)(F)F)cn2)CCCN1C(=O)c1ccccc1-n1nccn1] | (2-(2H-1,2,3-triazol-2-yl)phenyl)((2S,3R)-2-methyl-3-((5-(trifluoromethyl)pyrimidin-2-yl)oxy)piperidin-1-yl)methanone |

-continued

| Ex. | Structure | Compound Name |
|---|---|---|
| 104 | | ((2S,3R)-2-methyl-3-((5-(trifluoromethyl)pyrimidin-2-yl)oxy)piperidin-1-yl)(6-methyl-3-(2H-1,2,3-triazol-2-yl)pyridin-2-yl)methanone |
| 105 | | ((2S,3R)-2-methyl-3-((5-(trifluoromethyl)pyrazin-2-yl)oxy)piperidin-1-yl)(5-methyl-3-(2H-1,2,3-triazol-2-yl)pyridin-2-yl)methanone |
| 106 | | (2-(2H-1,2,3-triazol-2-yl)phenyl)((2S,3R)-2-methyl-3-((5-(trifluoromethyl)pyrazin-2-yl)oxy)piperidin-1-yl)methanone |

| Ex. | Structure | Compound Name |
|---|---|---|
| 107 | 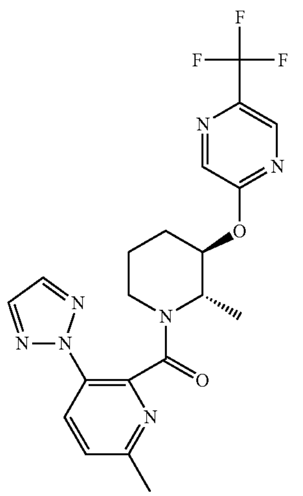 | ((2S,3R)-2-methyl-3-((5-(trifluoromethyl)pyrazin-2-yl)oxy)piperidin-1-yl)(6-methyl-3-(2H-1,2,3-triazol-2-yl)pyridin-2-yl)methanone |
| 108 | 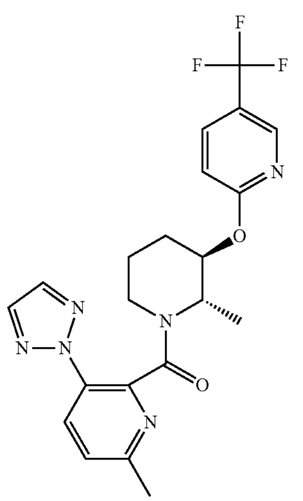 | ((2S,3R)-2-methyl-3-((5-(trifluoromethyl)pyridin-2-yl)oxy)piperidin-1-yl)(6-methyl-3-(2H-1,2,3-triazol-2-yl)pyridin-2-yl)methanone |
| 109 | 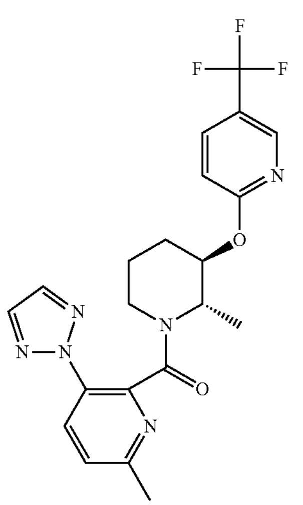 | (±)-trans-(2-methyl-3-((5-(trifluoromethyl)pyridin-2-yl)oxy)piperidin-1-yl)(6-methyl-3-(2H-1,2,3-triazol-2-yl)pyridin-2-yl)methanone |
| 110 | | (2-(2H-1,2,3-triazol-2-yl)phenyl)((2S,3R)-2-methyl-3-((5-(trifluoromethyl)pyridin-2-yl)oxy)piperidin-1-yl)methanone |
| 111 | | ((2S,3R)-2-methyl-3-((5-(trifluoromethyl)pyridin-2-yl)oxy)piperidin-1-yl)(5-methyl-3-(2H-1,2,3-triazol-2-yl)pyridin-2-yl)methanone |
| 112 | | (4-methyl-2-(2H-1,2,3-triazol-2-yl)phenyl)((2S,3R)-2-methyl-3-((5-(trifluoromethyl)pyridin-2-yl)oxy)piperidin-1-yl)methanone |

| Ex. | Structure | Compound Name |
|---|---|---|
| 113 | 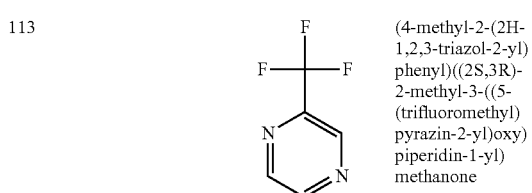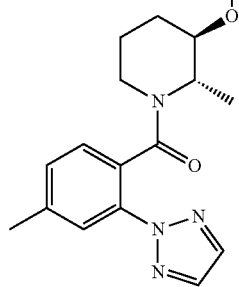 | (4-methyl-2-(2H-1,2,3-triazol-2-yl)phenyl)((2S,3R)-2-methyl-3-((5-(trifluoromethyl)pyrazin-2-yl)oxy)piperidin-1-yl)methanone |
| 114 | 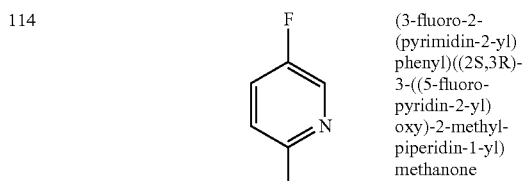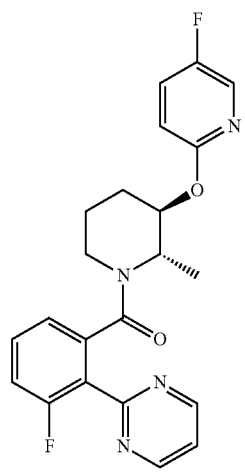 | (3-fluoro-2-(pyrimidin-2-yl)phenyl)((2S,3R)-3-((5-fluoropyridin-2-yl)oxy)-2-methyl-piperidin-1-yl)methanone |
| 115 | 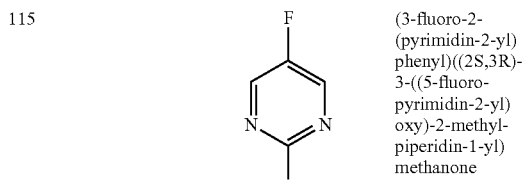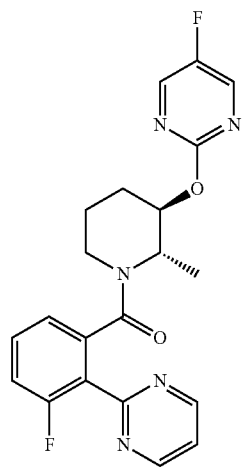 | (3-fluoro-2-(pyrimidin-2-yl)phenyl)((2S,3R)-3-((5-fluoropyrimidin-2-yl)oxy)-2-methyl-piperidin-1-yl)methanone |
| 116 | 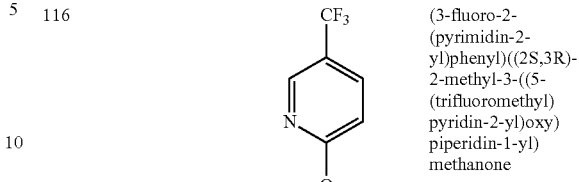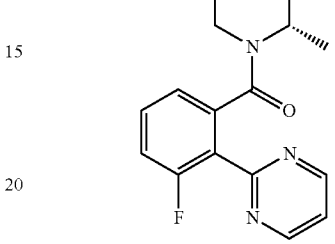 | (3-fluoro-2-(pyrimidin-2-yl)phenyl)((2S,3R)-2-methyl-3-((5-(trifluoromethyl)pyridin-2-yl)oxy)piperidin-1-yl)methanone |
| 117 | 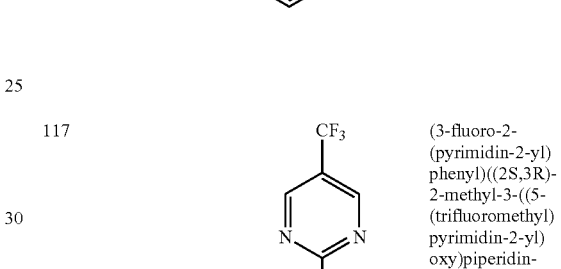 | (3-fluoro-2-(pyrimidin-2-yl)phenyl)((2S,3R)-2-methyl-3-((5-(trifluoromethyl)pyrimidin-2-yl)oxy)piperidin-1-yl)methanone |
| 118 | 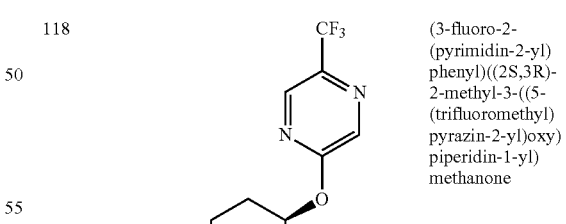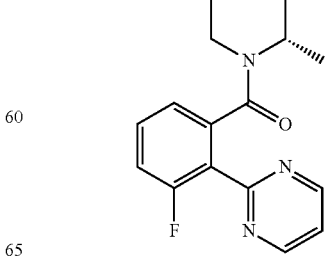 | (3-fluoro-2-(pyrimidin-2-yl)phenyl)((2S,3R)-2-methyl-3-((5-(trifluoromethyl)pyrazin-2-yl)oxy)piperidin-1-yl)methanone |

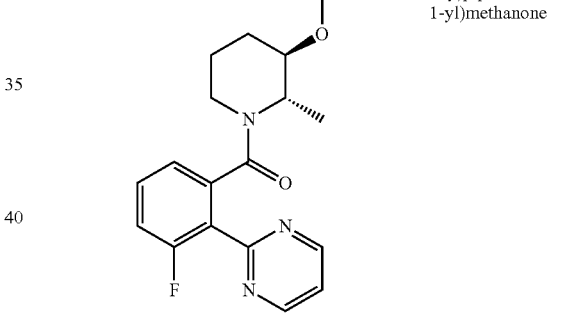

| Ex. | Structure | Compound Name |
|---|---|---|
| 119 | 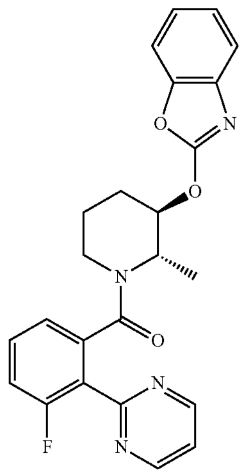 [SMILES: C[C@H]1[C@H](Oc2nc3ccccc3o2)CCCN1C(=O)c1cccc(F)c1-c1ncccn1] | ((2S,3R)-3-(benzo[d]oxazol-2-yloxy)-2-methyl-piperidin-1-yl)(3-fluoro-2-(pyrimidin-2-yl)phenyl)methanone |
| 120 | 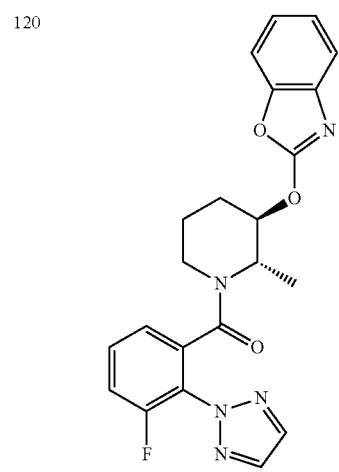 | ((2S,3R)-3-(benzo[d]oxazol-2-yloxy)-2-methyl-piperidin-1-yl)(3-fluoro-2-(2H-1,2,3-triazol-2-yl)phenyl)methanone |
| 121 | 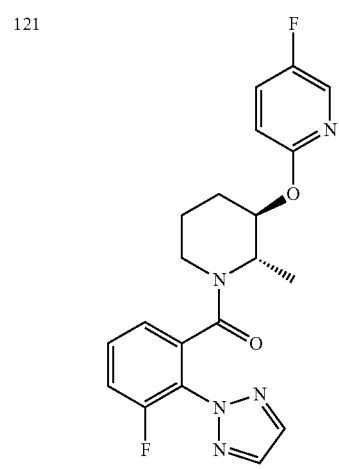 | (3-fluoro-2-(2H-1,2,3-triazol-2-yl)phenyl)((2S,3R)-3-((5-fluoropyridin-2-yl)oxy)-2-methylpiperidin-1-yl)methanone |

| Ex. | Structure | Compound Name |
|---|---|---|
| 122 | 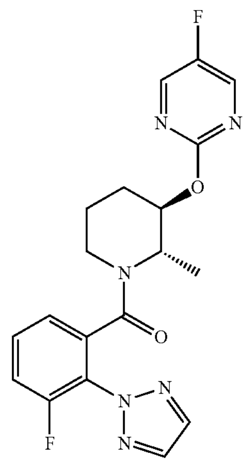 | (3-fluoro-2-(2H-1,2,3-triazol-2-yl)phenyl)((2S,3R)-3-((5-fluoropyrimidin-2-yl)oxy)-2-methylpiperidin-1-yl)methanone |
| 123 | 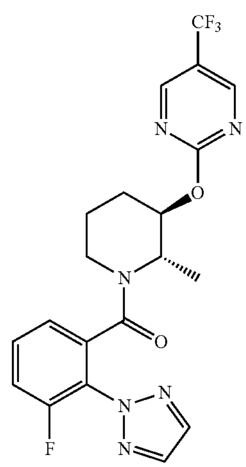 | (3-fluoro-2-(2H-1,2,3-triazol-2-yl)phenyl)((2S,3R)-2-methyl-3-((5-(trifluoromethyl)pyrimidin-2-yl)oxy)piperidin-1-yl)methanone |
| 124 | 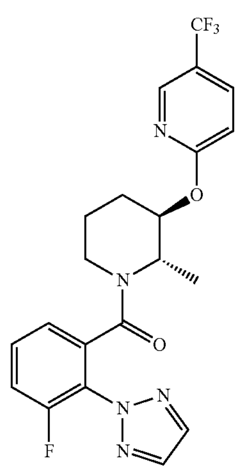 [SMILES: C[C@H]1[C@H](Oc2ccc(C(F)(F)F)cn2)CCCN1C(=O)c1cccc(F)c1-n1nccn1] | (3-fluoro-2-(2H-1,2,3-triazol-2-yl)phenyl)((2S,3R)-2-methyl-3-((5-(trifluoromethyl)pyridin-2-yl)oxy)piperidin-1-yl)methanone |

| Ex. | Compound Name |
|---|---|
| 125 | (3-fluoro-2-(2H-1,2,3-triazol-2-yl)phenyl)((2S,3R)-2-methyl-3-((5-(trifluoromethyl)pyrazin-2-yl)oxy)piperidin-1-yl)methanone |
| 126 | ((2S,3R)-3-(benzo[d]oxazol-2-yloxy)-2-methyl-piperidin-1-yl)(3-fluoro-2-(2H-1,2,3-triazol-2-yl)phenyl)methanone |
| 127 | ((2S,3R)-3-(benzo[d]oxazol-2-yloxy)-2-methylpiperidin-1-yl)(2-fluoro-6-(2H-1,2,3-triazol-2-yl)phenyl)methanone |
| 128 | (2-fluoro-6-(2H-1,2,3-triazol-2-yl)phenyl)((2S,3R)-3-((5-fluoro-pyridin-2-yl)oxy)-2-methylpiperidin-1-yl)methanone |
| 129 | (2-fluoro-6-(2H-1,2,3-triazol-2-yl)phenyl)((2S,3R)-3-((5-fluoro-pyrimidin-2-yl)oxy)-2-methyl-piperidin-1-yl)methanone |
| 130 | (2-fluoro-6-(2H-1,2,3-triazol-2-yl)phenyl)((2S,3R)-2-methyl-3-((5-(trifluoromethyl)pyrimidin-2-yl)oxy)piperidin-1-yl)methanone |

| Ex. | Structure | Compound Name |
|---|---|---|
| 131 | 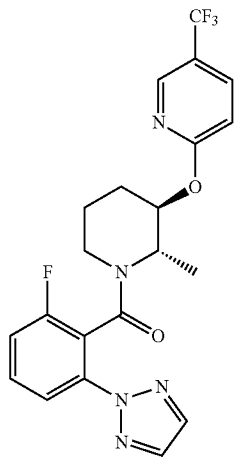 [SMILES: C[C@H]1[C@H](Oc2ccc(C(F)(F)F)cn2)CCCN1C(=O)c1c(F)cccc1-n1nccn1] | (2-fluoro-6-(2H-1,2,3-triazol-2-yl)phenyl)((2S,3R)-2-methyl-3-((5-(trifluoromethyl)pyridin-2-yl)oxy)piperidin-1-yl)methanone |
| 132 | 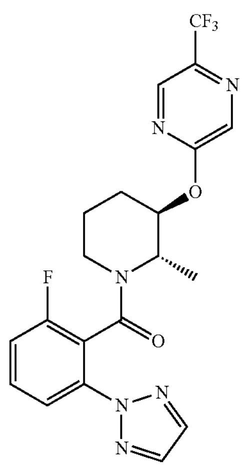 [SMILES: C[C@H]1[C@H](Oc2cnc(C(F)(F)F)cn2)CCCN1C(=O)c1c(F)cccc1-n1nccn1] | (2-fluoro-6-(2H-1,2,3-triazol-2-yl)phenyl)((2S,3R)-2-methyl-3-((5-(trifluoromethyl)pyrazin-2-yl)oxy)piperidin-1-yl)methanone |
| 133 | 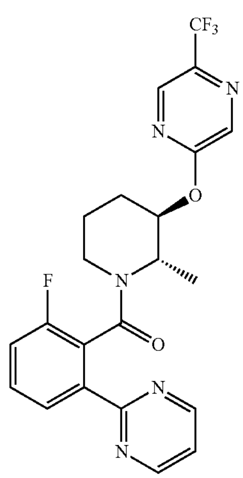 [SMILES: C[C@H]1[C@H](Oc2cnc(C(F)(F)F)cn2)CCCN1C(=O)c1c(F)cccc1-c1ncccn1] | (2-fluoro-6-(pyrimidin-2-yl)phenyl)((2S,3R)-2-methyl-3-((5-(trifluoromethyl)pyrazin-2-yl)oxy)piperidin-1-yl)methanone |
| 134 | | (2-fluoro-6-(pyrimidin-2-yl)phenyl)((2S,3R)-2-methyl-3-((5-(trifluoromethyl)pyridin-2-yl)oxy)piperidin-1-yl)methanone |
| 135 | | (2-fluoro-6-(pyrimidin-2-yl)phenyl)((2S,3R)-2-methyl-3-((5-(trifluoromethyl)pyrimidin-2-yl)oxy)piperidin-1-yl)methanone |
| 136 | | (2-fluoro-6-(pyrimidin-2-yl)phenyl)((2S,3R)-3-((5-fluoropyrimidin-2-yl)oxy)-2-methyl-piperidin-1-yl)methanone |

-continued

| Ex. | Structure | Compound Name |
|---|---|---|
| 137 | 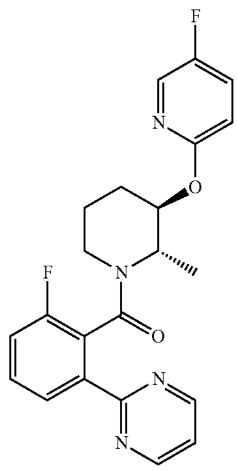 [SMILES: C[C@H]1[C@H](Oc2ccc(F)cn2)CCCN1C(=O)c1c(F)cccc1-c1ncccn1] | (2-fluoro-6-pyrimidin-2-yl)phenyl)((2S,3R)-3-((5-fluoro-pyridin-2-yl)oxy)-2-methyl-piperidin-1-yl)methanone |
| 138 | 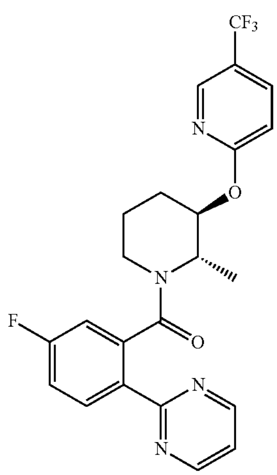 [SMILES: C[C@H]1[C@H](Oc2ccc(C(F)(F)F)cn2)CCCN1C(=O)c1cc(F)ccc1-c1ncccn1] | (5-fluoro-2-(pyrimidin-2-yl)phenyl)((2S,3R)-2-methyl-3-((5-(trifluoromethyl)pyridin-2-yl)oxy)piperidin-1-yl)methanone |
| 139 | 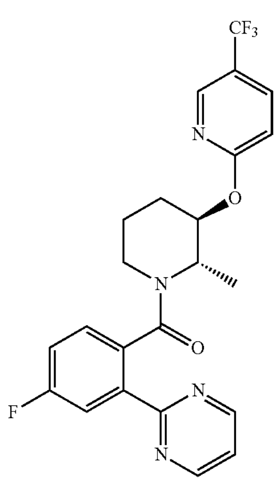 | (4-fluoro-2-(pyrimidin-2-yl)phenyl)((2S,3R)-2-methyl-3-((5-(trifluoromethyl)pyridin-2-yl)oxy)piperidin-1-yl)methanone |

-continued

| Ex. | Structure | Compound Name |
|---|---|---|
| 140 | 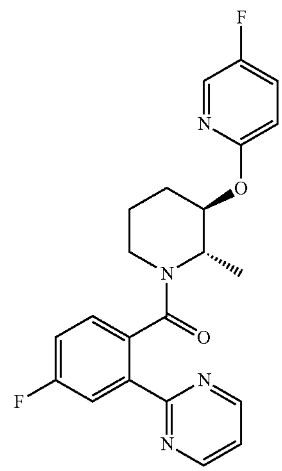 [SMILES: C[C@H]1[C@H](Oc2ccc(F)cn2)CCCN1C(=O)c1ccc(F)cc1-c1ncccn1] | (4-fluoro-2-(pyrimidin-2-yl)phenyl)((2S,3R)-2-methyl-3-((5-(trifluoromethyl)pyridin-2-yl)oxy)piperidin-1-yl)methanone |
| 141 | 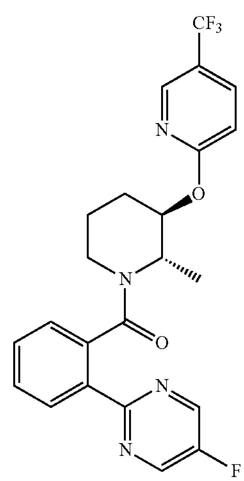 [SMILES: C[C@H]1[C@H](Oc2ccc(C(F)(F)F)cn2)CCCN1C(=O)c1ccccc1-c1ncc(F)cn1] | (4-fluoro-2-(pyrimidin-2-yl)phenyl)((2S,3R)-3-((5-fluoro-pyridin-2-yl)oxy)-2-methylpiperidin-1-yl)methanone |
| 142 | 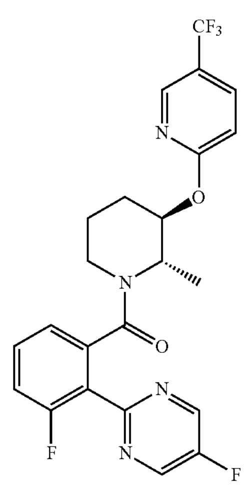 [SMILES: C[C@H]1[C@H](Oc2ccc(C(F)(F)F)cn2)CCCN1C(=O)c1cccc(F)c1-c1ncc(F)cn1] | (3-fluoro-2-(5-fluoropyrimidin-2-yl)phenyl)((2S,3R)-2-methyl-3-((5-(trifluoromethyl)pyridin-2-yl)oxy)piperidin-1-yl)methanone |

-continued

| Ex. | Structure | Compound Name |
|---|---|---|
| 143 | 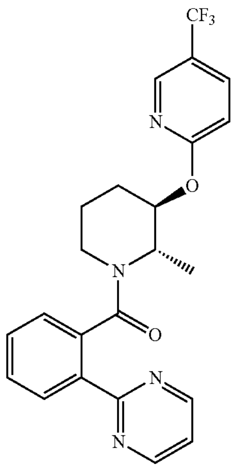 [SMILES: C[C@H]1[C@H](Oc2ccc(C(F)(F)F)cn2)CCCN1C(=O)c1ccccc1-c1ncccn1] | ((2S,3R)-2-methyl-3-((5-(trifluoromethyl)pyridin-2-yl)oxy)piperidin-1-yl)(2-(pyrimidin-2-yl)phenyl)methanone |
| 144 | 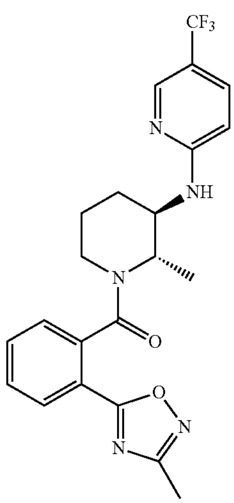 [SMILES: Cc1noc(-c2ccccc2C(=O)N2CCC[C@@H](Nc3ccc(C(F)(F)F)cn3)[C@@H]2C)n1] | (2-(3-methyl-1,2,4-oxadiazol-5-yl)phenyl)((2S,3R)-2-methyl-3-((5-(trifluoromethyl)pyridin-2-yl)amino)piperidin-1-yl)methanone |
| 145 | 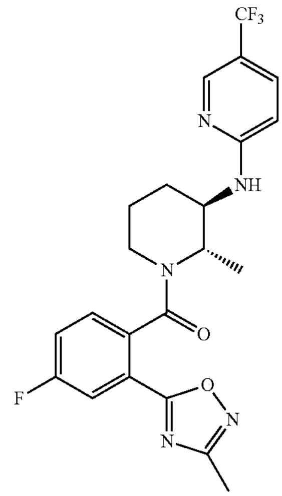 [SMILES: Cc1noc(-c2cc(F)ccc2C(=O)N2CCC[C@@H](Nc3ccc(C(F)(F)F)cn3)[C@@H]2C)n1] | (4-fluoro-2-(3-methyl-1,2,4-oxadiazol-5-yl)phenyl)((2S,3R)-2-methyl-3-((5-(trifluoromethyl)pyridin-2-yl)amino)piperidin-1-yl)methanone |
| 146 | 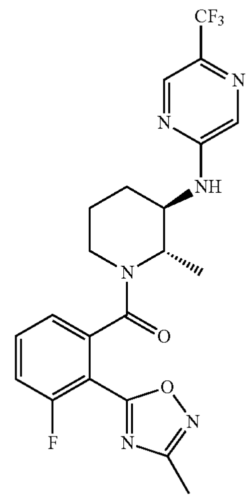 [SMILES: Cc1noc(-c2c(F)cccc2C(=O)N2CCC[C@@H](Nc3cnc(C(F)(F)F)cn3)[C@@H]2C)n1] | (3-fluoro-2-(3-methyl-1,2,4-oxadiazol-5-yl)phenyl)((2S,3R)-2-methyl-3-((5-(trifluoromethyl)pyrazin-2-yl)amino)piperidin-1-yl)methanone |

55. A pharmaceutical composition comprising a compound according claim 1 and at least one pharmaceutically acceptable excipient.

56. A method of treating a subject suffering from or diagnosed with a disease, disorder, or medical condition mediated by orexin receptor activity, wherein the disease, disorder, or medical condition is mood disorders, post-traumatic stress disorder, panic disorders, attention deficit disorders, cognitive deficiencies, or substance abuse, comprising administering to the subject a therapeutically effective amount of a compound according to claim 1.

57. The method of claim 56, wherein the disease, disorder, or medical condition is mood disorders.

* * * * *